United States Patent
Kim et al.

(10) Patent No.: US 10,937,967 B2
(45) Date of Patent: Mar. 2, 2021

(54) AMINE-BASED COMPOUND AND ORGANIC LIGHT-EMITTING DEVICE INCLUDING THE AMINE-BASED COMPOUND

(71) Applicant: Samsung Display Co., Ltd., Yongin-si (KR)

(72) Inventors: Youngkook Kim, Yongin-si (KR); Jongwoo Kim, Yongin-si (KR); Jangyeol Baek, Yongin-si (KR); Eunjae Jeong, Yongin-si (KR); Sanghyun Han, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 358 days.

(21) Appl. No.: 15/968,541

(22) Filed: May 1, 2018

(65) Prior Publication Data

US 2019/0115543 A1    Apr. 18, 2019

(30) Foreign Application Priority Data

Oct. 12, 2017    (KR) .......................... 10-2017-0132753

(51) Int. Cl.
| | | |
|---|---|---|
| *H01L 51/00* | (2006.01) | |
| *C07D 403/12* | (2006.01) | |
| *H01L 51/50* | (2006.01) | |
| *H01L 51/56* | (2006.01) | |

(52) U.S. Cl.
CPC ........ *H01L 51/0061* (2013.01); *C07D 403/12* (2013.01); *H01L 51/0072* (2013.01); *H01L 51/001* (2013.01); *H01L 51/5004* (2013.01); *H01L 51/506* (2013.01); *H01L 51/5012* (2013.01); *H01L 51/5064* (2013.01); *H01L 51/5088* (2013.01); *H01L 51/56* (2013.01); *H01L 2251/552* (2013.01); *H01L 2251/558* (2013.01)

(58) Field of Classification Search
CPC .................................................. H01L 51/0061
See application file for complete search history.

(56) References Cited

U.S. PATENT DOCUMENTS

| | | |
|---|---|---|
| 4,720,432 A | 1/1988 | VanSlyke et al. |
| 5,061,569 A | 10/1991 | VanSlyke et al. |
| 6,242,115 B1 | 6/2001 | Thomson et al. |
| 7,867,631 B2 | 1/2011 | Kim et al. |
| 8,021,764 B2 | 9/2011 | Hwang et al. |
| 2016/0149141 A1 | 5/2016 | Jung et al. |

FOREIGN PATENT DOCUMENTS

| | | | |
|---|---|---|---|
| JP | 11-144873 | | 5/1999 |
| JP | 2000-302756 | A | 10/2000 |
| JP | 2006-151979 | A | 6/2006 |
| JP | 2006-298898 | A | 11/2006 |
| JP | 2015-227316 | A | 12/2015 |
| KR | 10-2008-0067165 | | 7/2008 |
| KR | 10-2009-0129799 | | 12/2009 |
| KR | 20110111095 | A * | 10/2011 |
| KR | 10-2016-0061571 | | 6/2016 |

OTHER PUBLICATIONS

English machine translation of KR 2011-0111095A (Year: 2011).*

* cited by examiner

*Primary Examiner* — Peter F Godenschwager

(74) *Attorney, Agent, or Firm* — Lewis Roca Rothgerber Christie LLP

(57) ABSTRACT

Provided is an amine-based compound represented by one of Formulae 1-1 and 1-2. An organic light-emitting device includes: a first electrode; a second electrode facing the first electrode; and an organic layer disposed between the first electrode and the second electrode, where the organic layer includes an emission layer and at least one amine-based compound described above.

20 Claims, 4 Drawing Sheets

| 190 |
|-----|
| 150 |
| 110 |

| 190 |
|-----|
| 150 |
| 110 |
| 210 |

| 220 |
|:---:|
| 190 |
| 150 |
| 110 |

| |
|---|
| 220 |
| 190 |
| 150 |
| 110 |
| 210 |

AMINE-BASED COMPOUND AND ORGANIC LIGHT-EMITTING DEVICE INCLUDING THE AMINE-BASED COMPOUND

CROSS-REFERENCE TO RELATED APPLICATION

This application claims priority to and the benefit of Korean Patent Application No. 10-2017-0132753, filed on Oct. 12, 2017, in the Korean Intellectual Property Office, the entire content of which is incorporated herein by reference.

BACKGROUND

1. Field

One or more embodiments relates to an amine-based compound and an organic light-emitting device including the same.

2. Description of the Related Art

Organic light-emitting devices (OLEDs) are self-emission devices that have wide viewing angles, high contrast ratios, short response times, and excellent brightness, driving voltage, and response speed characteristics, and produce full-color images.

OLEDs may include a first electrode disposed on a substrate, and may include a hole transport region, an emission layer, an electron transport region, and a second electrode sequentially disposed on the first electrode. Holes provided from the first electrode may move toward the emission layer through the hole transport region. Electrons provided from the second electrode may move toward the emission layer through the electron transport region. Carriers, such as holes and electrons, may recombine in the emission layer to produce excitons. These excitons transit (or relax) from an excited state to a ground state to thereby generate light.

SUMMARY

One or more embodiments include an amine-based compound and an organic light-emitting device including the same.

Additional aspects of embodiments will be set forth in part in the description which follows and, in part, will be apparent from the description, or may be learned by practice of the presented embodiments.

According to one or more embodiments, an amine-based compound is represented by one of Formulae 1-1 and 1-2:

Formula 1-1

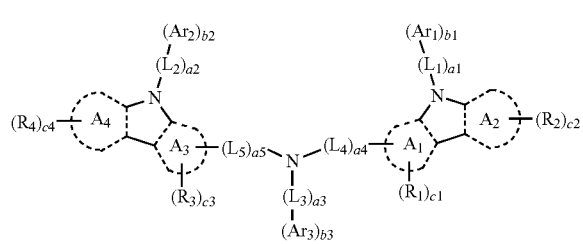

-continued

Formula 1-2

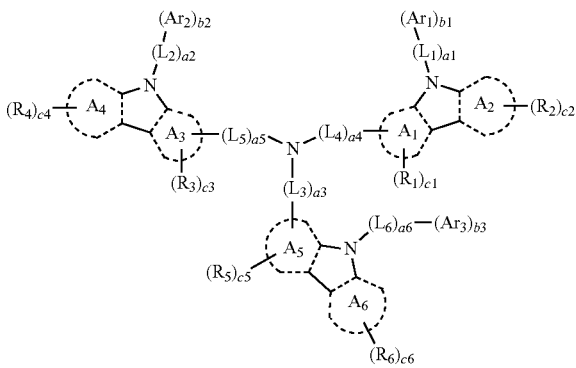

wherein, in Formulae 1-1 and 1-2, $A_1$ to $A_6$ are each independently selected from a $C_5$-$C_{30}$ cyclic group and a $C_1$-$C_{30}$ heterocyclic group, $L_1$ to $L_6$ are each independently selected from a substituted or unsubstituted $C_5$-$C_{60}$ carbocyclic group and a substituted or unsubstituted $C_1$-$C_{60}$ heterocyclic group, a1 to a6 are each independently an integer from 0 to 5, when a1 is 2 or greater, at least two $L_1$ groups are identical to or different from each other; when a2 is 2 or greater, at least two $L_2$ groups are identical to or different from each other; when a3 is 2 or greater, at least two $L_3$ groups are identical to or different from each other; when a4 is 2 or greater, at least two $L_4$ groups are identical to or different from each other; when a5 is 2 or greater, at least two $L_5$ groups are identical to or different from each other; when a6 is 2 or greater, at least two $L_6$ groups are identical to or different from each other, when a1 is 0, *-$(L_1)_{a1}$-*' is a single bond; when a2 is 0, *-$(L_2)_{a2}$-*' is a single bond; when a3 is 0, *-$(L_3)_{a3}$-' is a single bond; when a4 is 0, *-$(L_4)_{a4}$-*' is a single bond; when a5 is 0, *-$(L_5)_{a5}$-*' is a single bond; when a6 is 0, *-$(L_6)_{a6}$-*' is a single bond, $Ar_1$ to $Ar_3$ and $R_1$ to $R_6$ are each independently selected from hydrogen, deuterium, —F, —Cl, —Br, —I, a hydroxyl group, a cyano group, a nitro group, an amino group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —C(=O)($Q_1$), —N($Q_1$)($Q_2$), —P(=O)($Q_1$)($Q_2$), —P(=S)($Q_1$)($Q_2$), —S(=O)($Q_1$)($Q_2$), and —S(=O)$_2$($Q_1$)($Q_2$), b1 to b3 are each independently an integer from 1 to 5, when 1 is 2 or greater, at least two $Ar_1$ groups are identical to or different from each other; when b2 is 2 or greater, at least two $Ar_2$ groups are identical to or different from each other; when b3 is 2 or greater, at least two Ar$_3$ groups are identical to or different from each other, c1 to c6 are each independently an integer from 1 to 10, when c1 is 2 or greater, at least two R$_1$ groups are identical to or different from each other; when c2 is 2 or greater, at least two R$_2$ groups are identical to or different from each other; when c3 is 2 or greater, at least two R$_3$ groups are identical to or different from each other; when c4 is 2 or greater, at least two R$_4$ groups are identical to or different from each other, when c5 is 2 or greater, at least two R$_5$ groups are identical to or different from each other; when c6 is 2 or greater, at least two R$_6$ groups are identical to or different from each other, the amine-based compound represented by one of Formulae 1-1 and 1-2 includes at least one —F, provided that the amine-based compound represented by one of Formulae 1A-9 and 1A-10 is excluded from Formulae 1-1 and 1-2:

Formula 1A-9

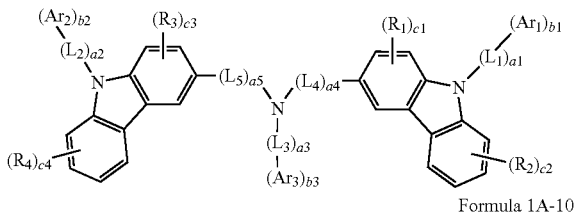

Formula 1A-10

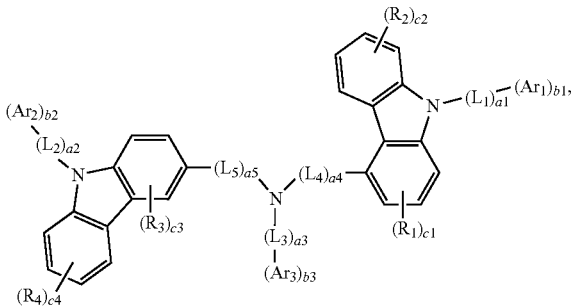

and at least one substituent of the substituted C$_5$-C$_{60}$ carbocyclic group, the substituted C$_2$-C$_{60}$ heterocyclic group, the substituted C$_1$-C$_{60}$ alkyl group, the substituted C$_2$-C$_{60}$ alkenyl group, the substituted C$_2$-C$_{60}$ alkynyl group, the substituted C$_1$-C$_{60}$ alkoxy group, the substituted C$_3$-C$_{10}$ cycloalkyl group, the substituted C$_1$-C$_{10}$ heterocycloalkyl group, the substituted C$_3$-C$_{10}$ cycloalkenyl group, the substituted C$_1$-C$_{10}$ heterocycloalkenyl group, the substituted C$_6$-C$_{60}$ aryl group, the substituted C$_6$-C$_{60}$ aryloxy group, the substituted C$_6$-C$_{60}$ arylthio group, the substituted C$_1$-C$_{60}$ heteroaryl group, the substituted C$_1$-C$_{60}$ heteroaryloxy group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amino group, an amidino group, a hydrazino group, a hydrazono group, a C$_1$-C$_{60}$ alkyl group, a C$_2$-C$_{60}$ alkenyl group, a C$_2$-C$_{60}$ alkynyl group, and a C$_1$-C$_{60}$ alkoxy group;

a C$_1$-C$_{60}$ alkyl group, a C$_2$-C$_{60}$ alkenyl group, a C$_2$-C$_{60}$ alkynyl group, and a C$_1$-C$_{60}$ alkoxy group, each substituted with at least one selected from deuterium, —F, —Cl, —Br, —I, a hydroxyl group, a cyano group, a nitro group, an amino group, an amidino group, a hydrazino group, a hydrazono group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{11}$)(Q$_{12}$)(Q$_{13}$), —N(Q$_{11}$)(Q$_{12}$), —B(Q$_{11}$)(Q$_{12}$), —C(=O)(Q$_{11}$), —S(=O)$_2$(Q$_{11}$), and —P(=O)(Q$_{11}$)(Q$_{12}$);

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, a biphenyl group, and a terphenyl group;

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazino group, a hydrazono group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, a biphenyl group, a terphenyl group, —Si(Q$_{21}$)(Q$_{22}$)(Q$_{23}$), —N(Q$_{21}$)(Q$_{22}$), —B(Q$_{21}$)(Q$_{22}$), —C(=O)(Q$_{21}$), —S(=O)$_2$(Q$_{21}$), and —P(=O)(Q$_{21}$)(Q$_{22}$); and —Si(Q$_3$O(Q$_{32}$)(Q$_{33}$), —N(Q$_{31}$)(Q$_{32}$), —B(Q$_3$O(Q$_{32}$), —C(=O)(Q$_{31}$), —S(=O)$_2$(Q$_{31}$), and —P(=O)(Q$_{31}$)(Q$_{32}$), wherein Q$_1$ to Q$_3$, Q$_{11}$ to Q$_{13}$, Q$_{21}$ to Q$_{23}$, and Q$_{31}$ to Q$_{33}$ are each independently selected from hydrogen, deuterium, —F, —Cl, —Br, —I, a hydroxyl group, a cyano group, a nitro group, an amino group, an amidino group, a hydrazino group, a hydrazono group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryl group substituted with a C$_1$-C$_{60}$ alkyl group, a C$_1$-C$_{60}$ heteroaryl group, a monovalent non-aromatic condensed polycyclic group, a monovalent non-aromatic condensed heteropolycyclic group, a biphenyl group, and a terphenyl group, and

* and *' each indicate a binding site to an adjacent atom.

According to one or more embodiments, an organic light-emitting device includes: a first electrode; a second electrode facing the first electrode; and an organic layer disposed between the first electrode and the second electrode, wherein the organic layer includes an emission layer and at least one amine-based compound described above.

BRIEF DESCRIPTION OF THE DRAWINGS

These and/or other aspects of embodiments will become apparent and more readily appreciated from the following description of the embodiments, taken in conjunction with the accompanying drawings in which:

FIG. 1 is schematic view of an organic light-emitting device according to an embodiment;

FIG. 2 is schematic view of an organic light-emitting device according to an embodiment;

FIG. 3 is schematic view of an organic light-emitting device according to an embodiment; and FIG. 4 is schematic view of an organic light-emitting device according to an embodiment.

DETAILED DESCRIPTION

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of embodiments of the present description. As used herein, the term "and/or" includes any and all combinations of one or more of the associated listed items. Expressions such as "at least one of," when preceding a list of elements, modify the entire list of elements and do not modify the individual elements of the list.

The present disclosure allows for various modifications of the described subject matter and includes various embodiments, example embodiments of which will be illustrated in the drawings and described in detail in the written description. Effects, features, and a method of preparing the subject matter of the present disclosure will become apparent by reference to the example embodiments of the present disclosure, together with the accompanying drawings. The subject matter of the present disclosure may, however, be embodied in many different forms and should not be construed as being limited to the example embodiments set forth herein.

Hereinafter, the subject matter of the present disclosure will be described in more detail by explaining example embodiments of the present disclosure with reference to the attached drawings. Like reference numerals in the drawings denote like elements, and thus repeated description thereof is not necessary.

In the embodiments described in the present specification, an expression used in the singular encompasses the expression of the plural, unless it has a clearly different meaning in the context.

In the present specification, it is to be understood that the terms such as "including," "having," and "comprising" are intended to indicate the existence of the features or components disclosed in the specification, and are not intended to preclude the possibility that one or more other features or components may exist or may be added.

It will be understood that when a layer, region, or component is referred to as being "on" or "onto" another layer, region, or component, it may be directly or indirectly formed over the other layer, region, or component. For example, intervening layers, regions, or components may be present.

Sizes of components in the drawings may be exaggerated for convenience of explanation. In other words, since sizes and thicknesses of components in the drawings may be arbitrarily illustrated for convenience of explanation, the following embodiments are not limited thereto.

An amine-based compound may be represented by one of Formulae 1-1 and 1-2:

Formula 1-1

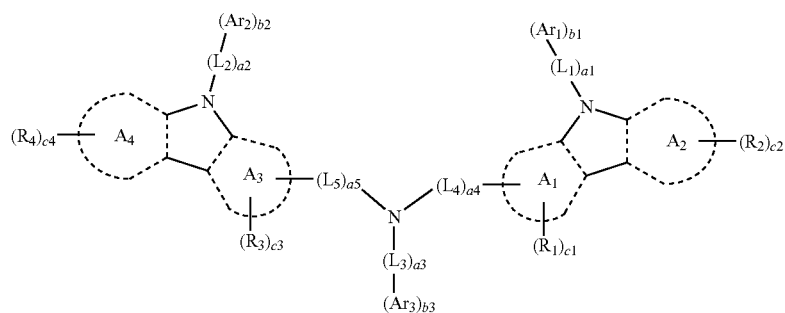

Formula 1-2

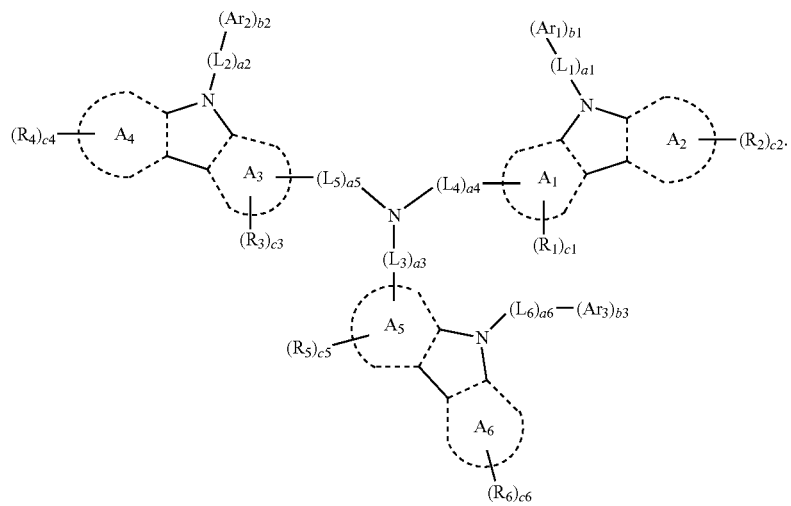

In Formulae 1-1 and 1-2, $A_1$ to $A_6$ may each independently be selected from a $C_5$-$C_{30}$ cyclic group and a $C_1$-$C_{30}$ heterocyclic group.

In some embodiments, $A_1$ to $A_6$ may each independently be selected from a benzene group, an indene group, a naphthalene group, an anthracene group, a fluorene group, a phenanthrene group, a triphenylene group, a pyrene group, a chrysene group, a naphthacene group, a pyrrole group, an imidazole group, a pyrazole group, a pyridine group, a pyrimidine group, a pyrazine group, a pyridazine group, an indole group, an isoindole group, an indazole group, a quinoline group, an isoquinoline group, a benzoquinoline group, a naphthyridine group, a quinoxaline group, a quinazoline group, a cinnoline group, a carbazole group, a phenanthridine group, an acridine group, a phenanthroline group, a phenazine group, a benzimidazole group, a furan group, a benzofuran group, a thiophene group, a benzothiophene group, a thiazole group, an isothiazole group, a benzothiazole group, an isoxazole group, an oxazole group, a triazole group, an oxadiazole group, a triazine group, a benzoxazole group, a dibenzofuran group, a dibenzothiophene group, a benzocarbazole group, and a dibenzocarbazole group.

In some embodiments, $A_1$ to $A_6$ may each independently be selected from a benzene group and a naphthalene group.

In some embodiments, $A_1$ to $A_6$ may be a benzene group, but embodiments are not limited thereto.

In Formulae 1-1 and 1-2, $L_1$ to $L_6$ may each independently be selected from a substituted or unsubstituted $C_5$-$C_{60}$ carbocyclic group and a substituted or unsubstituted $C_1$-$C_{60}$ heterocyclic group.

In some embodiments, $L_1$ to $L_6$ may each independently be selected from a benzene group, a pentalene group, an indene group, a naphthalene group, an azulene group, a heptalene group, an indacene group, an acenaphthalene group, a fluorene group, a spiro-bifluorene group, a benzofluorene group, a phenalene group, a phenanthrene group, an anthracene group, a fluoranthene group, a triphenylene group, a pyrene group, a chrysene group, a naphthacene group, a picene group, a perylene group, a pentaphenylene group, a hexacene group, a pentacene group, a rubicene group, a coronene group, an ovalene group, a pyrrole group, an imidazole group, a pyrazole group, a pyridine group, a pyrazine group, a pyrimidine group, a pyridazine group, an isoindole group, an indole group, an indazole group, a purine group, a quinoline group, an isoquinoline group, a benzoquinoline group, a phthalazine group, a naphthyridine group, a quinoxaline group, a quinazoline group, a cinnoline group, a carbazole group, a phenanthridine group, an acridine group, a phenanthroline group, a phenazine group, a benzoxazole group, a benzimidazole group, a furan group, a benzofuran group, a thiophene group, a benzothiophene group, a thiazole group, an isothiazole group, a benzothiazole group, an isoxazole group, an oxazole group, a triazole group, a tetrazole group, an oxadiazole group, a triazine group, a benzoxazole group, a dibenzofuran group, a dibenzothiophene group, a benzocarbazole group, and a dibenzocarbazole group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzoxazolyl group, a dibenzofuranyl group, a dibenzothiophenyl group, a benzocarbazolyl group, and a dibenzocarbazolyl group, but embodiments are not limited thereto.

In some embodiments, $L_1$ to $L_6$ may each independently be selected from groups represented by Formulae 3-1 to 3-46, but embodiments are not limited thereto:

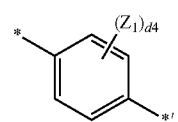

Formula 3-1

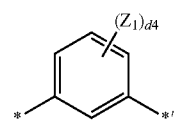

Formula 3-2

-continued
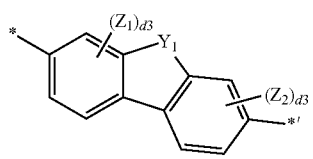
Formula 3-3
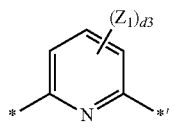
Formula 3-12
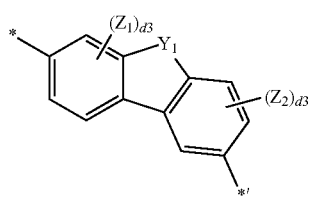
Formula 3-4
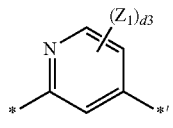
Formula 3-13
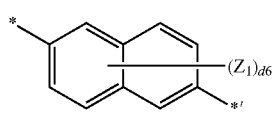
Formula 3-5
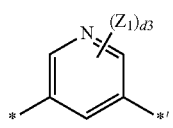
Formula 3-14
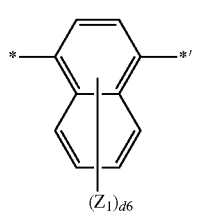
Formula 3-6
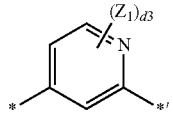
Formula 3-15
Formula 3-7
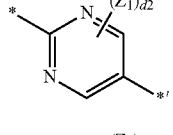
Formula 3-16

Formula 3-17
Formula 3-8
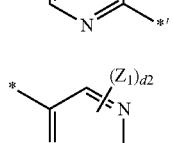
Formula 3-18
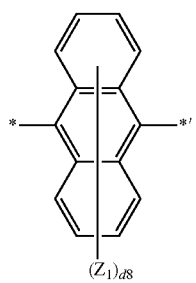
Formula 3-19
Formula 3-9
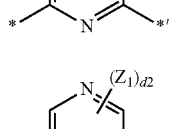
Formula 3-20
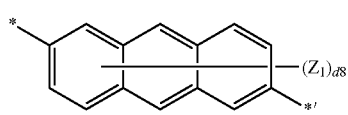
Formula 3-10
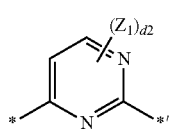
Formula 3-21

Formula 3-22
Formula 3-11
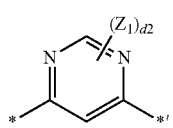
Formula 3-23
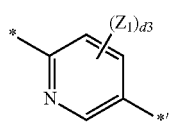

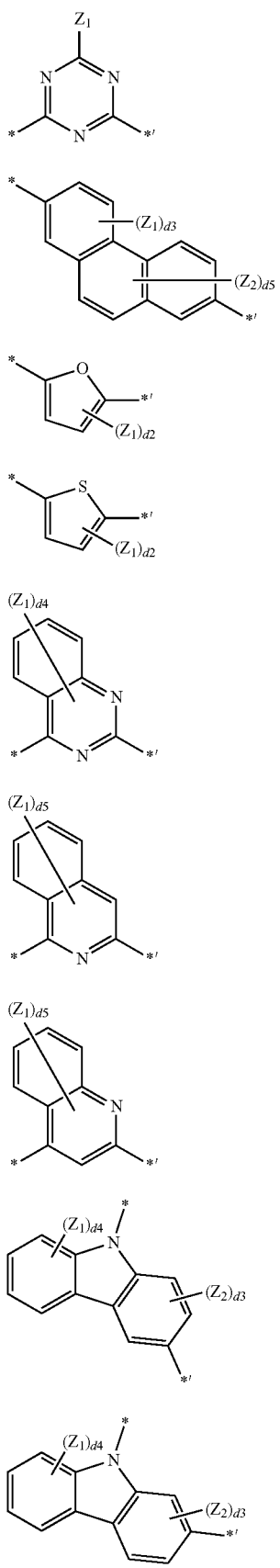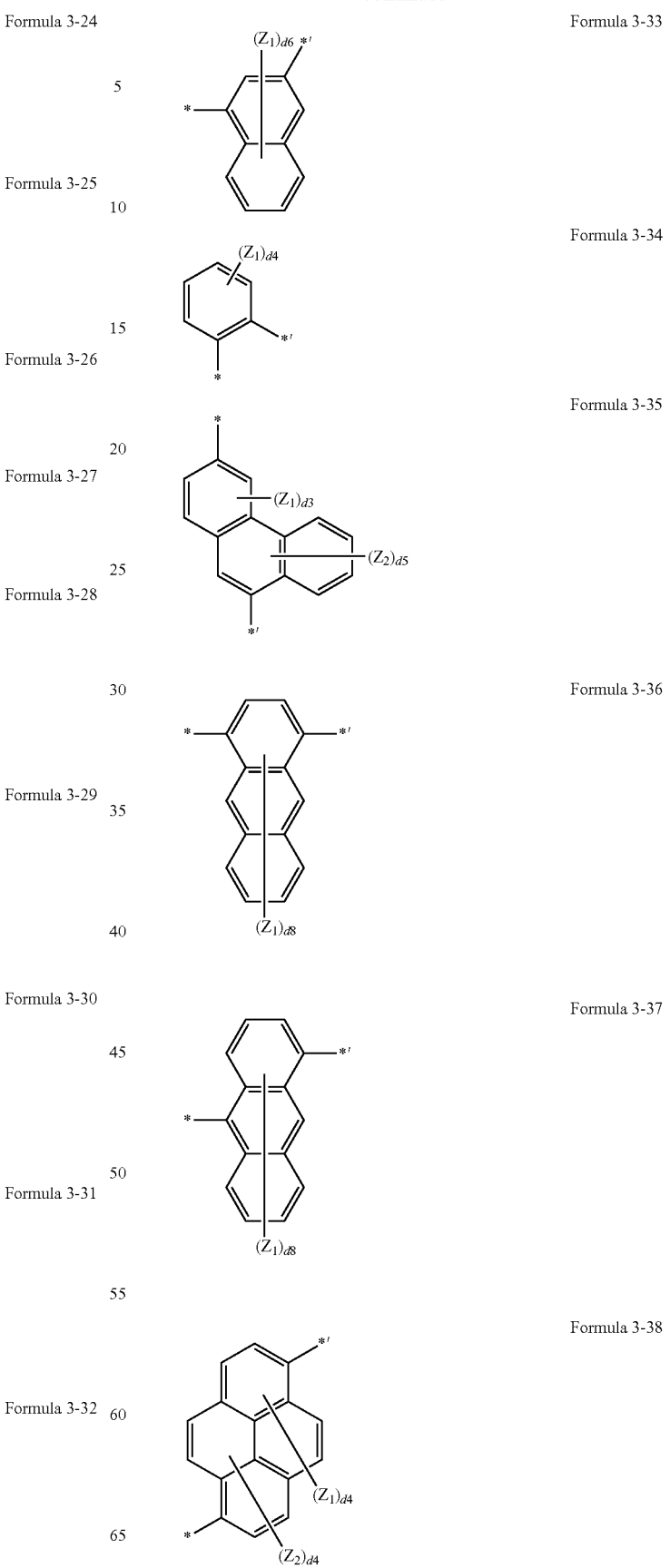

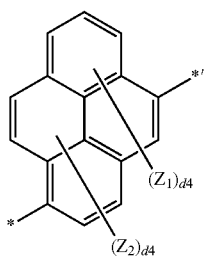

Formula 3-39

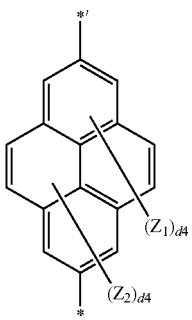

Formula 3-40

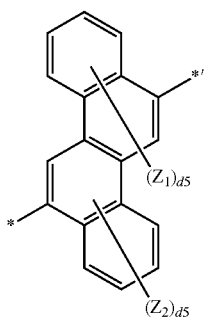

Formula 3-41

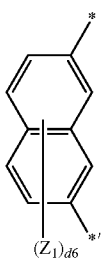

Formula 3-42

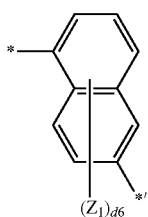

Formula 3-43

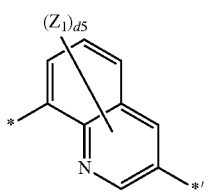

Formula 3-44

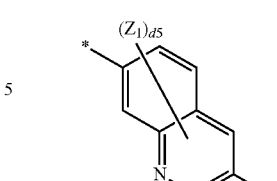

Formula 3-45

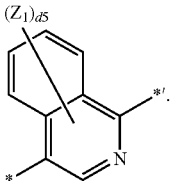

Formula 3-46 wherein, in Formulae 3-1 to 3-46, $Y_1$ may be selected from O, S, $C(Z_3)(Z_4)$, $N(Z_5)$, and $Si(Z_6)(Z_7)$, $Z_1$ to $Z_7$ may each independently be selected from hydrogen, deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group, d2 may be an integer from 0 to 2; when d2 is 2 or greater, at least two $Z_1$ groups may be identical to or different from each other, and d3 may be an integer from 0 to 3; when d3 is 2 or greater, at least two of each of groups represented by $Z_1$ and groups represented by $Z_2$ may be identical to or different from each other, d4 may be an integer from 0 to 4; when d4 is 2 or greater, at least two of each of groups represented by $Z_1$ and groups represented by $Z_2$ may be identical to or different from each other, d5 may be an integer from 0 to 5; when d5 is 2 or greater, at least two of each of groups represented by $Z_1$ and groups represented by $Z_2$ may be identical to or different from each other, d6 may be an integer from 0 to 6; when d6 is 2 or greater, at least two $Z_1$ groups may be identical to or different from each other, and d8 may be an integer from 0 to 8; when d8 is 2 or greater, at least two $Z_1$ groups may be identical to or different from each other, and

* indicates a binding site to an adjacent atom.

In some embodiments, $L_1$ to $L_6$ may each independently be selected from groups represented by Formulae 3-1, 3-2, and 3-34, but embodiments are not limited thereto.

In Formulae 1-1 and 1-2, a1 to a6 may each independently be an integer from 0 to 5. a1 indicates the number of $L_1$ groups; when a1 is 2 or greater, at least two $L_1$ groups may be identical to or different from each other. Descriptions for a2 to a6 may each be the same as those for a1 as described herein.

When a1 is 0, *-$(L_1)_{a1}$-*' may be a single bond; when a2 is 0, *-$(L_2)_{a2}$-*' may be a single bond; when a3 is 0, *-$(L_3)_{a3}$-*' may be a single bond; when a4 is 0, *-$(L_4)_{a4}$-*' may be a single bond; when a5 is 0, *-$(L_5)_{a5}$-*' may be a single bond; and when a6 is 0, *-$(L_6)_{a6}$-*' may be a single bond.

In some embodiments, a1 to a6 may each independently be selected from 0, 1, 2, and 3, but embodiments are not limited thereto.

In some embodiments, in Formula 1-1, a4 and a5 may not each be 0; or, in Formula 1-2, a3 to a5 may not each be 0, but embodiments are not limited thereto.

In Formulae 1-1 and 1-2, $Ar_1$ to $Ar_3$ and $R_1$ to $R_6$ may each independently be selected from hydrogen, deuterium, —F, —Cl, —Br, —I, a hydroxyl group, a cyano group, a nitro group, an amino group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —B$(Q_1)(Q_2)$, —C(=O)$(Q_1)$, —N$(Q_1)(Q_2)$, —P(=O)$(Q_1)(Q_2)$, —P(=S)$(Q_1)(Q_2)$, —S(=O)$(Q_1)(Q_2)$, and —S(=O)$_2(Q_1)(Q_2)$, wherein $Q_1$ to $Q_3$ may each independently be selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$ $C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group.

In some embodiments, $Ar_1$ to $Ar_3$ may each independently be selected from a benzene group, a pentalene group, an indene group, a naphthalene group, an azulene group, a heptalene group, an indacene group, an acenaphthalene group, a fluorene group, a spiro-bifluorene group, a benzofluorene group, a phenalene group, a phenanthrene group, an anthracene group, a fluoranthene group, a triphenylene group, a pyrene group, a chrysene group, a naphthacene group, a picene group, a perylene group, a pentaphenylene group, a hexacene group, a pentacene group, a rubicene group, a coronene group, an ovalene group, a pyrrole group, an imidazole group, a pyrazole group, a pyridine group, a pyrazine group, a pyrimidine group, a pyridazine group, an isoindole group, an indole group, an indazole group, a purine group, a quinoline group, an isoquinoline group, a benzoquinoline group, a phthalazine group, a naphthyridine group, a quinoxaline group, a quinazoline group, a cinnoline group, a carbazole group, a phenanthridine group, an acridine group, a phenanthroline group, a phenazine group, a benzoxazole group, a benzimidazole group, a furan group, a benzofuran group, a thiophene group, a benzothiophene group, a thiazole group, an isothiazole group, a benzothiazole group, an isoxazole group, an oxazole group, a triazole group, a tetrazole group, an oxadiazole group, a triazine group, a benzoxazole group, a dibenzofuran group, a dibenzothiophene group, a benzocarbazole group, and a dibenzocarbazole group; and a benzene group, a pentalene group, an indene group, a naphthalene group, an azulene group, a heptalene group, an indacene group, an acenaphthalene group, a fluorene group, a spiro-bifluorene group, a benzofluorene group, a phenalene group, a phenanthrene group, an anthracene group, a fluoranthene group, a triphenylene group, a pyrene group, a chrysene group, a naphthacene group, a picene group, a perylene group, a pentaphenylene group, a hexacene group, a pentacene group, a rubicene group, a coronene group, an ovalene group, a pyrrole group, an imidazole group, a pyrazole group, a pyridine group, a pyrazine group, a pyrimidine group, a pyridazine group, an isoindole group, an indole group, an indazole group, a purine group, a quinoline group, an isoquinoline group, a benzoquinoline group, a phthalazine group, a naphthyridine group, a quinoxaline group, a quinazoline group, a cinnoline group, a carbazole group, a phenanthridine group, an acridine group, a phenanthroline group, a phenazine group, a benzoxazole group, a benzimidazole group, a furan group, a benzofuran group, a thiophene group, a benzothiophene group, a thiazole group, an isothiazole group, a benzothiazole group, an isoxazole group, an oxazole group, a triazole group, a tetrazole group, an oxadiazole group, a triazine group, a benzoxazole group, a dibenzofuran group, a dibenzothiophene group, a benzocarbazole group, and a dibenzocarbazole group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzoxazolyl group, a dibenzofuranyl group, a dibenzothiophenyl group, a benzocarbazolyl group, and a dibenzocarbazolyl group, but embodiments are not limited thereto.
In some embodiments, $Ar_1$ to $Ar_3$ may each independently be selected from groups represented by Formulae 5-1 to 5-79, but embodiments are not limited thereto:
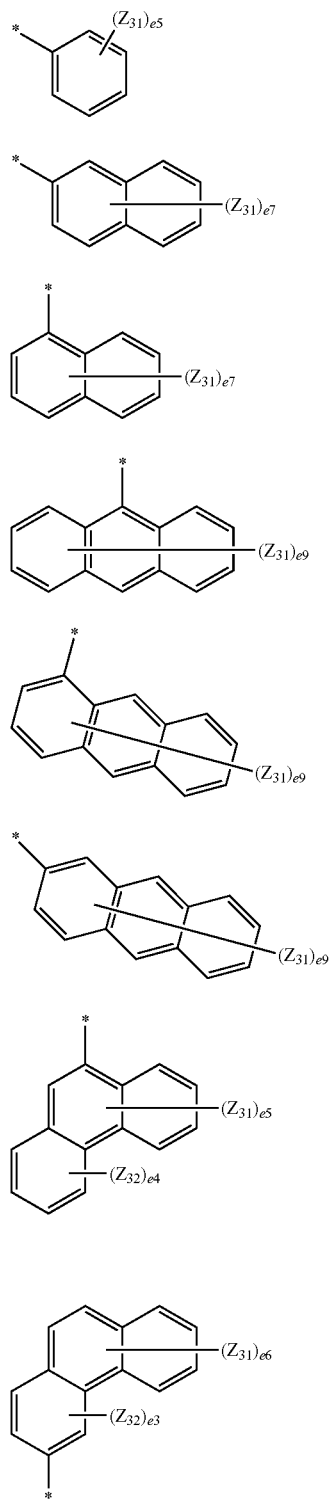
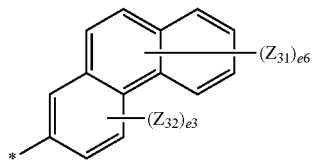
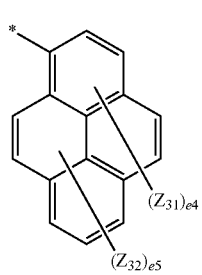
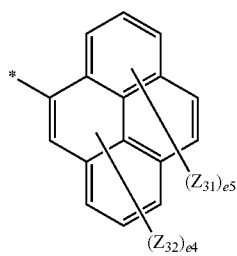
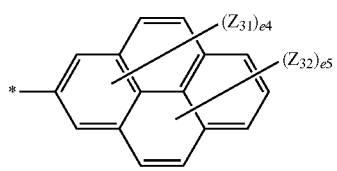
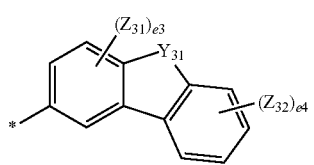
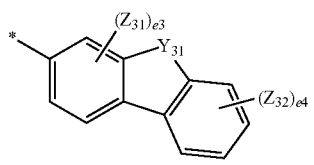
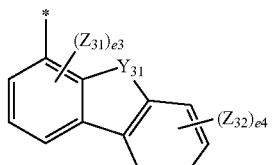
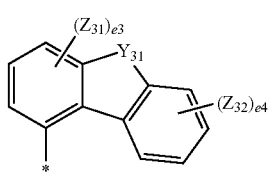

-continued
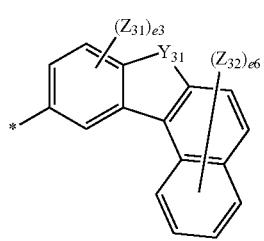
Formula 5-17
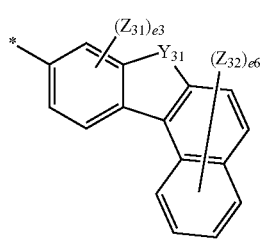
Formula 5-18
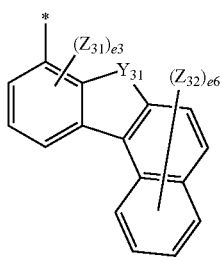
Formula 5-19
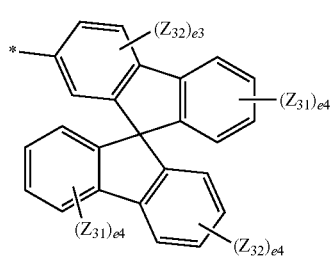
Formula 5-20
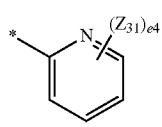
Formula 5-21
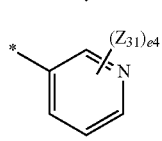
Formula 5-22
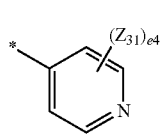
Formula 5-23
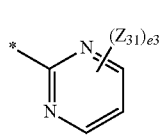
Formula 5-24
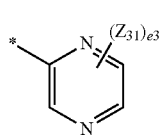
Formula 5-25
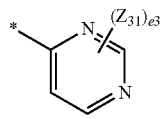
Formula 5-26
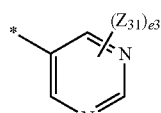
Formula 5-27
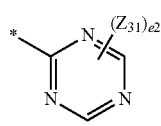
Formula 5-28
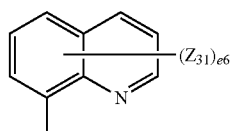
Formula 5-29
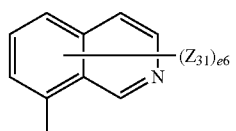
Formula 5-30
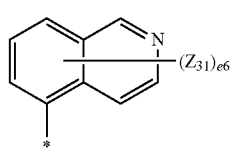
Formula 5-31
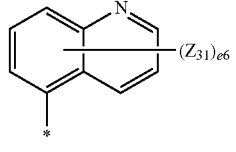
Formula 5-32
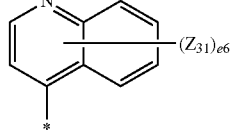
Formula 5-33
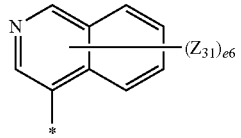
Formula 5-34
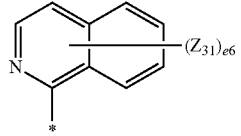
Formula 5-35
Formula 5-36

Formula 5-37
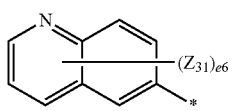
Formula 5-38
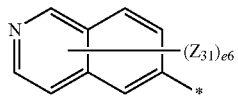
Formula 5-39
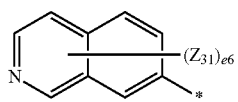
Formula 5-40
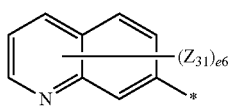
Formula 5-41
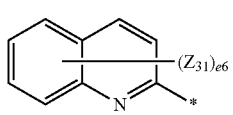
Formula 5-42
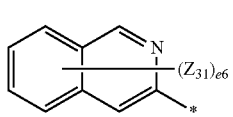
Formula 5-43
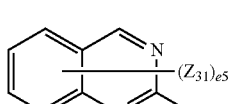
Formula 5-44
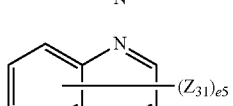
Formula 5-45
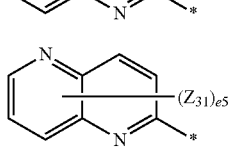
Formula 5-46
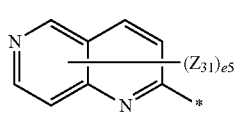
Formula 5-47
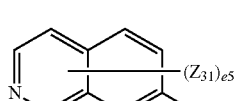
Formula 5-48
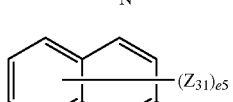
Formula 5-49
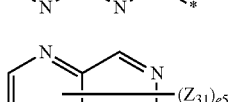
Formula 5-50
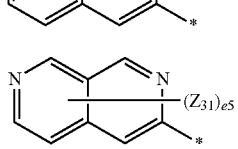
Formula 5-51
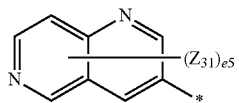
Formula 5-52
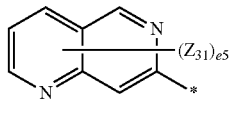
Formula 5-53
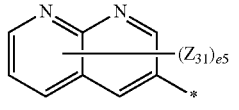
Formula 5-54
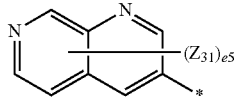
Formula 5-55
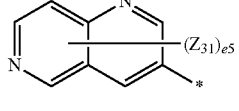
Formula 5-56
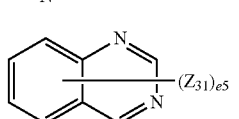
Formula 5-57
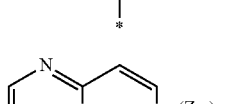
Formula 5-58
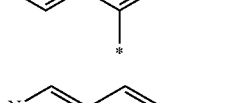
Formula 5-59
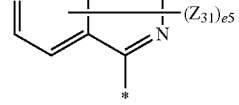
Formula 5-60
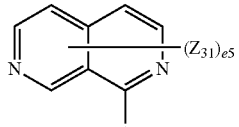
Formula 5-61
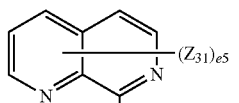
Formula 5-62
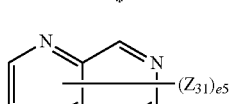
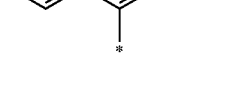

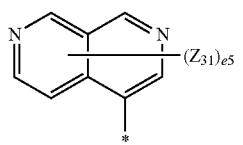
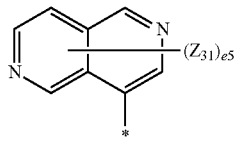
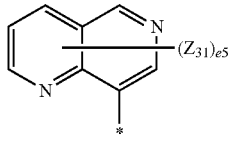
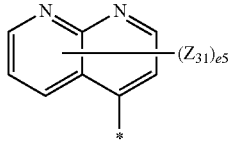
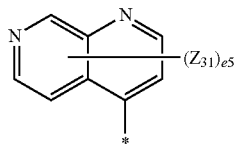
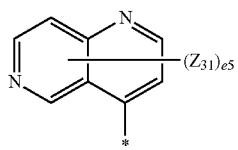
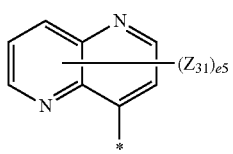
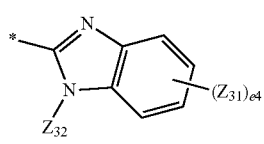
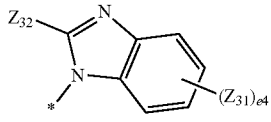
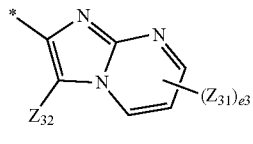
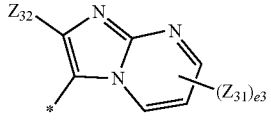

Formula 5-63
Formula 5-64
Formula 5-65
Formula 5-66
Formula 5-67
Formula 5-68
Formula 5-69
Formula 5-70
Formula 5-71
Formula 5-72
Formula 5-73

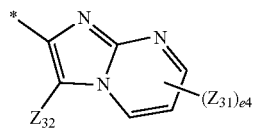

Formula 5-74

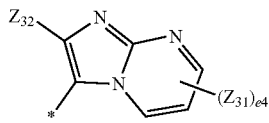

Formula 5-75

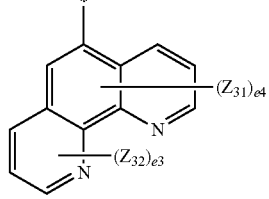

Formula 5-76

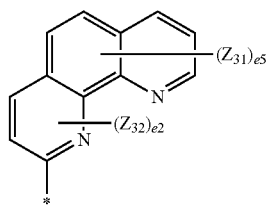

Formula 5-77

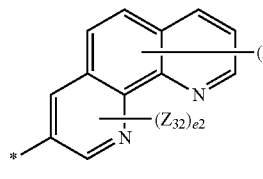

Formula 5-78

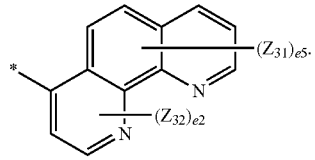

Formula 5-79 wherein, in Formulae 5-1 to 5-79, $Y_{31}$ may be selected from O, S, $C(Z_{33})(Z_{34})$, $N(Z_{35})$, and $Si(Z_{36})(Z_{37})$, $Z_{31}$ to $Z_{37}$ may each independently be selected from hydrogen, deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group, e2 may be an integer from 0 to 2; when e2 is 2 or greater, at least two of each of groups represented by $Z_{31}$ and groups represented by $Z_{32}$ may be identical to or different from each other, e3 may be an integer from 0 to 3; when e3 is 2 or greater, at least two of each of groups represented by $Z_{31}$ and groups represented by $Z_{32}$ may be identical to or different from each other, e4 may be an integer from 0 to 4; when e4 is 2 or greater, at least two of each of groups represented by $Z_{31}$ and groups represented by $Z_{32}$ may be identical to or different from each other, e5 may be an integer from 0 to 5; when e5 is 2 or greater, at least two of each of groups represented by $Z_{31}$ and groups represented by $Z_{32}$ may be identical to or different from each other, e6 may be an integer from 0 to 6; when e6 is 2 or greater, at least two of each of groups represented by $Z_{31}$ and groups represented by $Z_{32}$ may be identical to or different from each other, e7 may be an integer from 0 to 7; when e7 is 2 or greater, at least two $Z_{31}$ groups may be identical to or different from each other, e9 may be an integer from 0 to 9; when e9 is 2 or greater, at least two $Z_{31}$ groups may be identical to or different from each other, and

* indicates a binding site to an adjacent atom.

In some embodiments, $Ar_1$ to $Ar_3$ may each independently be selected from groups represented by Formulae 6-1 to 6-42, but embodiments are not limited thereto:

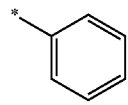

Formula 6-1

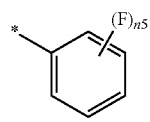

Formula 6-2

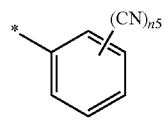

Formula 6-3

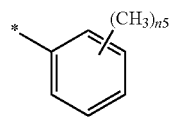

Formula 6-4

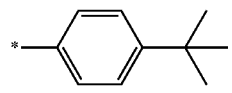

Formula 6-5

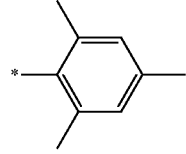

Formula 6-6

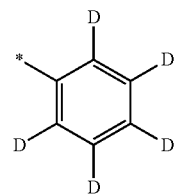

Formula 6-7

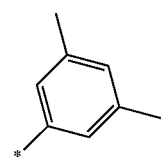

Formula 6-8

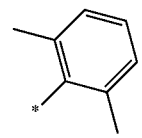

Formula 6-9

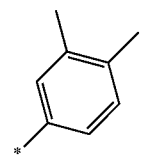

Formula 6-10

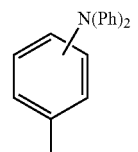

Formula 6-11

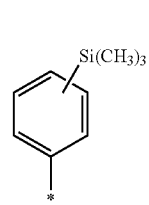

Formula 6-12

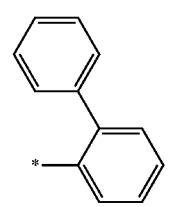

Formula 6-13

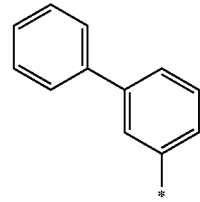

Formula 6-14

27
-continued
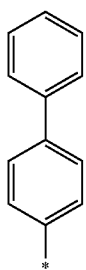
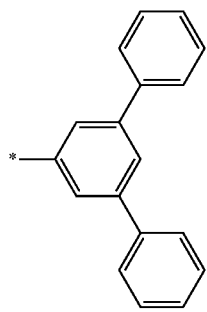
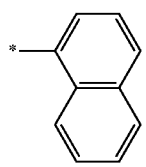
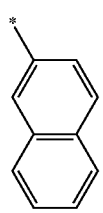
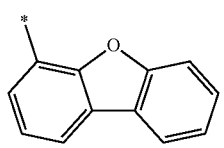
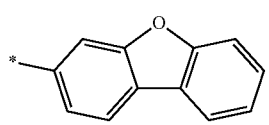
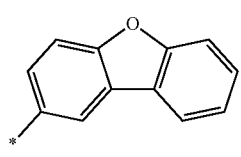
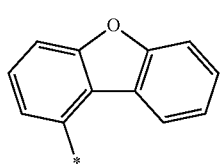
28
-continued
Formula 6-15
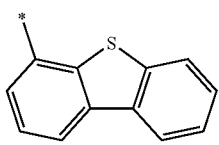
Formula 6-16
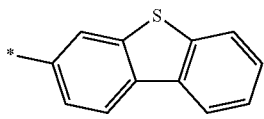
Formula 6-17
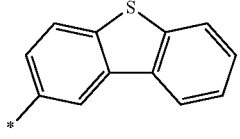
Formula 6-18
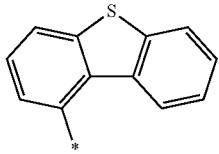
Formula 6-19
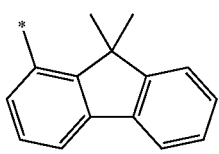
Formula 6-20
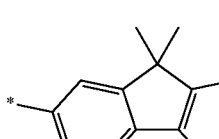
Formula 6-21
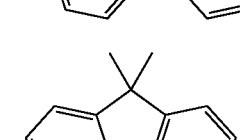
Formula 6-22
Formula 6-23
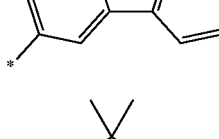
Formula 6-24
Formula 6-25
Formula 6-26
Formula 6-27
Formula 6-28
Formula 6-29
Formula 6-30
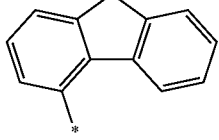
Formula 6-31
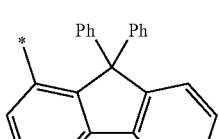
Formula 6-32
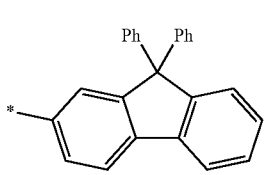

Formula 6-33 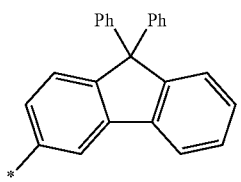

Formula 6-34 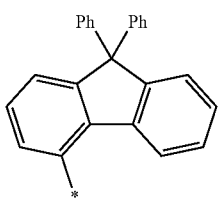

Formula 6-35 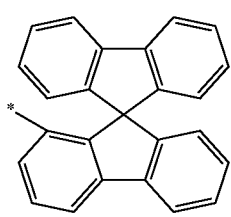

Formula 6-36 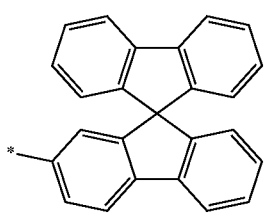

Formula 6-37 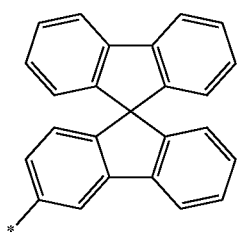

Formula 6-38 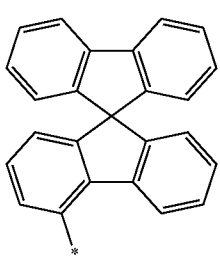

Formula 6-39 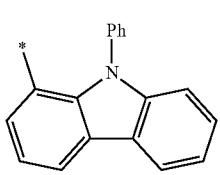

Formula 6-40 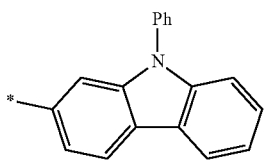

Formula 6-41 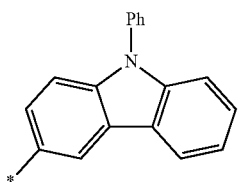

Formula 6-42 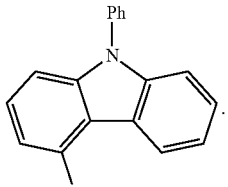

wherein, in Formulae 6-1 to 6-42, n5 may be an integer from 1 to 5,

"Ph" represents a phenyl group, and

* indicates a binding site to an adjacent atom.

In some embodiments, $Ar_1$ to $Ar_3$ may each independently be selected from groups represented by Formulae 6-1, 6-2, 6-13 to 6-16, 6-19 to 6-26, 6-28, 6-30, 6-32, 6-34, and 6-36.

In some embodiments, at least one of $Ar_1$ to $Ar_3$ may be selected from groups represented by Formulae 7-1 to 7-9:

Formula 7-1 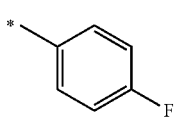

Formula 7-2 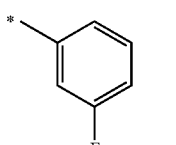

Formula 7-3 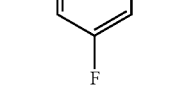

Formula 7-4 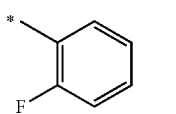

Formula 7-5 

-continued

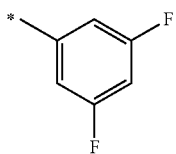
Formula 7-6

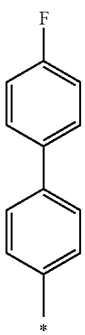
Formula 7-7

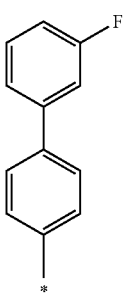
Formula 7-8

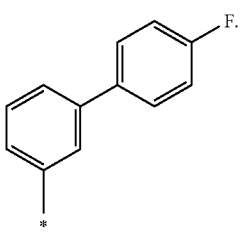
Formula 7-9 wherein, in Formulae 7-1 to 7-9, * indicates a binding site to an adjacent atom.

In Formulae 1-1 and 1-2, b1 to b3 may each independently be an integer from 1 to 5. b1 indicates the number of $Ar_1$ groups; when b1 is 2 or greater, at least two $Ar_1$ groups may be identical to or different from each other. Descriptions for b2 and b3 may each be the same as those for b1 as described herein.

In some embodiments, $R_1$ to $R_6$ may each independently be selected from hydrogen, deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group.

In some embodiments, $R_1$ to $R_6$ may each independently be selected from hydrogen, deuterium, —F, —Cl, —Br, —I, a hydroxyl group, a cyano group, a nitro group, an amino group, an amidino group, a hydrazino group, a hydrazono group, a methyl group, an ethyl group, a propyl group, an iso-propyl group, an n-butyl group, an isobutyl group, a sec-butyl group, a ter-butyl group, a pentyl group, an iso-amyl group, a hexyl group, a phenyl group, and a biphenyl group.

In Formulae 1-1 and 1-2, c1 to c6 may each independently be an integer from 1 to 10. c1 indicates the number of $R_1$ groups; when c1 is 2 or greater, at least two $R_1$ groups may be identical to or different from each other. Descriptions for c2 to c6 may each be the same as those for c1 as described herein.

In some embodiments, in Formula 1-1, at least one selected from $R_1$ group(s) in the number of c1, $R_2$ group(s) in the number of c2, $R_3$ group(s) in the number of c3, and $R_4$ group(s) in the number of c4 may be —F; or in Formula 1-2, at least one selected from $R_1$ group(s) in the number of c1, $R_2$ group(s) in the number of c2, $R_3$ group(s) in the number of c3, $R_4$ group(s) in the number of c4, $R_5$ group(s) in the number of c5, and $R_6$ group(s) in the number of c6 may be —F.

In some embodiments, at least one of $Ar_1$ to $Ar_3$ may be selected from groups represented by Formulae 7-1 to 7-9, i) in Formula 1-1, at least one selected from $R_1$ group(s) in the number of c1, $R_2$ group(s) in the number of c2, $R_3$ group(s) in the number of c3, and $R_4$ group(s) in the number of c4 may be —F; or ii) in Formula 1-2, at least one selected from $R_1$ group(s) in the number of c1, $R_2$ group(s) in the number of c2, $R_3$ group(s) in the number of c3, $R_4$ group(s) in the number of c4, $R_5$ group(s) in the number of c5, and $R_6$ group(s) in the number of c6 may be —F.

In some embodiments, at least one substituent of the substituted $C_5$-$C_{60}$ carbocyclic group, the substituted $C_2$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ heteroaryloxy group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group,

* and *' each indicate a binding site to an adjacent atom.

In some embodiments, the amine-based compound represented by one of Formulae 1-1 and 1-2 may be represented by one of Formulae 1A and 1B, but embodiments are not limited thereto:

Formula 1A

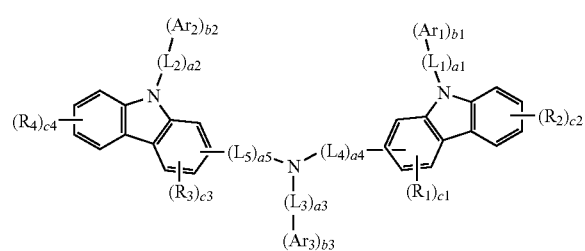

Formula 1B

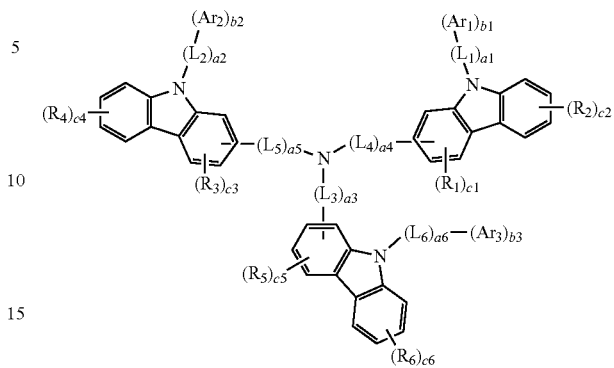

wherein, in Formulae 1A and 1B, $L_1$ to $L_6$, a1 to a6, $Ar_1$ to $Ar_3$, b1 to b3, and $R_1$ to $R_6$ may be defined the same as those described herein with reference to Formulae 1-1 and 1-2, c1, c3, and c5 may each independently be an integer from 1 to 3, and c2, c4, and c6 may each independently be an integer from 1 to 4.

In some embodiments, the amine-based compound represented by one of Formulae 1-1 and 1-2 may be represented by one of Formulae 1A-1 to 1A-8, but embodiments are not limited thereto:

Formula 1A-1

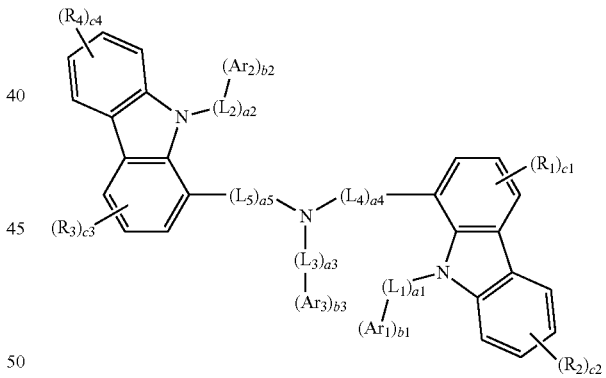

Formula 1A-2

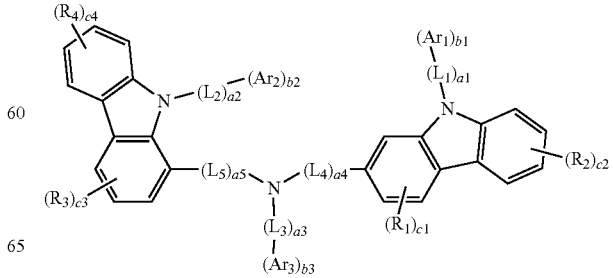

Formula 1A-3

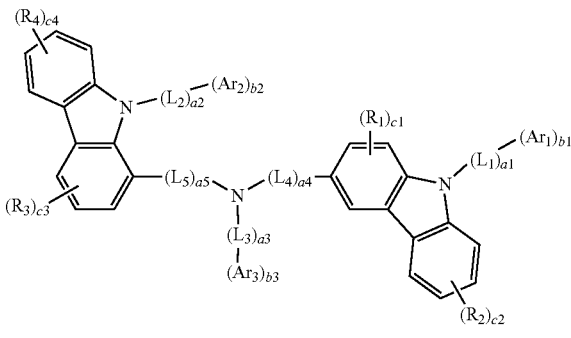

Formula 1A-4

Formula 1A-5

Formula 1A-6

Formula 1A-7

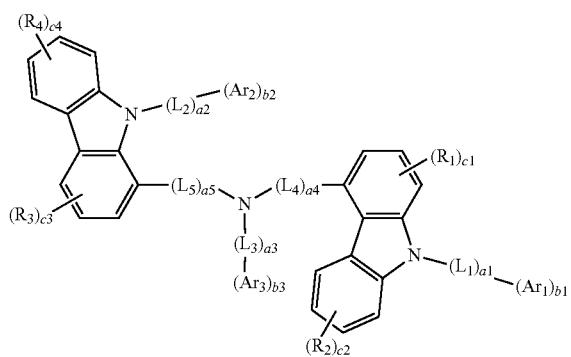

Formula 1A-8 wherein in Formulae 1A-1 to 1A-8, $L_1$ to $L_5$, a1 to a5, $Ar_1$ to $Ar_3$, b1 to b3, and $R_1$ to $R_4$ may be defined the same as those described herein with reference to Formulae 1-1 and 1-2, c1 and c3 may each independently be an integer from 1 to 3, and c2 and c4 may each independently be an integer from 1 to 4.

In some embodiments, in Formulae 1A-1 to 1A-8, a4 and a5 may each be 0.

In some embodiments, in Formulae 1A-1 to 1A-8, at least one of $Ar_1$ to $Ar_3$ may be selected from groups represented by Formulae 7-1 to 7-9.

The amine-based compound represented by one of Formulae 1A-9 and 1A-10 may be excluded from Formulae 1-1 and 1-2:

Formula 1A-9

Formula 1A-10 wherein in Formulae 1A-9 and 1A-10, $L_1$ to $L_5$, a1 to a5, $Ar_1$ to $Ar_3$, b1 to b3, $R_1$ to $R_4$, and c1 to c4 may be defined the same as those described herein with reference to Formulae 1A-1 to 1A-8.

In some embodiments, in Formulae 1A-1 to 1A-8, at least one selected from $R_1$ group(s) in the number of c1, $R_2$ group(s) in the number of c2, $R_3$ group(s) in the number of c3, and $R_4$ group(s) in the number of c4 may be —F.

In some embodiments, in Formula 1A-1 to 1A-8, at least one of $Ar_1$ to $Ar_3$ may be selected from groups represented by Formulae 7-1 to 7-9, and at least one selected from $R_1$ group(s) in the number of c1, $R_2$ group(s) in the number of c2, $R_3$ group(s) in the number of c3, and $R_4$ group(s) in the number of c4 may be —F.

In some embodiments, the amine-based compound represented by one of Formulae 1-1 and 1-2 may be represented by one of Formulae 1A-11 to 1A-18, but embodiments are not limited thereto:

Formula 1A-11

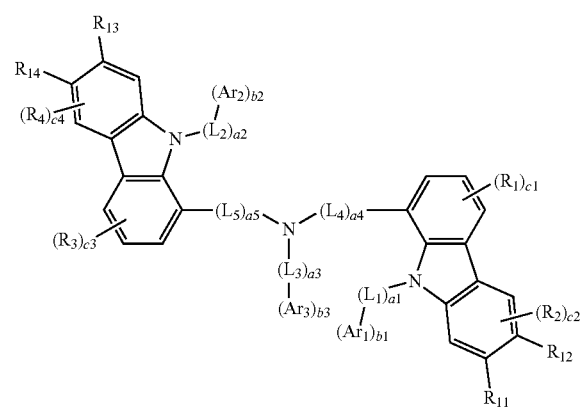

Formula 1A-12

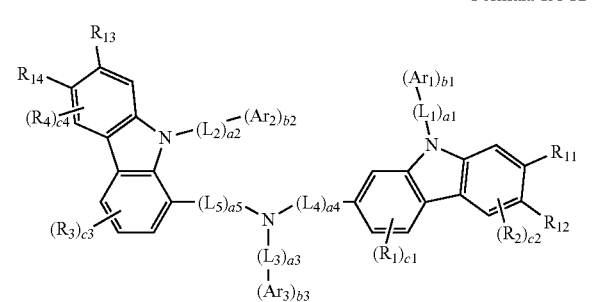

Formula 1A-13

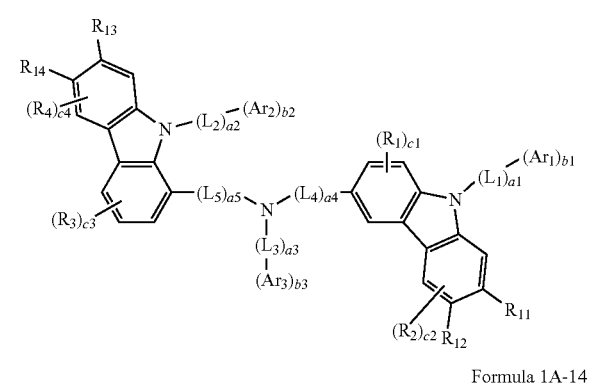

Formula 1A-14

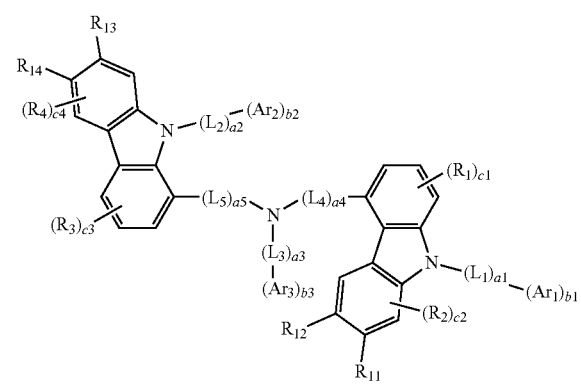

Formula 1A-15

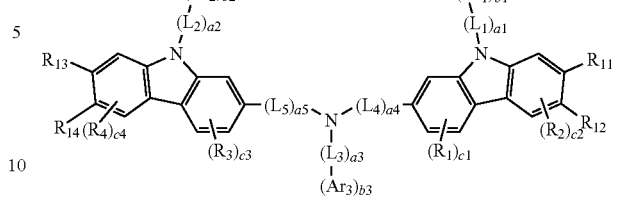

Formula 1A-16

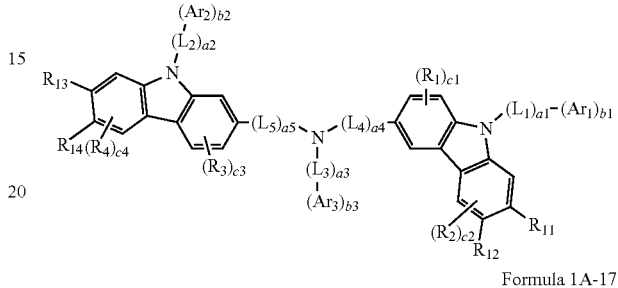

Formula 1A-17

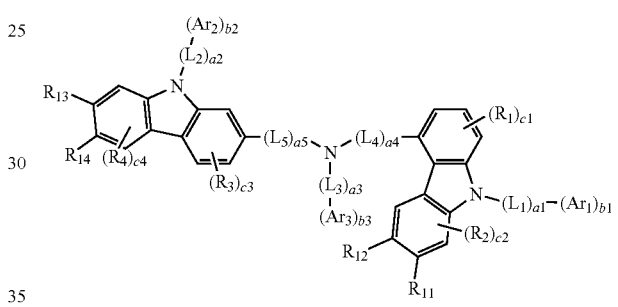

Formula 1A-18

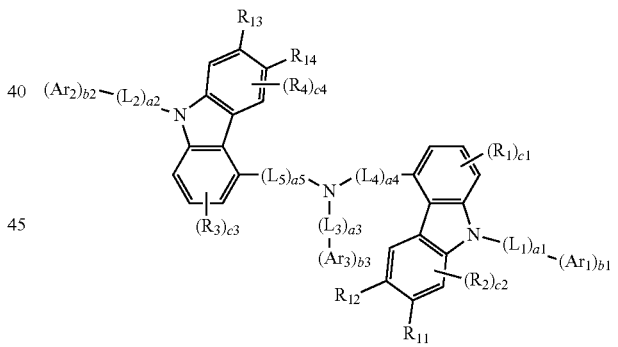

wherein, in Formulae 1A-11 to 1A-18, $L_1$ to $L_5$, a1 to a5, $Ar_1$ to $Ar_3$, b1 to b3, and $R_1$ to $R_4$ may be defined the same as those described herein with reference to Formulae 1-1 and 1-2, c1 and c3 may each independently be an integer from 1 to 3, c2 and c4 may each independently be an integer selected from 1 and 2, $R_{11}$ to $R_{14}$ may be defined the same as $R_1$ as described herein with reference to Formulae 1-1 and 1-2, and i) at least one of $Ar_1$ to $Ar_3$ may be selected from groups represented by Formulae 7-1 to 7-9;

ii) $R_{11}$ and/or $R_{13}$ may be —F;

iii) $R_{12}$ and/or $R_{14}$ may be —F;

iv) at least one of $Ar_1$ to $Ar_3$ may be selected from groups represented by Formulae 7-1 to 7-9, and $R_{11}$ and/or $R_{13}$ may be —F; or v) at least one of $Ar_1$ to $Ar_3$ may be selected from groups represented by Formulae 7-1 to 7-9, and $R_{12}$ and/or $R_{14}$ may be —F.

In some embodiments, the number of F(s) included in the amine-based compound may be selected from 1, 2, 3, 4, and 5, but embodiments are not limited thereto.

In some embodiments, the number of F(s) included in the amine-based compound may be selected from 1, 2, and 3.

In some embodiments, the amine-based compound represented by one of Formulae 1-1 and 1-2 may be selected from Compounds 1 to 232, but embodiments are not limited thereto:

1

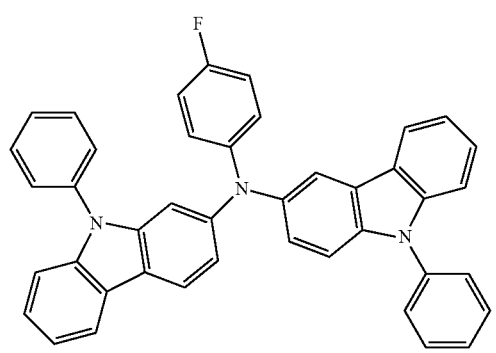

2

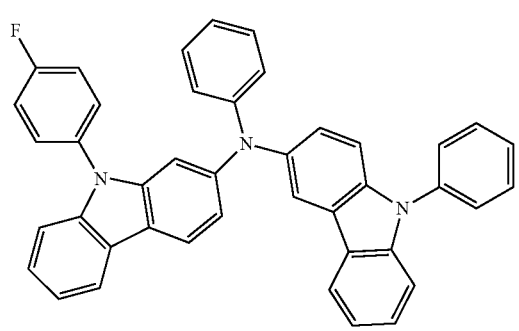

3

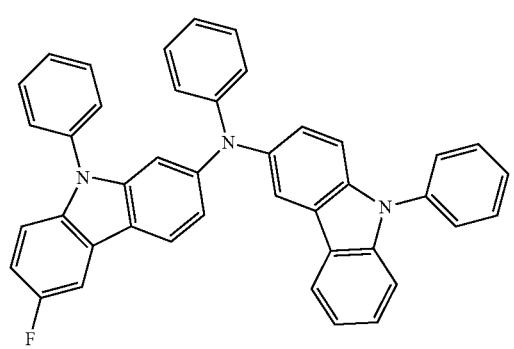

4

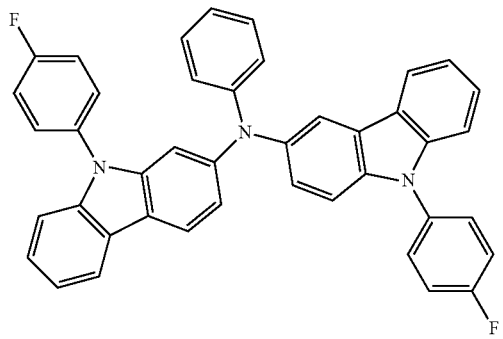

5

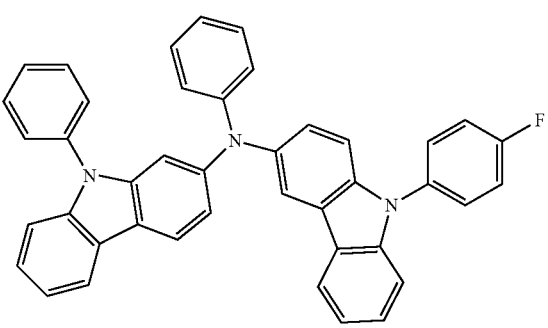

6

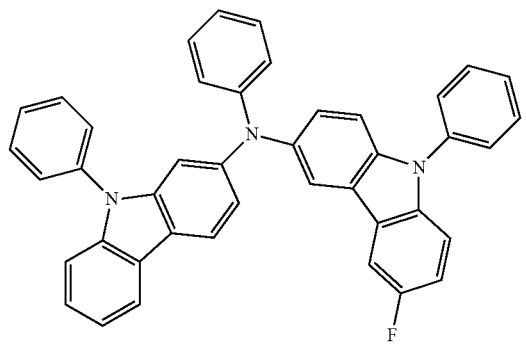

7

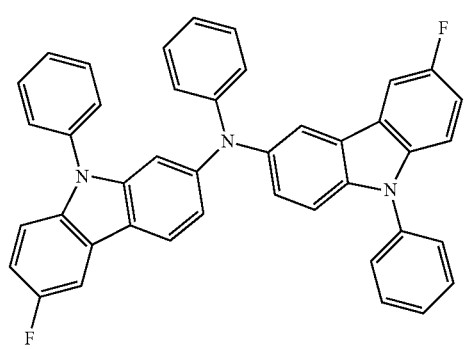

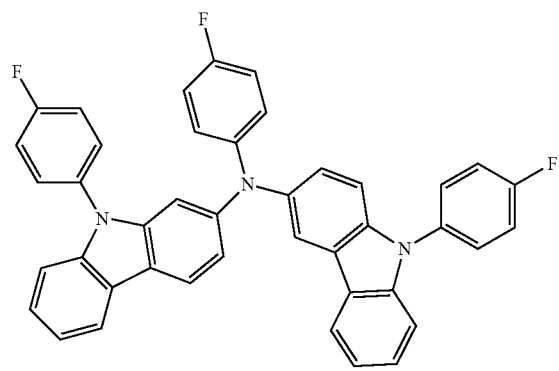
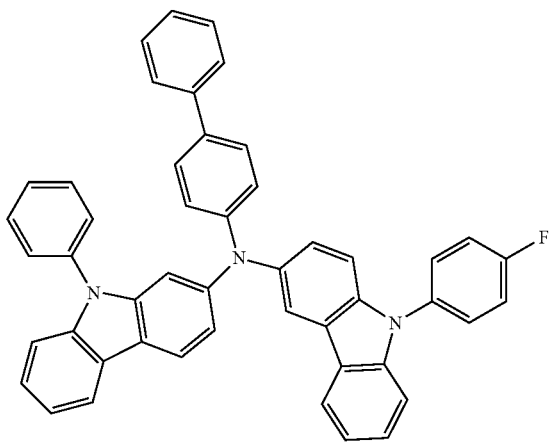
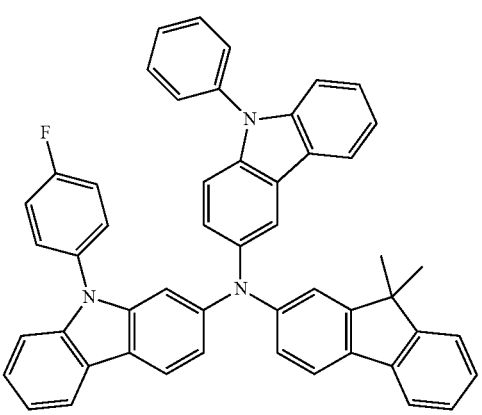
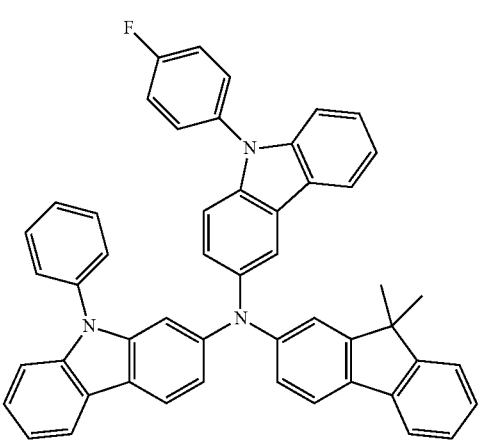

15
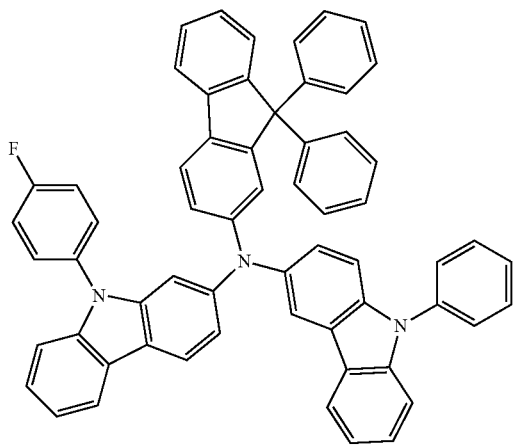
16
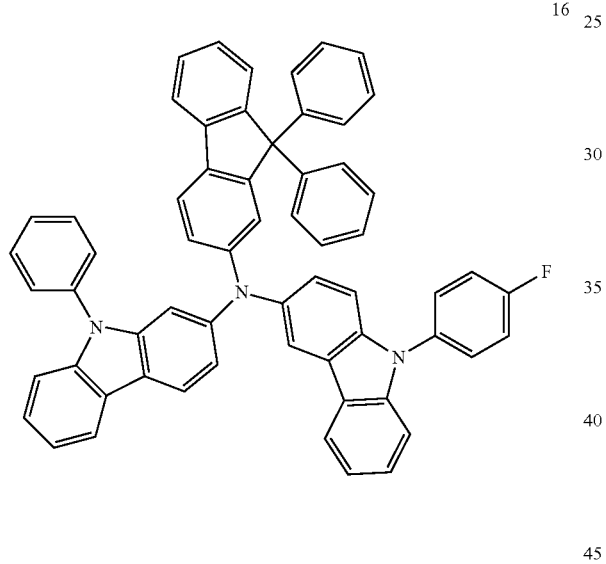
17
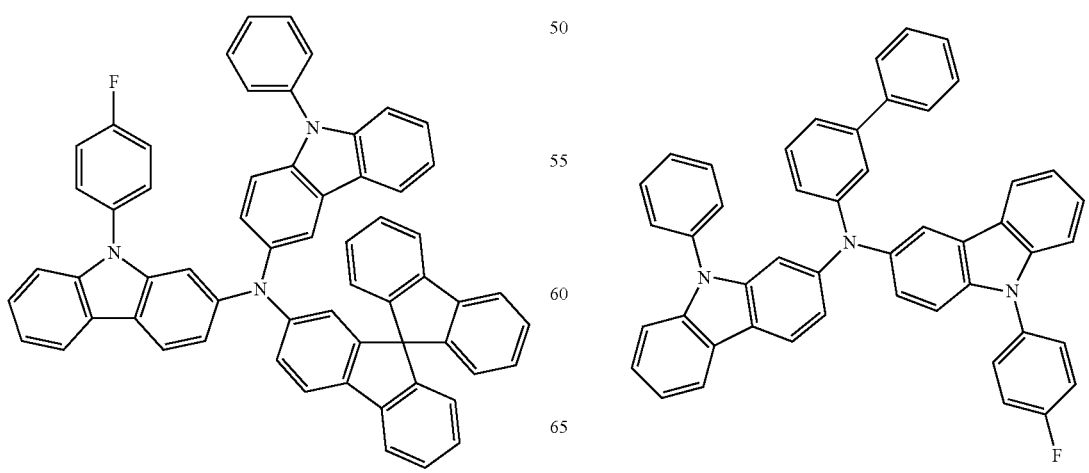
18
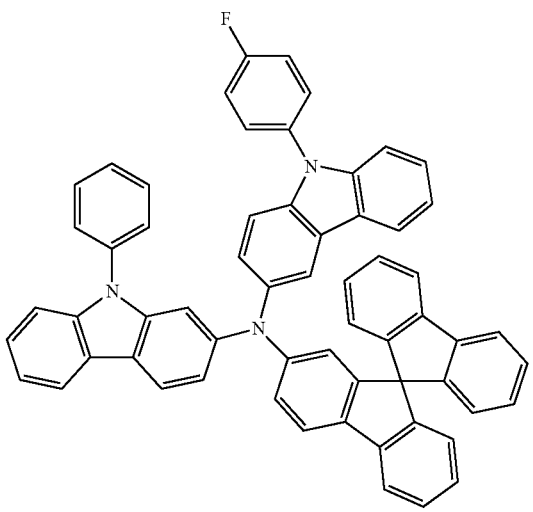
19
20

21
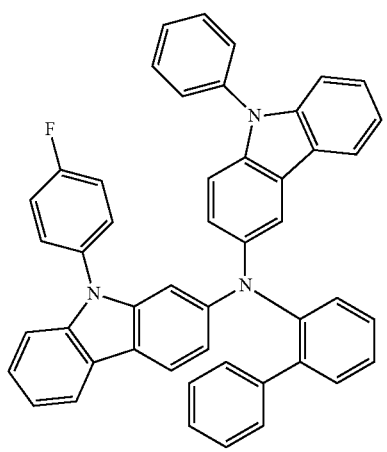
22
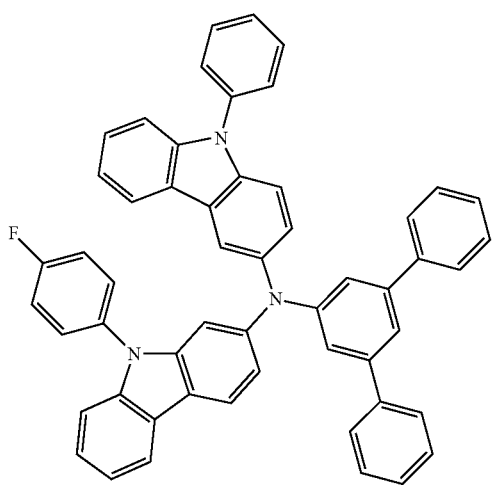
23
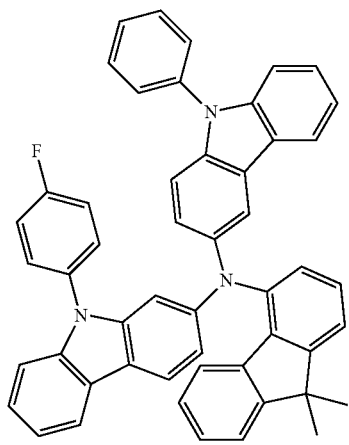
24
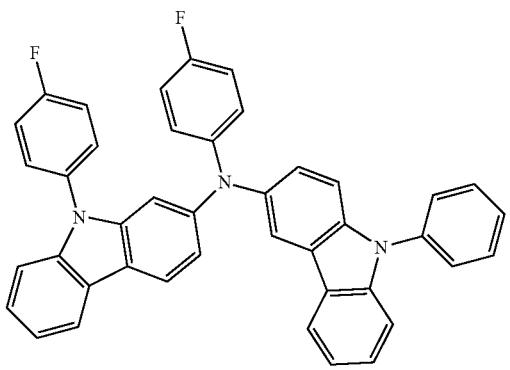
25
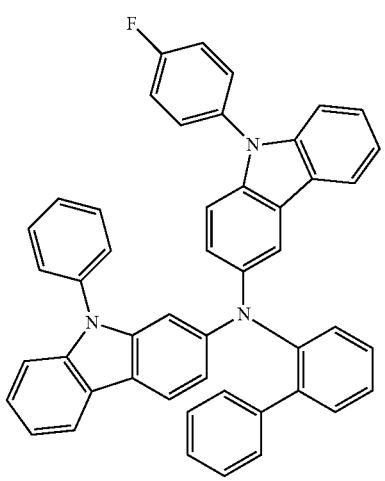
26
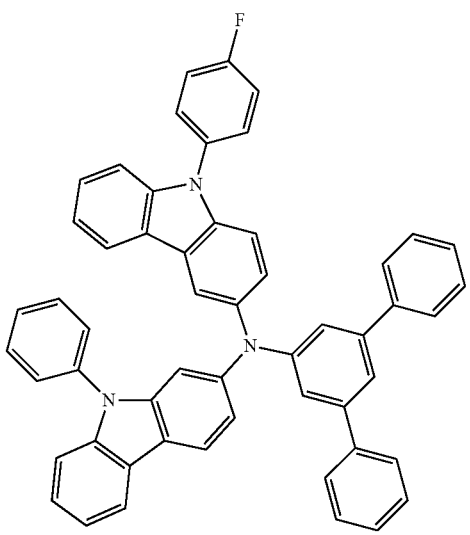

27
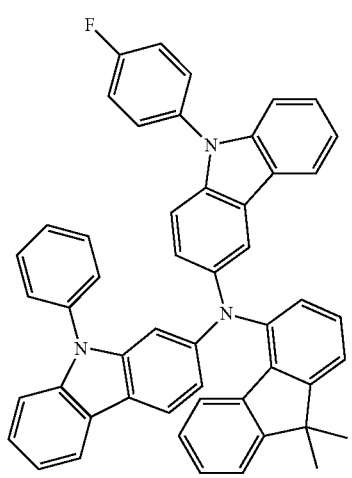
28
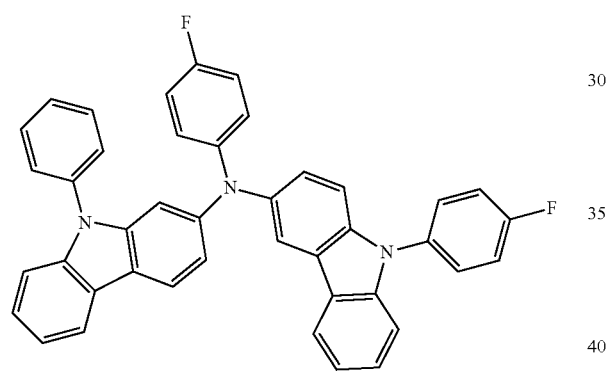
29
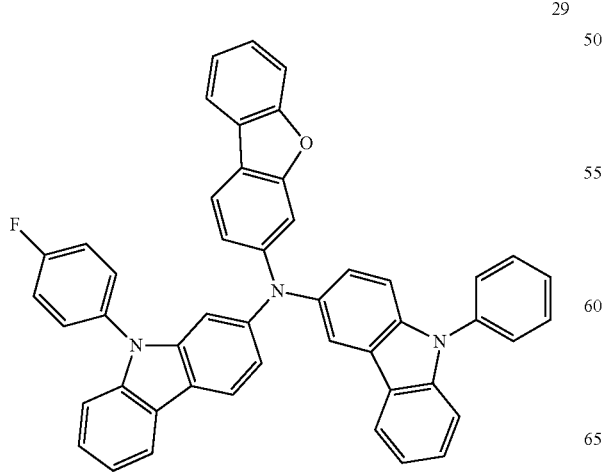
30
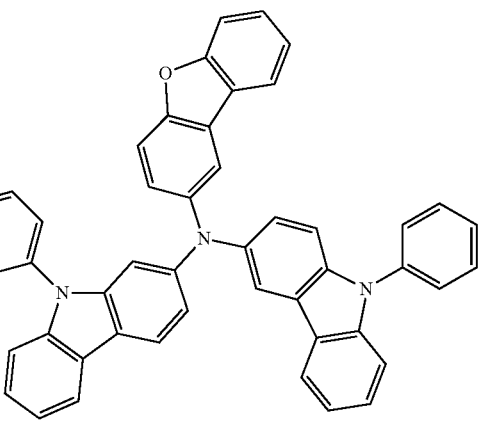
31
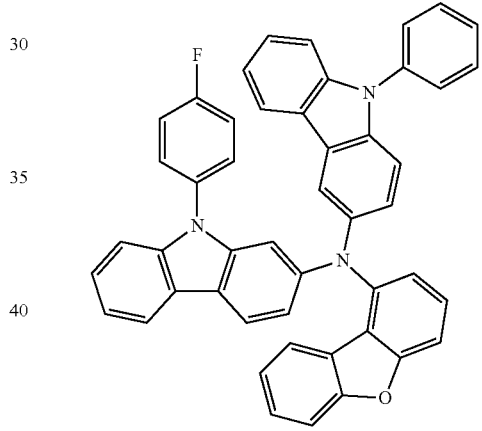
32
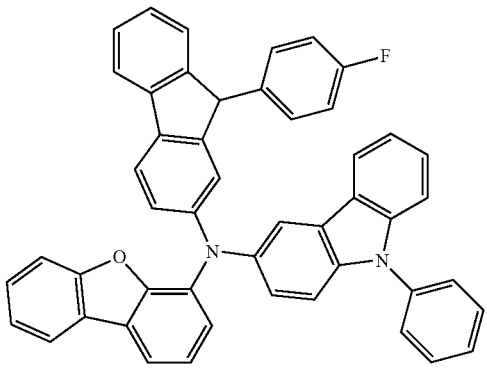

33
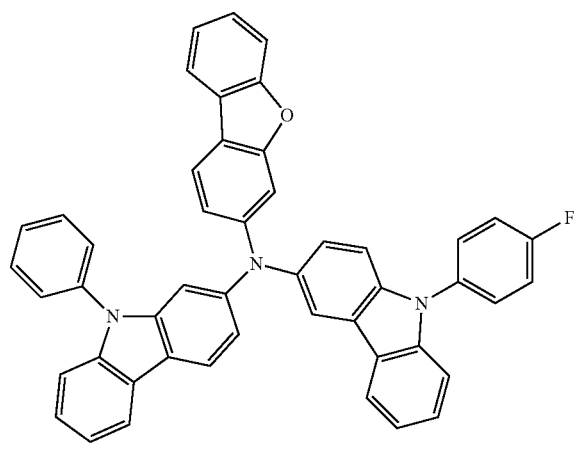
34
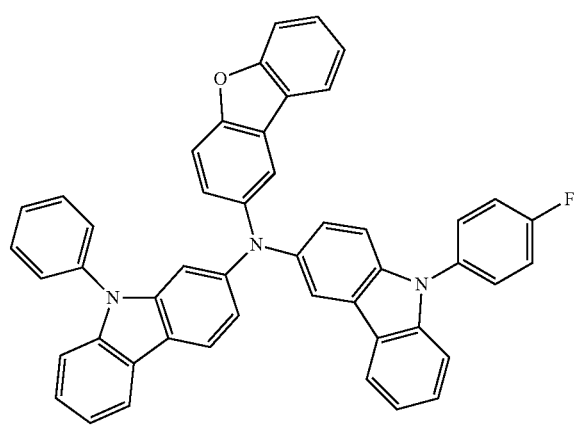
35
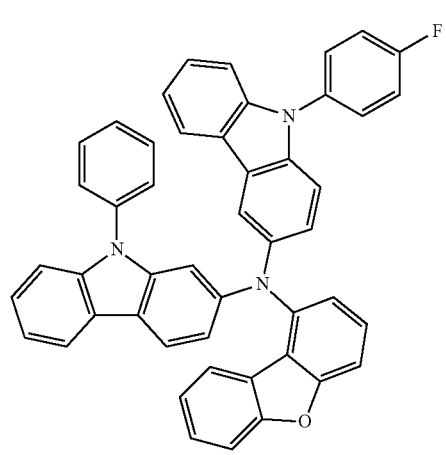
36
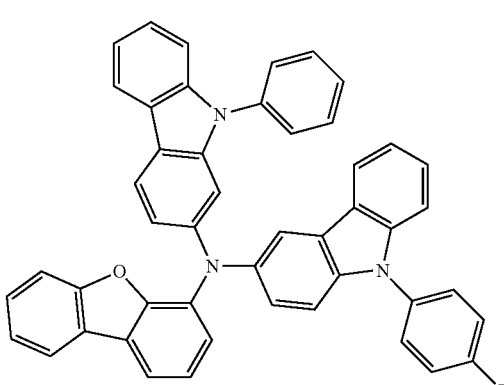
37
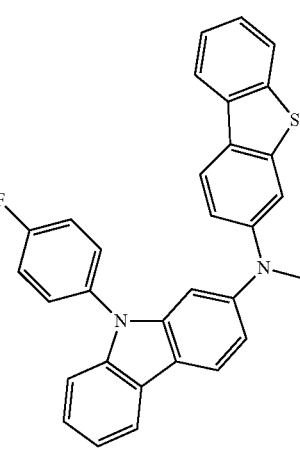
38
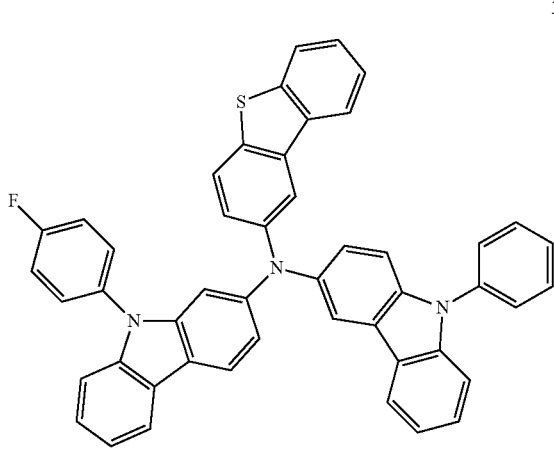

-continued
39
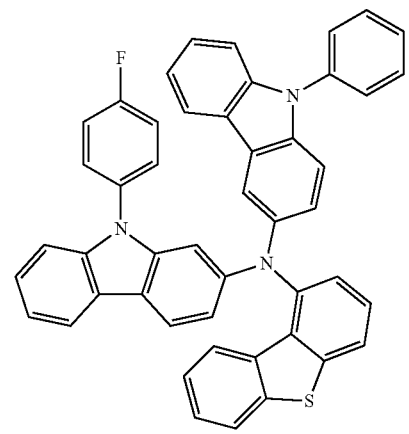
40
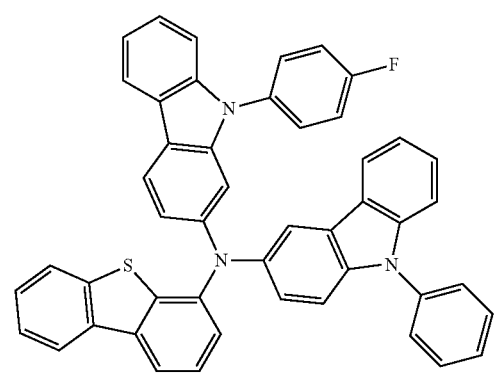
41
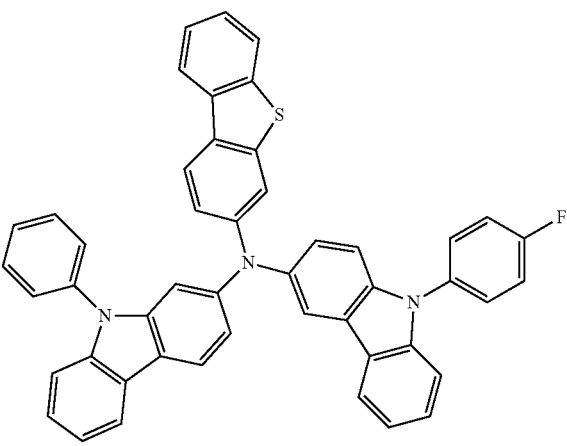
-continued
42
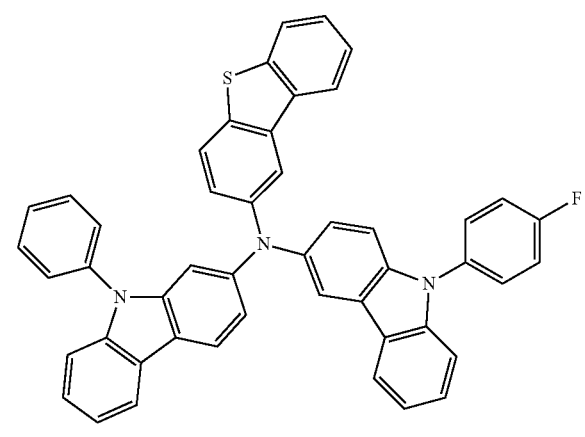
43
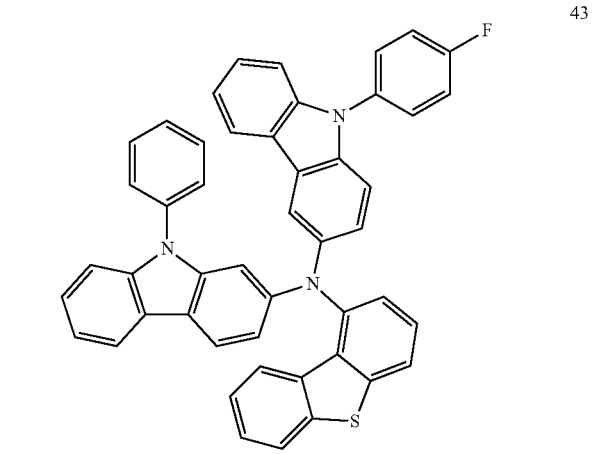
44
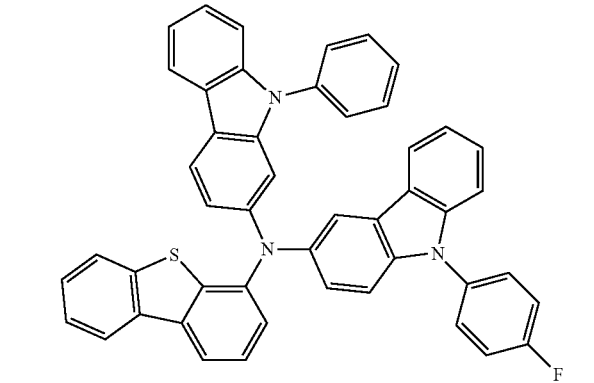
45
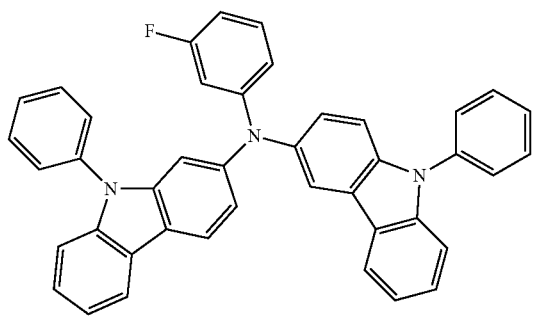

46
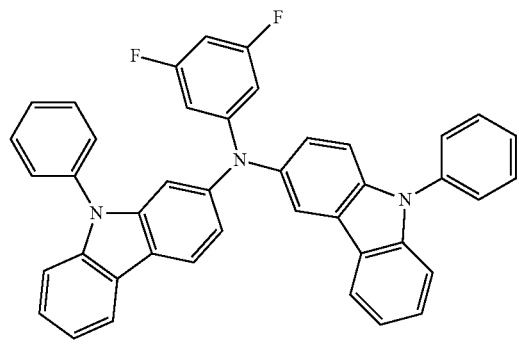
49
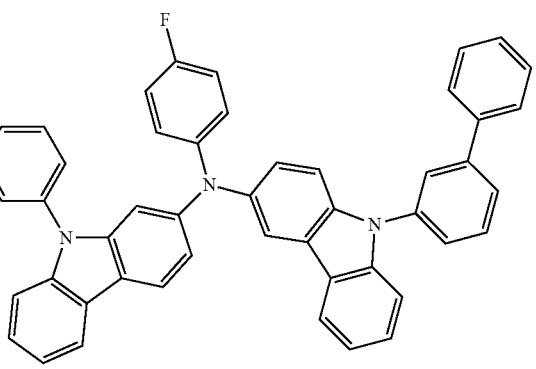
47
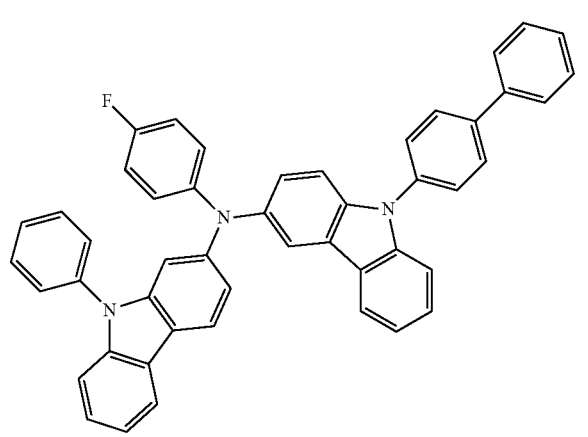
50
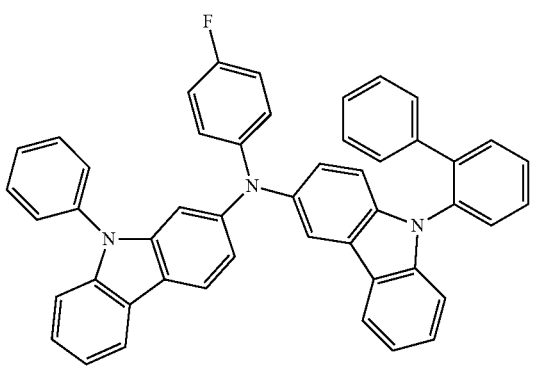
48
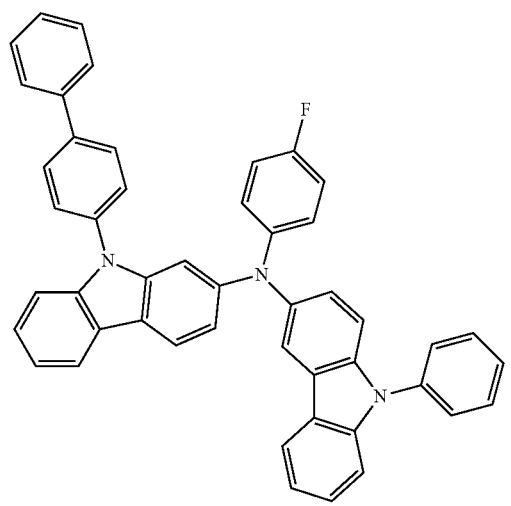
51
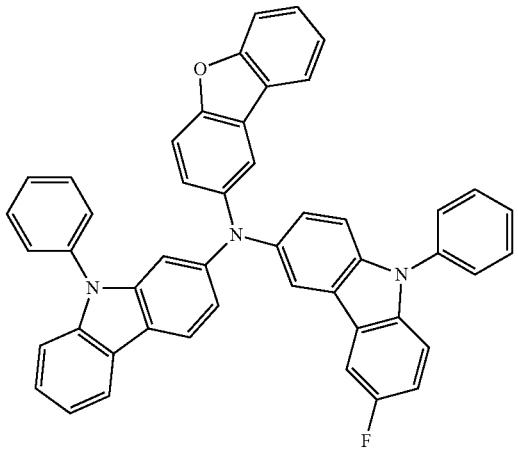

52
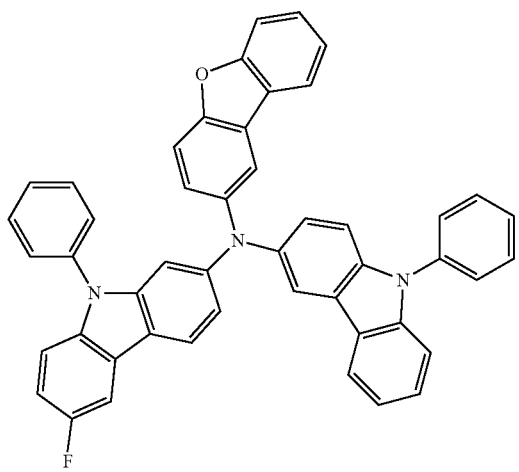
53
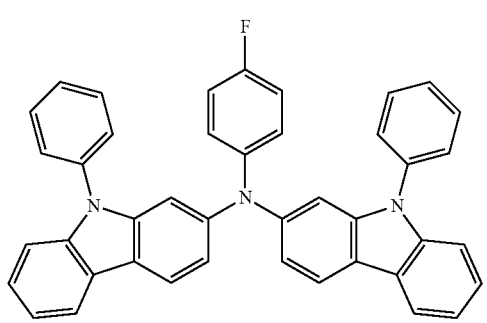
54
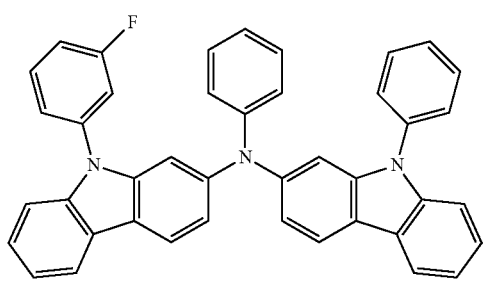
55
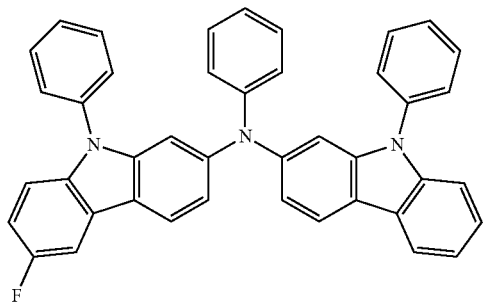
56
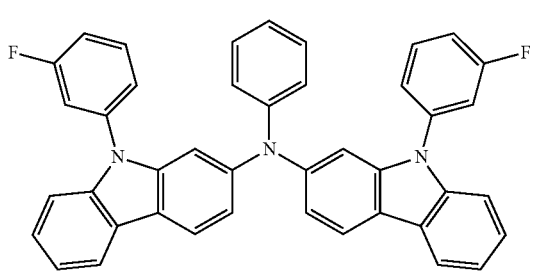
57
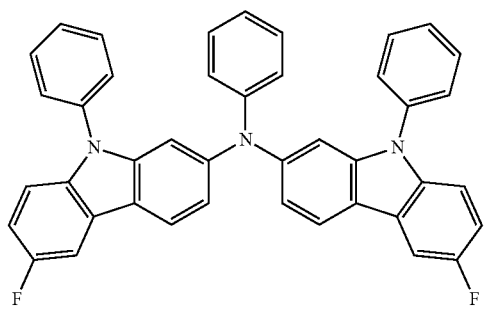
58
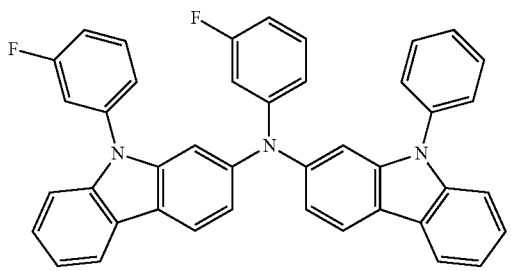
59
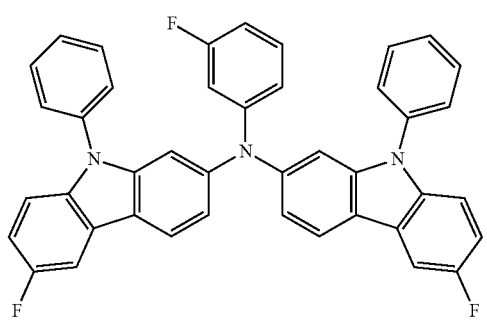
60
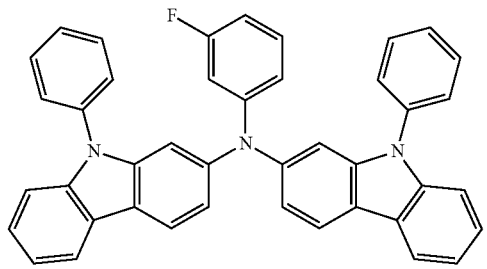

61
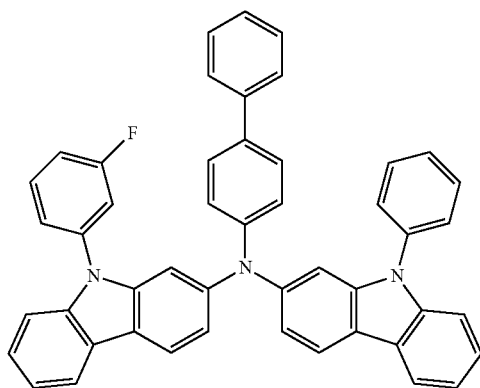
62
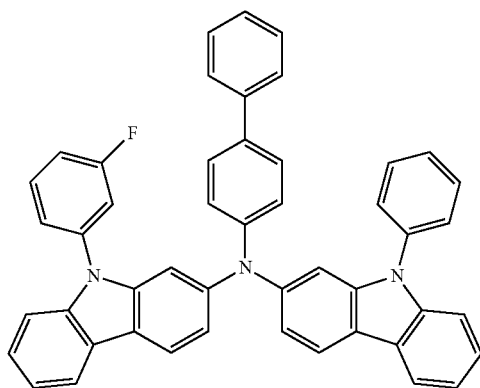
63
64
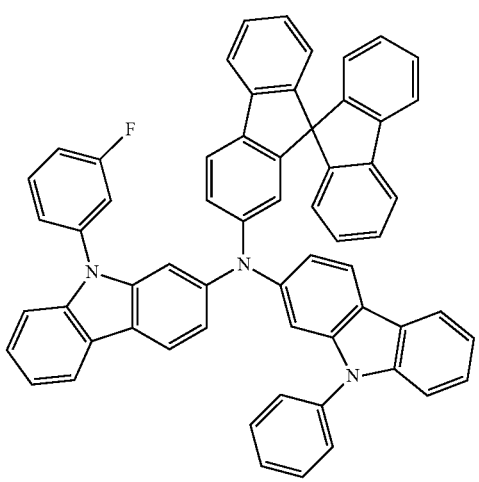
65
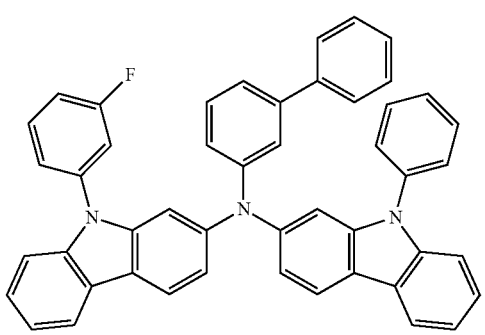
66
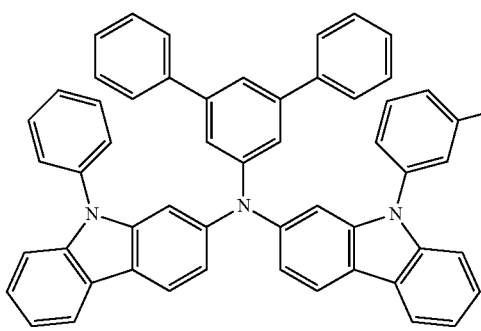
67
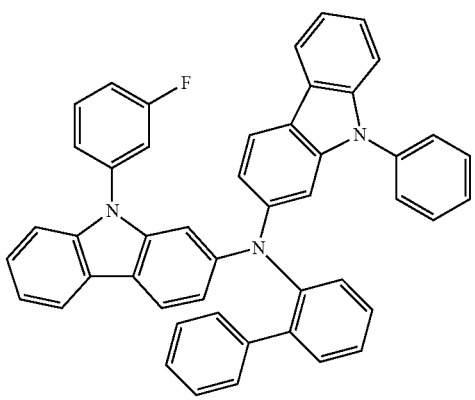

68
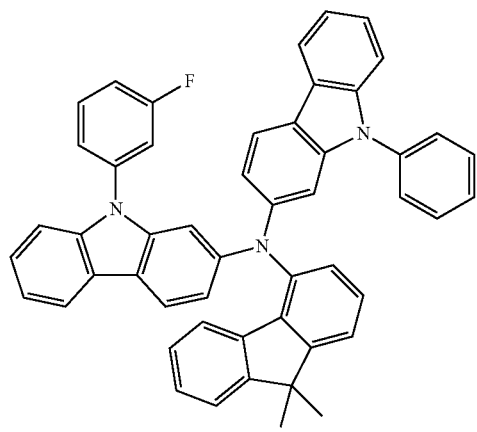
69
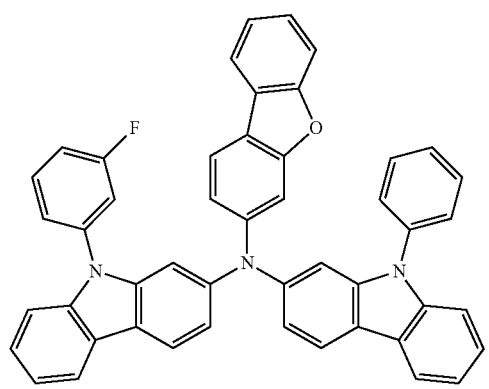
70
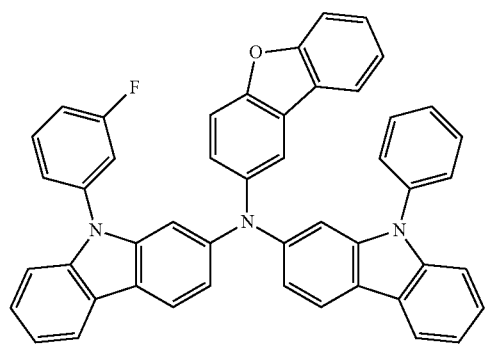
71
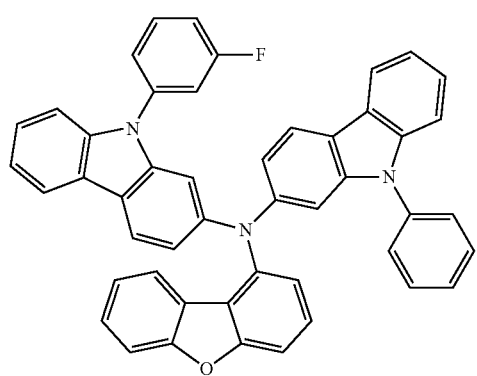
72
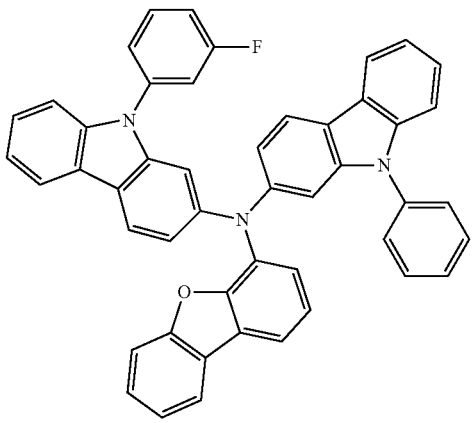
73
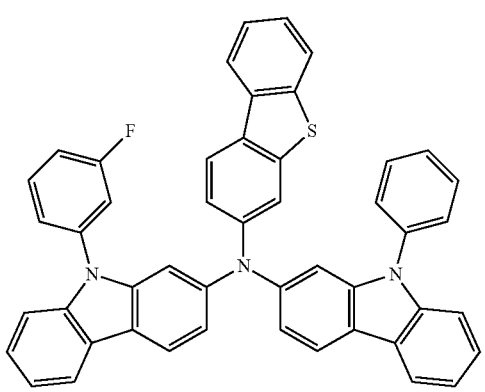
74
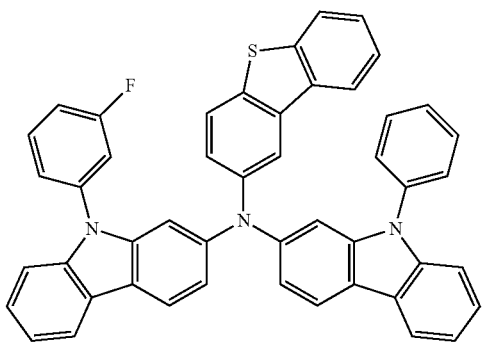
75
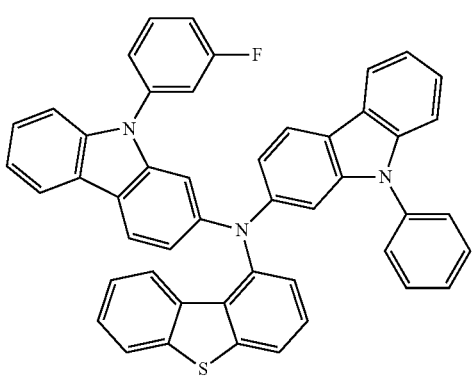

76
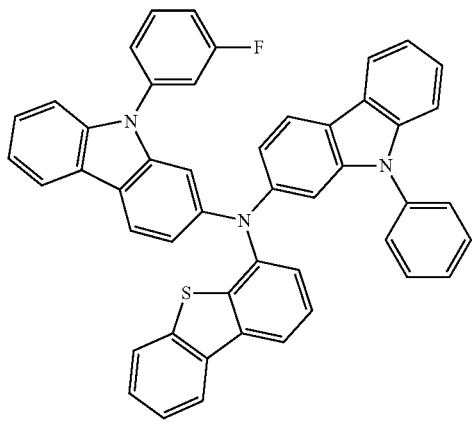
77
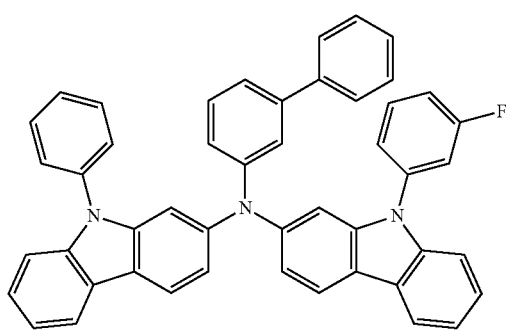
78
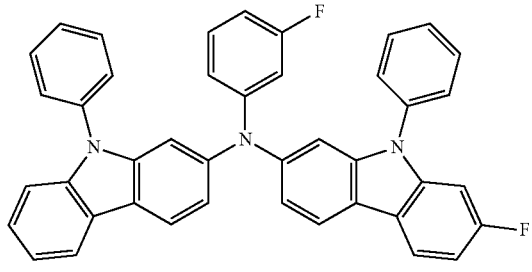
79
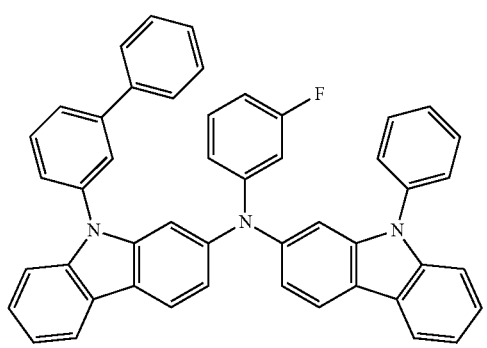
80
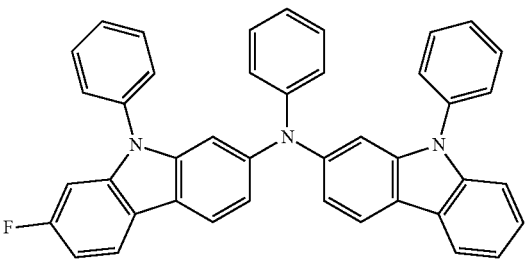
81
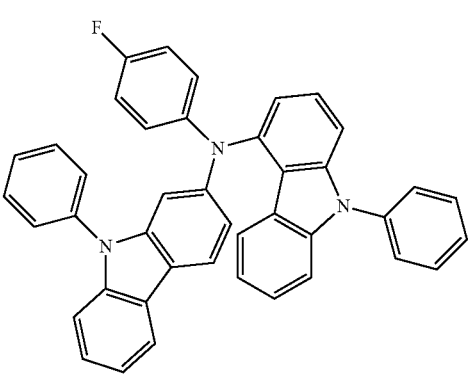
82
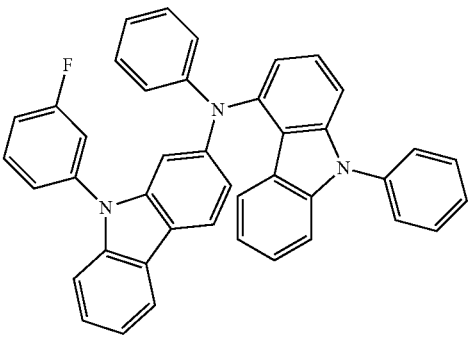
83
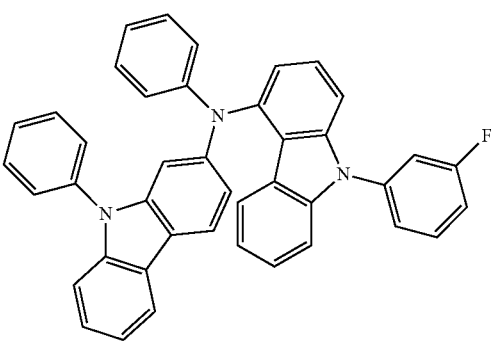

-continued
84
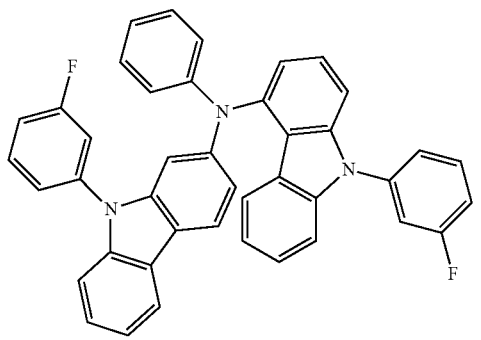
85
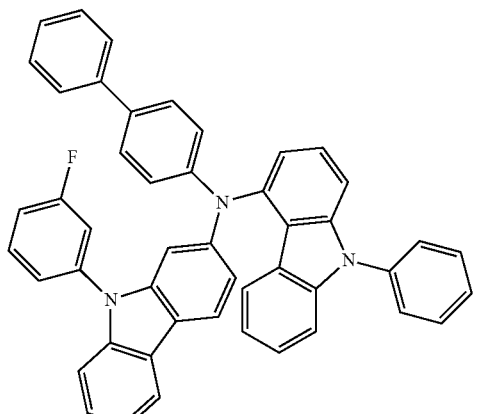
86
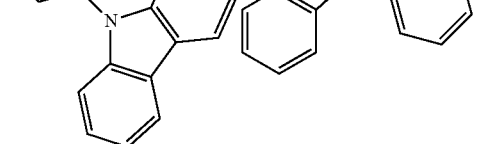
87
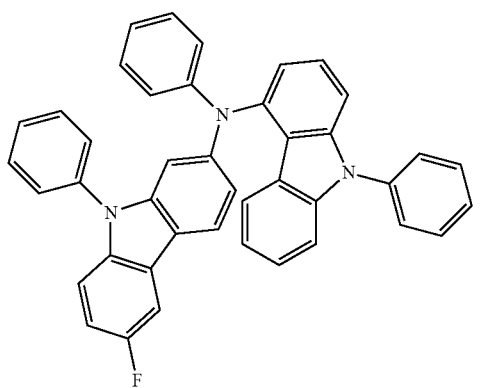
-continued
88
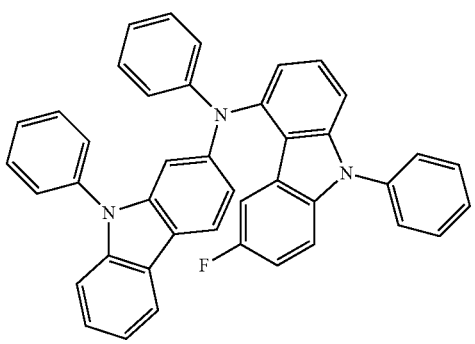
89
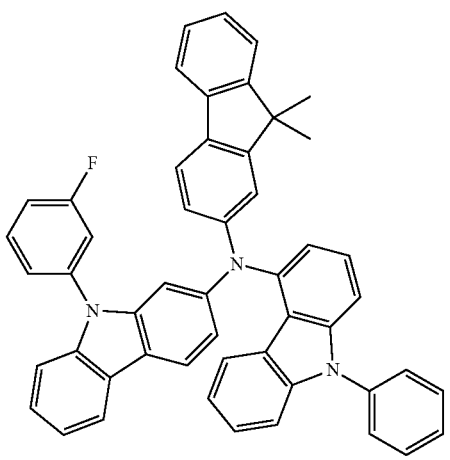
90
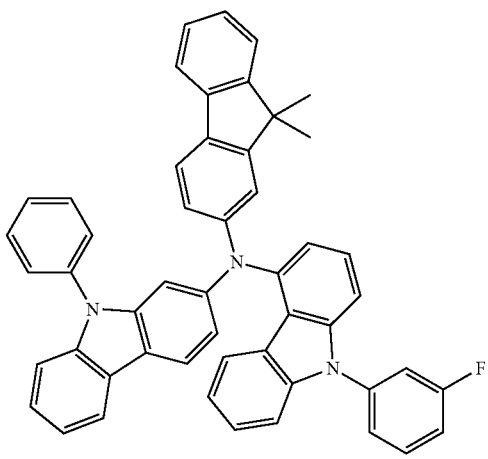

91
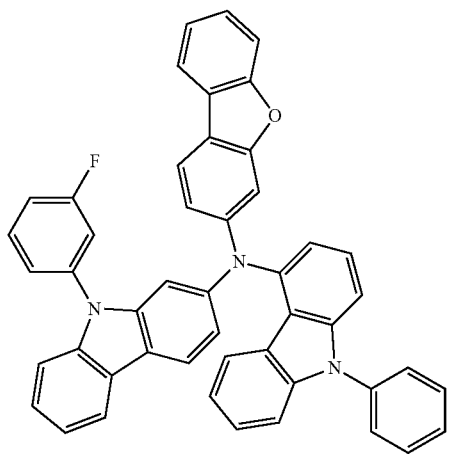
92
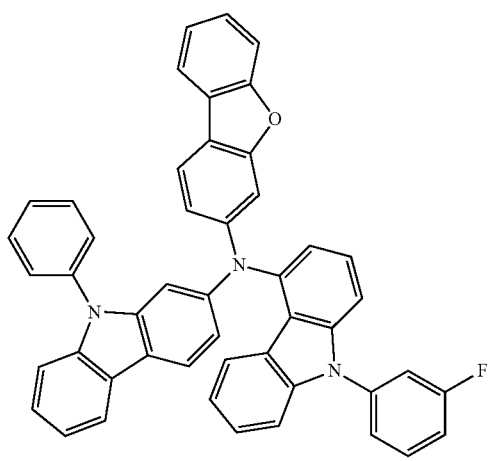
93
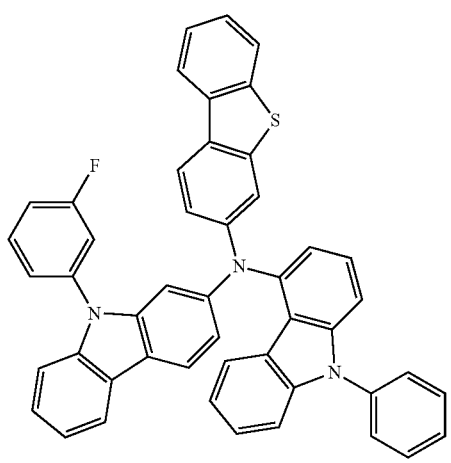
94
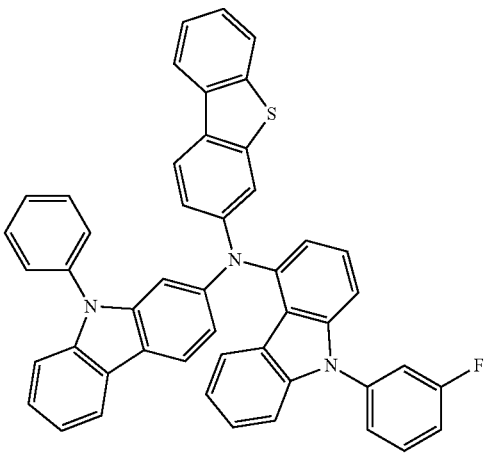
95
96
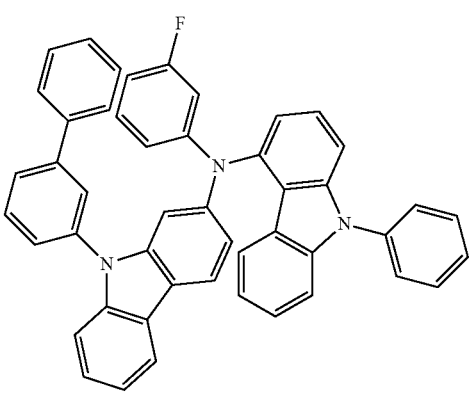
97
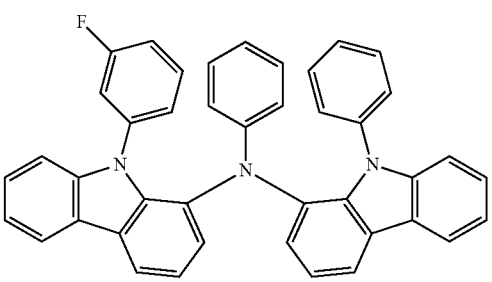

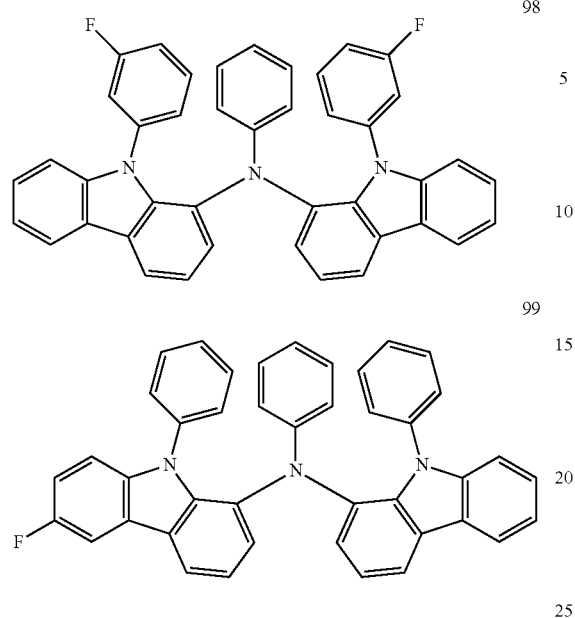
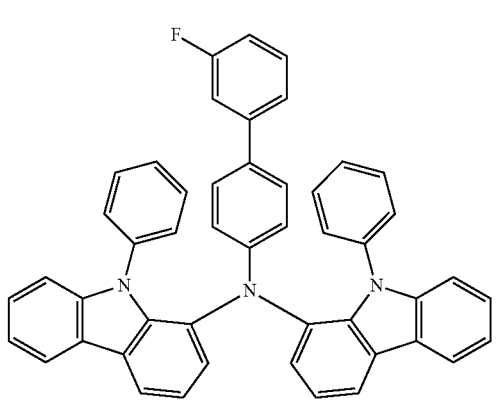
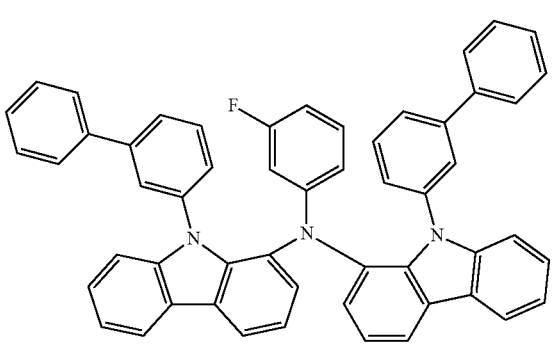
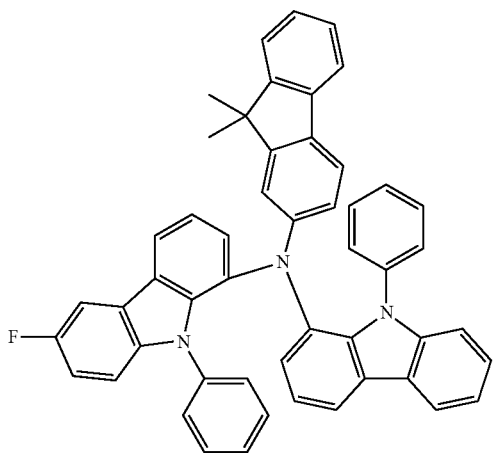

106
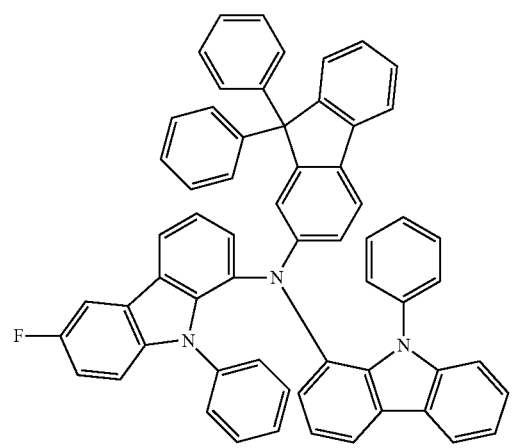
107
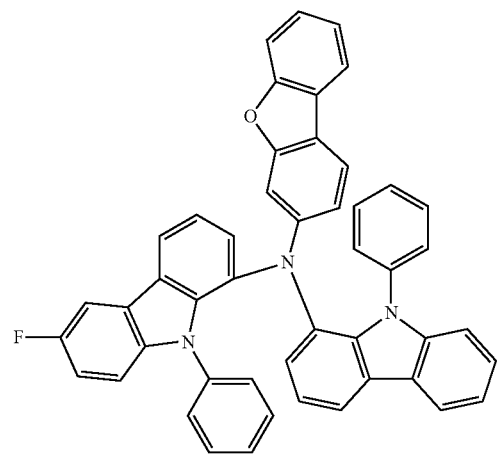
108
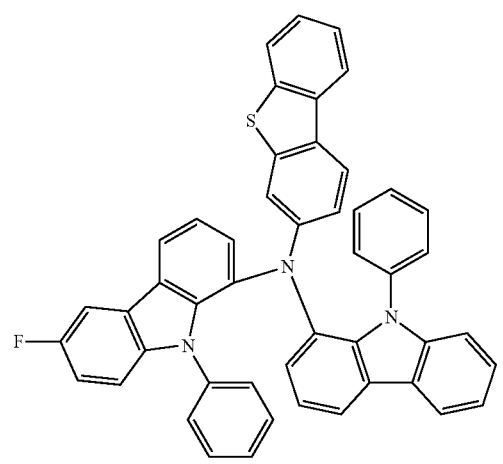
109
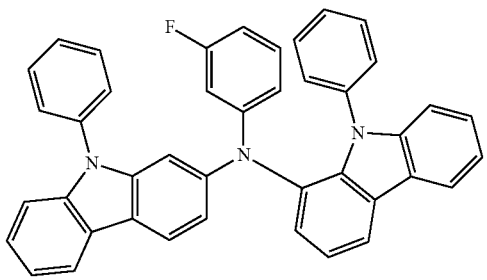
110
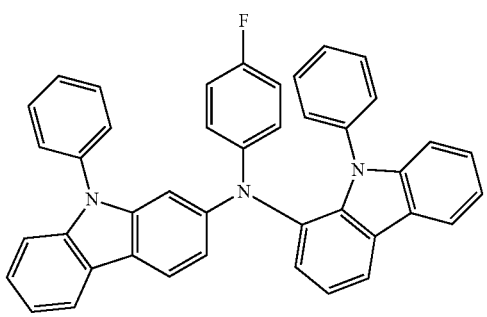
111
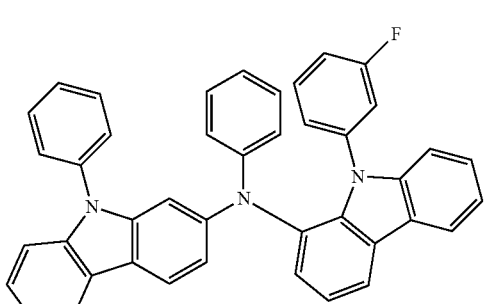
112
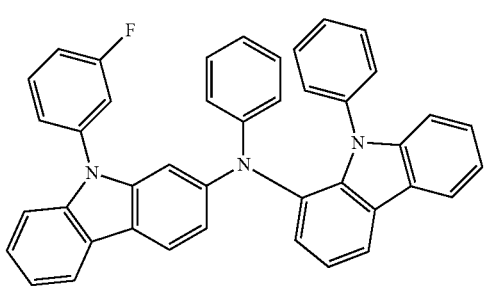
113
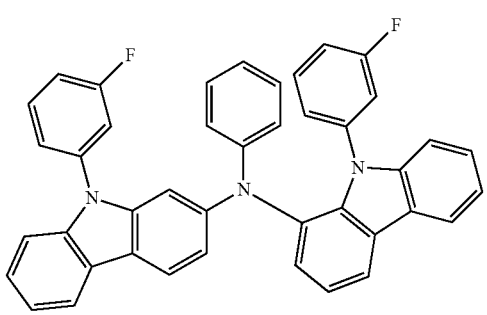

114
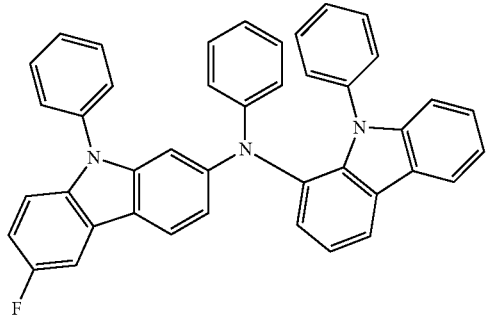
115
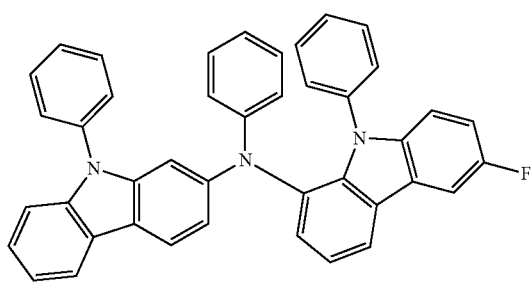
116
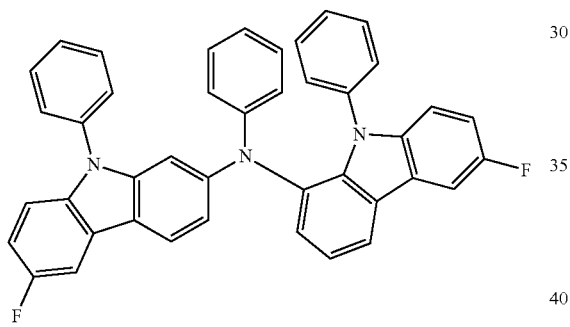
117
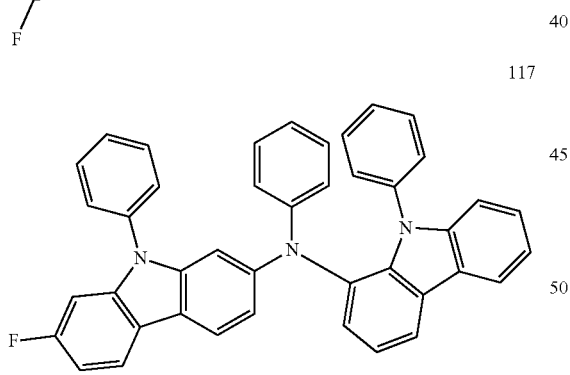
118
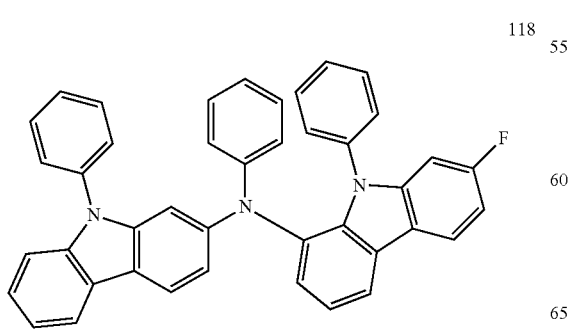
119
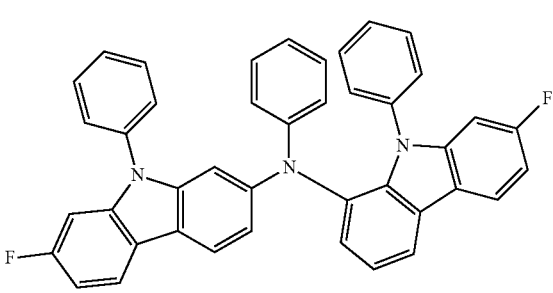
120
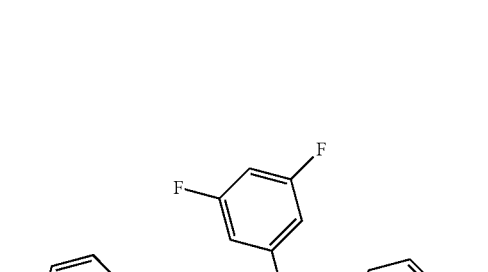
121
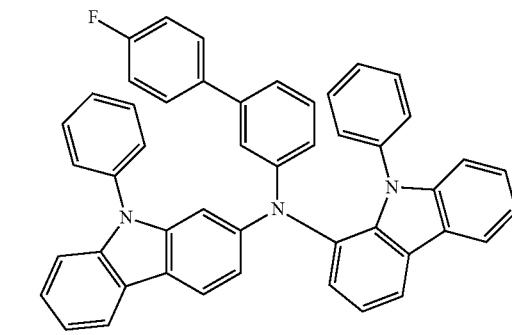
122
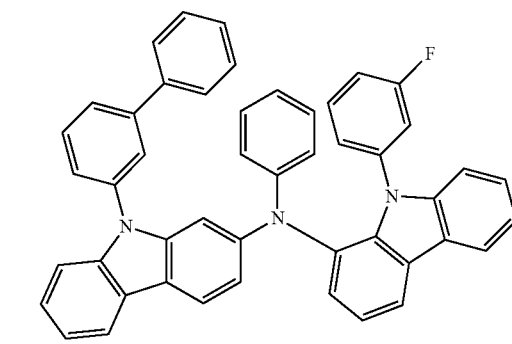

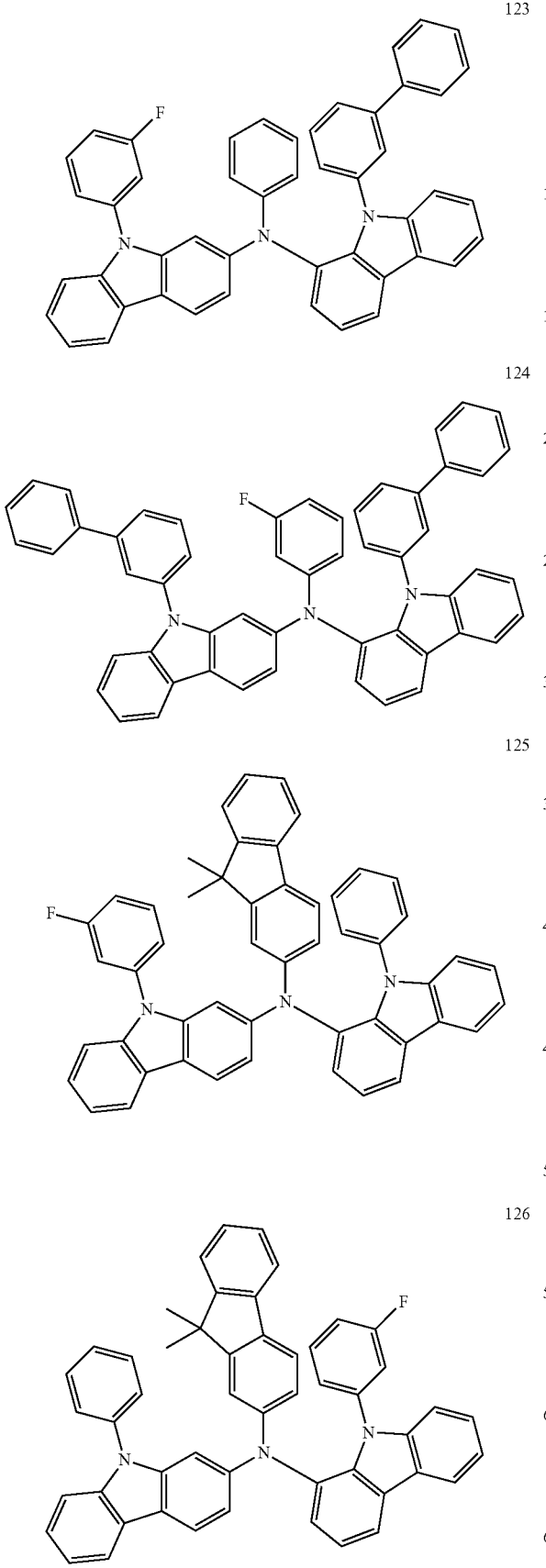
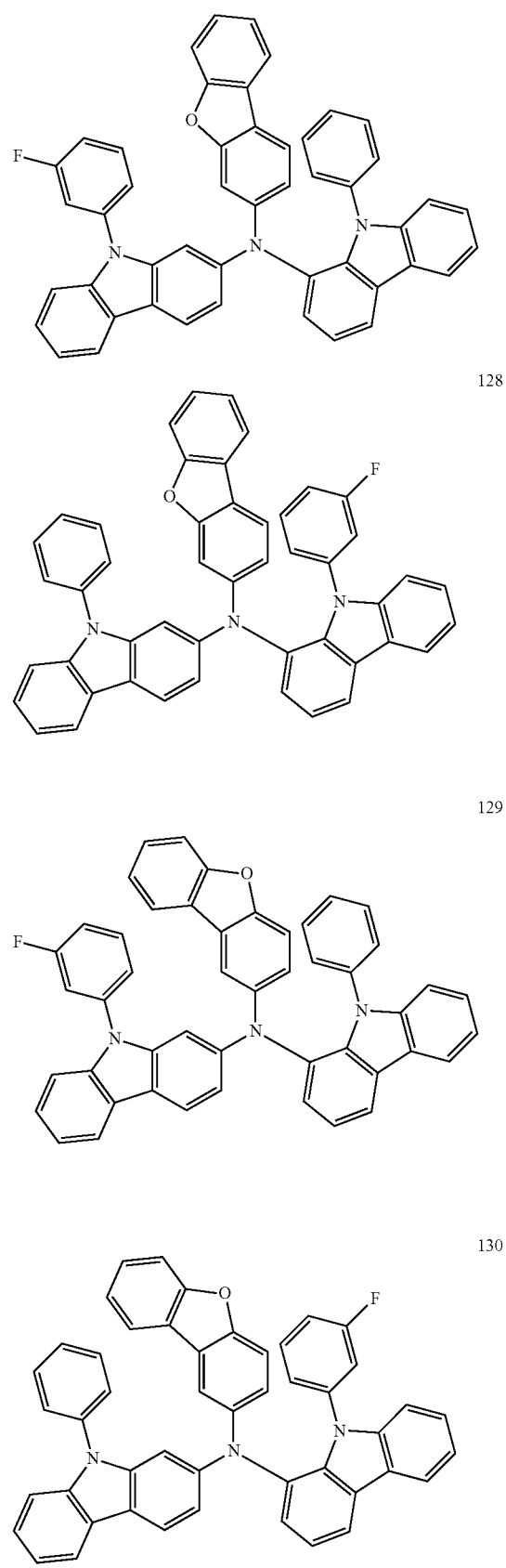

131
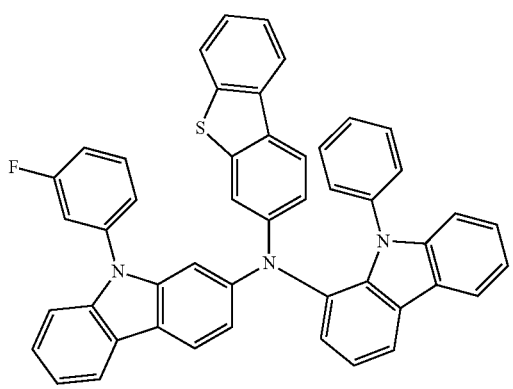
132
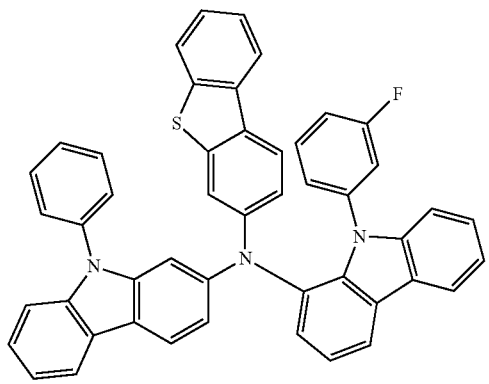
133
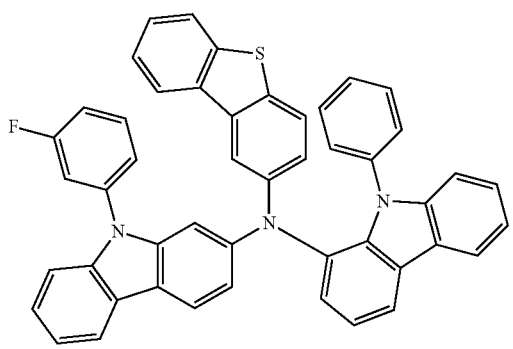
134
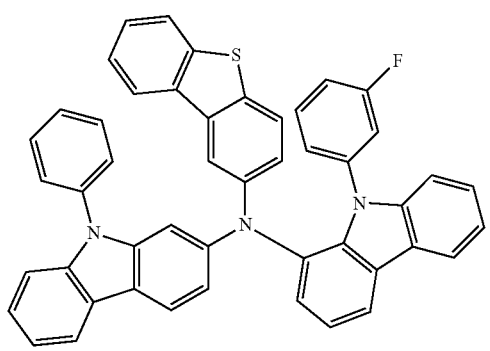
135
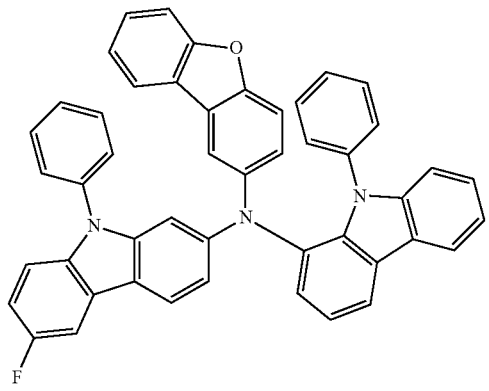
136
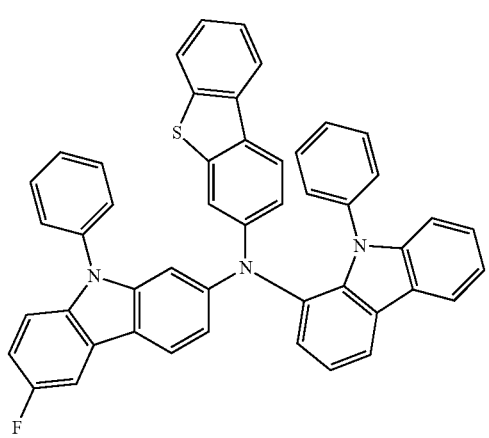
137
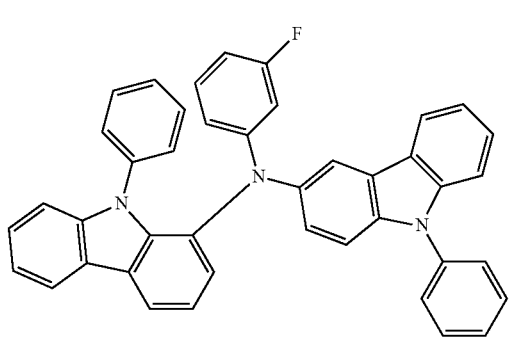
138
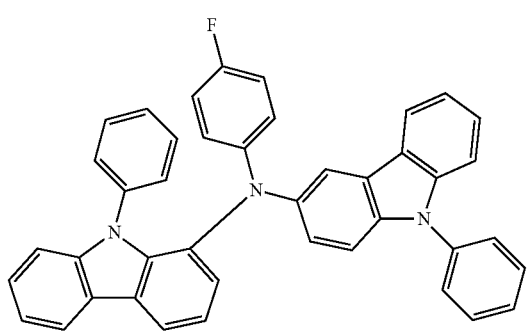

139
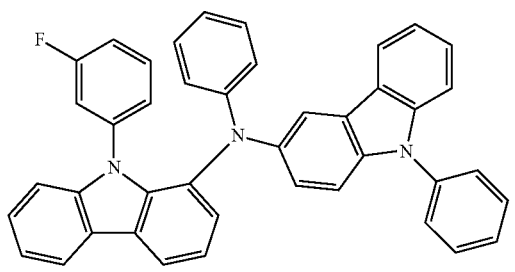
140
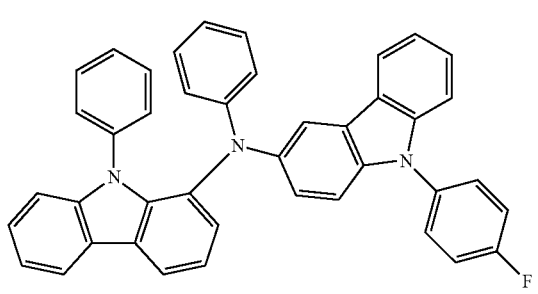
141
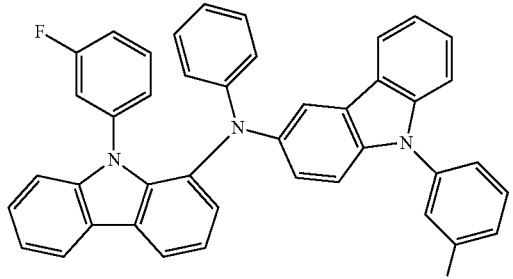
142
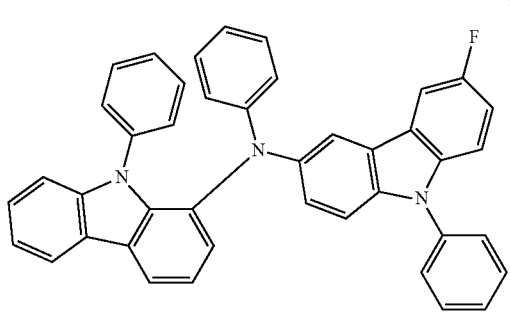
143
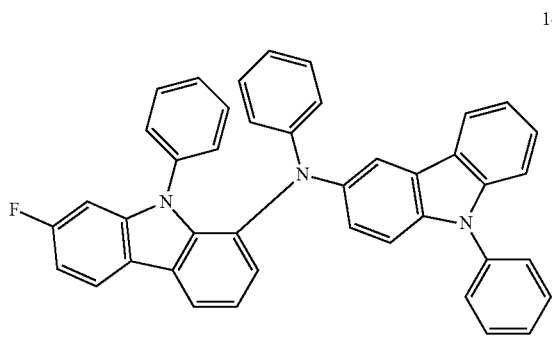
144
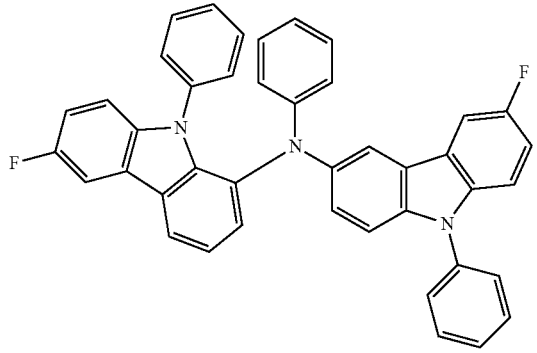
145
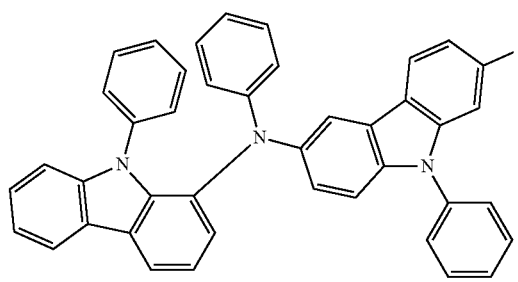
146
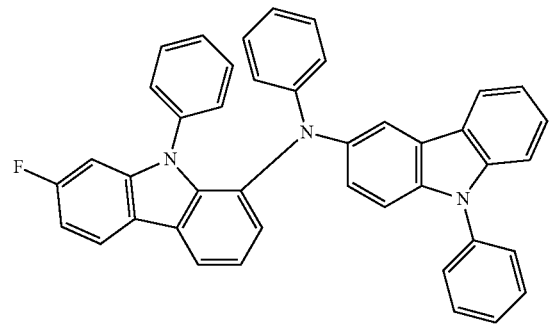
147
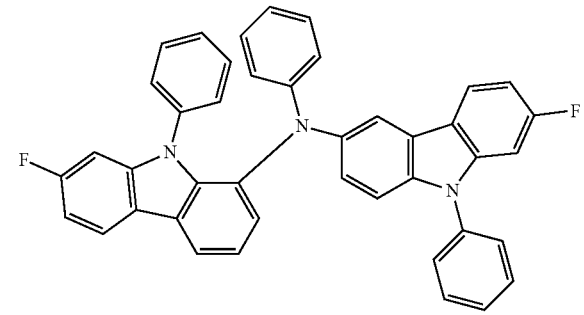

148
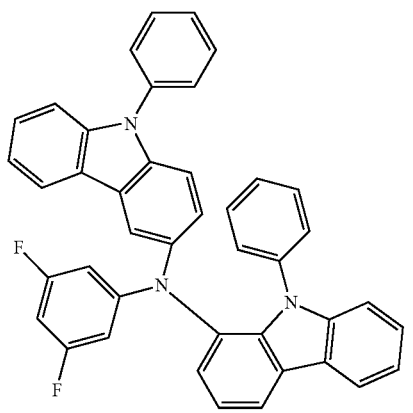
149
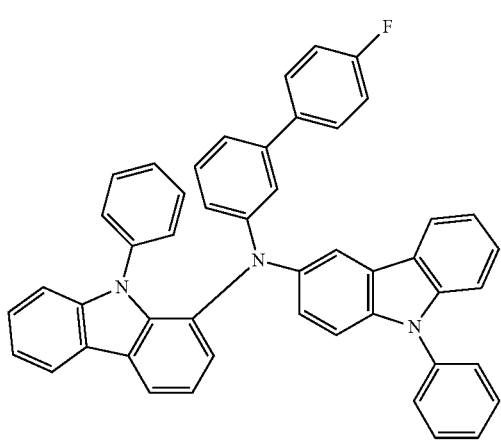
150
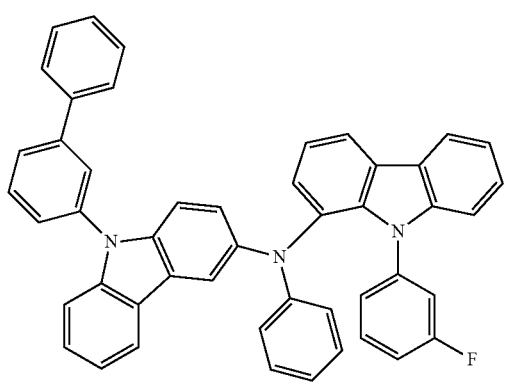
151
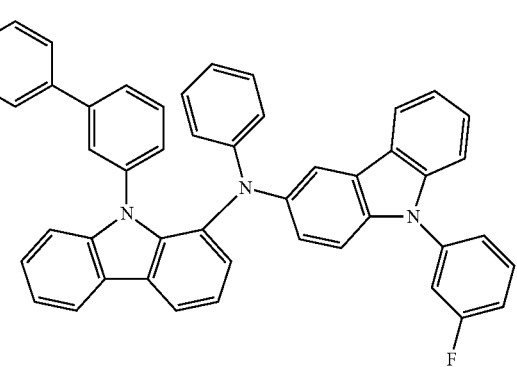
152
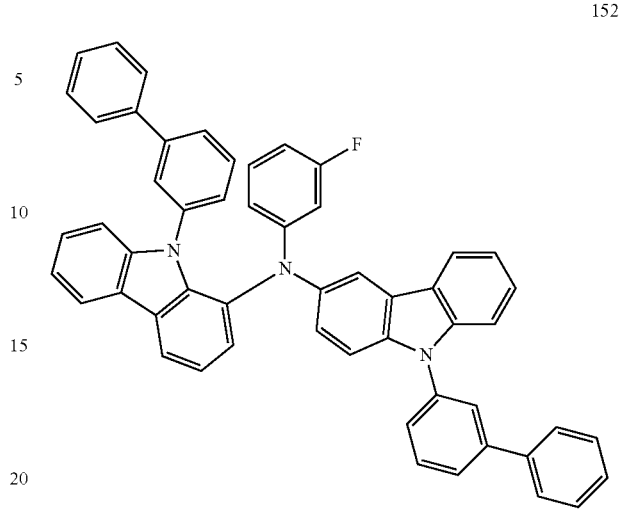
153
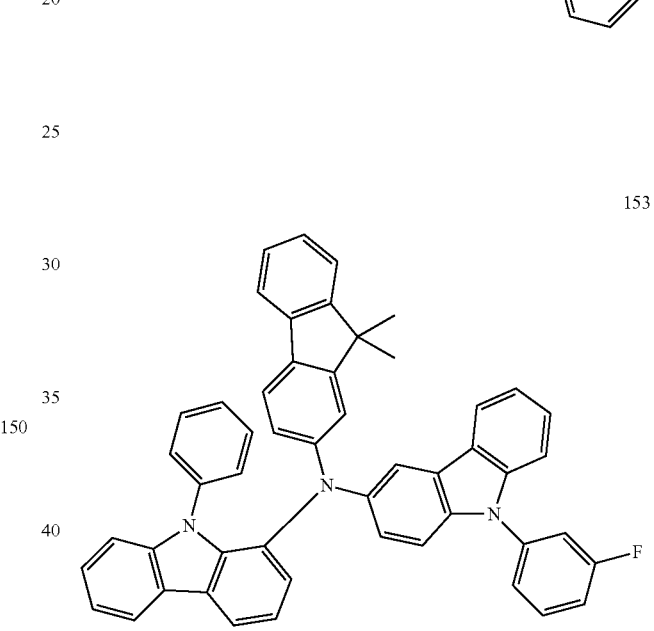
154
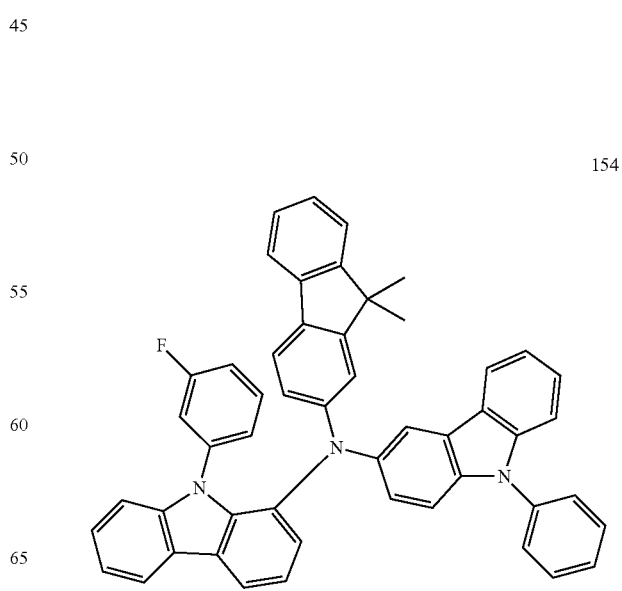

155
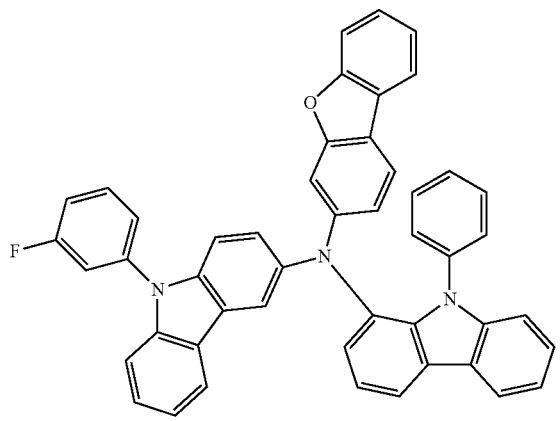
156
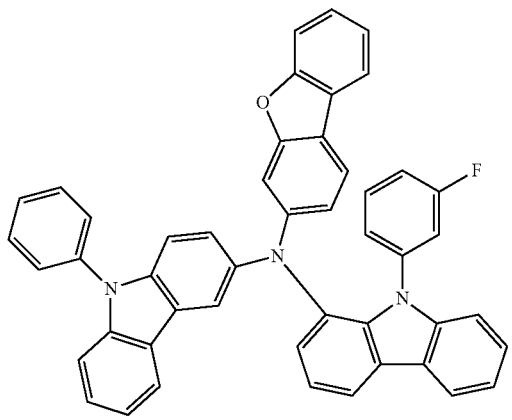
157
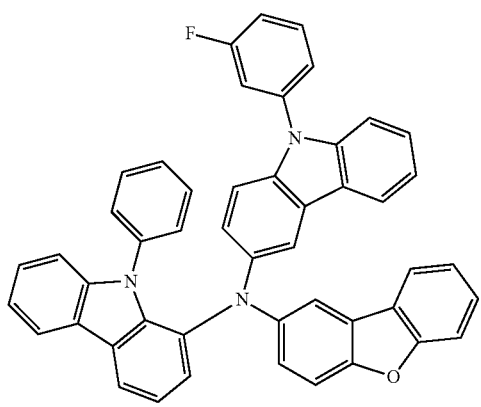
158
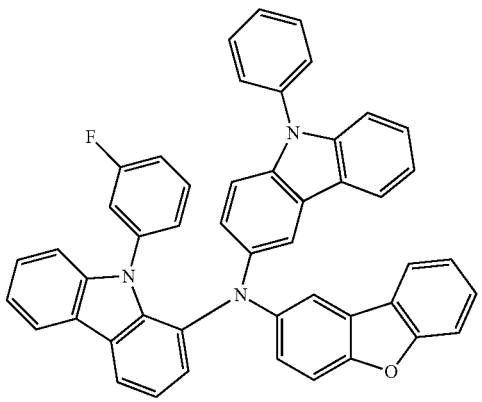
159
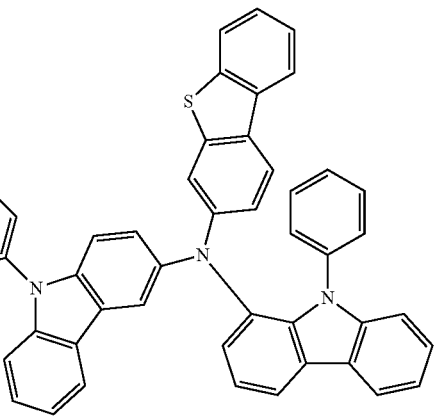
160
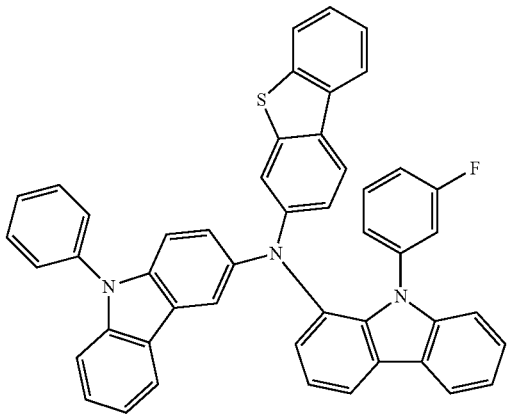

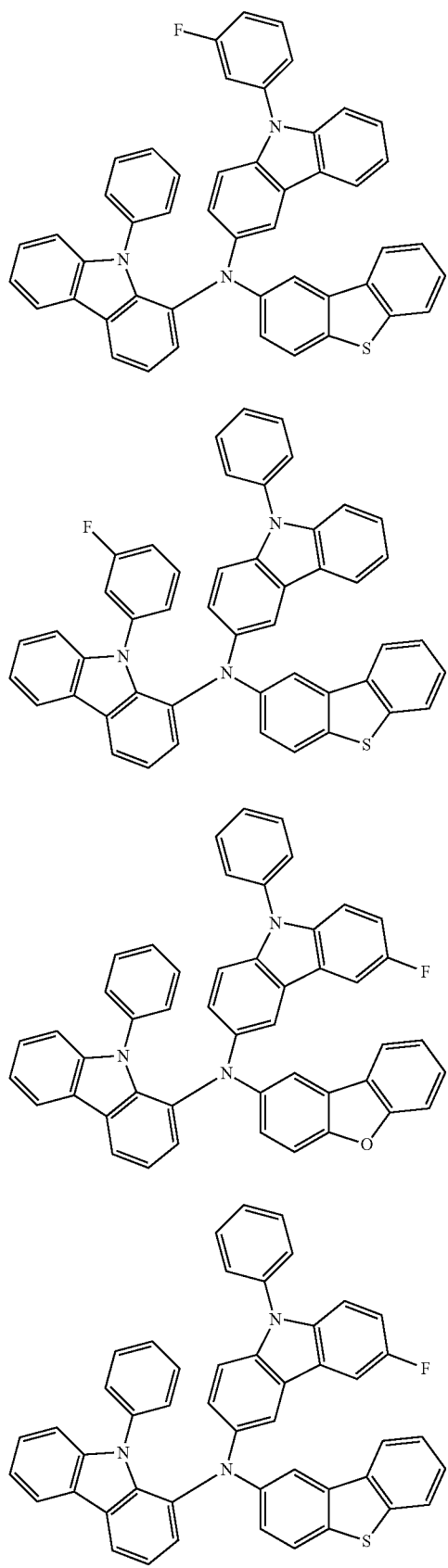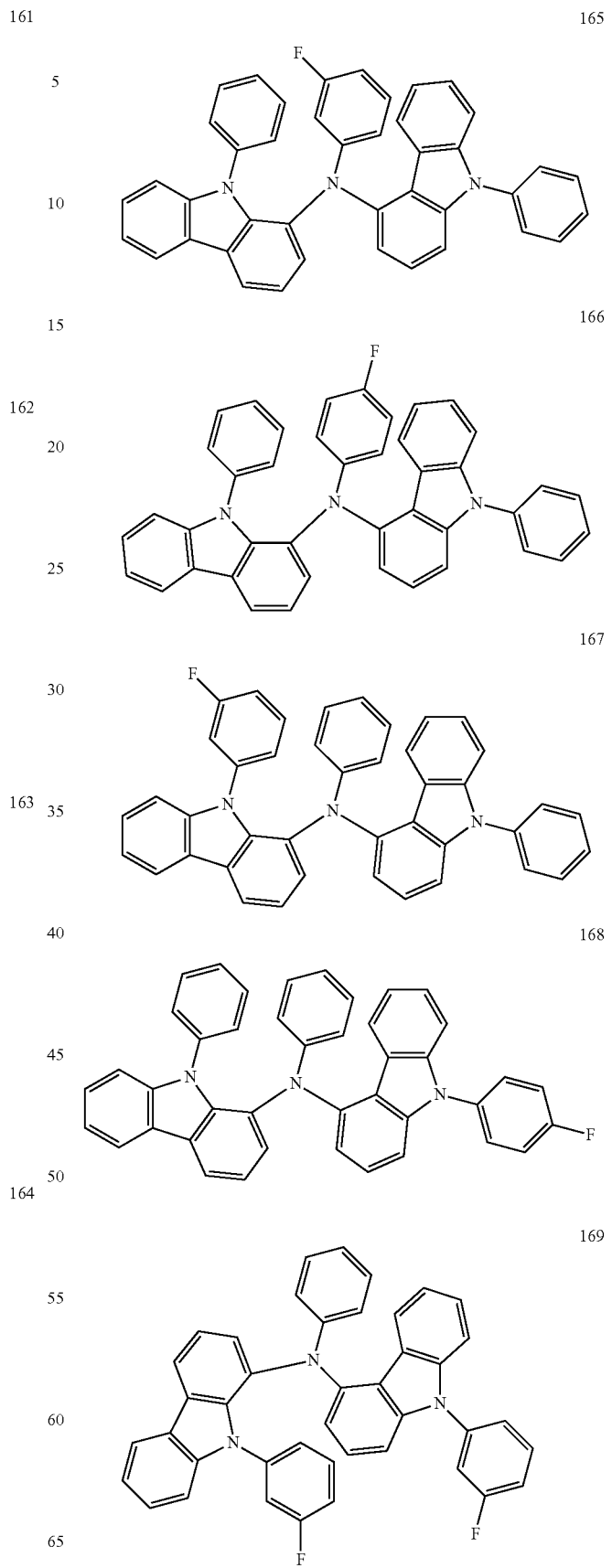

170
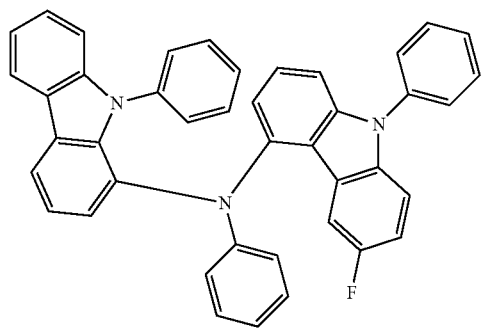
171
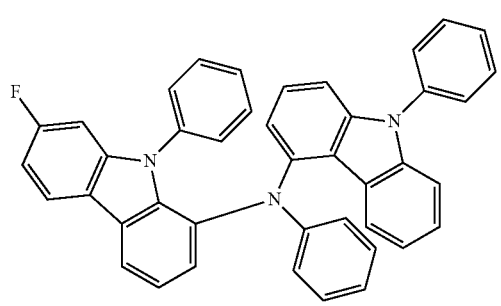
172
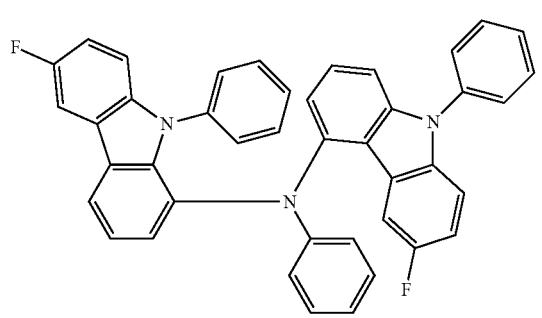
173
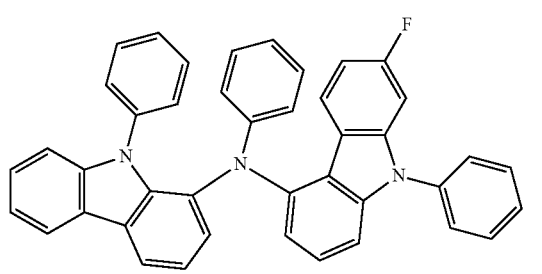
174
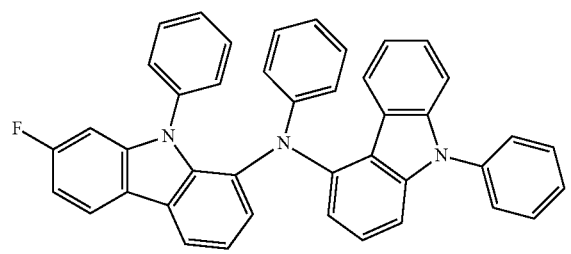
175
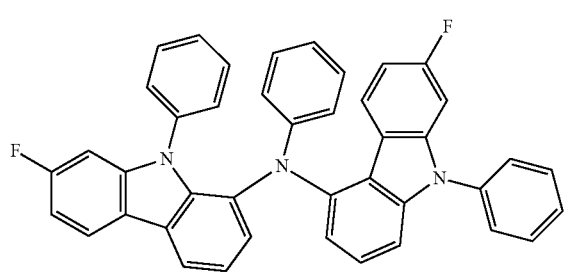
176
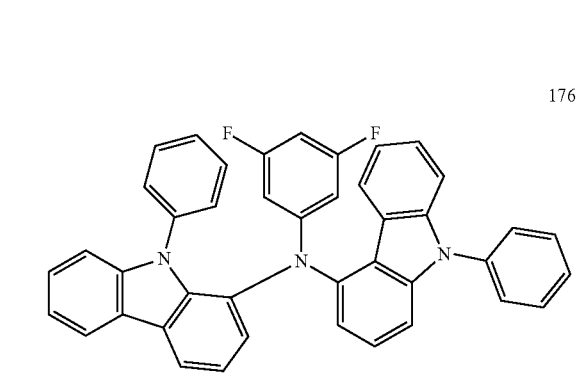
177
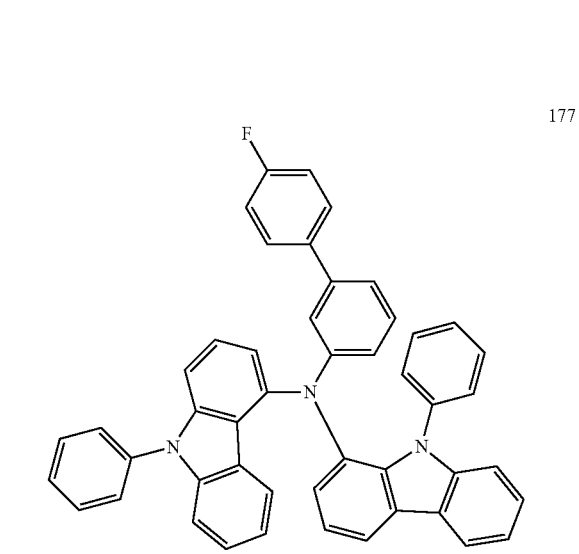
178
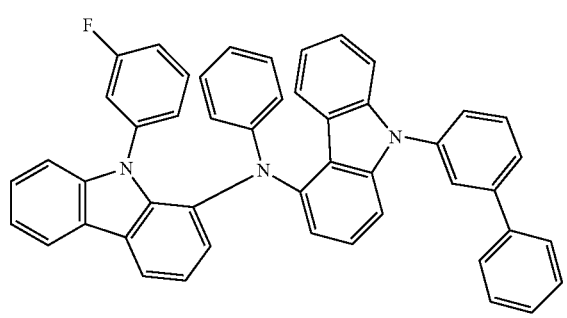

179
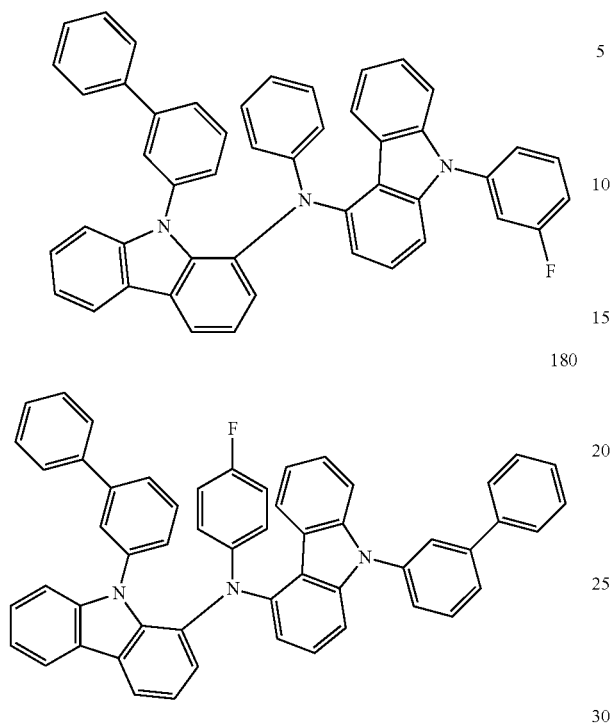
180
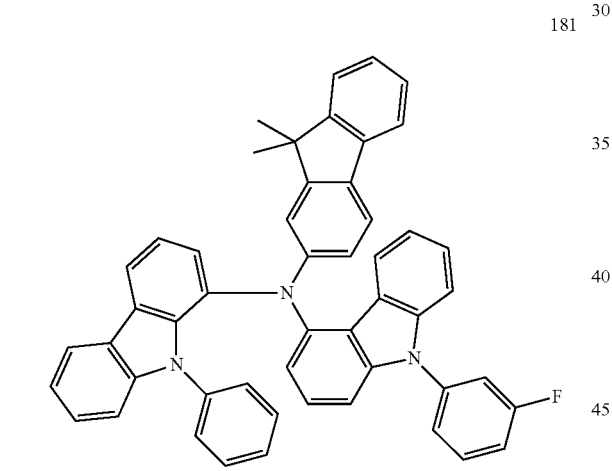
181
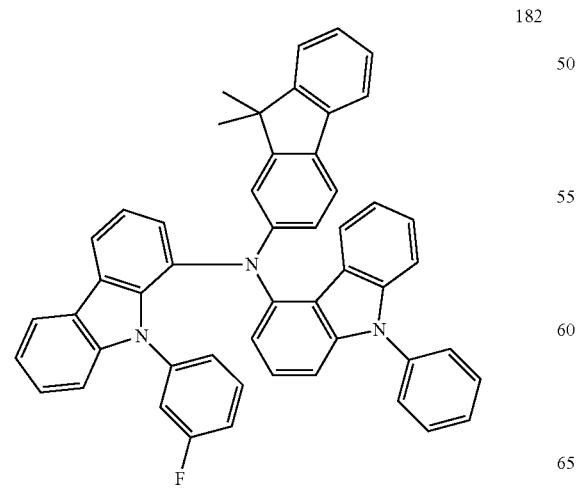
182
183
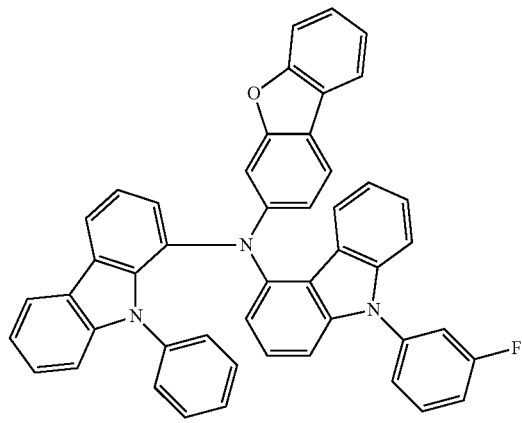
184
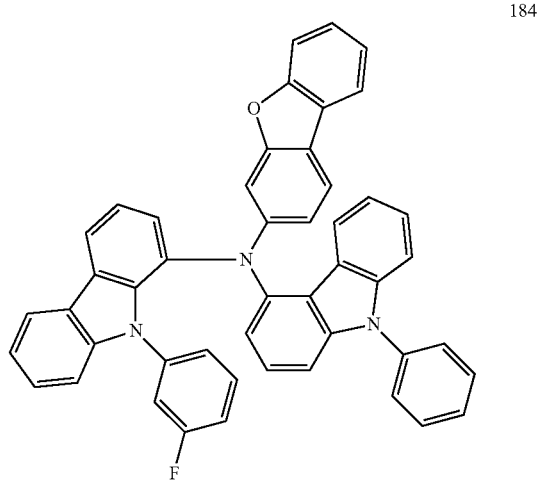
185
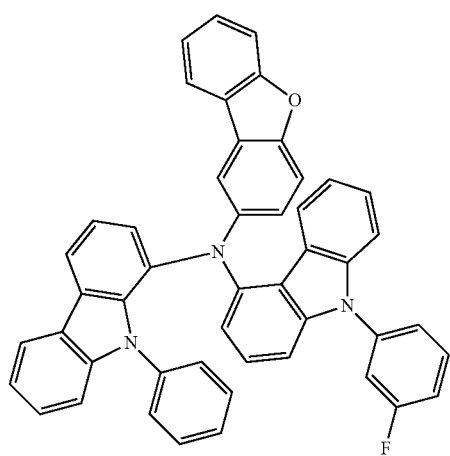

186
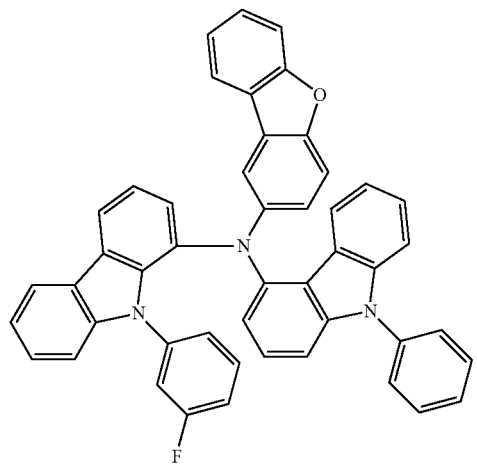
187
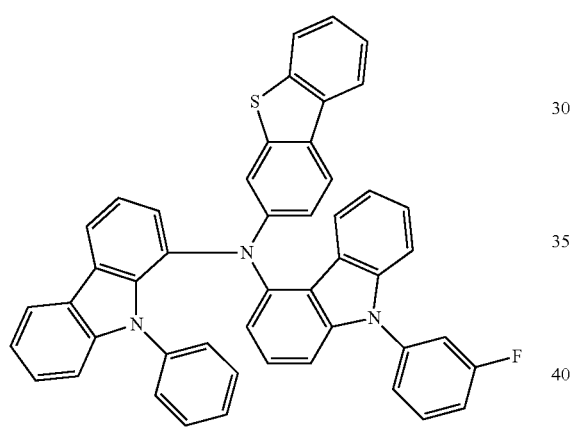
188
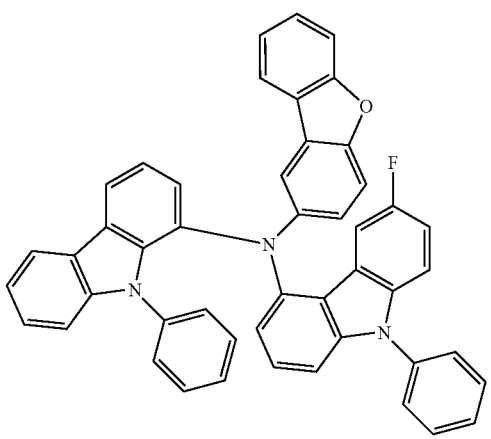
189
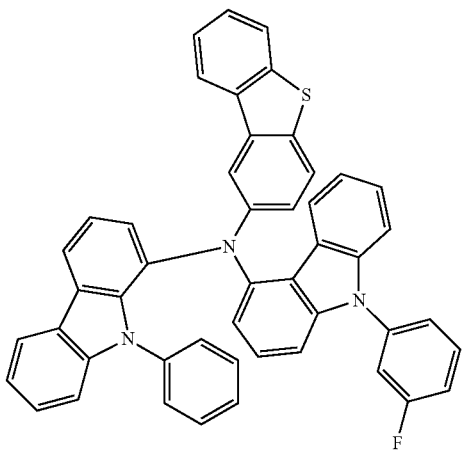
190
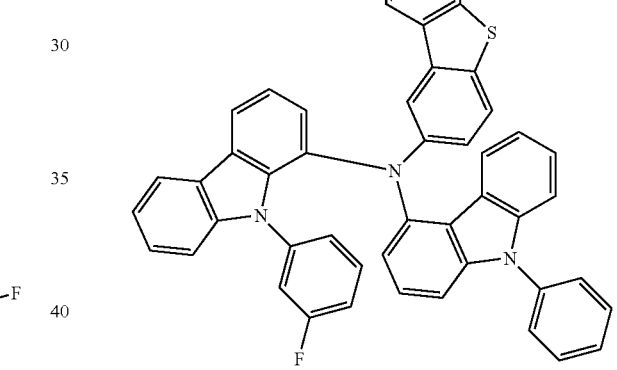
191

192
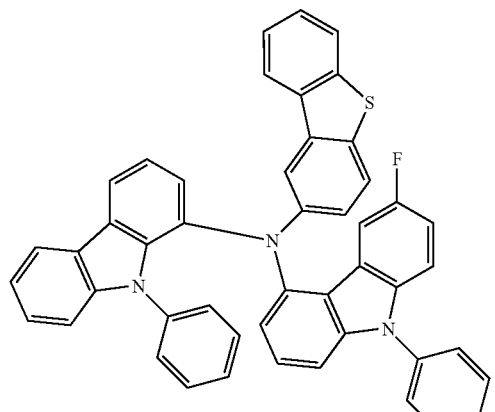
193
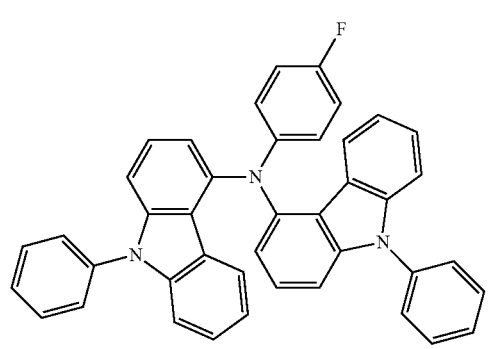
194
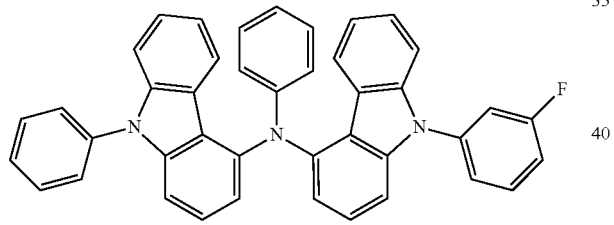
195
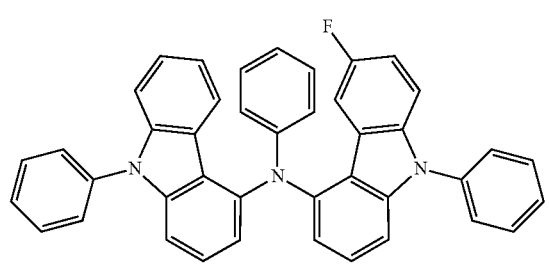
196
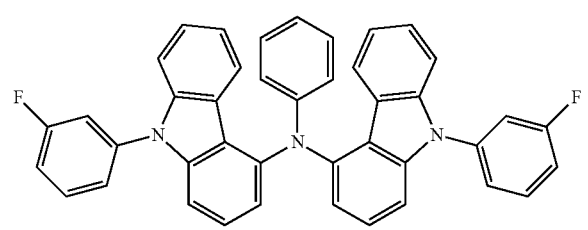
197
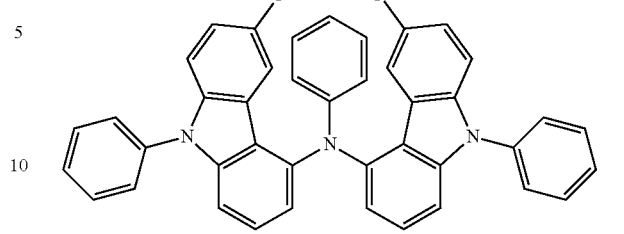
198
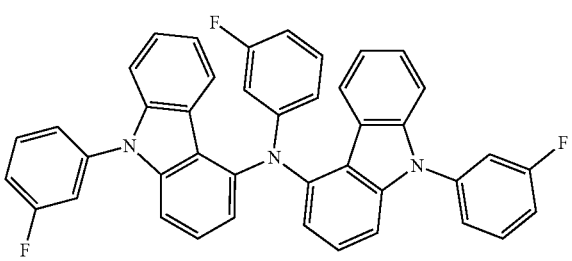
199
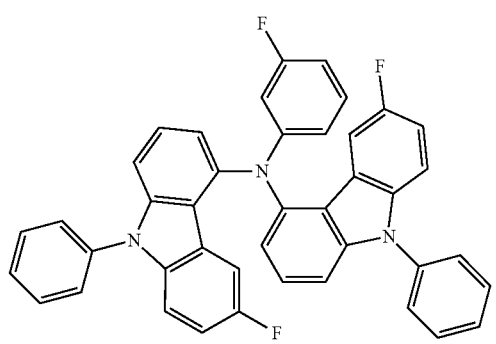
200
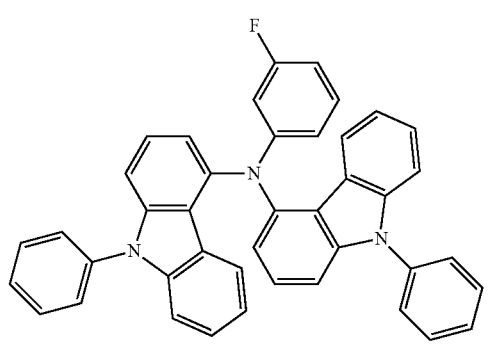
201
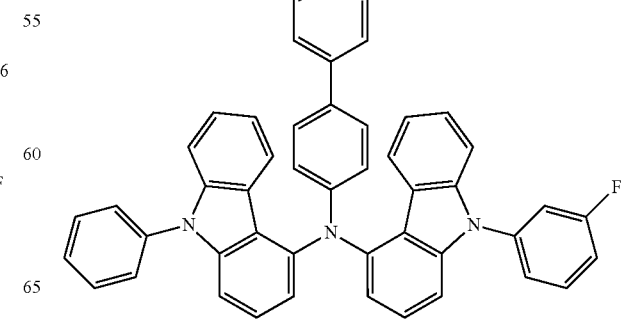

-continued
202
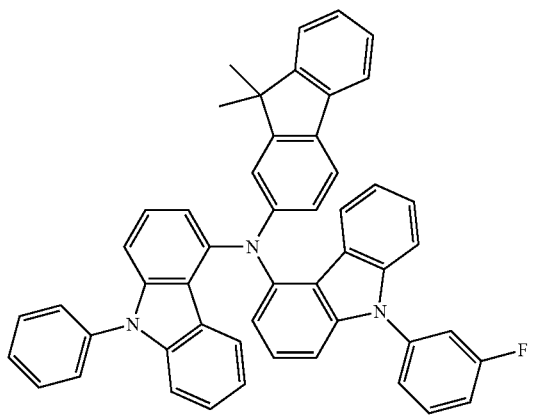
203
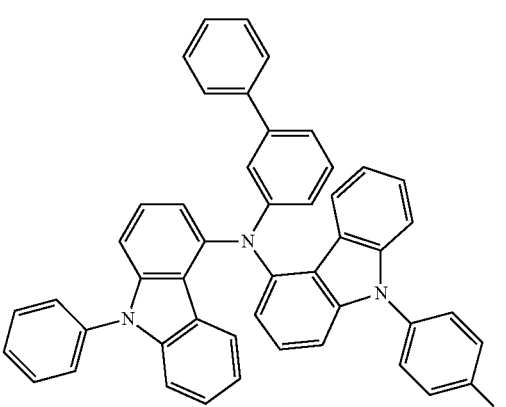
204
205
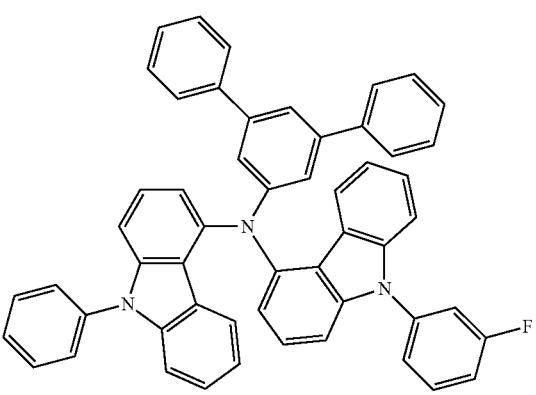
206
207
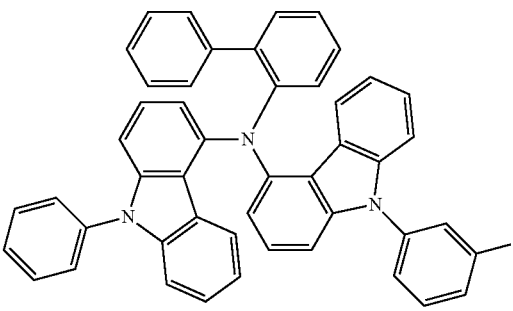
208
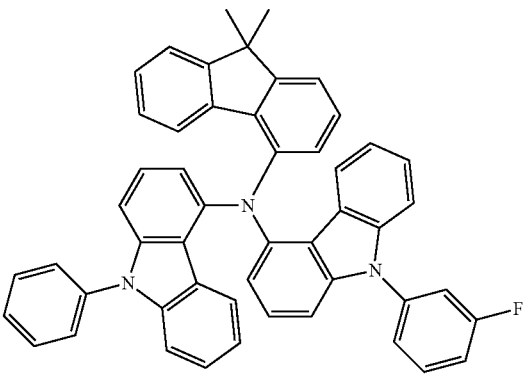

95
-continued
209
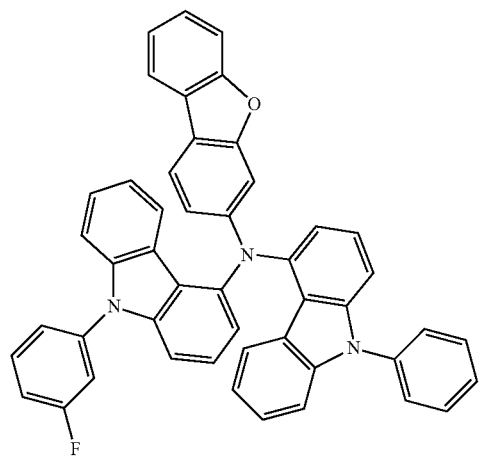
210
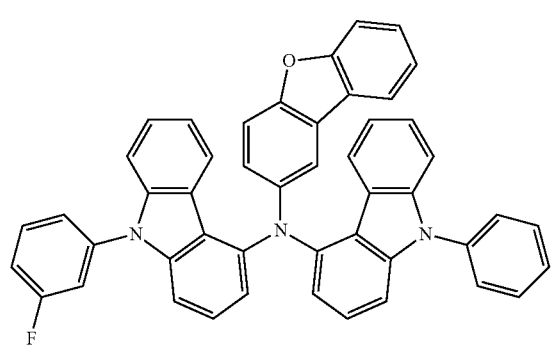
211
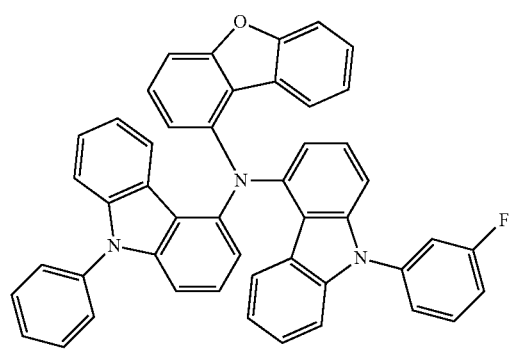
212
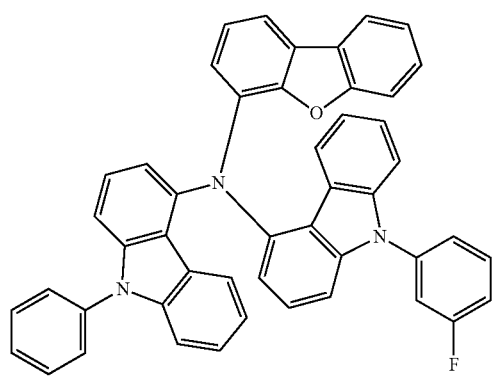
96
-continued
213
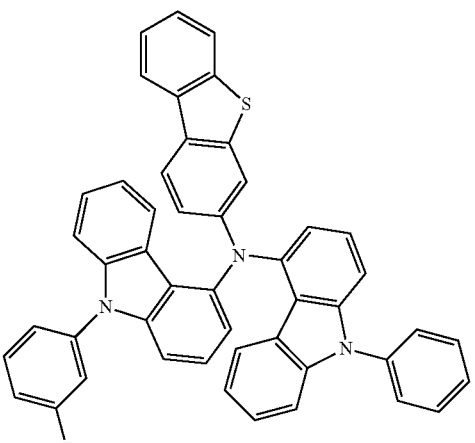
214
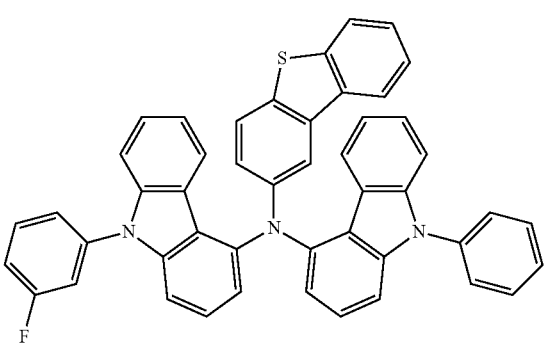
215
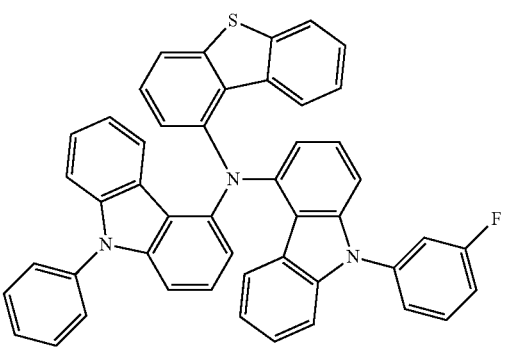
216
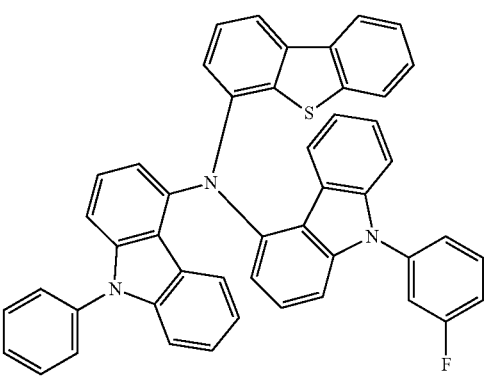

217
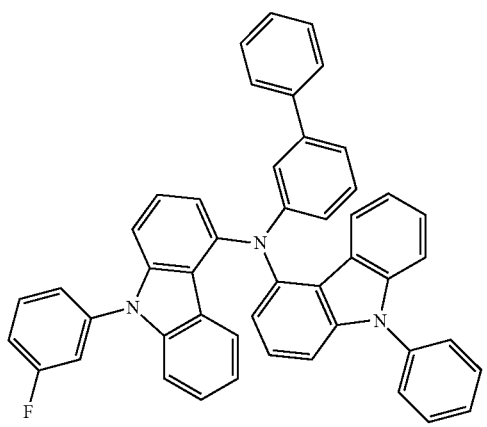
221
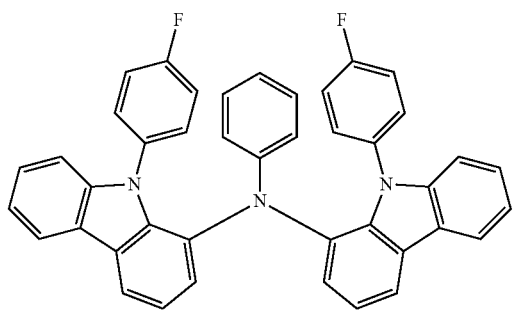
218
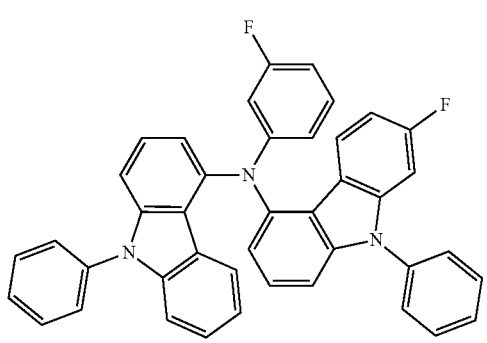
222
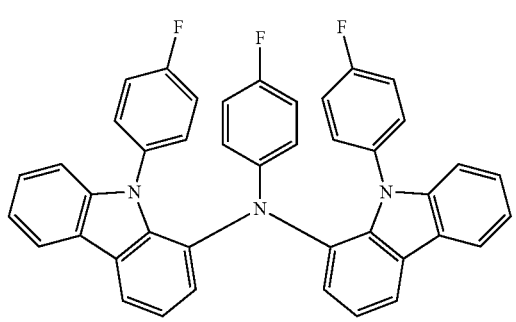
219
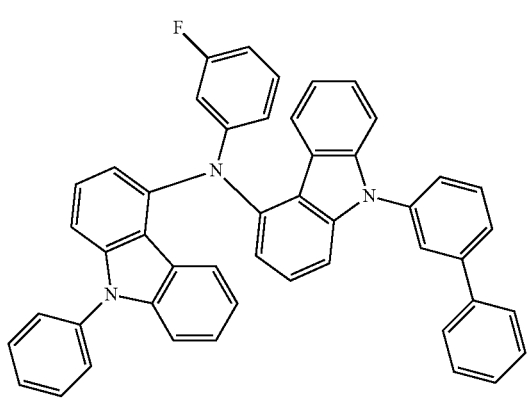
223
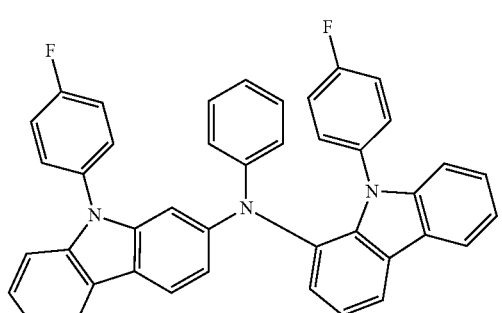
220
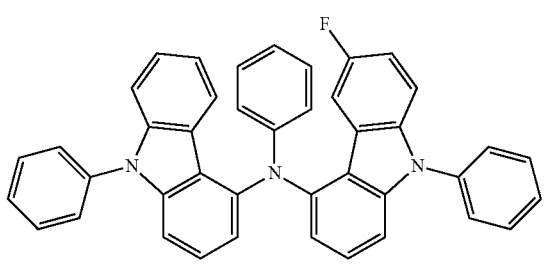
224
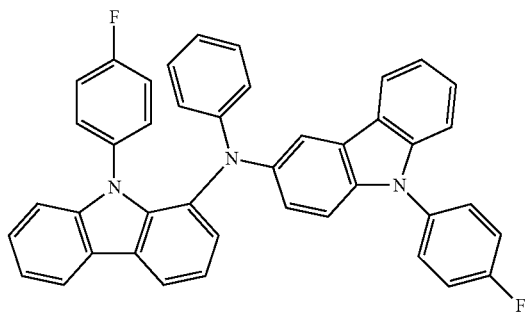

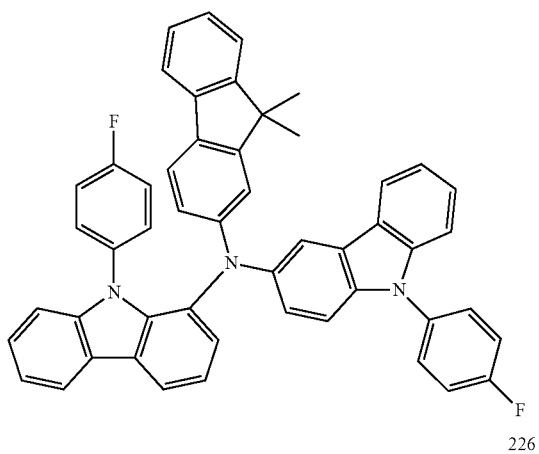
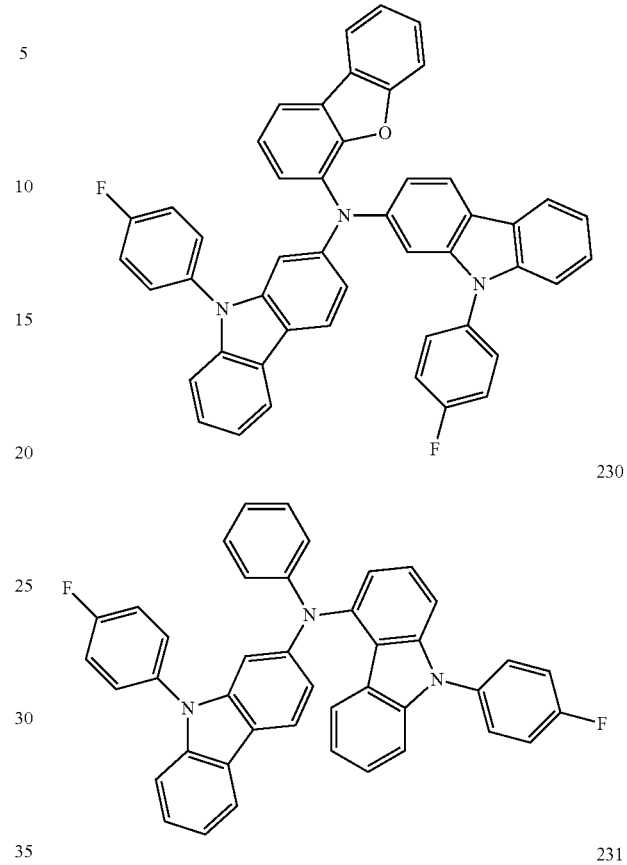
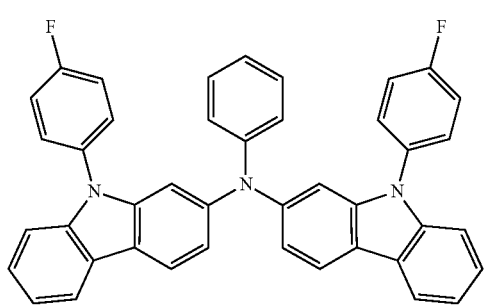
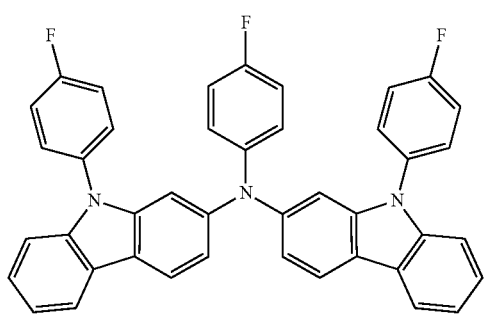
As the amine-based compound represented by one of Formulae 1-1 and 1-2 may include at least one fluorine, when a hole injection layer and/or a hole transport layer of an organic light-emitting device includes the amine-based compound, induced dipole in molecules may arise, which may consequently result in facilitation of acceptance of holes and electrons in an electric field. Thus, a low driving voltage may be achieved when driving the organic light-emitting device. For example, due to the strong electronegativity of the substituent, i.e., a fluorine atom, surplus electrons may be captured, which did not form excitons and are on migration from an emission layer to the hole transport layer. Accordingly, damage to the hole transport layer due to surplus electrons may decrease.

Therefore, an electronic device, e.g., an organic light-emitting device, employing the amine-based compound may have a low driving voltage, high efficiency, and long lifespan.

Methods of synthesizing the amine-based compound represented by one of Formulae 1-1 and 1-2 should be readily apparent to those of ordinary skill in the art by referring to Examples described herein.

At least one of the amine-based compounds represented by one of Formulae 1-1 and 1-2 may be included between a pair of electrodes in an organic light-emitting device. In some embodiments, the amine-based compound may be included in at least one selected from a hole transport region, an electron transport region, and an emission layer. In some embodiments, the amine-based compound represented by one of Formulae 1-1 and 1-2 may be used as a material for forming a capping layer, which is disposed on outer sides of a pair of electrodes in an organic light-emitting device.

Accordingly, there is provided an organic light-emitting device including a first electrode; a second electrode facing the first electrode; and an organic layer disposed between the first electrode and the second electrode, wherein the organic layer includes an emission layer and at least one amine-based compound represented by one of Formulae 1-1 and 1-2.

As used herein, the expression "(for example, the organic layer) including at least one amine-based compound" means that "(the organic layer) including an amine-based represented by one of Formulae 1-1 and 1-2, or at least two different amine-based compounds represented by one of Formulae 1-1 and 1-2".

For example, the organic layer may include only Compound 1 as the amine-based compound. In this embodiment, Compound 1 may be included in the emission layer of the organic light-emitting device. In some embodiments, the organic layer may include Compound 1 and Compound 2 as the amine-based compounds. In this embodiment, Compounds 1 and 2 may be present in the same layer (for example, Compounds 1 and 2 may be both present in an emission layer), or in different layers (for example, Compound 1 may be present in an emission layer, and Compound 2 may be present in an electron transport layer).

In some embodiments, the first electrode may be an anode, the second electrode may be a cathode, and the organic layer may further include a hole transport region disposed between the first electrode and the emission layer and an electron transport region disposed between the emission layer and the second electrode, wherein the hole transport region may include a hole injection layer, a first hole transport layer, a second hole transport layer, an emission auxiliary layer, an electron blocking layer, or a combination thereof, and the electron transport region may include a hole blocking layer, an electron transport layer, an electron injection layer, or a combination thereof.

In some embodiments, the hole transport region may include a multi-layered structure of hole injection layer/first hole transport layer/second hole transport layer, which are sequentially stacked in this stated order from a first electrode, but embodiments are not limited thereto.

In some embodiments, the hole transport region may include the amine-based compound.

In some embodiments, the hole transport region may include a first hole transport layer, wherein the first hole transport layer may include the amine-based compound.

In some embodiments, the hole transport region may include a hole injection layer, a first hole transport layer, and a second hole transport layer, wherein the second hole transport layer may be disposed between the first hole transport layer and an emission layer, the hole injection layer and the first hole transport layer may each include the amine-based compound, and the amine-based compound in the hole injection layer and the amine-based compound in the first hole transport layer may be identical to or different from each other.

In some embodiments, the amine-based compound in the hole injection layer and the amine-based compound in the first hole transport layer may be identical to or different from each other.

In some embodiments, the second hole transport layer may include the amine-based compound, wherein the amine-based compound in the hole injection layer and the amine-based compound in the second hole transport layer may be identical to or different from each other, and the amine-based compound in the first hole transport layer and the amine-based compound in the second hole transport layer may be identical to or different from each other.

In some embodiments, the amine-based compound in the hole injection layer and the amine-based compound in the second hole transport layer may be different from each other, and the amine-based compound in the first hole transport layer and the amine-based compound in the second hole transport layer may be different from each other.

In some embodiments, the hole transport region may include a p-dopant, wherein the p-dopant may have the lowest unoccupied molecular orbital (LUMO) level of −3.5 electron Volts (eV) or less.

For example, the p-dopant may include a quinone derivative.

In some embodiments, the hole transport region may include a hole injection layer, wherein the hole injection layer may include the p-dopant.

The term "organic layer" as used herein refers to a single and/or a plurality of layers disposed between the first electrode and the second electrode in an organic light-emitting device. A material included in the "organic layer" is not limited to an organic material.

Description of FIG. 1

Figure 1:
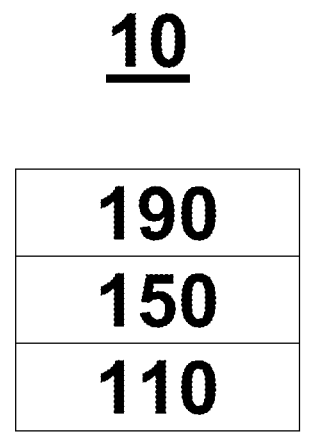

FIG. 1 illustrates a schematic cross-sectional view of an organic light-emitting device 10 according to an embodiment. The organic light-emitting device 10 may include a first electrode 110, an organic layer 150, and a second electrode 190.

Hereinafter, the structure of the organic light-emitting device 10 according to an embodiment and a method of manufacturing an organic light-emitting device according to an embodiment will be described in connection with FIG. 1.

First Electrode 110

Referring to FIG. 1, a substrate may be additionally disposed under the first electrode 110 or over the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering, onto the substrate, a material for forming the first electrode 110. When the first electrode 110 is an anode, the material for forming the first electrode 110 may be selected from materials with a high work function that facilitate hole injection.

The first electrode 110 may be a reflective electrode, a semi-transmissive electrode, or a transmissive electrode. When the first electrode 110 is a transmissive electrode, a material for forming the first electrode 110 may be selected from indium tin oxide (ITO), indium zinc oxide (IZO), tin oxide ($SnO_2$), zinc oxide (ZnO), and any combinations thereof, but embodiments are not limited thereto. In some embodiments, when the first electrode 110 is a semi-transmissive electrode or a reflective electrode, as a material for forming the first electrode 110, at least one of magnesium (Mg), silver (Ag), aluminum (Al), aluminum-lithium (Al—Li), calcium (Ca), magnesium-indium (Mg—In), magnesium-silver (Mg—Ag), and any combination thereof may be used, but embodiments are not limited thereto.

The first electrode 110 may have a single-layered structure, or a multi-layered structure including two or more layers. In some embodiments, the first electrode 110 may have a triple-layered structure of ITO/Ag/ITO, but embodiments are not limited thereto.

Organic Layer 150

The organic layer 150 may be on the first electrode 110. The organic layer 150 may include an emission layer.

The organic layer 150 may further include a hole transport region between the first electrode 110 and the emission layer and an electron transport region between the emission layer and the second electrode 190.

Hole Transport Region in Organic Layer 150

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one selected from a hole injection layer, an emission auxiliary layer, and an electron blocking layer.

For example, the hole transport region may have a single-layered structure including a single layer including a plurality of different materials or a multi-layered structure, e.g., a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/ electron blocking layer structure, wherein layers of each structure are sequentially stacked on the first electrode 110 in each stated order, but embodiments are not limited thereto.

The hole transport region may include an amine-based compound represented by one of Formulae 1-1 and 1-2.

The hole transport region may include, in addition to the amine-based compound represented by one of Formulae 1-1 and 1-2, at least one selected from m-MTDATA, TDATA, 2-TNATA, NPB (NPD), β-NPB, TPD, a spiro-TPD, a spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), (polyaniline)/poly(4-styrenesulfonate) (PANI/PSS), a compound represented by Formula 201, and a compound represented by Formula 202:

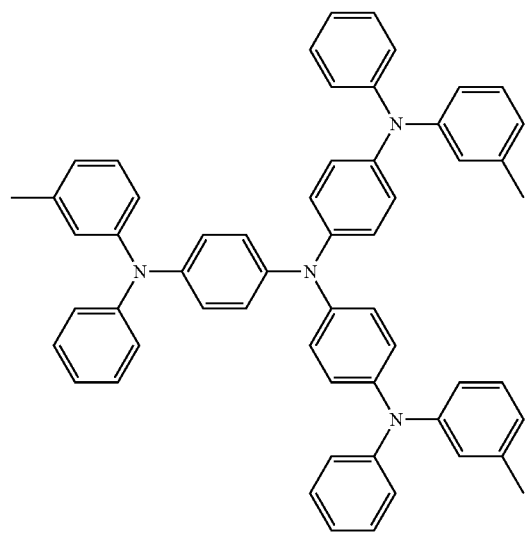

m-MTDATA

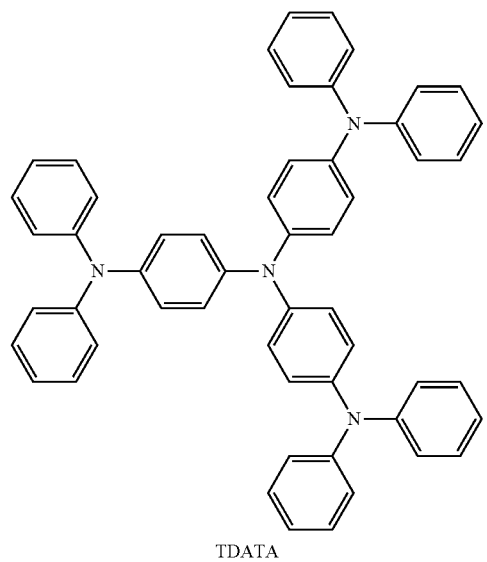

TDATA

-continued
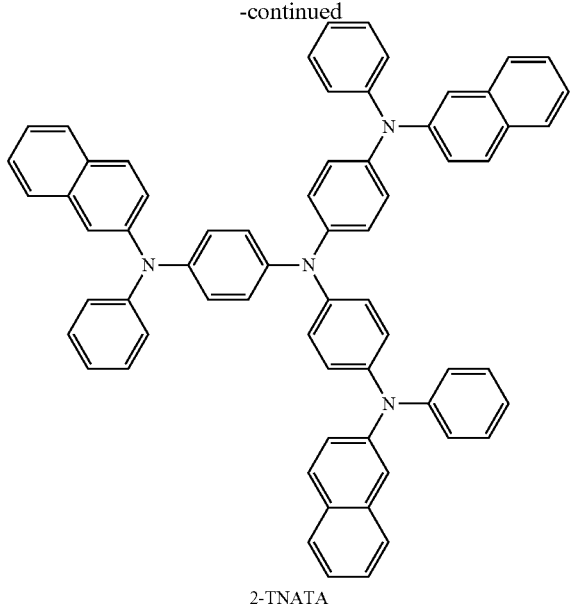
2-TNATA
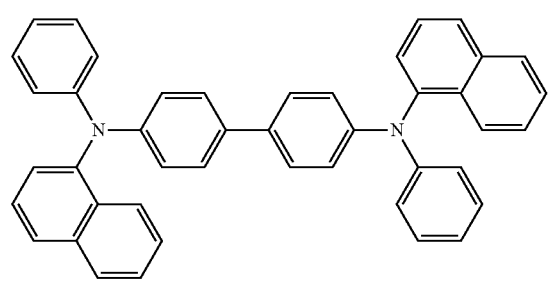
NPB
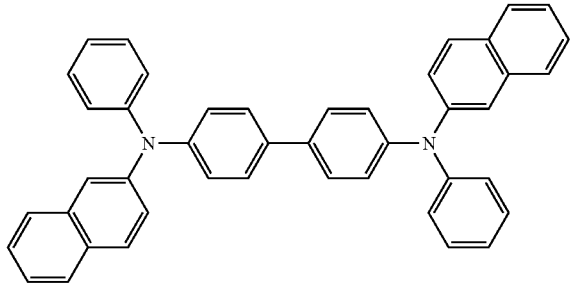
β-NPB
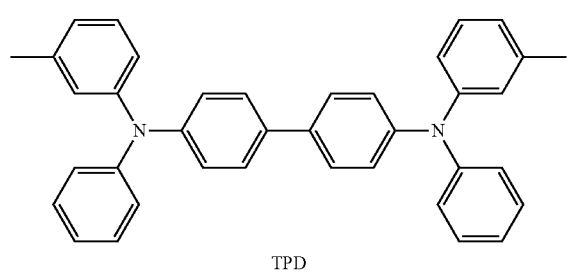
TPD
-continued
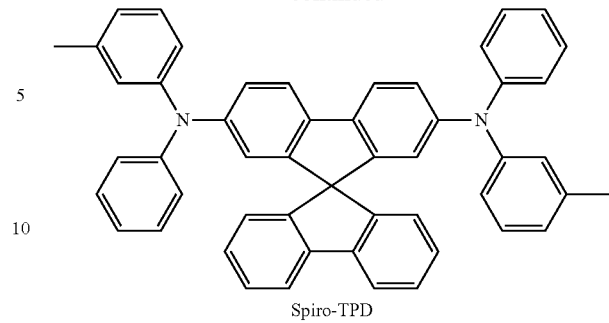
Spiro-TPD
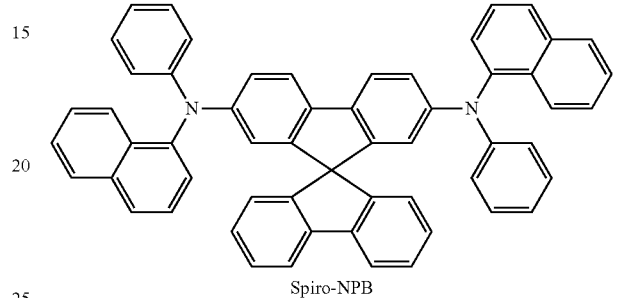
Spiro-NPB
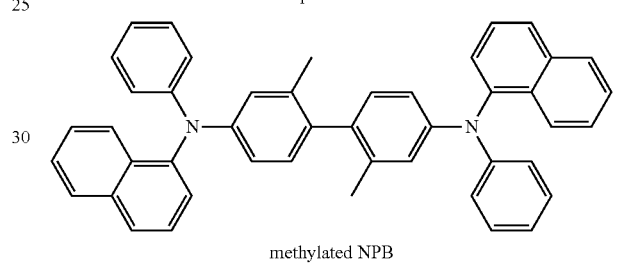
methylated NPB
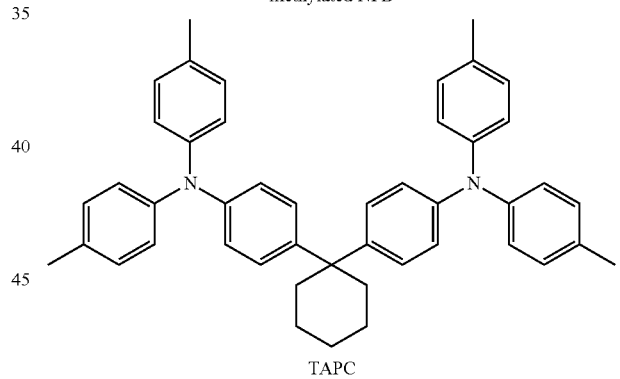
TAPC
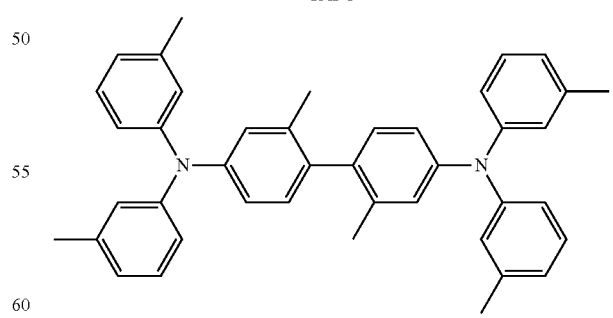
HMTPD
Formula 201
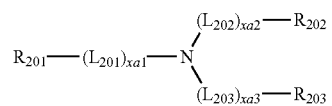

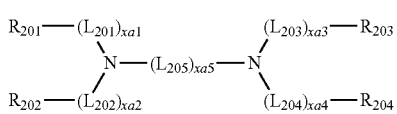

Formula 202 wherein, in Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formula 202, $R_{201}$ and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In one embodiment, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may be the same as those described herein.

In one or more embodiments, in Formula 201, at least one of $R_{201}$ to $R_{203}$ may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments are not limited thereto.

In one or more embodiments, in Formula 202, i) $R_{201}$ may be linked to $R_{202}$ via a single bond, and/or ii) $R_{203}$ may be linked to $R_{204}$ via a single bond.

In one or more embodiments, in Formula 202, at least one of $R_{201}$ to $R_{204}$ may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments are not limited thereto.

The compound represented by Formula 201 may be represented by Formula 201A:

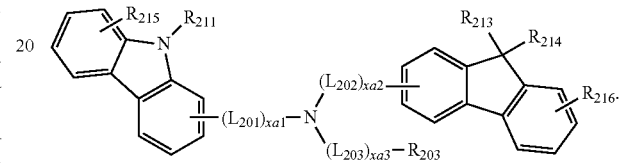

Formula 201A

In some embodiments, the compound represented by Formula 201 may be represented by Formula 201A(1), but embodiments are not limited thereto:

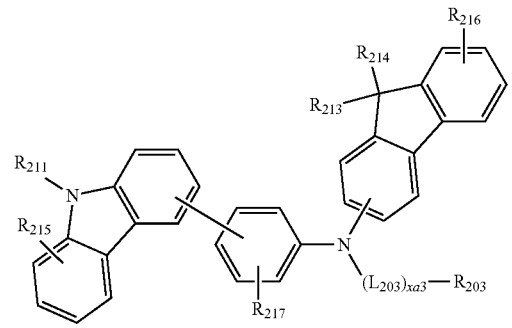

Formula 201A(1)

In some embodiments, the compound represented by Formula 201 may be represented by Formula 201A-1, but embodiments are not limited thereto:

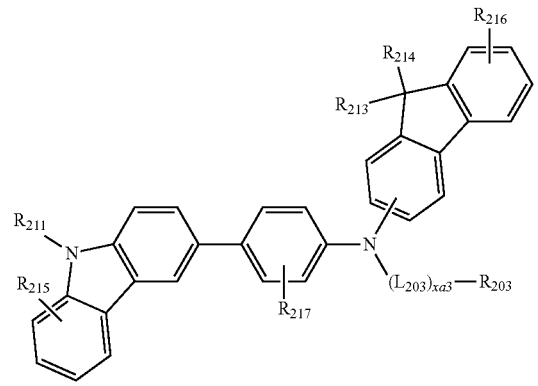

Formula 201A-1

In some embodiments, the compound represented by Formula 202 may be represented by Formula 202A:

Formula 202A

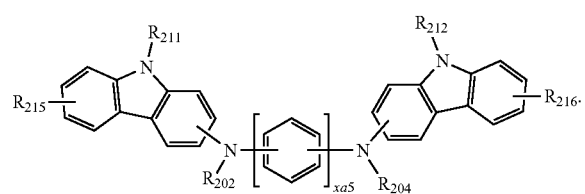

In some embodiments, the compound represented by Formula 202 may be represented by Formula 202A-1:

Formula 202A-1

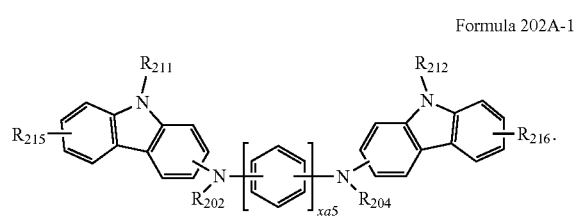

In Formulae 201A, 201A(1), 201A-1, 202A, and 202A-1, $L_{201}$ to $L_{203}$, xa1 to xa3, xa5, and $R_{202}$ to $R_{204}$ may each be the same as those described herein, descriptions for $R_{211}$ and $R_{212}$ may each be the same as those for $R_{203}$ described herein, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments are not limited thereto:

HT1

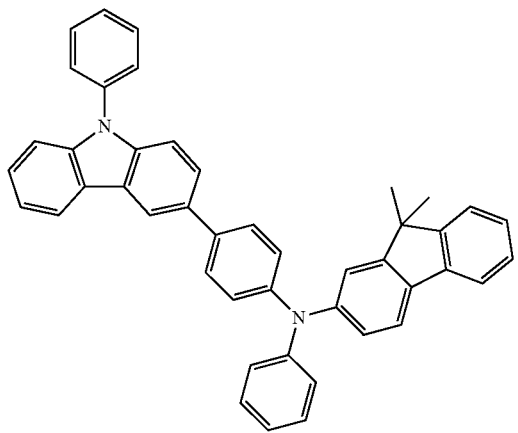

HT2

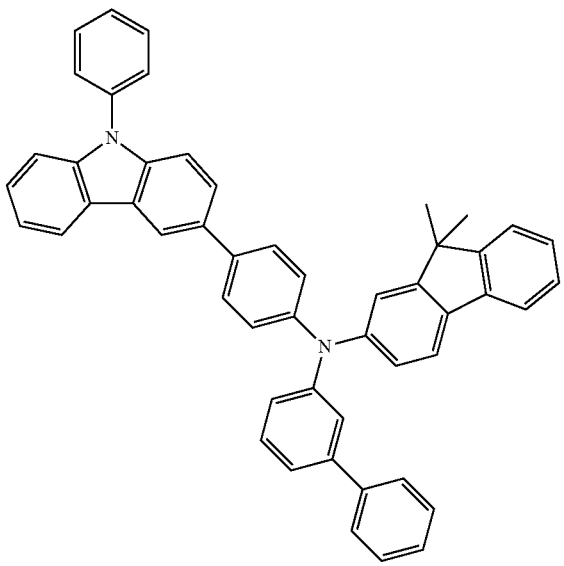

-continued
HT3
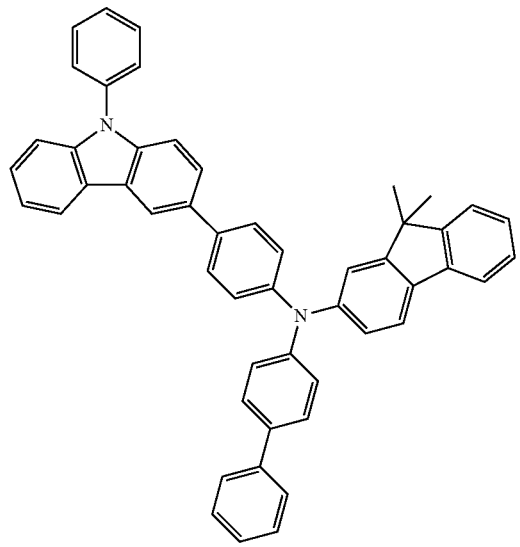
HT4
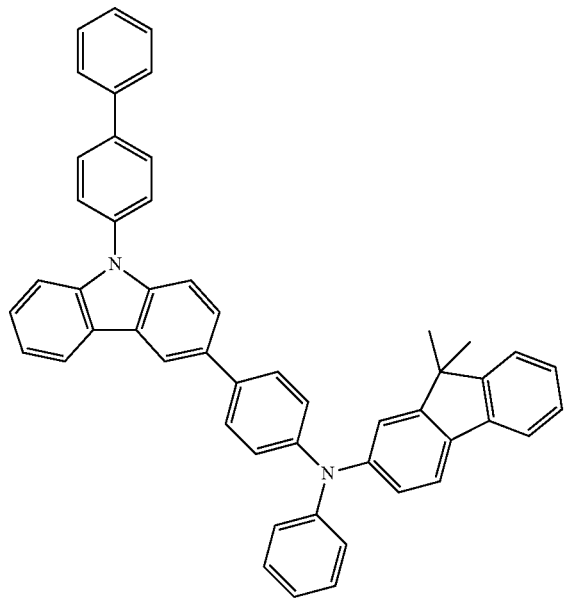
HT5
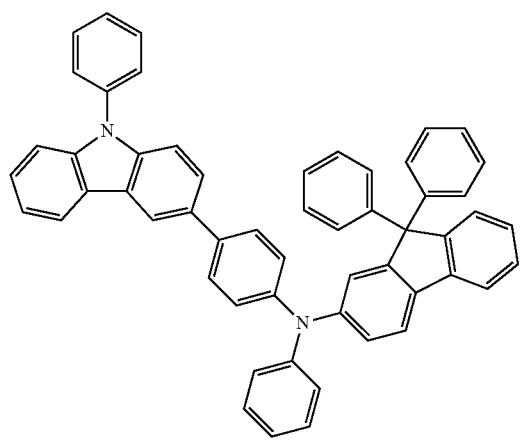
HT6
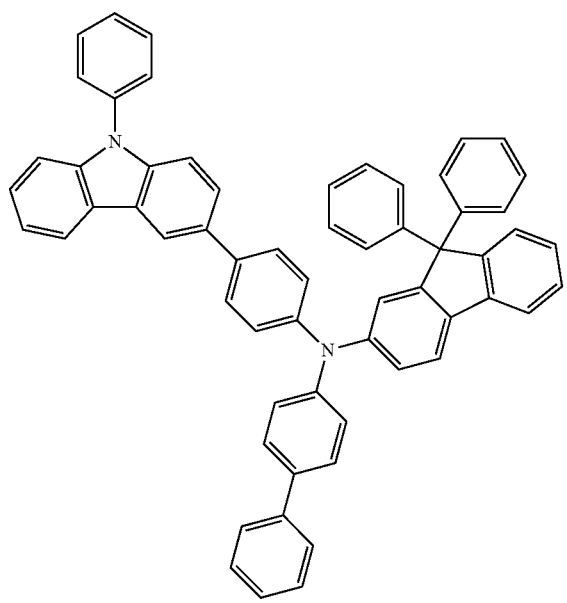

-continued
HT7
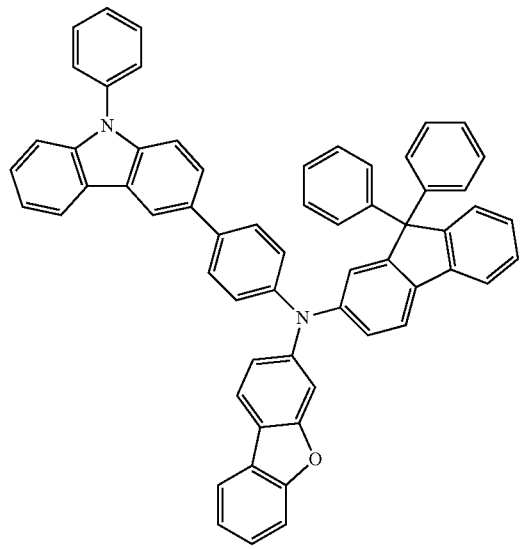
HT8
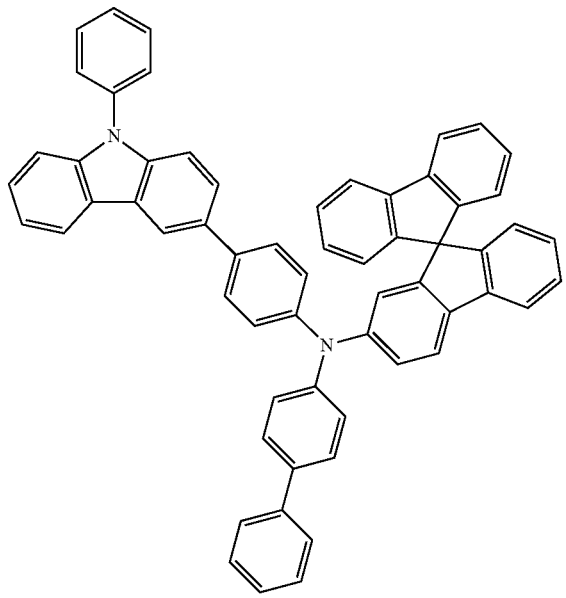
HT9
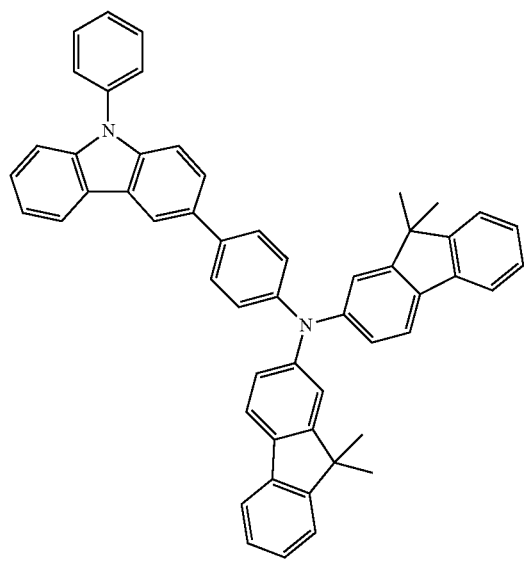
HT10
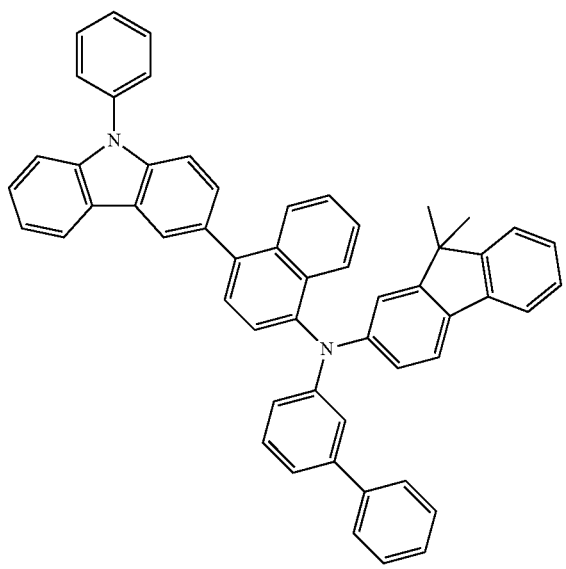

-continued
HT11
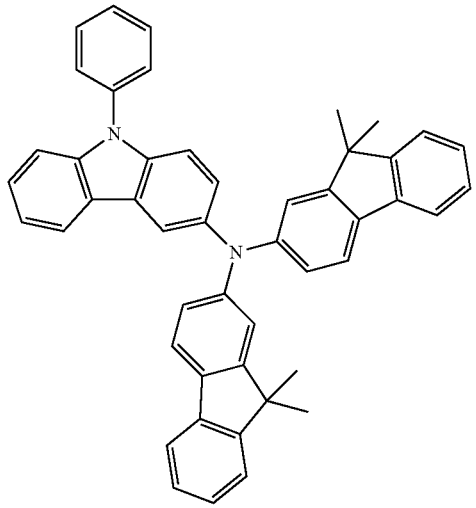
HT12
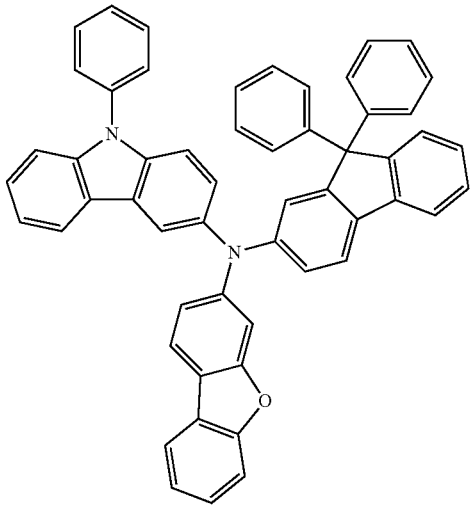
HT13
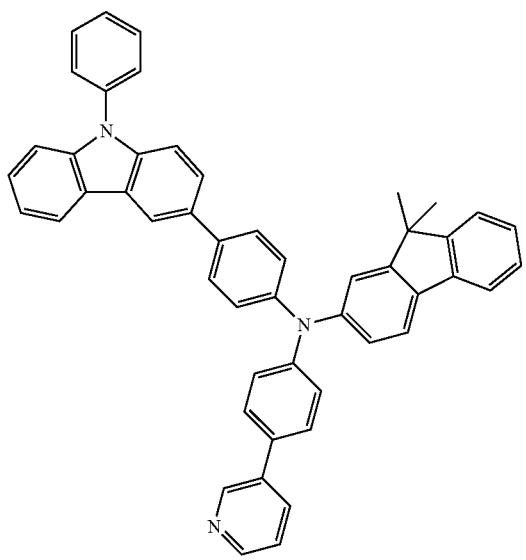
HT14
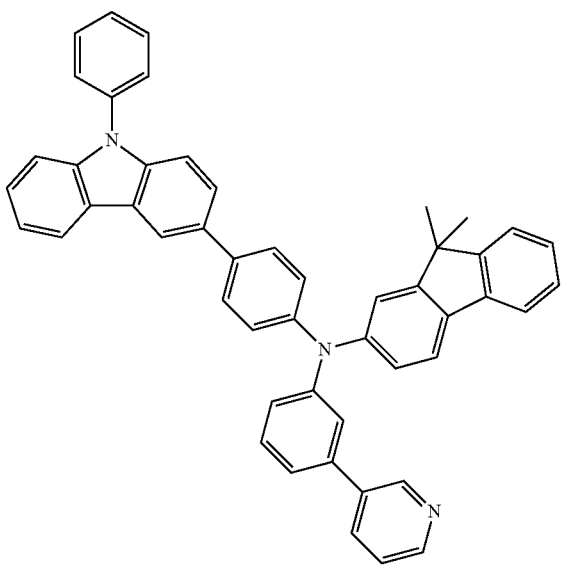
HT15
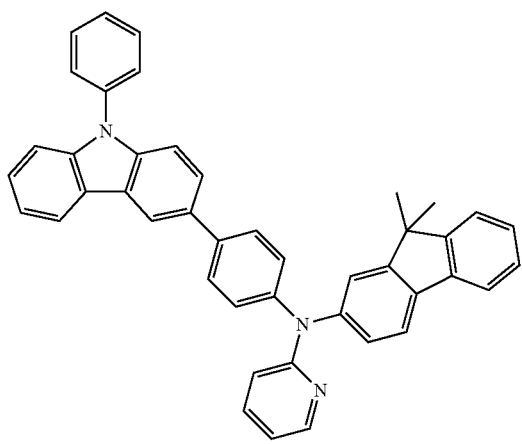
HT16
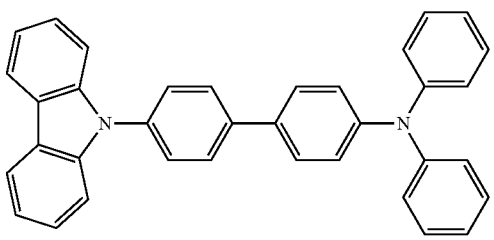

-continued
HT17
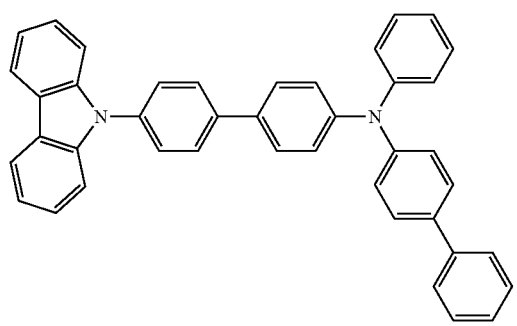
HT18
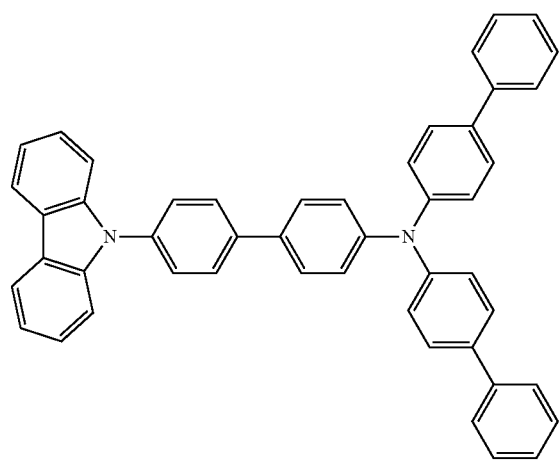
HT19
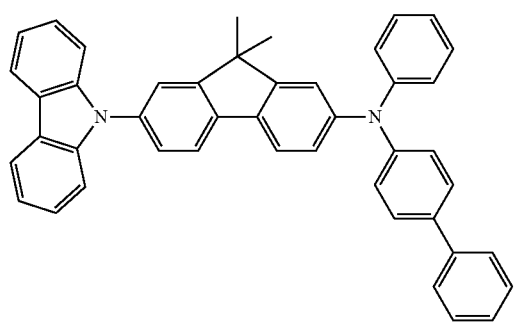
HT20
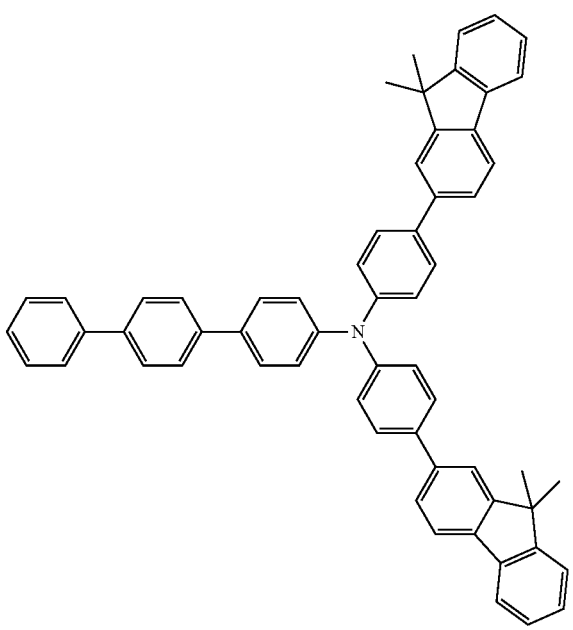

-continued
HT21
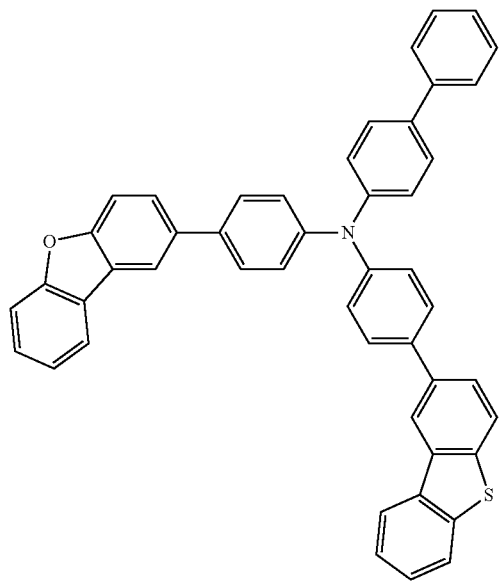
HT22
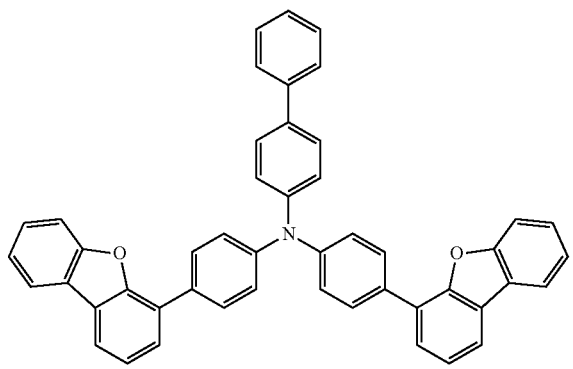
HT23
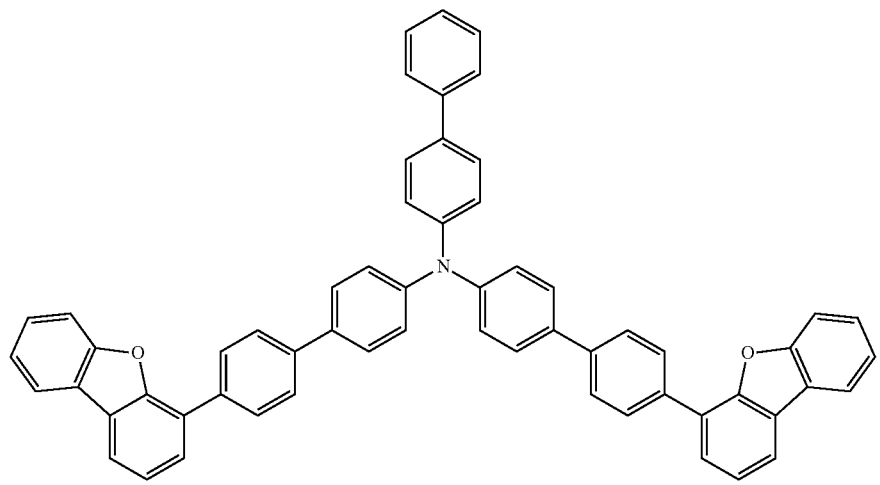

-continued
HT24
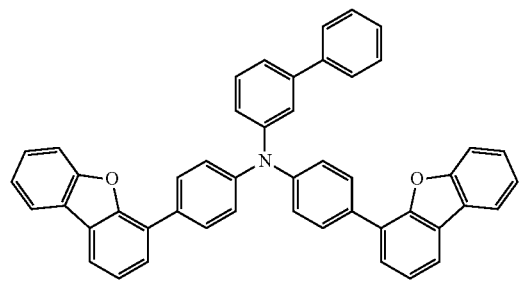
HT25
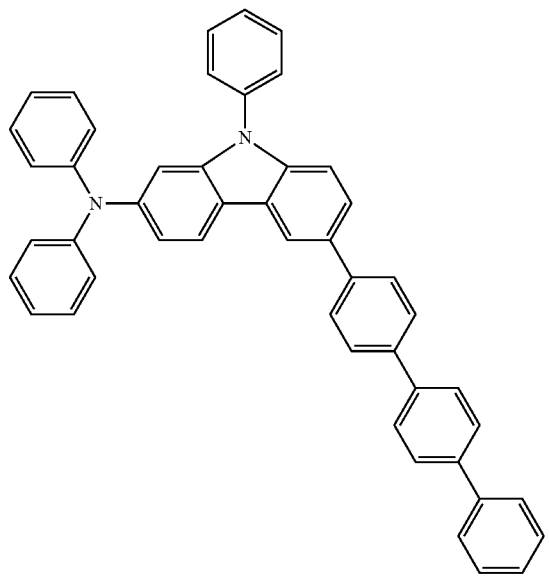
HT26
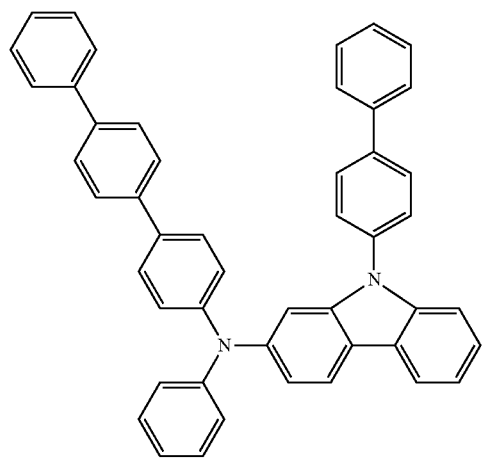
HT27
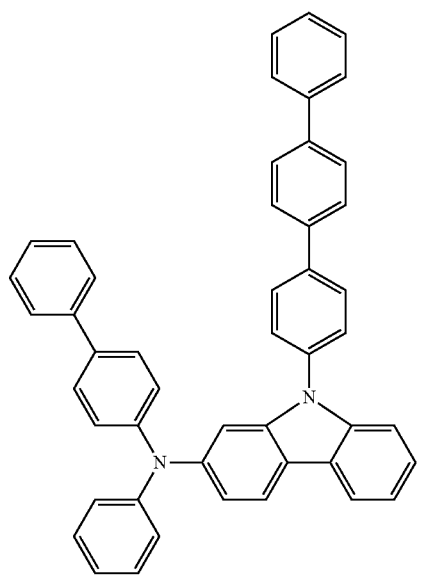
HT28
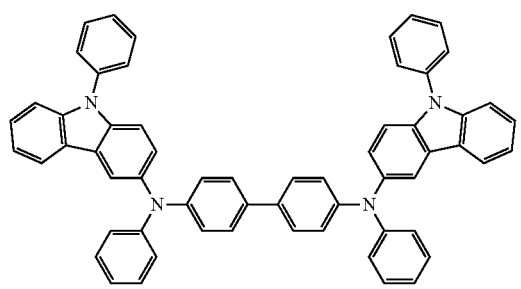
HT29
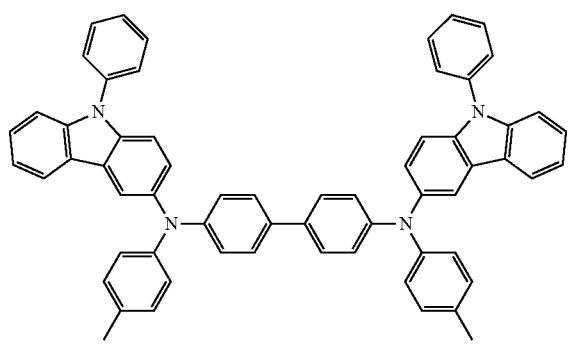

-continued
HT30
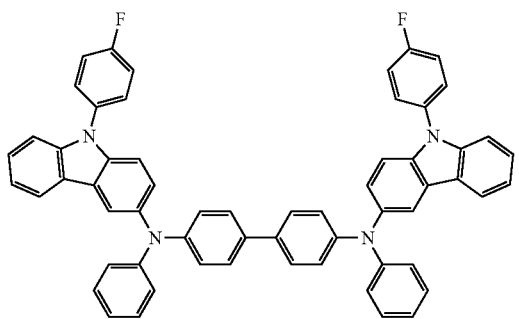
HT31
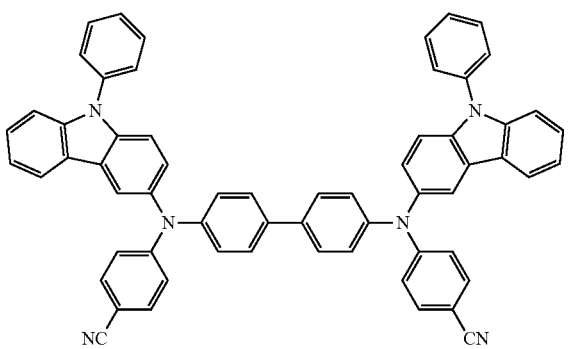
HT32
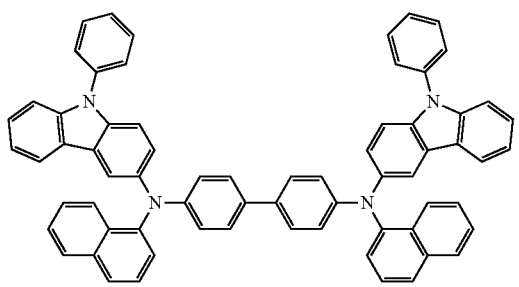
HT33
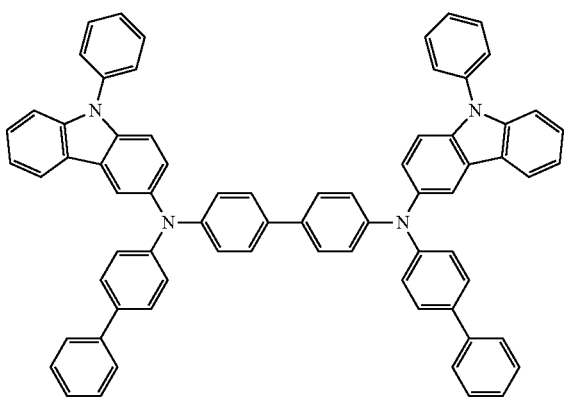
HT34
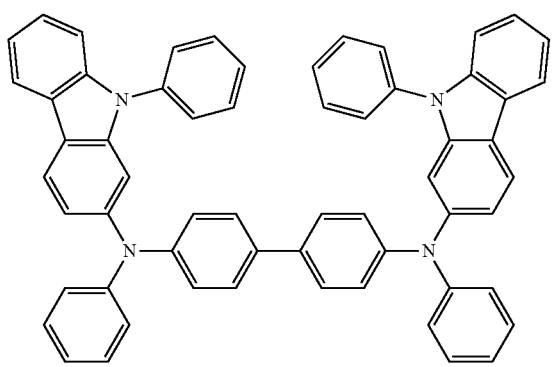
HT35
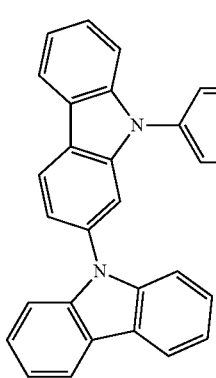

-continued

HT36

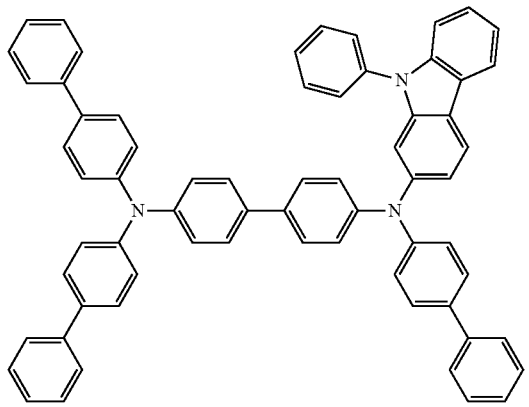

HT37

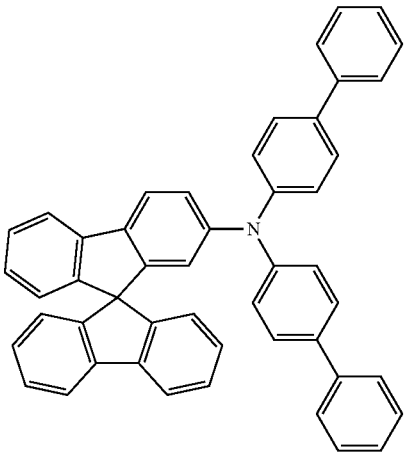

HT38

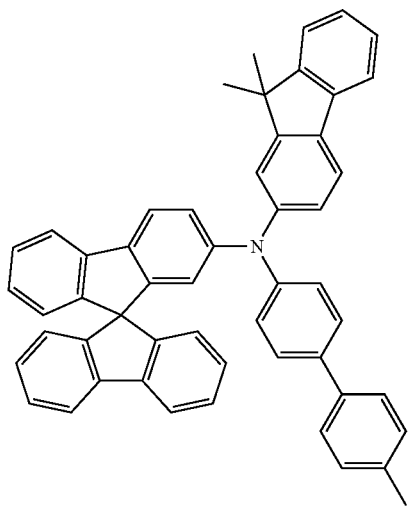

HT39

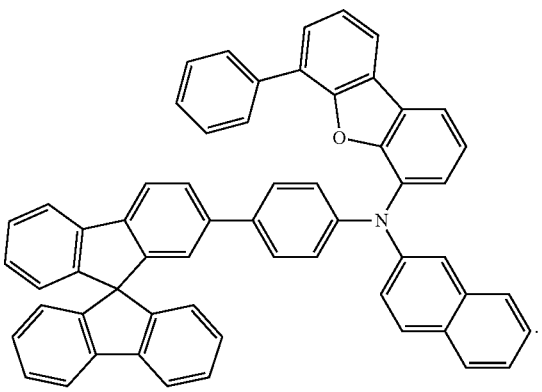

The thickness of the hole transport region may be in a range of about 100 (Angstroms) Å to about 10,000 Å, and in some embodiments, about 100 Å to about 1,000 Å. When the hole transport region includes at least one selected from a hole injection layer and a hole transport layer, the thickness of the hole injection layer may be in a range of about 100 Å to about 9,000 Å, and in some embodiments, about 100 Å to about 1,000 Å, and the thickness of the hole transport layer may be in a range of about 50 Å to about 2,000 Å, and in some embodiments, about 100 Å to about 1,500 Å. When the thicknesses of the hole transport region, the hole injection layer, and the hole transport layer are within any of these ranges, excellent hole transport characteristics may be obtained without a substantial increase in driving voltage.

The emission auxiliary layer may increase light emission efficiency by compensating for an optical resonance distance according to the wavelength of light emitted by an emission layer. The electron blocking layer may reduce or eliminate the flow of electrons from an electron transport region. The emission auxiliary layer and the electron blocking layer may include the aforementioned materials.

p-Dopant

The hole transport region may include a charge generating material as well as the aforementioned materials, to improve conductive properties of the hole transport region. The charge generating material may be substantially homogeneously or non-homogeneously dispersed in the hole transport region.

The charge generating material may include, for example, a p-dopant.

In some embodiments, the LUMO of the p-dopant may be about −3.5 eV or less.

The p-dopant may include at least one selected from a quinone derivative, a metal oxide, and a cyano group-containing compound, but embodiments are not limited thereto.

In some embodiments, the p-dopant may include at least one selected from a quinone derivative, such as tetracyanoquinodimethane (TCNQ) or 2,3,5,6-tetrafluoro-7,7,8,8-tetracyanoquinodimethane (F4-TCNQ);

a metal oxide, such as tungsten oxide or molybdenum oxide;

1,4,5,8,9,11-hexaazatriphenylene-hexacarbonitrile (HAT-CN); and a compound represented by Formula 221, but embodiments are not limited thereto:

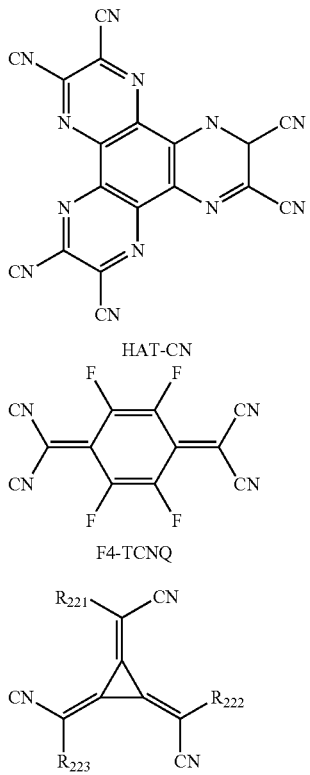

HAT-CN

F4-TCNQ

Formula 221 wherein, in Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one selected from $R_{221}$ to $R_{223}$ may include at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer in Organic Layer 150

When the organic light-emitting device 10 is a full color organic light-emitting device, the emission layer may be patterned into a red emission layer, a green emission layer, or a blue emission layer, according to a sub-pixel. In one or more embodiments, the emission layer may have a stacked structure. The stacked structure may include two or more layers selected from a red emission layer, a green emission layer, and a blue emission layer. The two or more layers may be in direct contact with each other. In some embodiments, the two or more layers may be separated from each other. In one or more embodiments, the emission layer may include two or more materials. The two or more materials may include a red light-emitting material, a green light-emitting material, or a blue light-emitting material. The two or more materials may be mixed with each other in a single layer. The two or more materials mixed with each other in the single layer may emit white light.

The emission layer may include a host and a dopant. The dopant may include at least one of a fluorescent dopant and a phosphorescent dopant.

The amount of the dopant in the emission layer may be, in general, in a range of about 0.01 parts to about 15 parts by weight based on 100 parts by weight of the host, but embodiments are not limited thereto.

The thickness of the emission layer may be in a range of about 100 Å to about 1,000 Å, and in some embodiments, about 200 Å to about 600 Å. When the thickness of the emission layer is within any of these ranges, improved luminescence characteristics may be obtained without a substantial increase in driving voltage.

Host in Emission Layer

The host may include a compound represented by Formula 301:

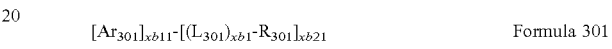

Formula 301 wherein, in Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), and xb21 may be an integer from 1 to 5, wherein $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

In some embodiments, $Ar_{301}$ in Formula 301 may be selected from a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

When xb11 in Formula 301 is 2 or greater, at least two $Ar_{301}$ groups may be linked via a single bond.

In one or more embodiments, the compound represented by Formula 301 may be represented by Formula 301-1 or 301-2:

$X_{301}$ may be O, S, or N-[($L_{304}$)$_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$, and $Q_{31}$ to $Q_{33}$ may each independently be the same as those described herein, descriptions for $L_{302}$ to $L_{304}$ may each independently be the same as those for $L_{301}$ described herein, descriptions for xb2 to xb4 may each independently be the same as those for xb1 described herein, and descriptions for $R_{302}$ to $R_{304}$ may each independently be the same as those for $R_{301}$ described herein.

In some embodiments, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofura-

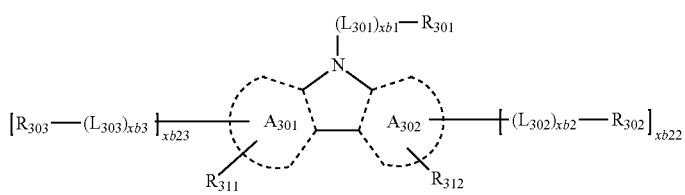

Formula 301-1

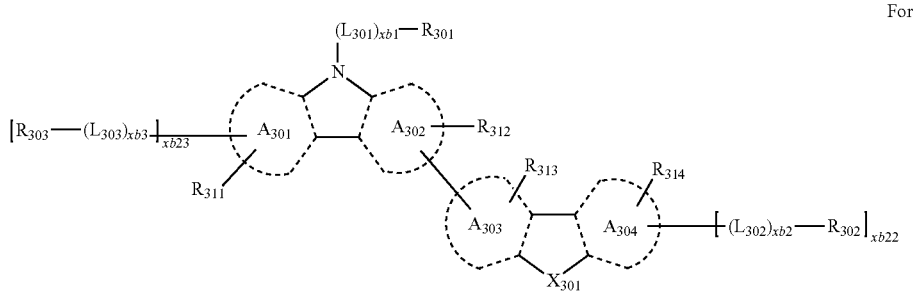

Formula 301-2 wherein, in Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonapthothiophene group, and a dinaphthothiophene group, nylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be the same as those described herein.

In some embodiments, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be the same as those described herein.

In some embodiments, the host may include an alkaline earth metal complex. For example, the host may include a beryllium (Be) complex, e.g., Compound H55, a magnesium (Mg) complex, or a zinc (Zn) complex.

The host may include at least one selected from 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments are not limited thereto:

H1
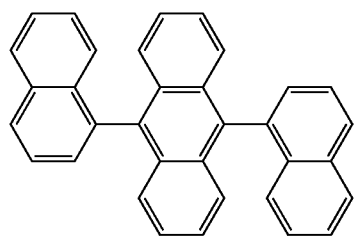

H2
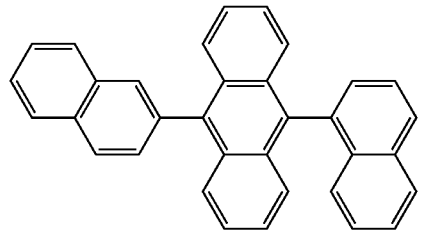

H3
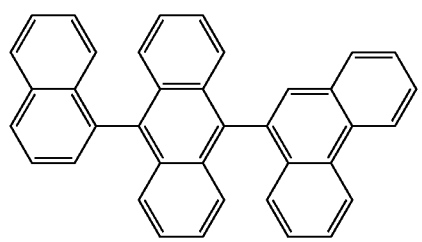

H4
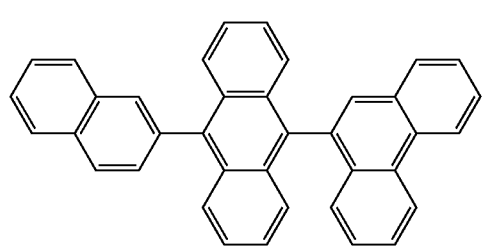

H5
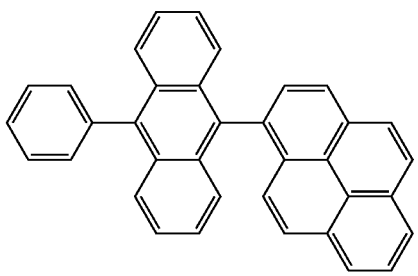

H6
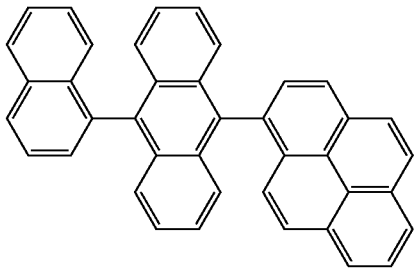

H7
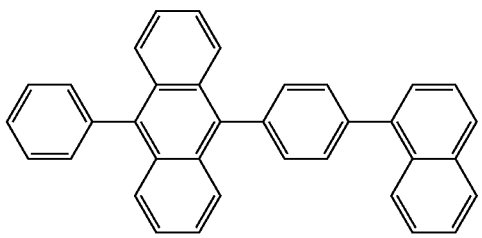

H8
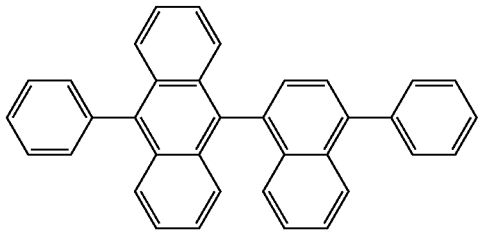

H9
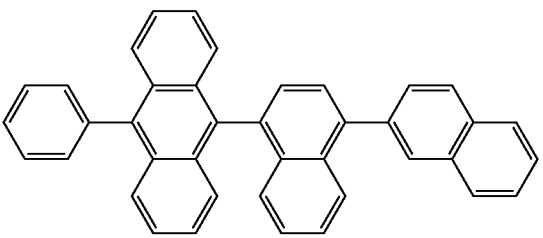

H10
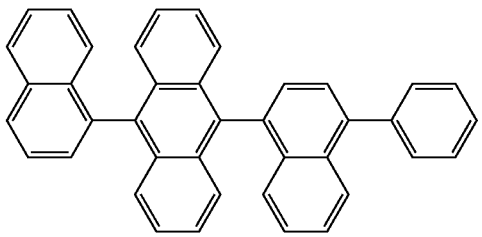

-continued
H11
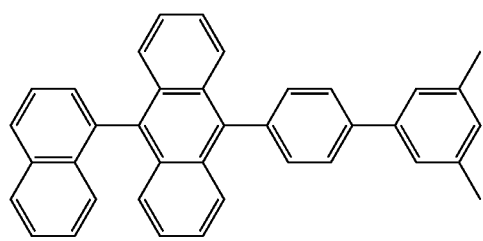
H12
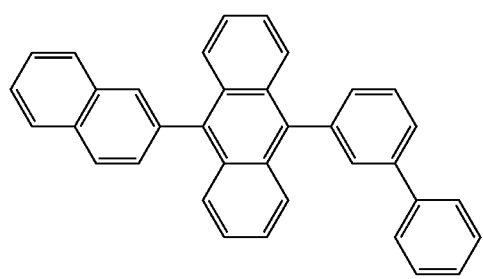
H13
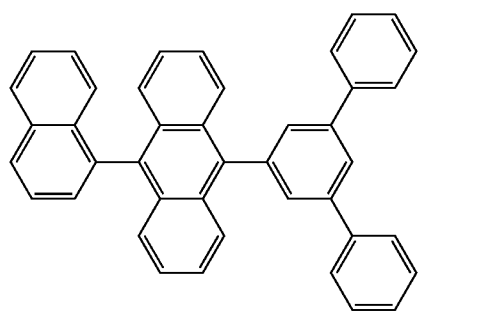
H14
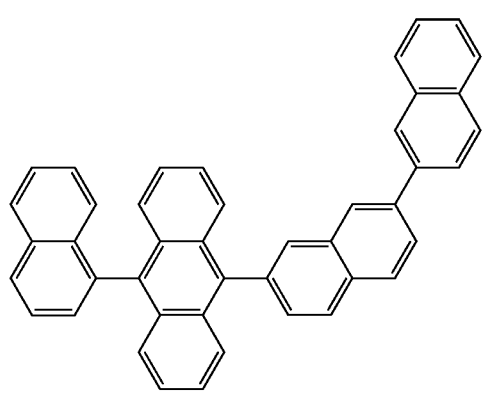
H15
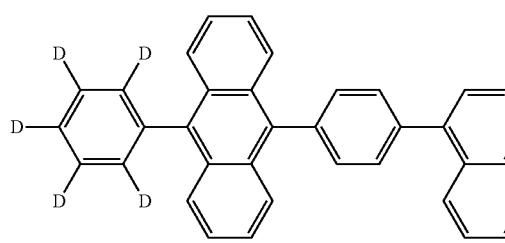
H16
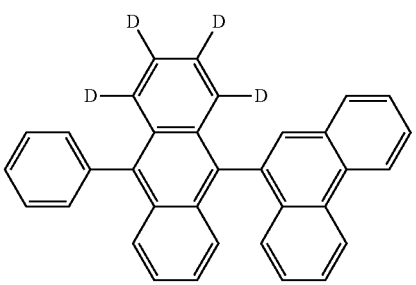
H17
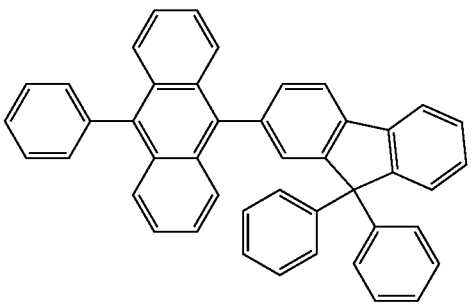
H18
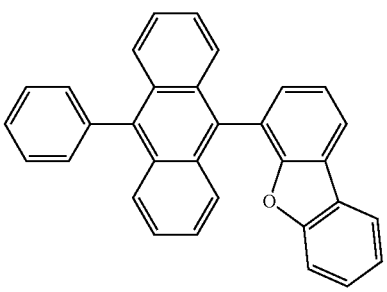
H19
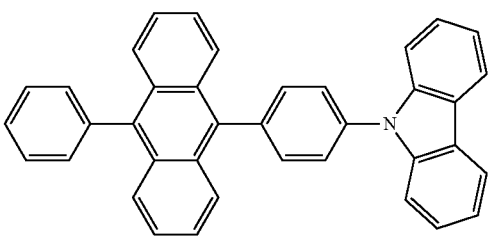
H20
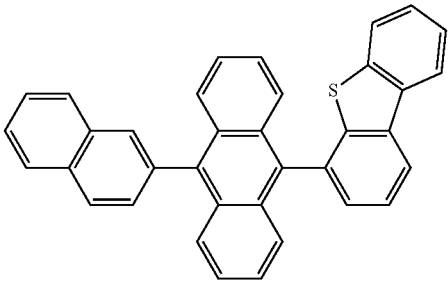

-continued
H21
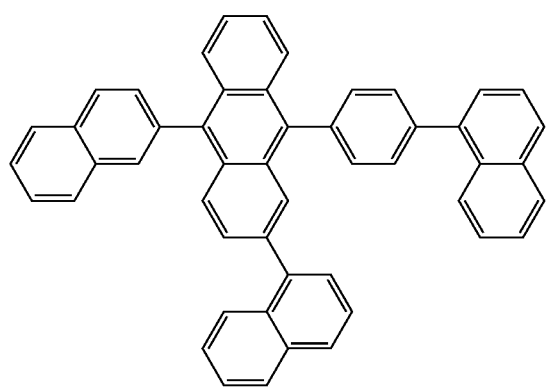
H22
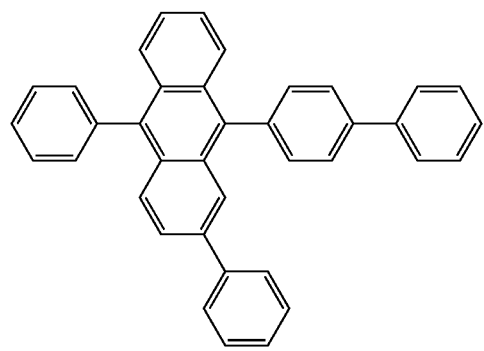
H23
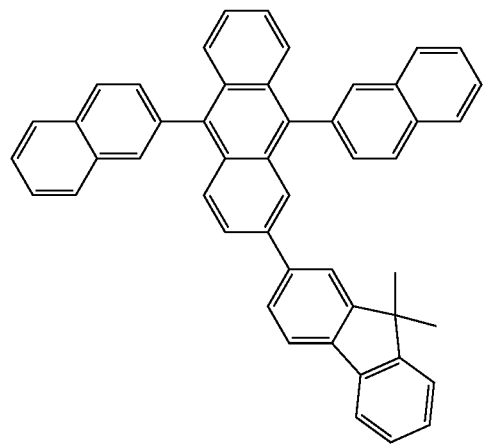
H24
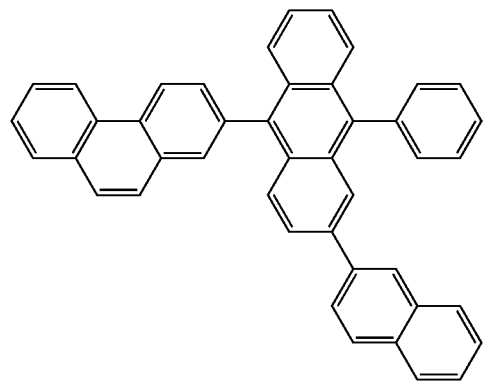
-continued
H25
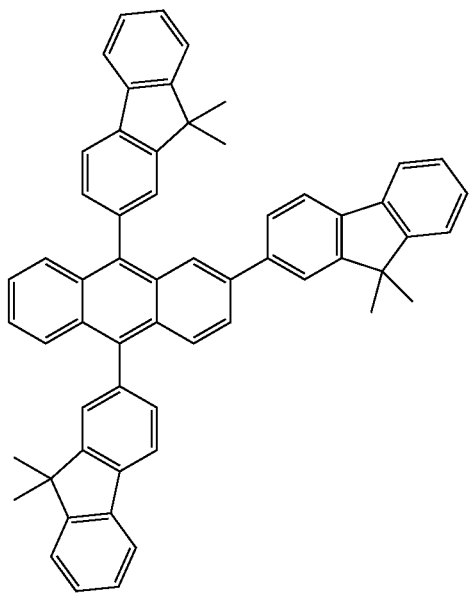
H26
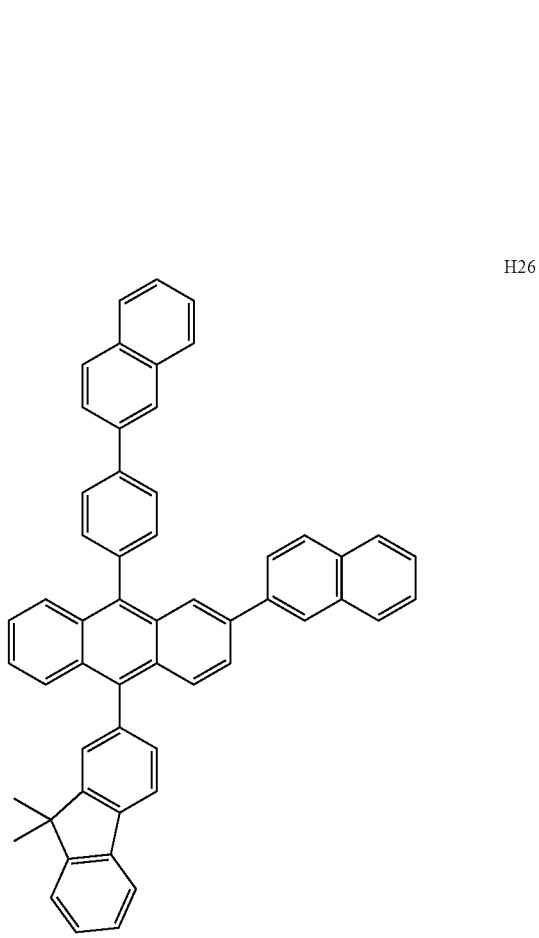

-continued
H27
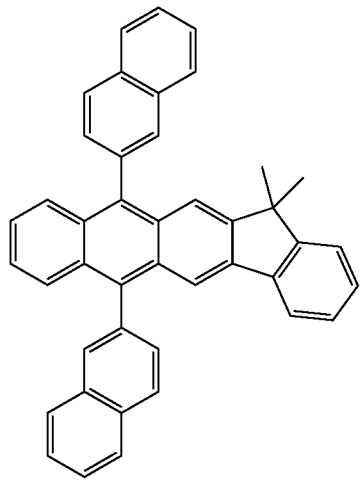
H28
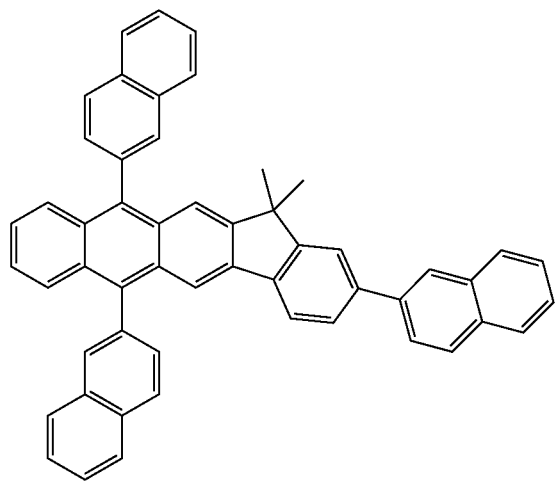
H29
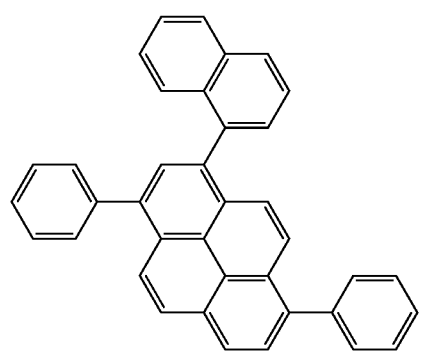
-continued
H30
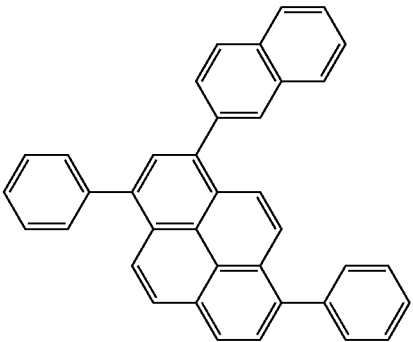
H31
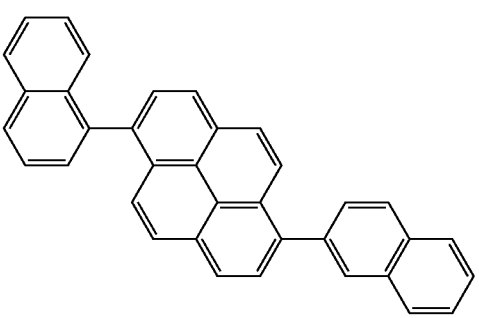
H32
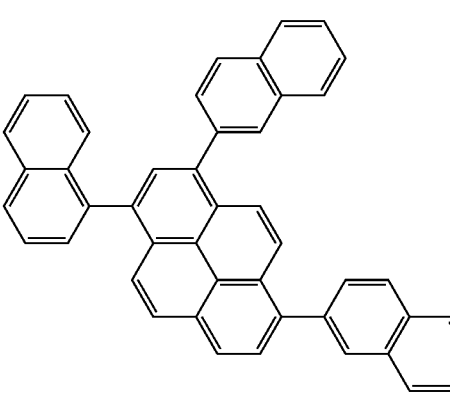
H33
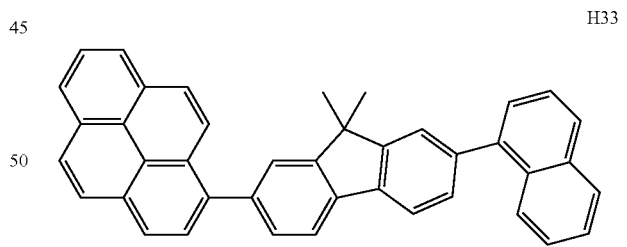
H34
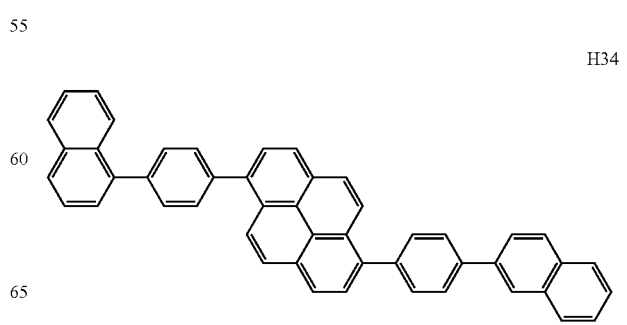

H35
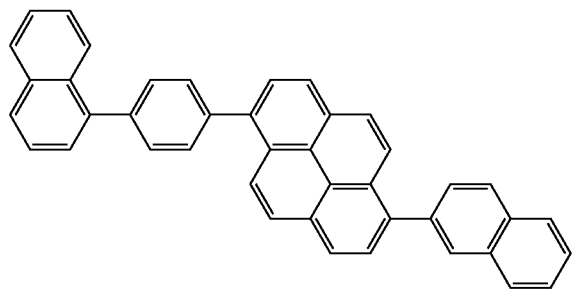
H36
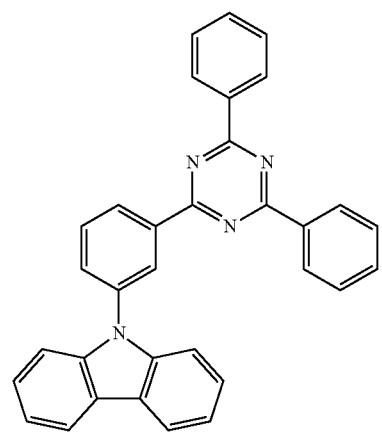
H37
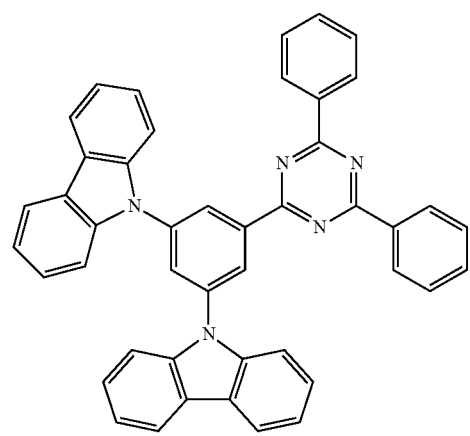
H38
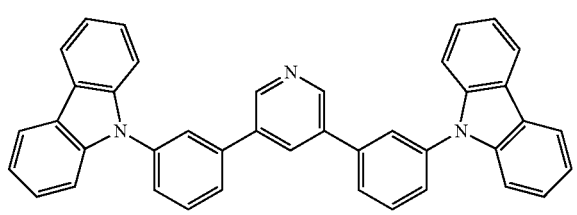
H39
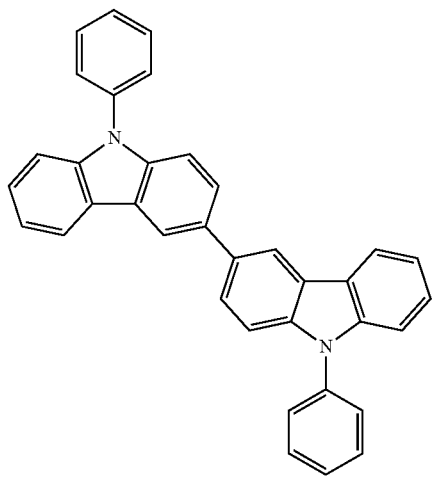
H40
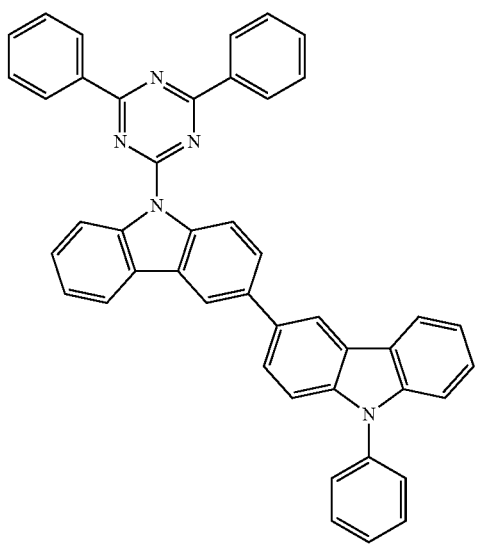
H41
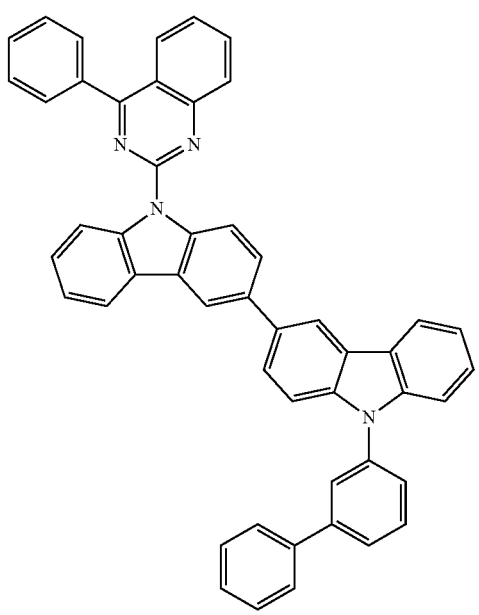

H42 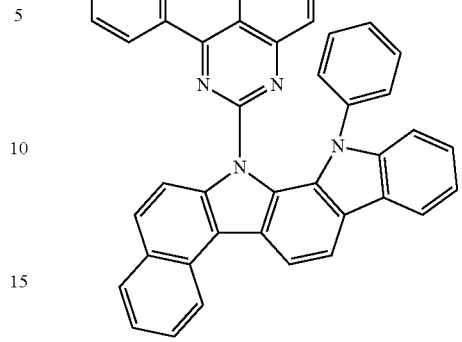
H43 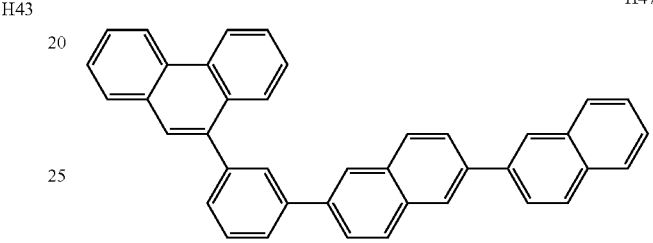
H44 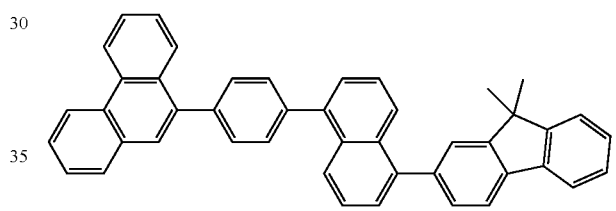
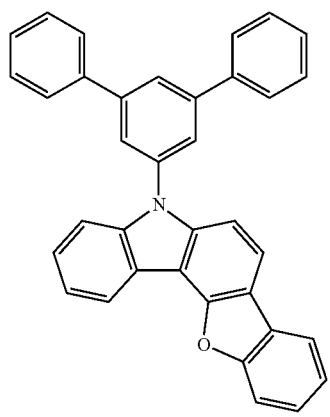
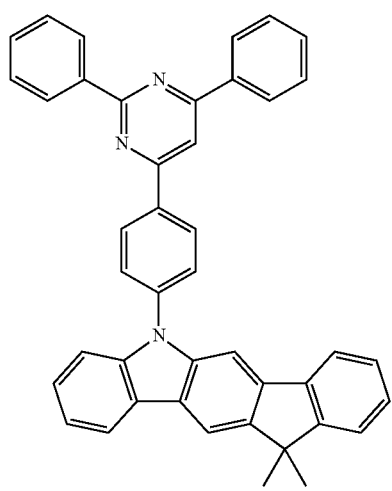
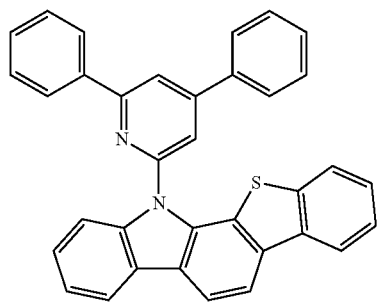
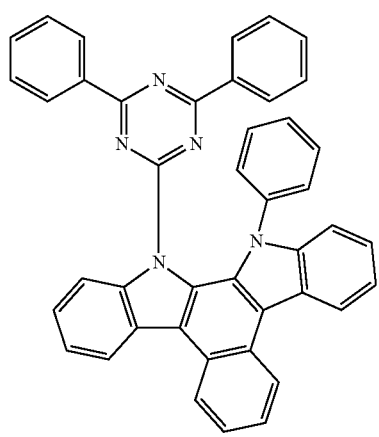
H46 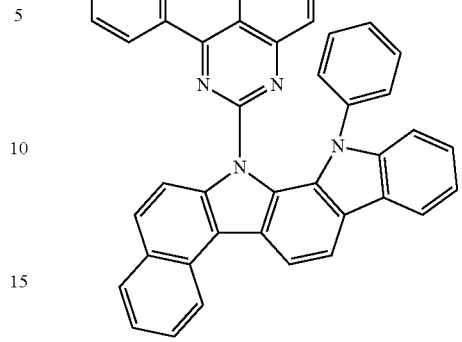
H47 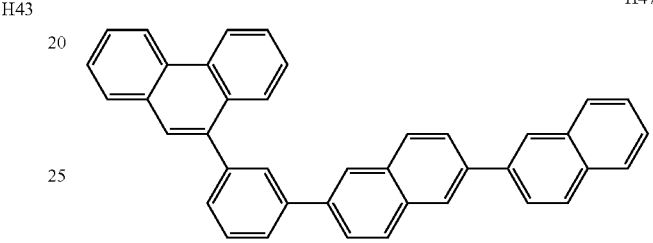
H48 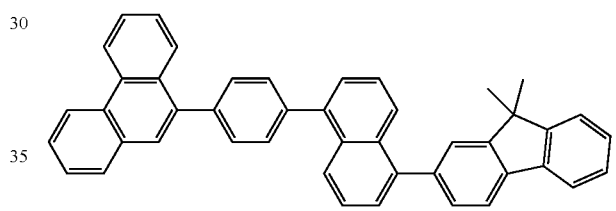
H49 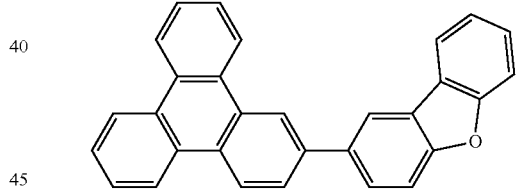
H50 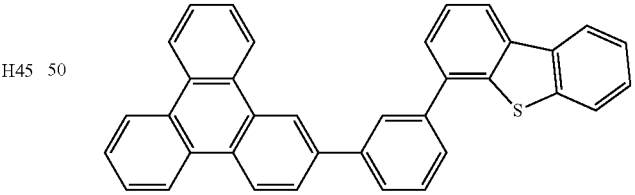
H51 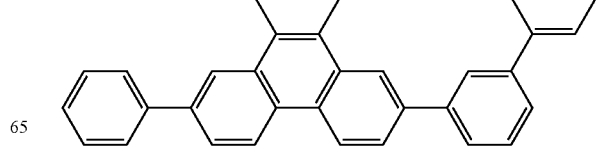

H52 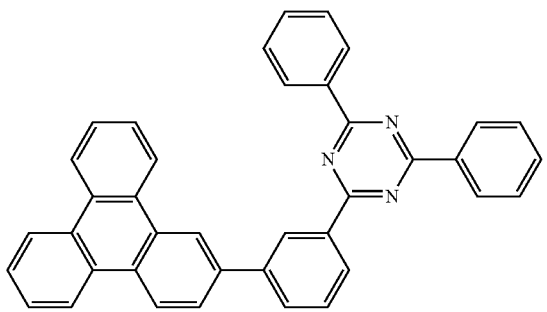

H53 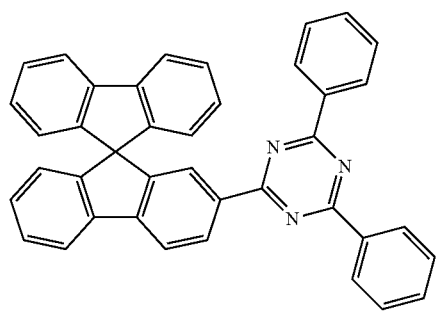

H54 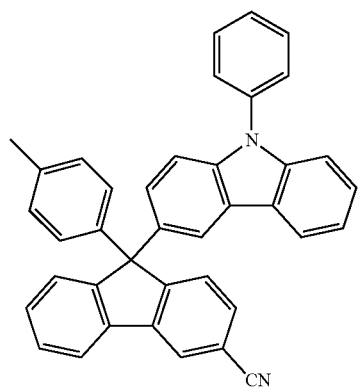

H55 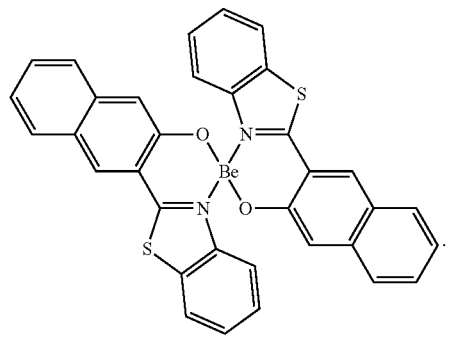

Phosphorescent Dopant Included in Emission Layer of Organic Layer 150

The phosphorescent dopant may include an organometallic complex represented by Formula 401:

$$M(L_{401})_{xc1}(L_{402})_{xc2} \quad \text{Formula 401}$$

Formula 402 wherein, in Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, xc1 may be an integer from 1, 2, and 3; when xc1 is two or greater, at least two $L_{401}$ groups may be identical to or different from each other, $L_{402}$ may be an organic ligand, xc2 may be an integer from 0 to 4; when xc2 is 2 or greater, at least two $L_{402}$ groups may be identical to or different from each other, $X_{401}$ to $X_{404}$ may each independently be nitrogen (N) or carbon (C), $X_{401}$ and $X_{403}$ may be linked via a single bond or a double bond, $X_{402}$ and $X_{404}$ may be linked via a single bond or a double bond, $A_{401}$ and $A_{402}$ may each independently be a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)—*', *—C($Q_{411}$)($Q_{412}$)—*', *—C($Q_{411}$)=C($Q_{412}$)—*', *—C($Q_{411}$)'*', or *=C($Q_{411}$)=*', wherein $Q_{411}$ and $Q_{412}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{401}$)($Q_{402}$)($Q_{403}$), —N($Q_{401}$) ($Q_{402}$), —B($Q_{401}$)($Q_{402}$), —C(=O)($Q_{401}$), —S(=O)$_2$ ($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and

* and *' in Formula 402 each indicate a binding site to M in Formula 401.

In some embodiments, in Formula 402, $A_{401}$ and $A_{402}$ may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen.

In one or more embodiments, in Formula 402, $R_{401}$ and $R_{402}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantyl group, a norbornanyl group, and a norbornenyl group;

a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments are not limited thereto.

In one or more embodiments, when xc1 in Formula 401 is 2 or greater, two $A_{401}$ groups of at least two $L_{401}$ groups may optionally be linked to each other via $X_{407}$ as a linking group; or two $A_{402}$ groups may optionally be linked to each other via $X_{408}$ as a linking group (see Compounds PD1 to PD4 and PD7). $X_{407}$ and $X_{408}$ may each independently be selected from a single bond, *—S—*', *—C(=O)—*', *—N($Q_{413}$)-*', *—C($Q_{413}$)($Q_{414}$)-*', and *—C($Q_{413}$)=C($Q_{414}$)-*', wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, but embodiments are not limited thereto.

$L_{402}$ in Formula 401 may be any suitable monovalent, divalent, or trivalent organic ligand available in the art. For example, $L_{402}$ may be selected from halogen, diketone (e.g., acetylacetonate), a carboxylic acid (e.g., picolinate), —C(=O), isonitrile, —CN, and phosphorus (e.g., phosphine or phosphite), but embodiments are not limited thereto.

In some embodiments, the phosphorescent dopant may include, for example, at least one selected from Compounds PD1 to PD25, but embodiments are not limited thereto:

PD1

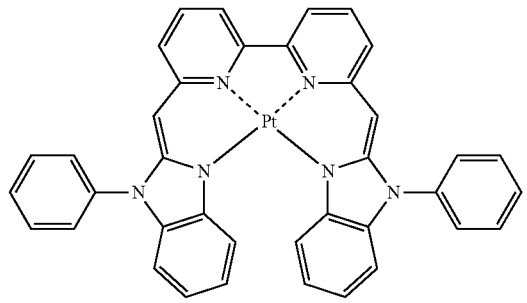

PD2

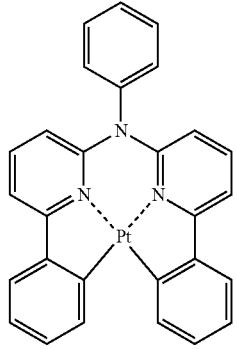

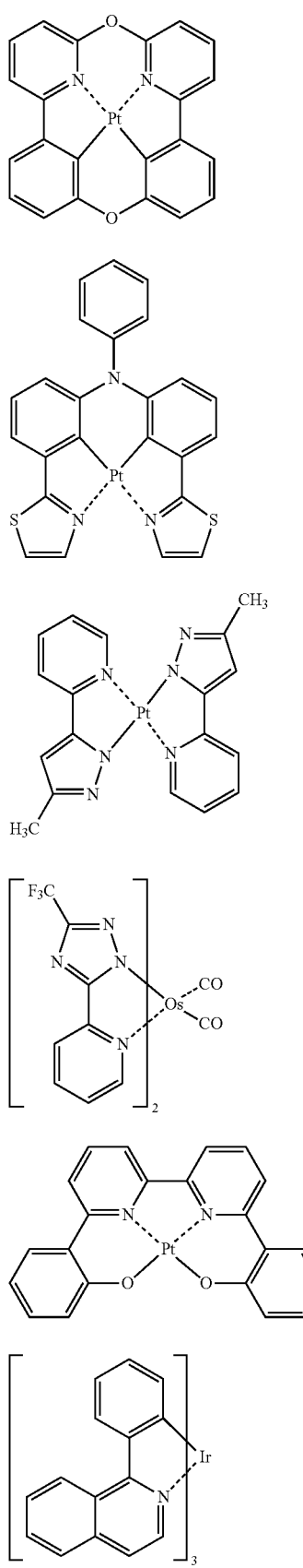

-continued
PD14
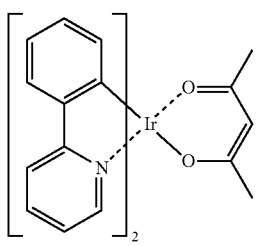
PD15
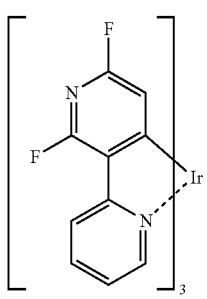
PD16
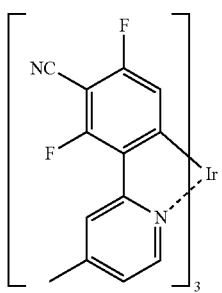
PD17
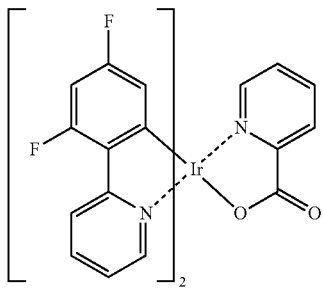
PD18
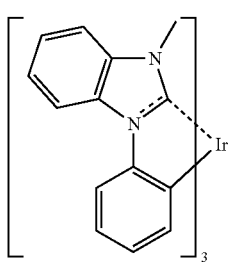
-continued
PD19
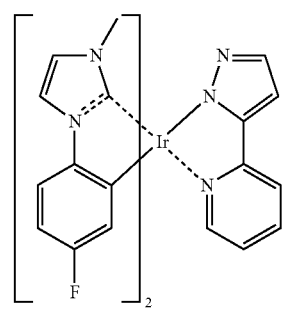
PD20
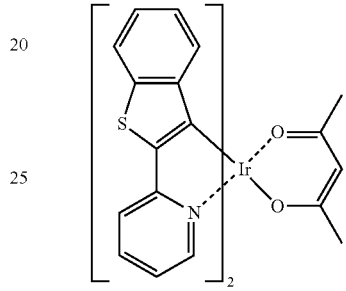
PD21
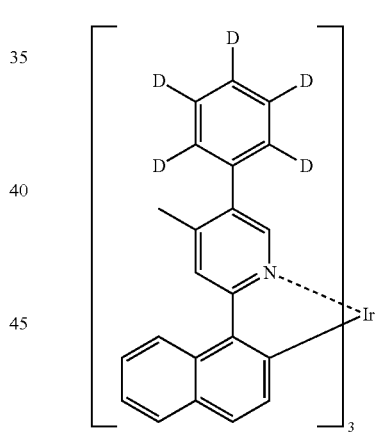
PD22
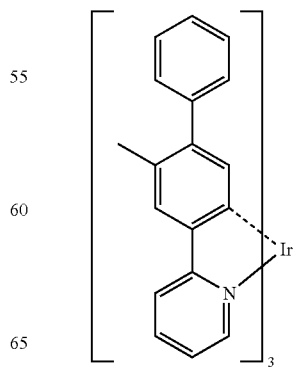

-continued

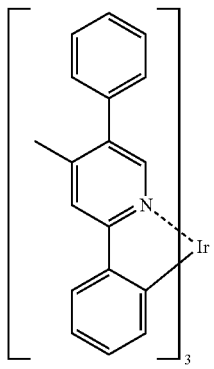
PD23

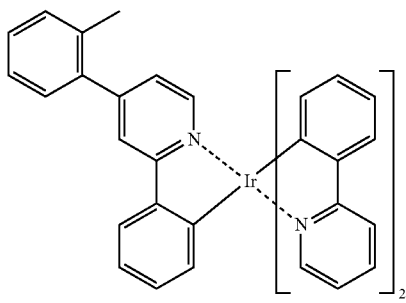
PD24

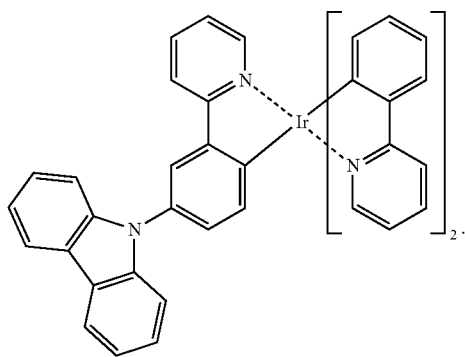
PD25

Fluorescent Dopant in Emission Layer

The fluorescent dopant may include an arylamine compound or a styrylamine compound.

In some embodiments, the fluorescent dopant may include a compound represented by Formula 501:

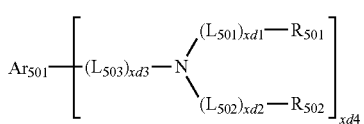
Formula 501 wherein, in Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer from 1 to 6.

In some embodiments, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, in Formula 501, $L_{501}$ to $L_{503}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, in Formula 501, $R_{501}$ and $R_{502}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments are not limited thereto.

In some embodiments, the fluorescent dopant may be selected from Compounds FD1 to FD22:

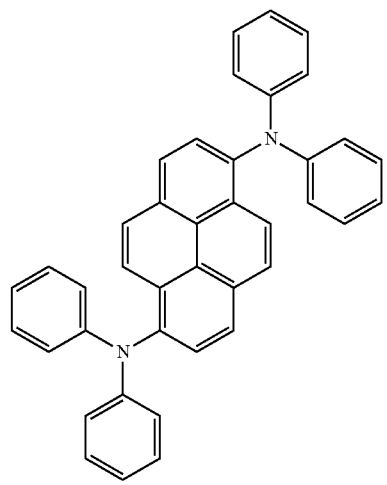

FD1

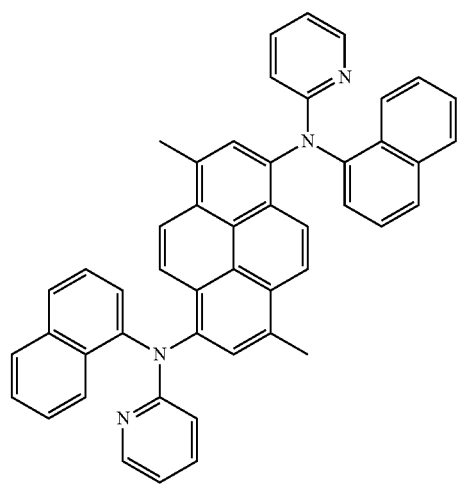

FD2

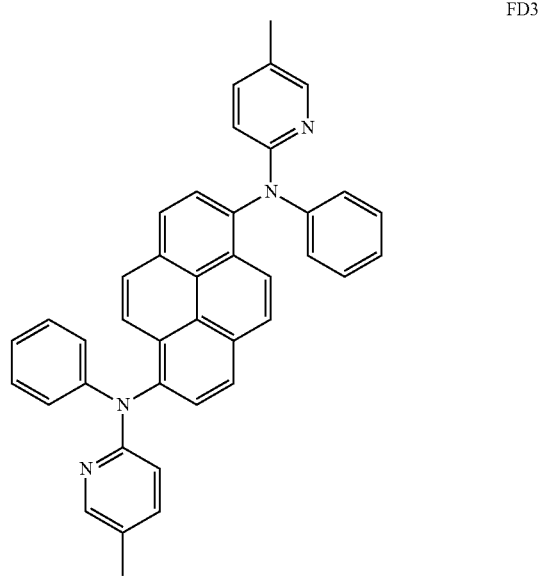

FD3

FD4
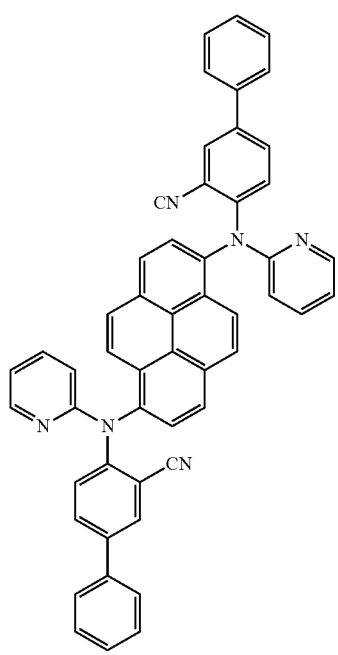
FD7
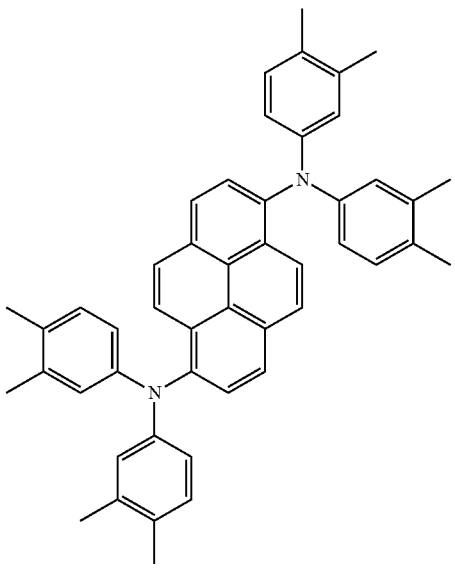
FD5
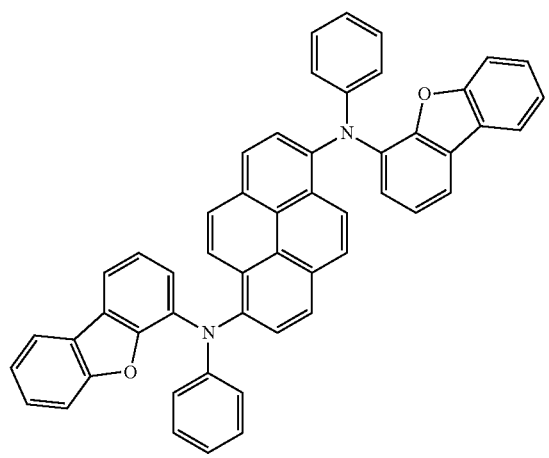
FD8
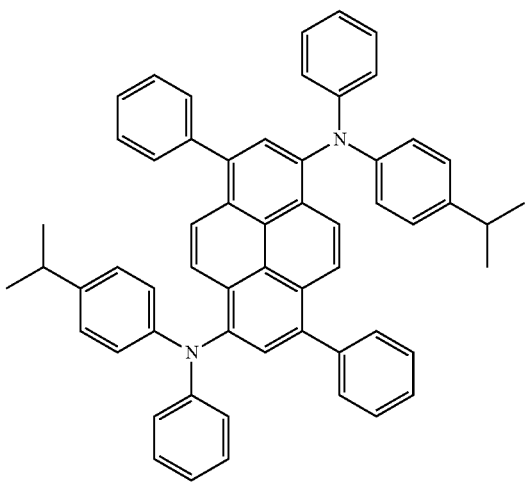
FD6
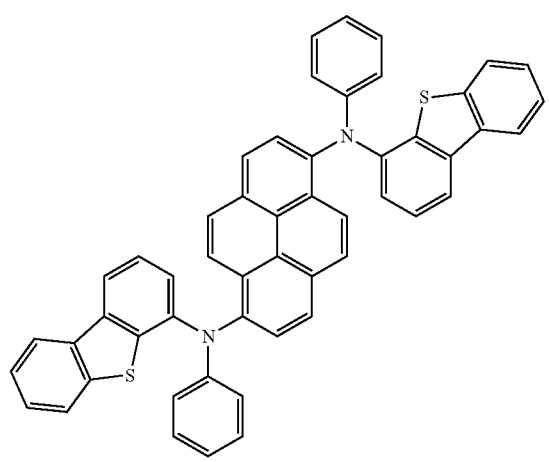
FD9
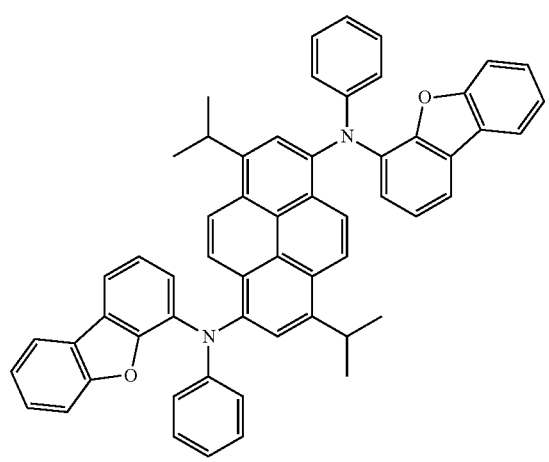

FD10
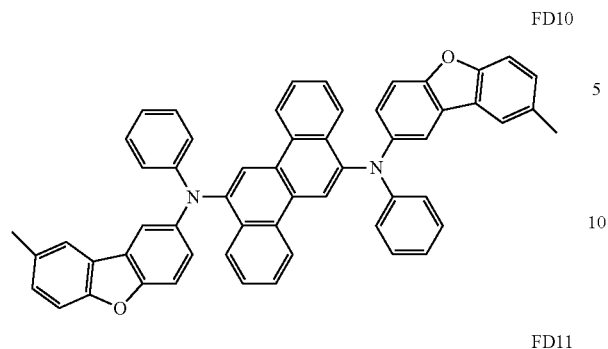
FD11
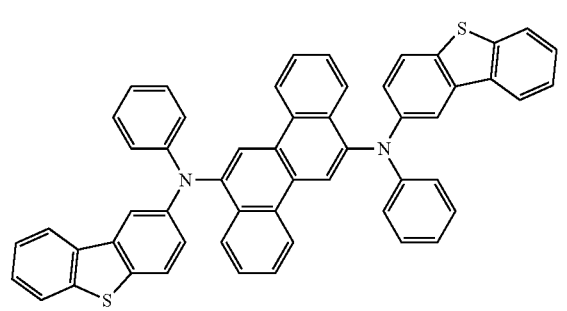
FD12
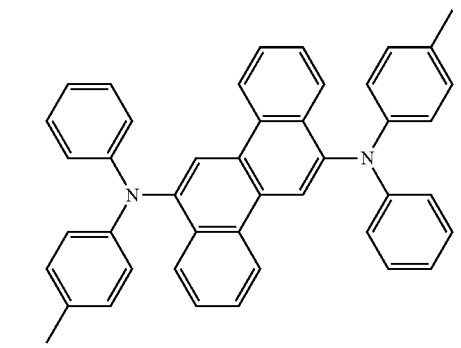
FD13
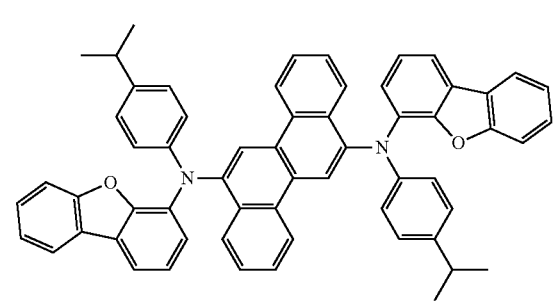
FD14
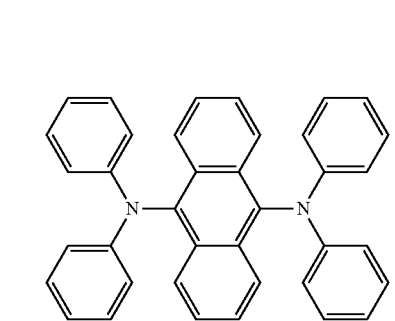
FD15
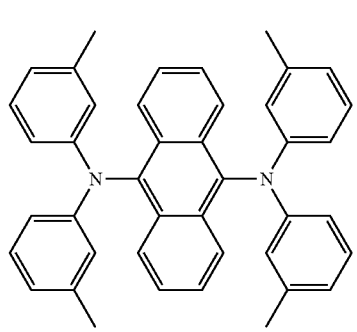
FD16
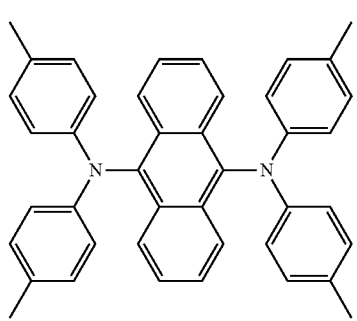
FD17
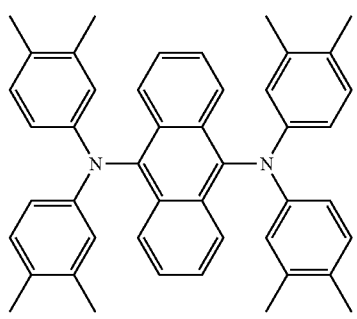
FD18
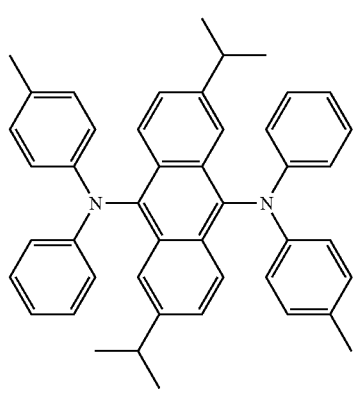

FD19
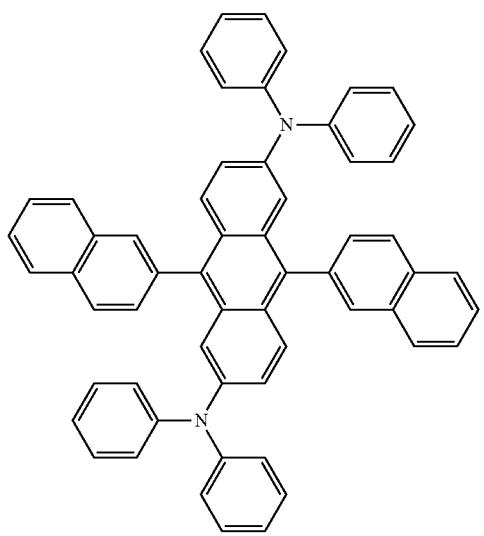
FD21
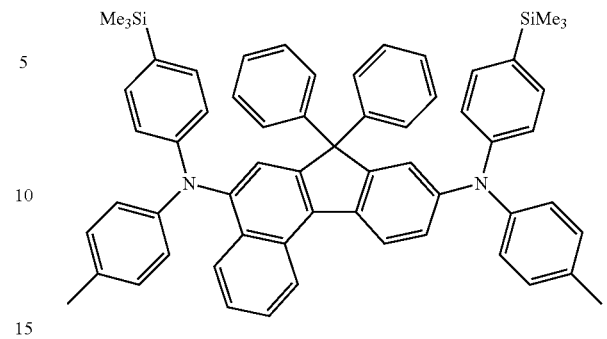
FD20
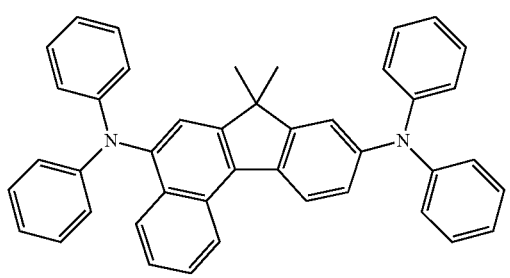
FD22
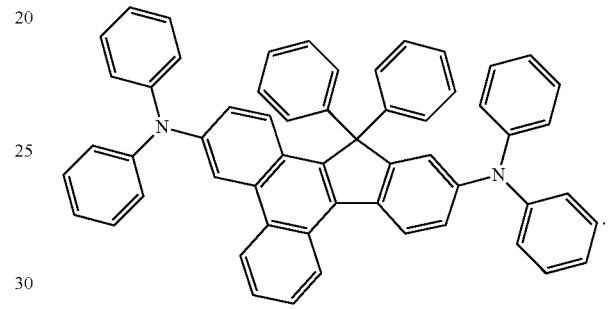
In some embodiments, the fluorescent dopant may be selected from the following compounds, but embodiments are not limited thereto:
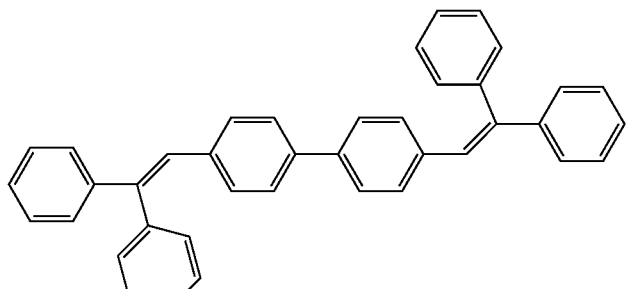
DPVBi
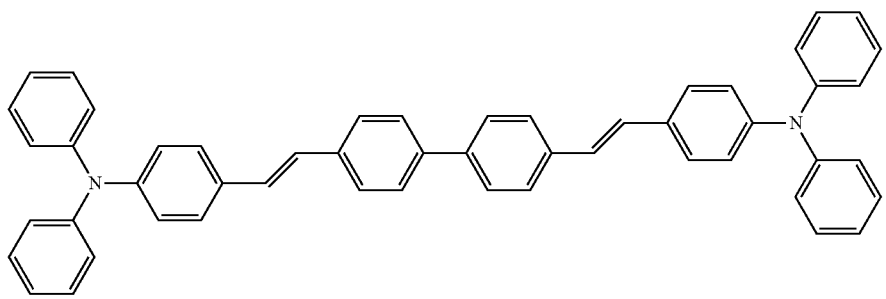
DPAVBi -continued

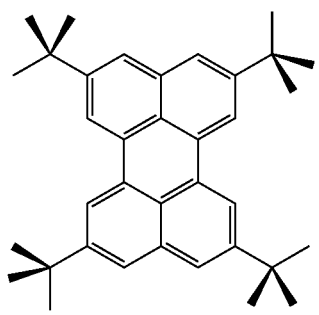
TBPe

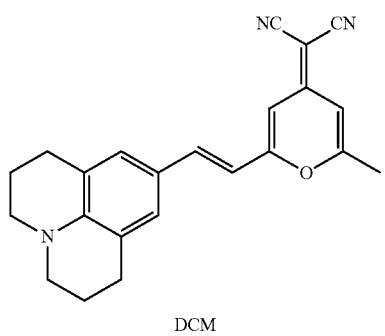
DCM

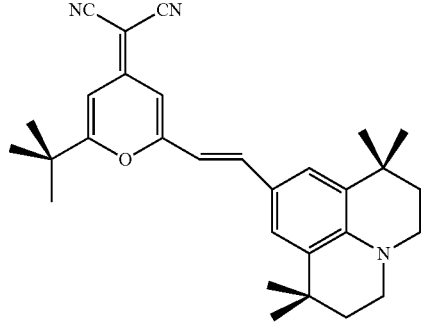
DCJTB

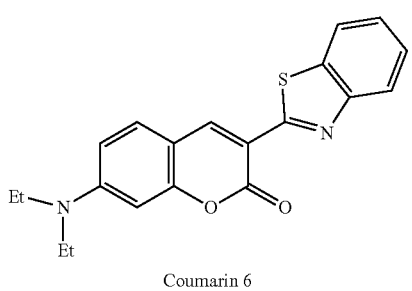
Coumarin 6

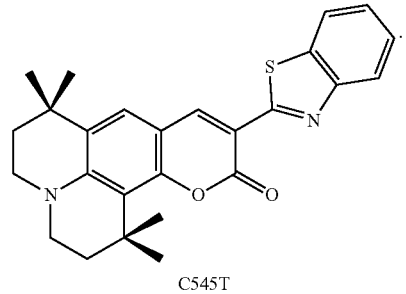
C545T

Electron Transport Region in Organic Layer 150

The electron transport region may have i) a single-layered structure including a single layer including a single material, ii) a single-layered structure including a single layer including a plurality of different materials, or iii) a multi-layered structure each having a plurality of layers, each having a plurality of different materials.

The electron transport region may include at least one selected from a buffer layer, a hole blocking layer, an electron control layer, an electron transport layer, and an electron injection layer, but embodiments are not limited thereto.

In some embodiments, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein layers of each structure are sequentially stacked on the emission layer in each stated order, but embodiments are not limited thereto.

The electron transport region, e.g., a buffer layer, a hole blocking layer, an electron control layer, or an electron transport layer in the electron transport region, may include a metal-free compound. The metal-free compound may include at least one π electron-depleted nitrogen-containing ring.

The term "π electron-depleted nitrogen-containing ring" as used herein refers to a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed, or iii) a heteropolycyclic group in which at least one 5-membered to 7-membered heteromonocyclic group having at least one *—N=*' moiety is condensed with at least one $C_5$-$C_{60}$ carbocyclic group.

Examples of the π electron-depleted nitrogen-containing ring may include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an iso-benzothiazole, a benzoxazole, an isobenzoxazole, a triazole, a tetrazole, an oxadiazole, a triazine, a thiadiazole, an imidazopyridine, an imidazopyrimidine, and an azacarbazole, but embodiments are not limited thereto.

In some embodiments, the electron transport region may include a compound represented by Formula 601:

$$[Ar_{601}]_{xe11}\text{-}[(L_{601})_{xe1}\text{-}R_{601}]_{xe21} \quad \text{Formula 601}$$

wherein, in Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), wherein $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one embodiment, at least one of $Ar_{601}$ groups in the number of xe11 and $R_{601}$ groups in the number of xe21 may include the π electron-depleted nitrogen-containing ring.

In some embodiments, $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is 2 or greater, at least two $Ar_{601}$ groups may be linked via a single bond.

In one or more embodiments, $Ar_{601}$ in Formula 601 may be an anthracene group.

In some embodiments, the compound represented by Formula 601 may be represented by Formula 601-1:

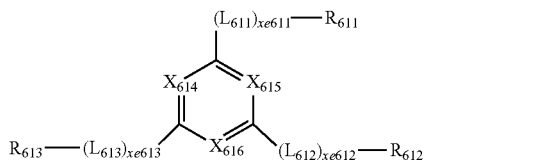

Formula 601-1 wherein, in Formula 601-1, $X_{614}$ may be N or C($R_{614}$), $X_{615}$ may be N or C($R_{615}$), $X_{616}$ may be N or C($R_{616}$), and at least one selected from $X_{614}$ to $X_{616}$ may be N, descriptions for $L_{611}$ to $L_{613}$ may each independently be the same as those for $L_{601}$ as described herein, descriptions for xe611 to xe613 may each independently be the same as those for xe1 as described herein, descriptions for $R_{611}$ to $R_{613}$ may each independently be the same as those for $R_{601}$ as described herein, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazone group, a $C_1$-$C_{20}$ alkyl group, a $C_1$-$C_{20}$ alkoxy group, a phenyl group, a biphenyl group, a terphenyl group, and a naphthyl group.

In one embodiment, in Formulae 601 and 601-1, $L_{601}$ and $L_{611}$ to $L_{613}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments are not limited thereto.

In one or more embodiments, in Formulae 601 and 601-1, xe1 and xe611 to xe613, may each independently be 0, 1, or 2.

In one or more embodiments, in Formulae 601 and 601-1, $R_{601}$ and $R_{611}$ to $R_{613}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), wherein Q$_{601}$ and Q$_{602}$ may each independently be the same as those described herein.

The electron transport region may include at least one compound selected from Compounds ET1 to ET36, but embodiments are not limited thereto:

ET1

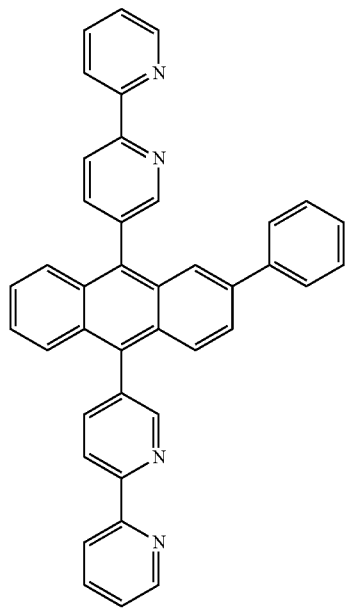

ET2

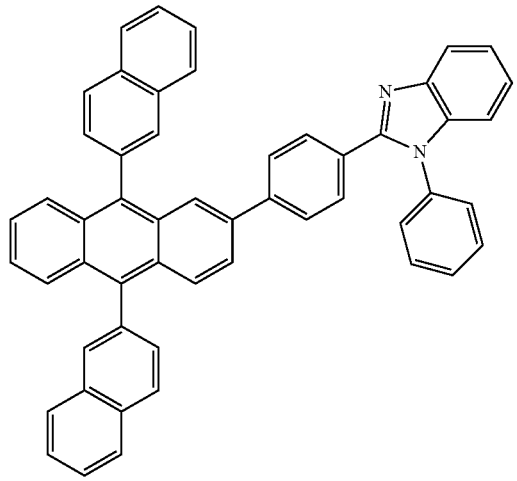

ET3

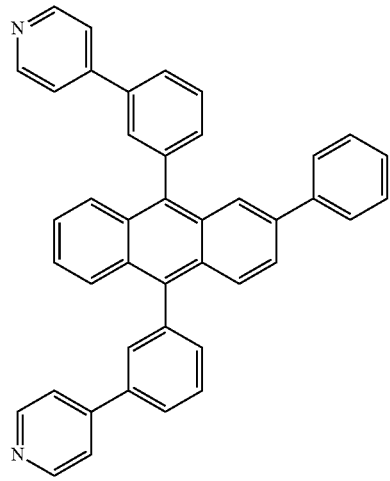

ET4

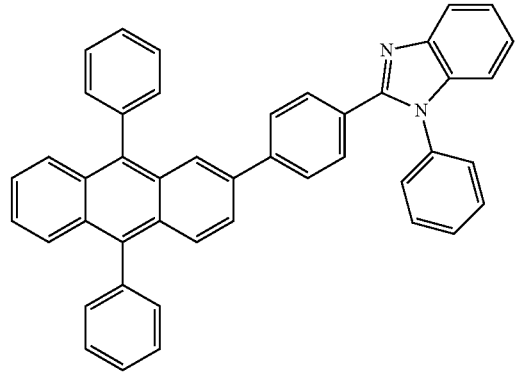

ET5

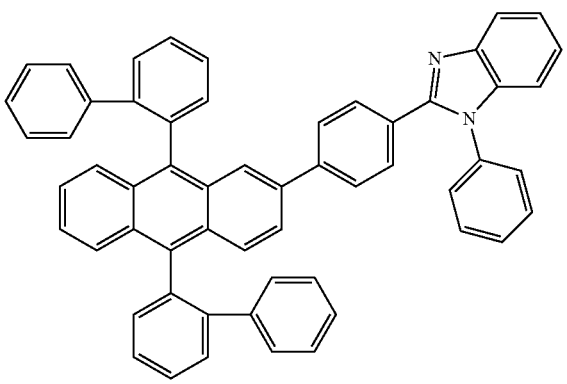

ET6
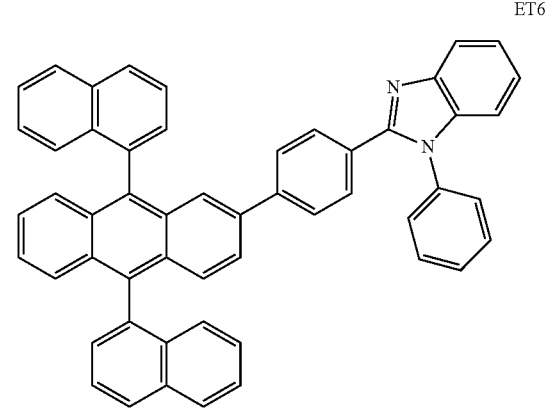
ET7
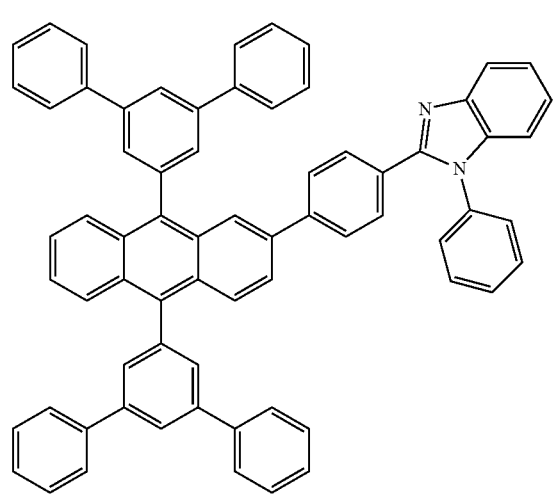
ET8
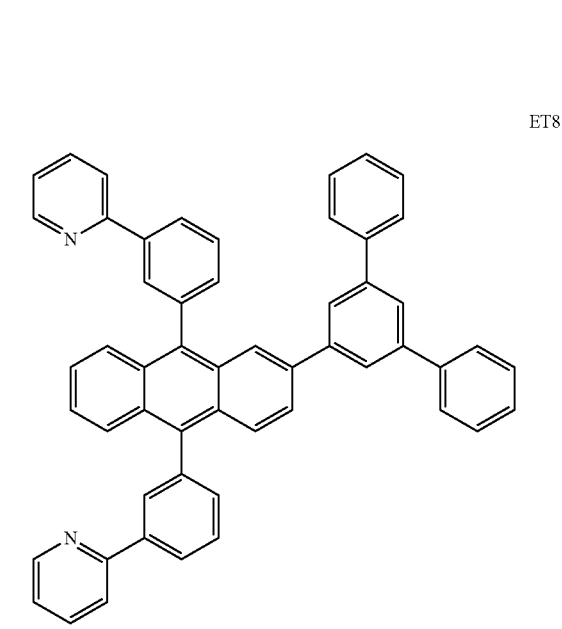
ET9
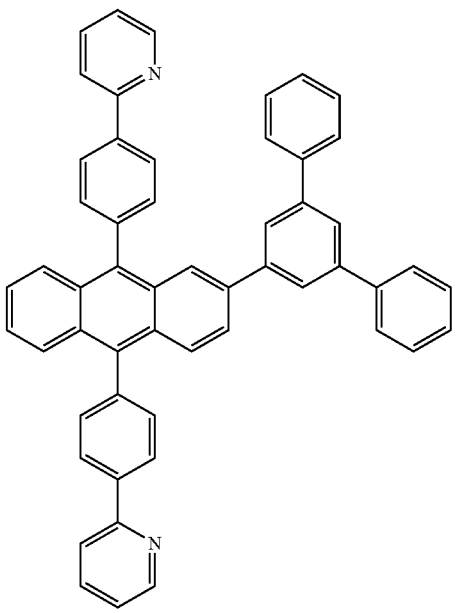
ET10
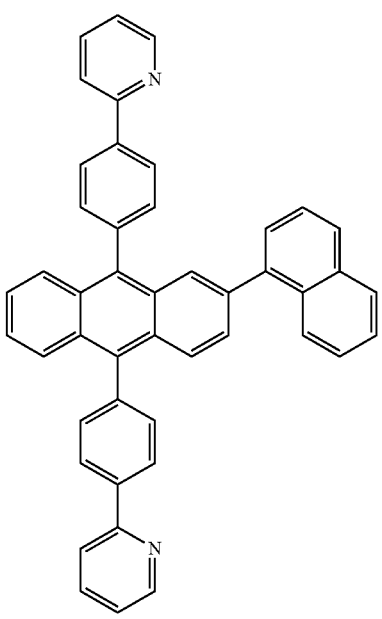

ET11
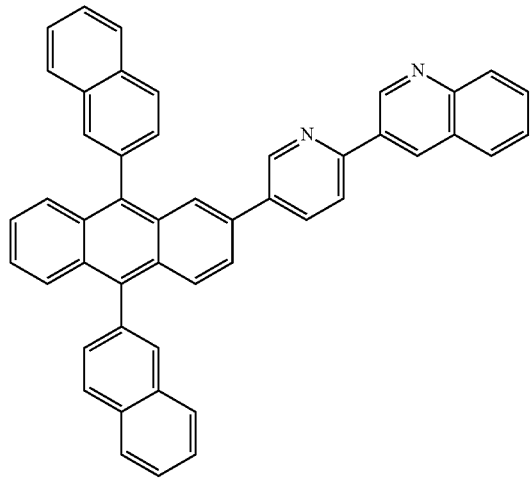
ET12
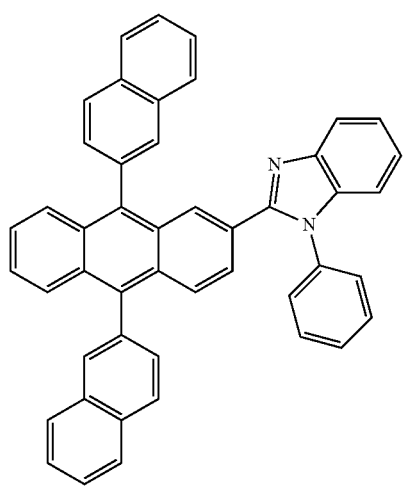
ET13
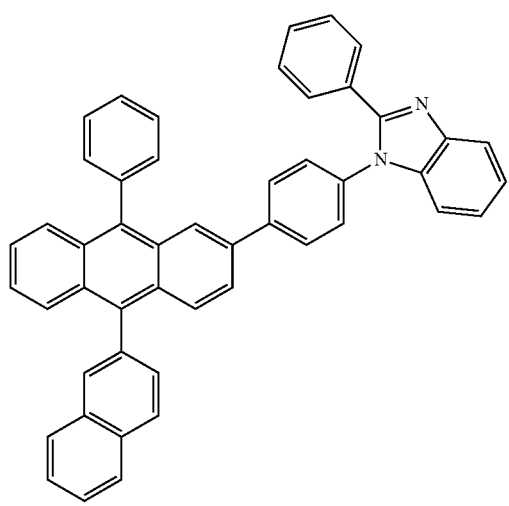
ET14
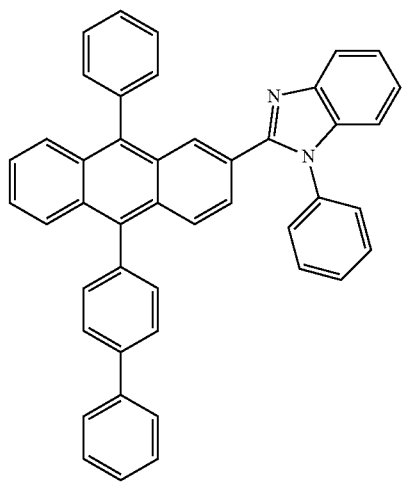
ET15
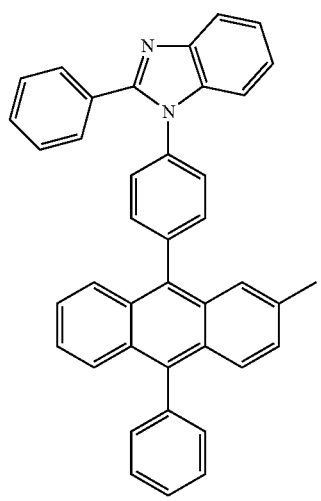
ET16
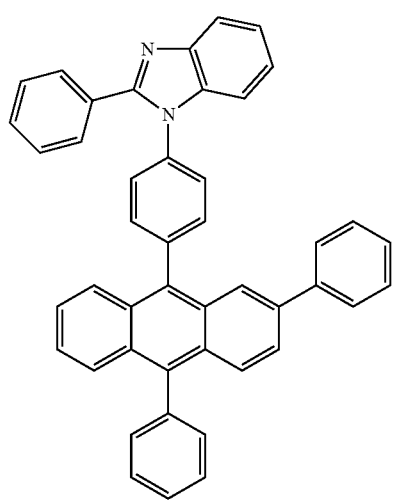

ET17 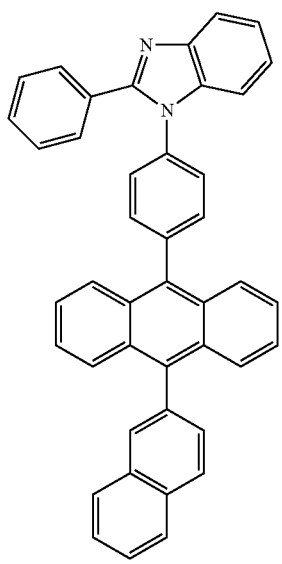
ET20 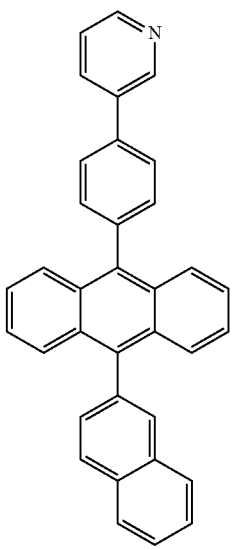
ET18 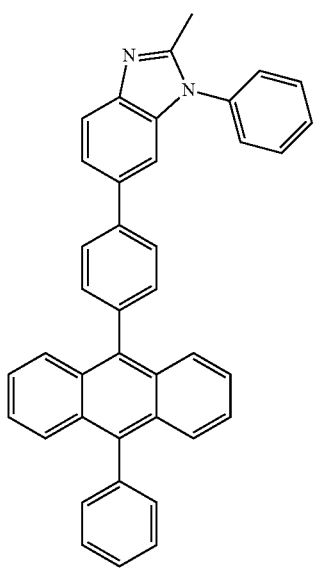
ET21 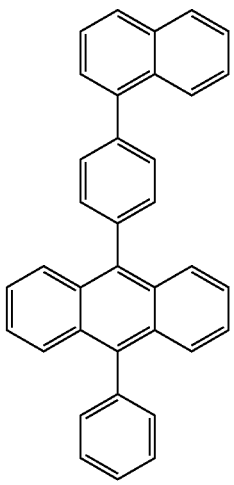
ET19 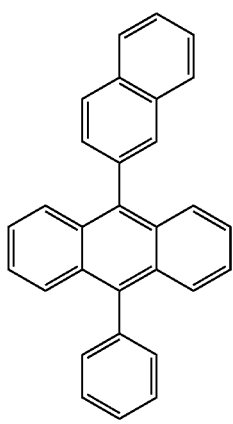
ET22 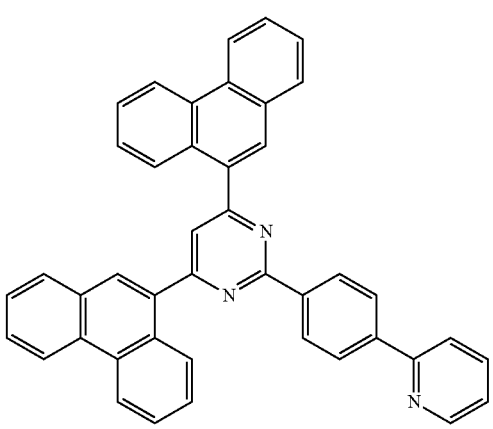

-continued

ET23

ET24

ET25

-continued

ET26

ET27

ET28

ET29
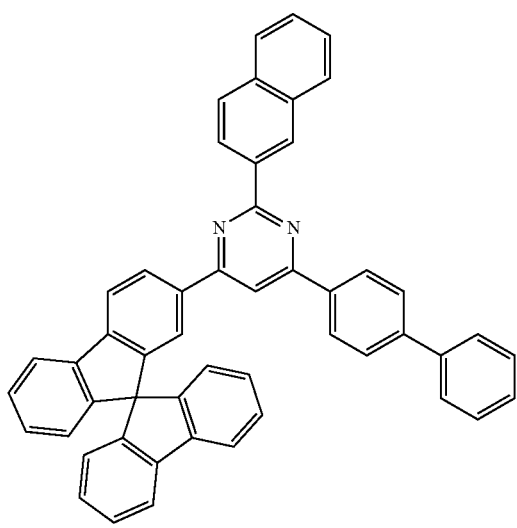
ET30
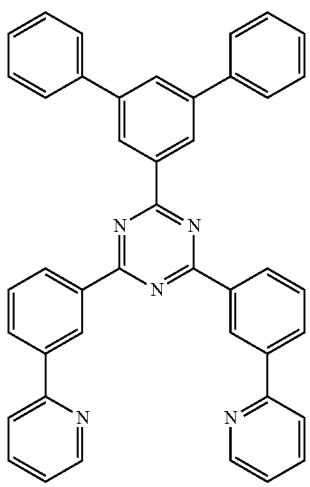
ET31
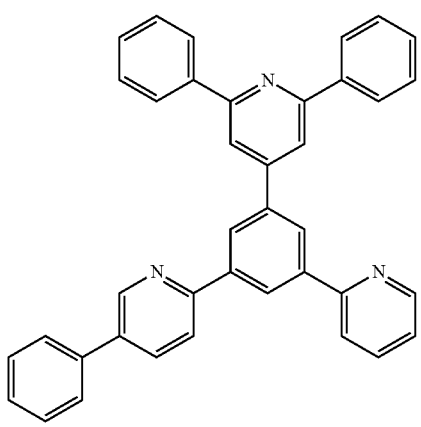
ET32
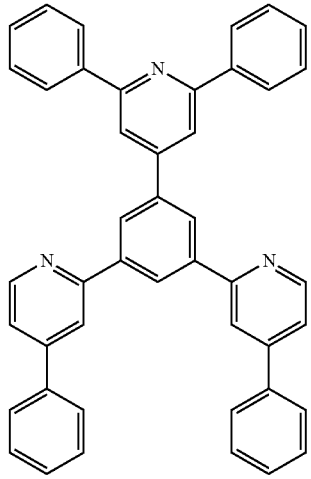
ET33
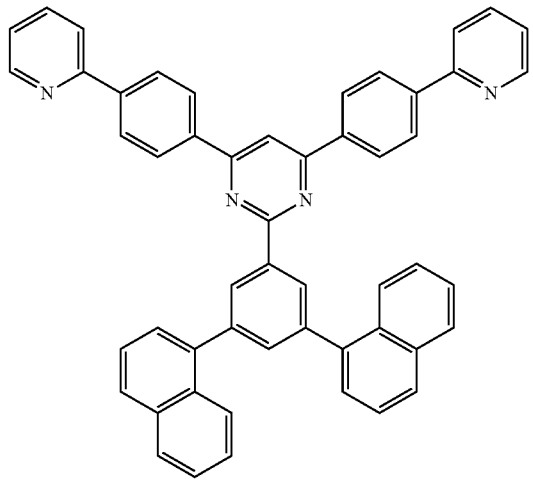
ET34
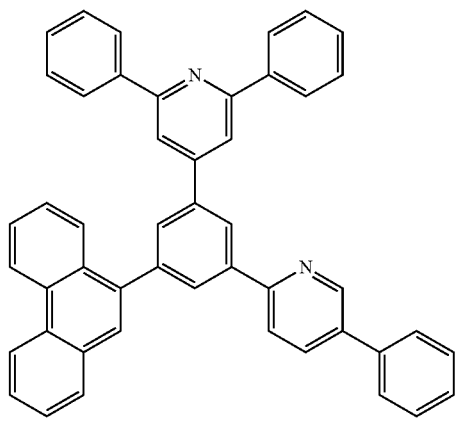

ET35

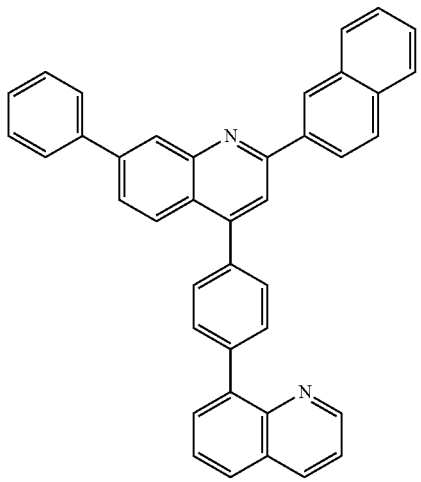

ET36

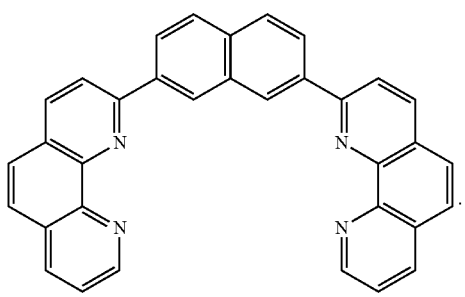

-continued

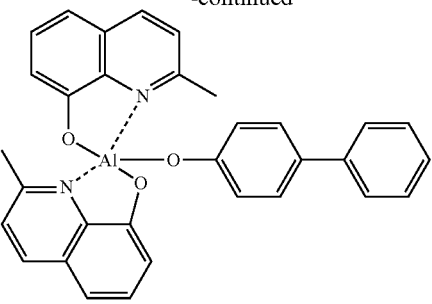
BAlq

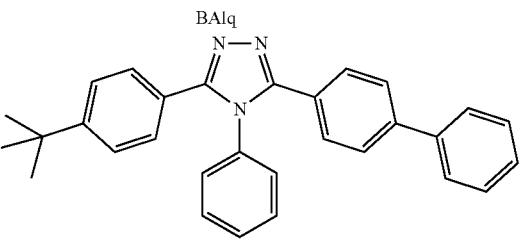
TAZ

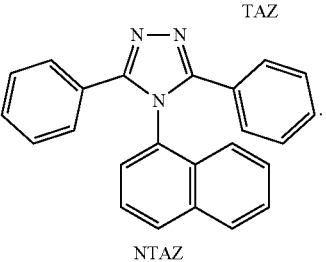
NTAZ

The thickness of the buffer layer, the hole blocking layer, or the electron control layer may each independently be in a range of about 20 Å to about 1,000 Å, and in some embodiments, about 30 Å to about 300 Å. When the thicknesses of the buffer layer, the hole blocking layer or the electron control layer are within any of these ranges, excellent hole blocking characteristics or excellent electron controlling characteristics may be obtained without a substantial increase in driving voltage.

The thickness of the electron transport layer may be in a range of about 100 Å to about 1,000 Å, and in some embodiments, about 150 Å to about 500 Å. When the thickness of the electron transport layer is within any of these ranges, excellent electron transport characteristics may be obtained without a substantial increase in driving voltage.

The electron transport region (e.g., the electron transport layer in the electron transport region) may further include, in addition to the materials described above, a material including metal.

The material including metal may include at least one selected from an alkali metal complex and an alkaline earth metal complex. The alkali metal complex may include a metal ion selected from a lithium (Li) ion, a sodium (Na) ion, a potassium (K) ion, a rubidium (Rb) ion, and a cesium (Cs) ion. The alkaline earth metal complex may include a metal ion selected from a beryllium (Be) ion, a magnesium (Mg) ion, a calcium (Ca) ion, an strontium (Sr) ion, and a barium (Ba) ion. Each ligand coordinated with the metal ion of the alkali metal complex and the alkaline earth metal complex may independently be selected from a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxydiphenyl In some embodiments, the electron transport region may include at least one compound selected from 2,9-dimethyl-4,7-diphenyl-1,10-phenanthroline (BCP), 4,7-diphenyl-1,10-phenanthroline (Bphen), Alq₃, BAlq, 3-(biphenyl-4-yl)-5-(4-tert-butylphenyl)-4-phenyl-4H-1,2,4-triazole (TAZ), and NTAZ:

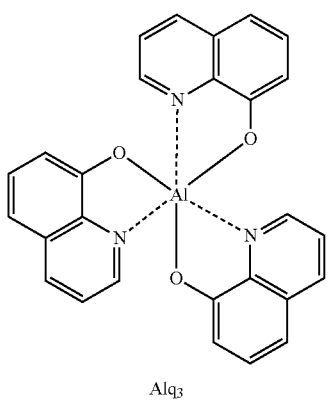
Alq₃ oxadiazole, a hydroxydiphenyl thiadiazole, a hydroxyphenyl pyridine, a hydroxyphenyl benzimidazole, a hydroxyphenyl benzothiazole, a bipyridine, a phenanthroline, and a cyclopentadiene, but embodiments are not limited thereto.

For example, the material including metal may include a Li complex. The Li complex may include, e.g., Compound ET-D1 (lithium quinolate, LiQ) or Compound ET-D2:

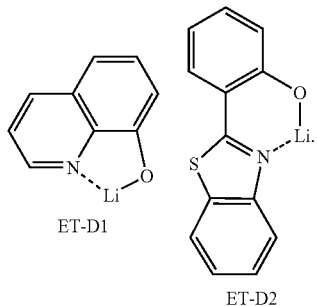

ET-D1

ET-D2

The electron transport region may include an electron injection layer that facilitates injection of electrons from the second electrode 190. The electron injection layer may be in direct contact with the second electrode 190.

The electron injection layer may have i) a single-layered structure including a single layer including a single material, ii) a single-layered structure including a single layer including a plurality of different materials, or iii) a multi-layered structure having a plurality of layers, each including a plurality of different materials.

The electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof.

The alkali metal may be selected from Li, Na, K, Rb, and Cs. In one embodiment, the alkali metal may be Li, Na, or Cs. In one or more embodiments, the alkali metal may be Li or Cs, but embodiments are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth metal compound, and the rare earth metal compound may each independently be selected from oxides and halides (e.g., fluorides, chlorides, bromides, or iodines) of the alkali metal, the alkaline earth metal, and the rare earth metal, respectively.

The alkali metal compound may be selected from alkali metal oxides, such as $Li_2O$, $Cs_2O$, or $K_2O$, and alkali metal halides, such as LiF, NaF, CsF, KF, LiI, NaI, CsI, KI, or RbI. In one embodiment, the alkali metal compound may be selected from LiF, $Li_2O$, NaF, LiI, NaI, CsI, and KI, but embodiments are not limited thereto.

The alkaline earth metal compound may be selected from alkaline earth metal compounds such as BaO, SrO, CaO, $Ba_xSr_{1-x}O$ (where 0<x<1), and $Ba_xCa_{1-x}O$ (where 0<x<1). In one embodiment, the alkaline earth metal compound may be selected from BaO, SrO, and CaO, but embodiments are not limited thereto.

The rare earth metal compound may be selected from $YbF_3$, $ScF_3$, $ScO_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$, but embodiments are not limited thereto.

The alkali metal complex, the alkaline earth metal complex, and the rare earth metal complex may each include ions of the above-described alkali metal, alkaline earth metal, and rare earth metal. Each ligand coordinated with the metal ion of the alkali metal complex, the alkaline earth metal complex, and the rare earth metal complex may independently be selected from a hydroxyquinoline, a hydroxyisoquinoline, a hydroxybenzoquinoline, a hydroxyacridine, a hydroxyphenanthridine, a hydroxyphenyl oxazole, a hydroxyphenyl thiazole, a hydroxydiphenyl oxadiazole, a hydroxydiphenyl thiadiazole, a hydroxyphenyl pyridine, a hydroxyphenyl benzimidazole, a hydroxyphenyl benzothiazole, a bipyridine, a phenanthroline, and a cyclopentadiene, but embodiments are not limited thereto.

The electron injection layer may consist of an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof, as described above. In some embodiments, the electron injection layer may further include an organic material. When the electron injection layer further includes an organic material, the alkali metal, the alkaline earth metal, the rare earth metal, the alkali metal compound, the alkaline earth metal compound, the rare earth metal compound, the alkali metal complex, the alkaline earth metal complex, the rare earth metal complex, or a combination thereof may be homogeneously or non-homogeneously dispersed in a matrix including the organic material.

The thickness of the electron injection layer may be in a range of about 1 Å to about 100 Å, and in some embodiments, about 3 Å to about 90 Å. When the thickness of the electron injection layer is within any of these ranges, excellent electron injection characteristics may be obtained without a substantial increase in driving voltage.

Second Electrode 190

The second electrode 190 may be disposed on the organic layer 150. In an embodiment, the second electrode 190 may be a cathode that is an electron injection electrode. In this embodiment, a material for forming the second electrode 190 may be a material having a low work function, for example, a metal, an alloy, an electrically conductive compound, or a combination thereof.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments are not limited thereto. The second electrode 190 may be a transmissive electrode, a semi-transmissive electrode, or a reflective electrode.

The second electrode 190 may have a single-layered structure, or a multi-layered structure including two or more layers.

Figure 3:
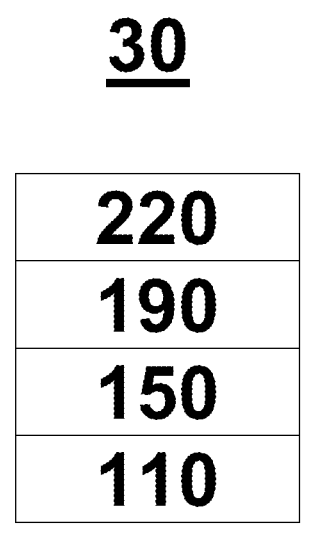
Figure 4:
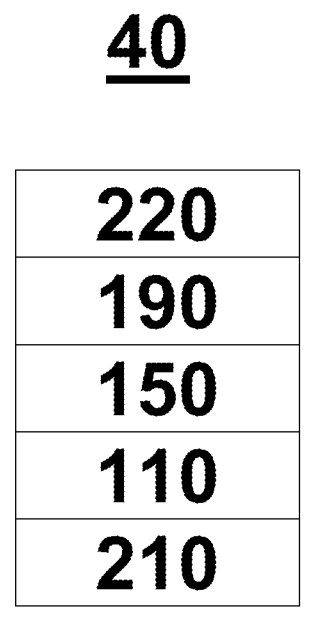

Description of FIGS. 2 to 4

Figure 2:
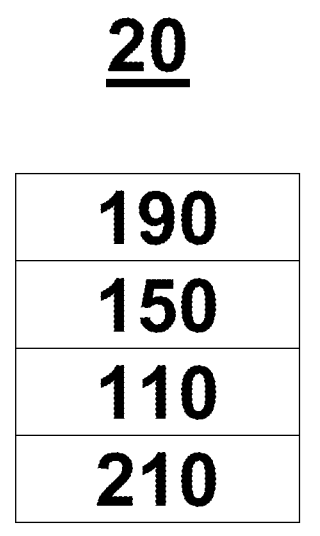

Referring to FIG. 2, an organic light-emitting device 20 has a first capping layer 210, the first electrode 110, the organic layer 150, and the second electrode 190 structure, wherein the layers are sequentially stacked in this stated order. Referring to FIG. 3, an organic light-emitting device 30 has the first electrode 110, the organic layer 150, the second electrode 190, and a second capping layer 220 structure, wherein the layers are sequentially stacked in this stated order. Referring to FIG. 4, an organic light-emitting device 40 has the first capping layer 210, the first electrode 110, the organic layer 150, the second electrode 190, and the second capping layer 220 structure, wherein the layers are stacked in this stated order.

The first electrode 110, the organic layer 150, and the second electrode 190 illustrated in FIGS. 2 to 4 may be substantially the same as those illustrated in FIG. 1.

In the organic light-emitting devices 20 and 40, light emitted from the emission layer in the organic layer 150 may pass through the first electrode 110 (which may be a semi-transmissive electrode or a transmissive electrode) and through the first capping layer 210 to the outside. In the organic light-emitting devices 30 and 40, light emitted from the emission layer in the organic layer 150 may pass through the second electrode 190 (which may be a semi-transmissive electrode or a transmissive electrode) and through the second capping layer 220 to the outside.

The first capping layer 210 and the second capping layer 220 may improve the external luminescence efficiency based on the principle of constructive interference.

The first capping layer 210 and the second capping layer 220 may each independently be a capping layer including an organic material, an inorganic capping layer including an inorganic material, or a composite capping layer including an organic material and an inorganic material.

At least one of the first capping layer 210 and the second capping layer 220 may each independently include at least one material selected from carbocyclic compounds, heterocyclic compounds, amine-based compounds, porphine derivatives, phthalocyanine derivatives, naphthalocyanine derivatives, alkali metal complexes, and alkaline earth metal complexes. The carbocyclic compound, the heterocyclic compound, and the amine-based compound may optionally be substituted with a substituent containing at least one element selected from O, N, S, Se, Si, F, Cl, Br, and I. In one embodiment, at least one of the first capping layer 210 and the second capping layer 220 may each independently include an amine-based compound.

In one or more embodiments, at least one of the first capping layer 210 and the second capping layer 220 may each independently include a compound represented by Formula 201 or a compound represented by 202.

In one or more embodiments, at least one of the first capping layer 210 and the second capping layer 220 may each independently include a compound selected from Compounds HT28 to HT33 and Compound CP1 to CP5, but embodiments are not limited thereto:

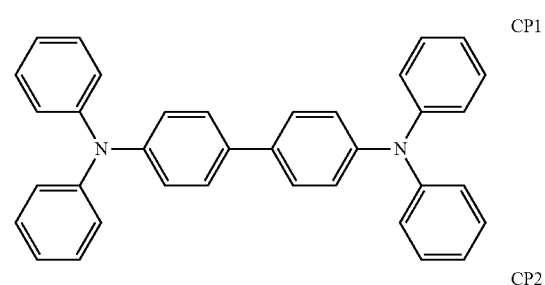

CP1

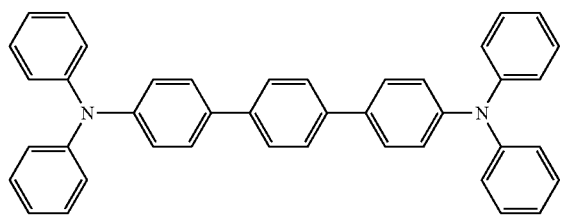

CP2

-continued

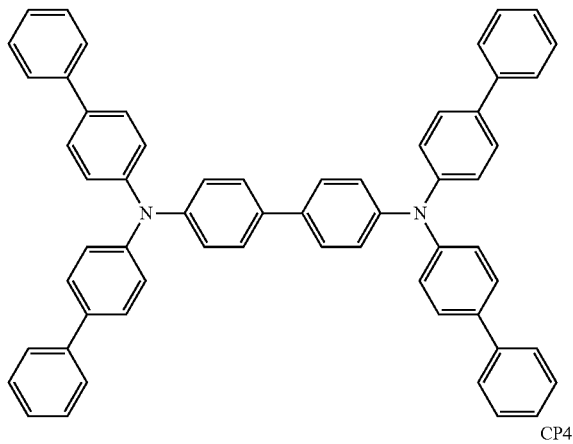

CP3

CP4

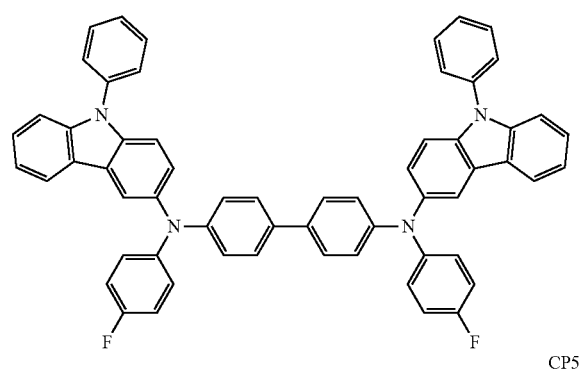

CP5

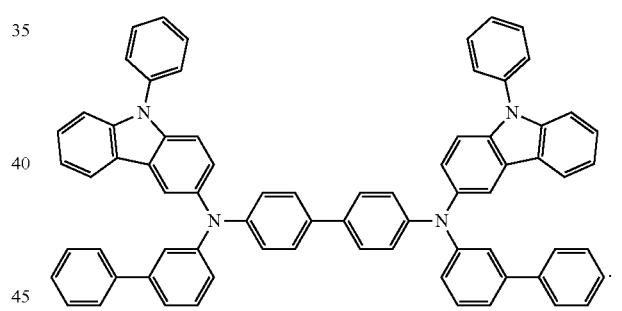

Hereinbefore, the organic light-emitting device has been described with reference to FIGS. 1 to 4, but embodiments are not limited thereto.

The layers constituting the hole transport region, the emission layer, and the layers constituting the electron transport region may be formed in a set or specific region by using one or more suitable methods such as vacuum deposition, spin coating, casting, Langmuir-Blodgett (LB) deposition, ink-jet printing, laser printing, and laser-induced thermal imaging.

When the layers constituting the hole transport region, the emission layer, and the layers constituting the electron transport region are each formed by vacuum deposition, the vacuum deposition may be performed at a deposition temperature in a range of about 100° C. to about 500° C. at a vacuum degree in a range of about $10^{-8}$ torr to about $10^{-3}$ torr, and at a deposition rate in a range of about 0.01 Angstroms per second (Å/sec) to about 100 Å/sec, depending on the material to be included in each layer and the structure of each layer to be formed.

When the layers constituting the hole transport region, the emission layer, and the layers constituting the electron transport region are each formed by spin coating, the spin coating may be performed at a coating rate of about 2,000 revolutions per minute (rpm) to about 5,000 rpm and at a heat treatment temperature of about 80° C. to about 200° C., depending on the material to be included in each layer and the structure of each layer to be formed.

General Definitions of Some of the Substituents

The term "$C_1$-$C_{60}$ alkyl group," as used herein, refers to a linear or branched aliphatic hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a hydrocarbon group having at least one carbon-carbon double bond at a main chain (e.g., in the middle) or at the terminus of the $C_2$-$C_{60}$ alkyl group. Examples thereof include an ethenyl group, a propenyl group, and a butenyl group. The term "$C_2$-$C_{60}$ alkenylene group," as used herein, refers to a divalent group having substantially the same structure as the $C_2$-$C_{60}$ alkenyl group.

The term "$C_2$-$C_{60}$ alkynyl group," as used herein, refers to a hydrocarbon group having at least one carbon-carbon triple bond at a main chain (e.g., in the middle) or at the terminus of the $C_2$-$C_{60}$ alkyl group. Examples thereof include an ethynyl group and a propynyl group. The term "$C_2$-$C_{60}$ alkynylene group," as used herein, refers to a divalent group having substantially the same structure as the $C_2$-$C_{60}$ alkynyl group.

The term "$C_1$-$C_{60}$ alkoxy group," as used herein, refers to a monovalent group represented by —$OA_{101}$ (wherein $A_{101}$ is a $C_1$-$C_{60}$ alkyl group). Examples thereof include a methoxy group, an ethoxy group, and an isopropyloxy group.

The term "$C_3$-$C_{10}$ cycloalkyl group," as used herein, refers to a monovalent monocyclic saturated hydrocarbon group including 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent monocyclic group including at least one heteroatom selected from N, O, Si, P, and S as a ring-forming atom and 1 to 10 carbon atoms. Examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_3$-$C_{10}$ cycloalkenyl group," as used herein, refers to a monovalent monocyclic group that has 3 to 10 carbon atoms and at least one double bond in its ring, and is not aromatic (e.g., the entire group or molecule is non-aromatic). Examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent monocyclic group including at least one heteroatom selected from N, O, Si, P, and S as a ring-forming atom, 1 to 10 carbon atoms, and at least one double bond in its ring. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_6$-$C_{60}$ aryl group," as used herein, refers to a monovalent group having a carbocyclic aromatic system having 6 to 60 carbon atoms. The term "$C_6$-$C_{60}$ arylene group," as used herein, refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused (e.g., combined together).

The term "$C_1$-$C_{60}$ heteroaryl group," as used herein, refers to a monovalent group having a heterocyclic aromatic system having at least one heteroatom selected from N, O, Si, P, and S as a ring-forming atom and 1 to 60 carbon atoms. The term "$C_1$-$C_{60}$ heteroarylene group," as used herein, refers to a divalent group having a heterocyclic aromatic system having at least one heteroatom selected from N, O, Si, P, and S as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be fused (e.g., combined together).

The term "$C_6$-$C_{60}$ aryloxy group," as used herein, refers to a group represented by —$OA_{102}$ (where $A_{102}$ is a $C_6$-$C_{60}$ aryl group). The term "$C_6$-$C_{60}$ arylthio group," as used herein, refers to a group represented by —$SA_{103}$ (where $A_{103}$ is a $C_6$-$C_{60}$ aryl group).

The term "monovalent non-aromatic condensed polycyclic group," as used herein, refers to a monovalent group that has two or more rings condensed (e.g., combined together) and only carbon atoms as ring forming atoms (e.g., 8 to 60 carbon atoms), wherein the entire molecular structure is non-aromatic. An example of the monovalent non-aromatic condensed polycyclic group may be a fluorenyl group. The term "divalent non-aromatic condensed polycyclic group," as used herein refers to a divalent group having substantially the same structure as the monovalent non-aromatic condensed polycyclic group.

The term "monovalent non-aromatic condensed heteropolycyclic group," as used herein, refers to a monovalent group that has two or more condensed rings and at least one heteroatom selected from N, O, Si, P, and S, in addition to carbon atoms (e.g., 1 to 60 carbon atoms), as a ring-forming atom, wherein the entire molecular structure is non-aromatic. An example of the monovalent non-aromatic condensed heteropolycyclic group is a carbazolyl group. The term "divalent non-aromatic condensed heteropolycyclic group," as used herein, refers to a divalent group having substantially the same structure as the monovalent non-aromatic condensed heteropolycyclic group.

The term "$C_5$-$C_{60}$ carbocyclic group," as used herein, refers to a monocyclic or polycyclic group having 5 to 60 carbon atoms only as ring-forming atoms. The $C_5$-$C_{60}$ carbocyclic group may be an aromatic carbocyclic group or a non-aromatic carbocyclic group. The term "$C_5$-$C_{60}$ carbocyclic group," as used herein, refers to a ring (e.g., a benzene group), a monovalent group (e.g., a phenyl group), or a divalent group (e.g., a phenylene group). In one or more embodiments, depending on the number of substituents coupled or connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group," as used herein, refers to a group having substantially the same structure as the $C_1$-$C_{60}$ carbocyclic group, except that at least one heteroatom selected from N, O, Si, P, and S is used as a ring-forming atom, in addition to carbon atoms (e.g., 1 to 60 carbon atoms).

In the present specification, at least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_r$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($O_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph" as used herein represents a phenyl group. The term "Me" as used herein represents a methyl group. The term "Et" as used herein represents an ethyl group. The term "ter-Bu" or "Bu$^t$" as used herein represents a tert-butyl group. The term "OMe" as used herein represents a methoxy group.

The term "biphenyl group" as used herein refers to a phenyl group substituted with a phenyl group. In other words, the "biphenyl group" may be a substituted phenyl group having a $C_6$-$C_{60}$ aryl group as a substituent.

The term "terphenyl group" as used herein refers to a phenyl group substituted with a biphenyl group. In other words, the "terphenyl group" may be a substituted phenyl group having a $C_6$-$C_{60}$ aryl group substituted with a $C_6$-$C_{60}$ aryl group as a substituent.

The symbols * and *' as used herein, unless defined otherwise, refer to a binding site to an adjacent atom in a corresponding formula.

Hereinafter, compounds and an organic light-emitting device according to one or more embodiments will be described in more detail with reference to Synthesis Examples and Examples. The wording "B was used instead of A" used in describing Synthesis Examples refers to that an identical (or substantially identical) number of molar equivalents of B was used in place of A.

SYNTHESIS EXAMPLES

Synthesis Example 1: Synthesis of Compound 1

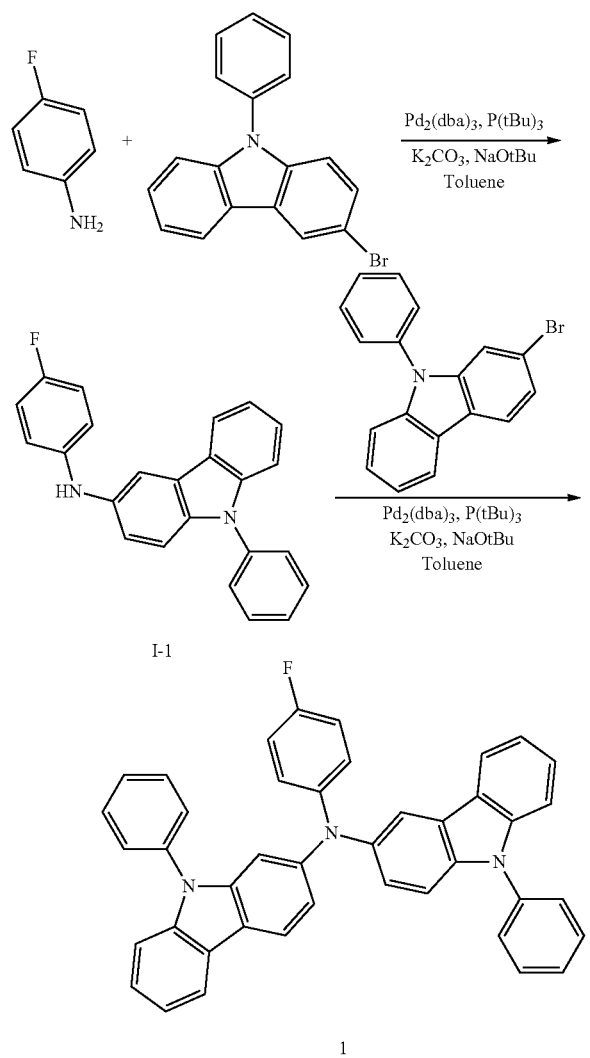

I-1

1

Synthesis of Intermediate I-1

1.2 grams (g) (11.0 millimole (mmol)) of 4-fluoroaniline, 3.2 g (10.0 mmol) of 3-bromo-9-phenyl-9H-carbazole, 0.46 g (0.5 mmol) of $Pd_2(dba)_3$, 0.1 g (0.5 mmol) of $P(tBu)_3$, and 1.44 g (15.0 mmol) of NaOtBu were dissolved in 30 milliliters (mL) of toluene, followed by heating for 5 hours under reflux. The reaction solution was cooled to room temperature, and an organic layer was extracted using 30 mL of diethylether. The separated organic layer was dried using anhydrous magnesium sulfate, followed by a distillation process performed thereon under reduced pressure. The residual was separated and purified through silica gel column chromatography, thereby obtaining 2.96 g of Intermediate I-1 (yield: 85%). The obtained compound was identified by liquid chromatography-mass spectrometry (LC-MS). ($C_{24}H_{17}FN_2$ M+ cal.: 352.1 found 353.1).

Synthesis of Compound 1

2.96 g (8.5 mmol) of Intermediate I-1, 2.73 g (8.5 mmol) of 2-bromo-9-phenyl-9H-carbazole, 0.39 g (0.43 mmol) of $Pd_2(dba)_3$, 0.08 g (0.43 mmol) of $P(tBu)_3$, and 1.23 g (12.8 mmol) of NaOtBu were dissolved in 30 mL of toluene, and followed by heating for 5 hours under reflux. The reaction solution was cooled to room temperature, and an organic layer was extracted using 30 mL of diethylether. The separated organic layer was dried using anhydrous magnesium sulfate, followed by a distillation process performed thereon under reduced pressure. The residual was separated and purified through silica gel column chromatography, thereby obtaining 4.18 g of Compound 1 (yield: 83%). The obtained compound was identified by LC-MS and $^1$H nuclear magnetic resonance (NMR). ($C_{42}H_{28}FN_3$ M+ cal.: 593.2 found 594.2).

$^1$H NMR (CDCl$_3$, 400 MHz) δ=8.12-8.05 (m, 2H), 7.87-7.85 (m, 1H), 7.55-7.46 (m, 8H), 7.41-7.23 (m, 10H), 7.17-7.08 (m, 4H), 6.96-6.84 (m, 3H)

The compounds according to one or more embodiments may be synthesized in substantially the same manner as in Synthesis of Compound 1. Each amine compound reacted with the corresponding aryl bromide compound according to Buchwald-Hartwig amination to thereby synthesize secondary amine Intermediate. Subsequently, the second Buchwald-Hartwig amination was performed with the introduction of the corresponding aryl bromide to synthesize the desired compounds with a high yield. Intermediates I-1 to I-31 used in Synthesis Examples 1 to 36 to synthesize the compound are as follows:

Synthetic secondary amine Intermediates I-1 to I-31

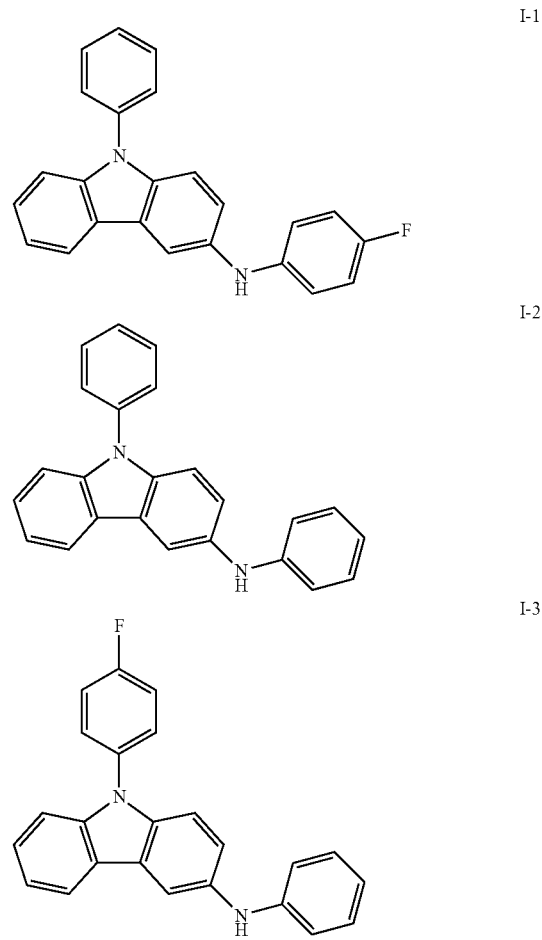

-continued
I-4
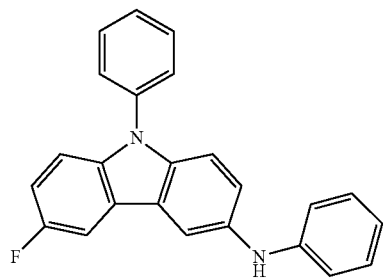
I-5
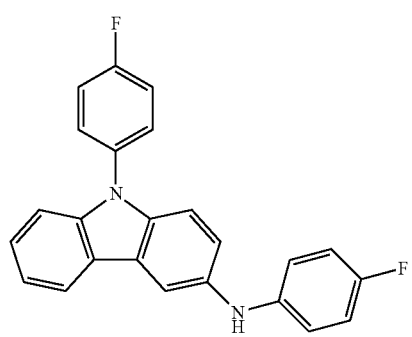
I-6
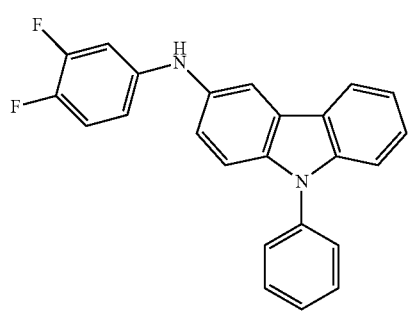
I-7
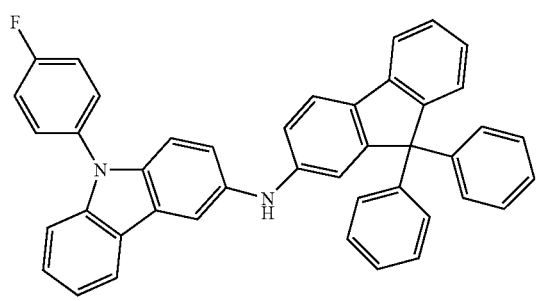
I-8
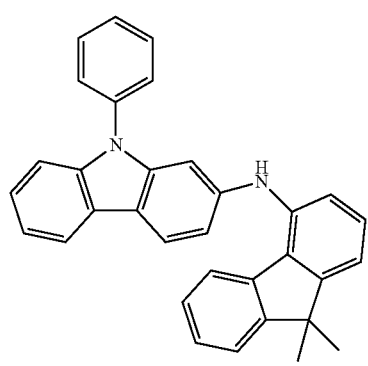
-continued
I-9
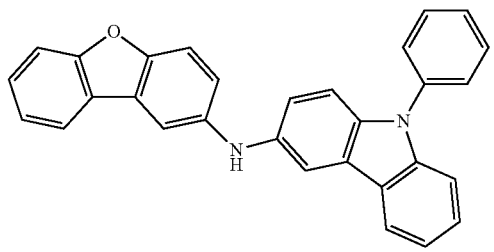
I-10
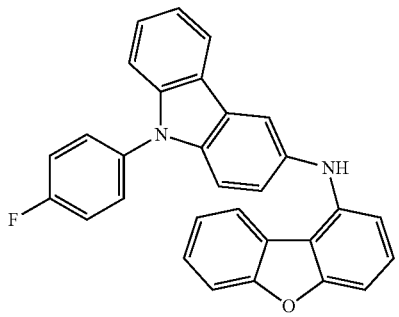
I-11
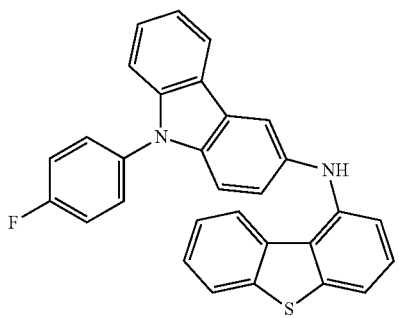
I-12
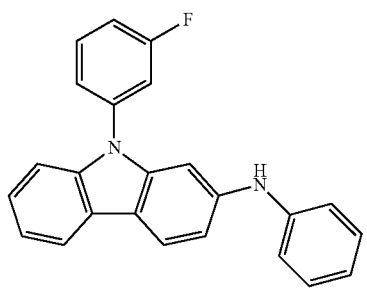
I-13
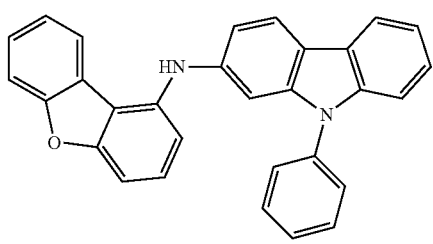

-continued
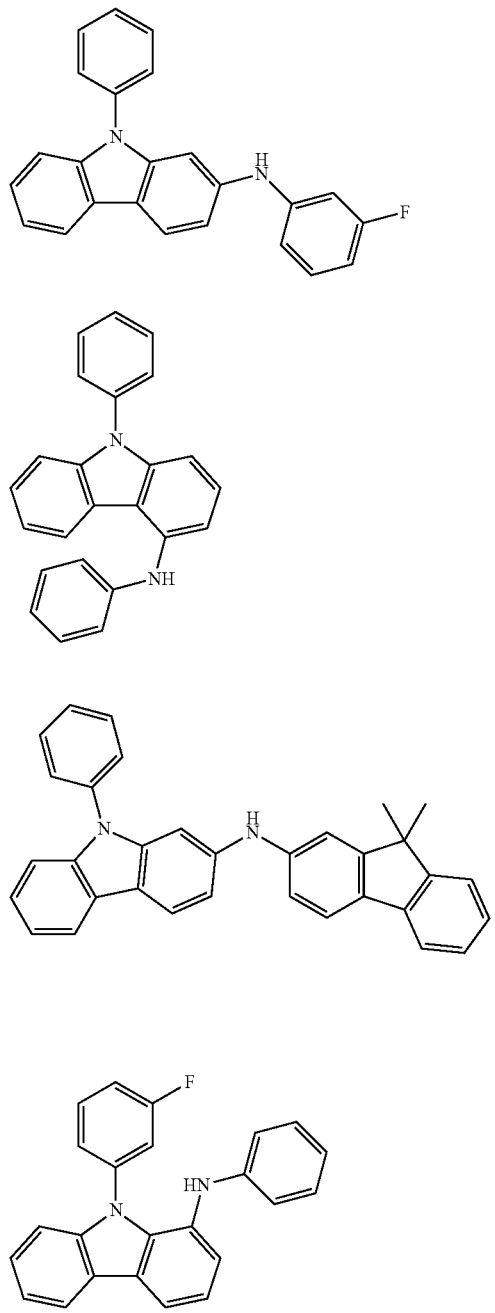
I-14
I-15
I-16
I-17
I-18
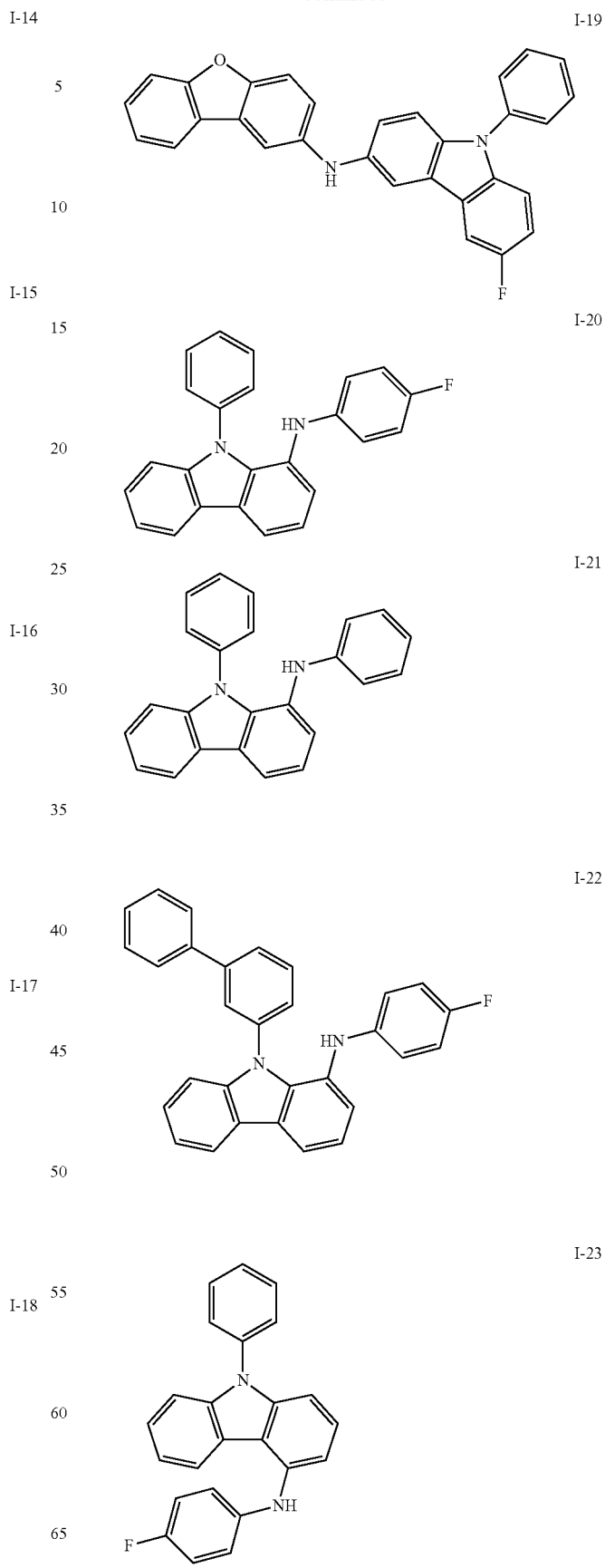
I-19
I-20
I-21
I-22
I-23

I-24
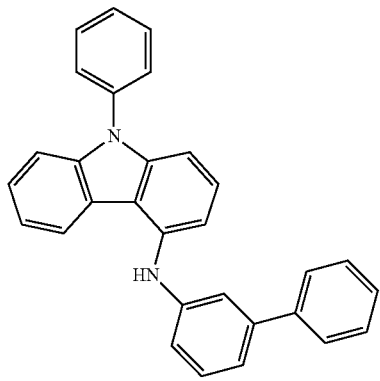
I-25
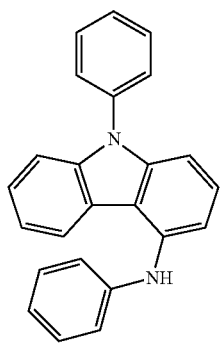
I-26
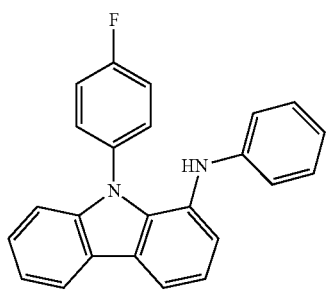
I-27
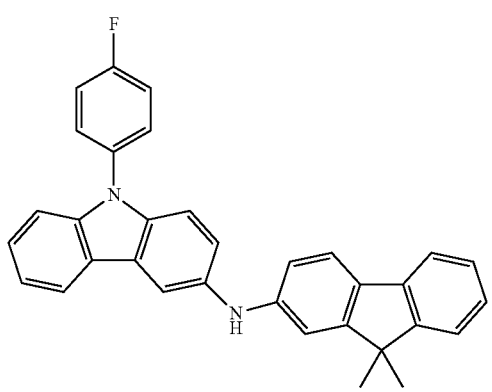
I-28
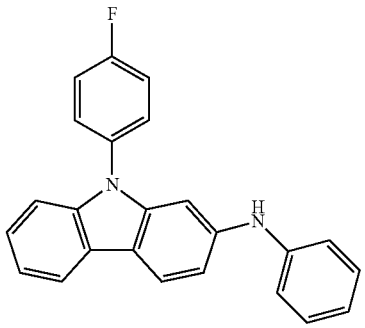
I-29
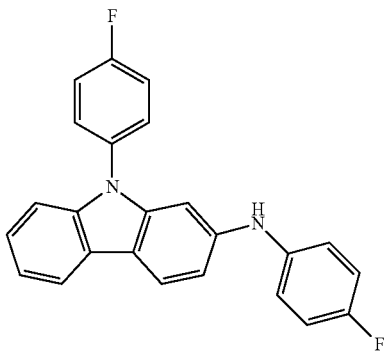
I-30
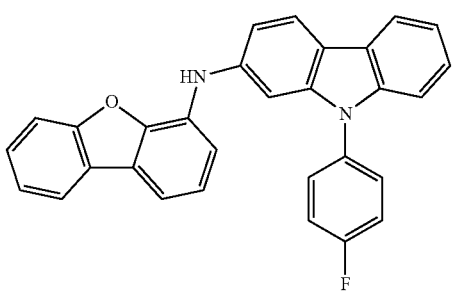
I-31
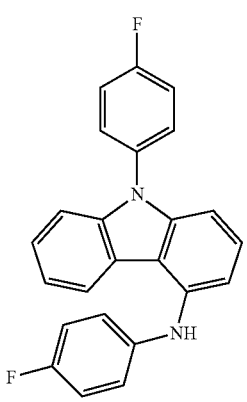
Synthesis Example 2: Synthesis of Compound 2
Compound 2 was synthesized in substantially the same manner as in Synthesis of Compound 1, except that Intermediate I-2 was reacted with 2-bromo-9-(4-fluorophenyl)-9H-carbazole (yield: 81%). The obtained compound was identified by LC-MS and $^1$H NMR. ($C_{42}H_{28}FN_3$ M+ cal.: 593.2 found 594.2).

¹H NMR (CDCl₃, 400 MHz) δ=12-8.05 (m, 2H), 7.87-7.85 (m, 1H), 7.55-7.46 (m, 4H), 7.41-7.23 (m, 11H), 7.19-7.11 (m, 4H), 7.07-6.96 (m, 3H), 6.92-6.87 (m, 1H), 6.84-6.79 (m, 2H)

Synthesis Example 3: Synthesis of Compound 4

Compound 4 was synthesized in substantially the same manner as in Synthesis of Compound 1, except that Intermediate I-3 was reacted with 2-bromo-9-(4-fluorophenyl)-9H-carbazole (yield: 81%). The obtained compound was identified by LC-MS and ¹H NMR. ($C_{42}H_{27}F_2N_3$ M+ cal.: 611.2 found 612.2).
¹H NMR (CDCl₃, 400 MHz) δ=8.12-8.05 (m, 2H), 7.87-7.85 (m, 1H), 7.40-7.23 (m, 12H), 7.16-7.06 (m, 6H), 6.99-6.89 (m, 3H), 6.87-6.83 (m, 1H), 6.79-6.77 (m, 2H)

Synthesis Example 4: Synthesis of Compound 5

Compound 5 was synthesized in substantially the same manner as in Synthesis of Compound 1, except that Intermediate I-3 was reacted with 2-bromo-9-phenyl-9H-carbazole (yield: 84%). The obtained compound was identified by LC-MS and ¹H NMR. ($C_{42}H_{28}FN_3$ M+ cal.: 593.2 found 594.2).
¹H NMR (CDCl₃, 400 MHz) δ=8.12-8.05 (m, 2H), 7.87-7.85 (m, 1H), 7.55-7.48 (m, 4H), 7.40-7.23 (m, 11H), 7.18-7.09 (m, 4H), 6.99-6.89 (m, 3H), 6.89-6.84 (m, 1H), 6.80-6.78 (m, 2H)

Synthesis Example 5: Synthesis of Compound 7

Compound 7 was synthesized in substantially the same manner as in Synthesis of Compound 1, except that Intermediate I-4 was reacted with 2-bromo-6-fluoro-9-phenyl-9H-carbazole (yield: 82%). The obtained compound was identified by LC-MS and ¹H NMR. ($C_{42}H_{27}F_2N_3$ M+ cal.: 611.2 found 612.2).
¹H NMR (CDCl₃, 400 MHz) δ=7.97 (d, 1H), 7.91-7.85 (m, 2H), 7.56-7.43 (m, 9H), 7.38-7.27 (m, 5H), 7.21 (dd, 1H), 7.15-7.04 (m, 6H), 6.89-6.83 (m, 1H), 6.80-6.76 (m, 2H)

Synthesis Example 6: Synthesis of Compound 8

Compound 8 was synthesized in substantially the same manner as in Synthesis of Compound 1, except that Intermediate I-5 was reacted with 2-bromo-9-(4-fluorophenyl)-9H-carbazole (yield: 82%). The obtained compound was identified by LC-MS and ¹H NMR. ($C_{42}H_{26}F_3N_3$ M+ cal.: 629.2 found 630.2).
¹H NMR (CDCl₃, 400 MHz) δ=8.12-8.05 (m, 2H), 7.87-7.85 (m, 1H), 7.40-7.23 (m, 12H), 7.14-7.09 (m, 4H), 7.01-6.93 (m, 4H), 6.86-6.77 (m, 3H)

Synthesis Example 7: Synthesis of Compound 10

Compound 10 was synthesized in substantially the same manner as in Synthesis of Compound 1, except that Intermediate I-6 was reacted with 2-bromo-9-phenyl-9H-carbazole (yield: 78%). The obtained compound was identified by LC-MS and ¹H NMR. ($C_{42}H_{27}F_2N_3$ M+ cal.: 611.2 found 612.2).
¹H NMR (CDCl₃, 400 MHz) δ=8.12-8.05 (m, 2H), 7.92-7.90 (m, 1H), 7.55-7.47 (m, 8H), 7.40-7.21 (m, 10H), 7.15-7.06 (m, 2H), 6.96 (dd, 1H), 6.92-6.85 (m, 2H), 6.72-6.69 (m, 1H)

Synthesis Example 8: Synthesis of Compound 16

Compound 16 was synthesized in substantially the same manner as in Synthesis of Compound 1, except that Intermediate I-7 was reacted with 2-bromo-9-phenyl-9H-carbazole (yield: 78%). The obtained compound was identified by LC-MS and ¹H NMR. ($C_{61}H_{40}FN_3$ M+ cal.: 833.3. found 834.3).
¹H NMR (CDCl₃, 400 MHz) δ=8.12-8.05 (m, 2H), 7.92-7.85 (m, 2H), 7.55-7.19 (m, 17H), 7.18-7.04 (m, 13H), 6.98 (d, 1H), 6.93-6.87 (m, 3H), 6.83-6.75 (m, 2H)

Synthesis Example 9: Synthesis of Compound 27

Compound 27 was synthesized in substantially the same manner as in Synthesis of Compound 1, except that Intermediate I-8 was reacted with 2-bromo-9-phenyl-9H-carbazole (yield: 83%). The obtained compound was identified by LC-MS and ¹H NMR. ($C_{51}H_{36}FN_3$ M+ cal.: 709.3. found 710.3).
¹H NMR (CDCl₃, 400 MHz) δ=8.14-8.06 (m, 2H), 7.95-7.93 (m, 1H), 7.62-7.48 (m, 5H), 7.40-7.22 (m, 13H), 7.14-7.06 (m, 3H), 6.99-6.84 (m, 5H), 6.68 (d, 1H), 1.61 (s, 6H)

Synthesis Example 10: Synthesis of Compound 30

Compound 30 was synthesized in substantially the same manner as in Synthesis of Compound 1, except that Intermediate I-9 was reacted with 2-bromo-9-(4-fluorophenyl)-9H-carbazole (yield: 81%). The obtained compound was identified by LC-MS and ¹H NMR. ($C_{48}H_{30}FN_3O$ M+ cal.: 683.2. found 684.2).
¹H NMR (CDCl₃, 400 MHz) δ=8.13-8.06 (m, 2H), 7.92 (d, 1H), 7.84 (d, 1H), 7.74 (d, 1H), 7.64-7.47 (m, 7H), 7.44-7.21 (m, 12H), 7.13-7.08 (m, 2H), 6.98-6.93 (m, 3H), 6.78-6.74 (m, 1H)

Synthesis Example 11: Synthesis of Compound 35

Compound 35 was synthesized in substantially the same manner as in Synthesis of Compound 1, except that Intermediate I-10 was reacted with 2-bromo-9-phenyl-9H-carbazole (yield: 80%). The obtained compound was identified by LC-MS and ¹H NMR. ($C_{48}H_{30}FN_3O$ M+ cal.: 683.2. found 684.2).
¹H NMR (CDCl₃, 400 MHz) δ=8.12-8.05 (m, 2H), 7.95 (d, 1H), 7.79 (d, 1H), 7.73 (d, 1H), 7.55-7.23 (m, 19H), 7.4-7.06 (m, 2H), 6.98-6.93 (m, 2H), 6.87-6.78 (m, 2H)

Synthesis Example 12: Synthesis of Compound 43

Compound 43 was synthesized in substantially the same manner as in Synthesis of Compound 1, except that Intermediate I-11 was reacted with 2-bromo-9-phenyl-9H-carbazole (yield: 80%). The obtained compound was identified by LC-MS and ¹H NMR. ($C_{48}H_{30}FN_3S$ M+ cal.: 699.2. found 700.2).
¹H NMR (CDCl₃, 400 MHz) δ=8.12-8.05 (m, 2H), 7.96-7.93 (m, 2H), 7.80 (dd, 1H), 7.67 (d, 1H), 7.56-7.21 (m, 18H), 7.13-7.07 (m, 2H), 7.02-6.94 (m, 2H), 6.89-6.82 (m, 2H)

Synthesis Example 13: Synthesis of Compound 56

Compound 56 was synthesized in substantially the same manner as in Synthesis of Compound 1, except that Intermediate I-12 was reacted with 2-bromo-9-(3-fluorophenyl)-9H-carbazole (yield: 84%). The obtained compound was identified by LC-MS and $^1$H NMR. ($C_{42}H_{27}F_2N_3$ M+ cal.: 611.2. found 612.2).

$^1$H NMR (CDCl$_3$, 400 MHz) δ=8.07-8.03 (m, 2H), 7.92 (d, 2H), 7.43-7.19 (m, 12H), 7.12-7.01 (m, 6H), 6.97 (d, 2H), 6.87-6.73 (m, 3H)

Synthesis Example 14: Synthesis of Compound 71

Compound 71 was synthesized in substantially the same manner as in Synthesis of Compound 1, except that Intermediate I-13 was reacted with 2-bromo-9-(4-fluorophenyl)-9H-carbazole (yield: 82%). The obtained compound was identified by LC-MS and $^1$H NMR. ($C_{48}H_{30}FN_3O$ M+ cal.: 683.2. found 684.2).

$^1$H NMR (CDCl$_3$, 400 MHz) δ=8.07-8.03 (m, 2H), 7.94 (d, 1H), 7.79-7.70 (m, 3H), 7.55-7.19 (m, 18H), 7.11-6.99 (m, 2H), 6.96-6.91 (m, 3H), 6.86-6.81 (m, 1H)

Synthesis Example 15: Synthesis of Compound 79

Compound 79 was synthesized in substantially the same manner as in Synthesis of Compound 1, except that Intermediate I-14 was reacted with 9-([1,1'-biphenyl]-3-yl)-2-bromo-9H-carbazole (yield: 81%). The obtained compound was identified by LC-MS and $^1$H NMR. ($C_{48}H_{32}FN_3$ M+ cal.: 669.3. found 670.3).

$^1$H NMR (CDCl$_3$, 400 MHz) δ=8.07-8.03 (m, 2H), 7.97-7.90 (m, 2H), 7.74-7.66 (m, 3H), 7.55-7.17 (m, 17H), 7.08-6.96 (m, 5H), 6.89-6.81 (m, 2H), 6.74-6.71 (m, 1H)

Synthesis Example 16: Synthesis of Compound 82

Compound 82 was synthesized in substantially the same manner as in Synthesis of Compound 1, except that Intermediate I-15 was reacted with 2-bromo-9-(3-fluorophenyl)-9H-carbazole (yield: 84%). The obtained compound was identified by LC-MS and $^1$H NMR. ($C_{42}H_{28}FN_3$ M+ cal.: 593.2. found 594.2).

$^1$H NMR (CDCl$_3$, 400 MHz) δ=8.07-8.03 (m, 1H), 7.99 (d, 1H), 7.95 (dd, 1H), 7.59-7.17 (m, 15H), 7.11-6.99 (m, 5H), 6.93-6.87 (m, 3H), 6.73-6.70 (m, 2H)

Synthesis Example 17: Synthesis of Compound 90

Compound 90 was synthesized in substantially the same manner as in Synthesis of Compound 1, except that Intermediate I-16 was reacted with 4-bromo-9-(4-fluorophenyl)-9H-carbazole (yield: 78%). The obtained compound was identified by LC-MS and $^1$H NMR. ($C_{51}H_{36}FN_3$ M+ cal.: 709.3. found 710.3).

$^1$H NMR (CDCl$_3$, 400 MHz) δ=8.07-8.03 (m, 1H), 7.99 (d, 1H), 7.94 (d, 1H), 7.78 (dd, 1H), 7.65 (dd, 1H), 7.57-7.19 (m, 17H), 7.14-6.98 (m, 4H), 6.92 (d, 1H), 6.82-6.74 (m, 3H), 1.62 (s, 6H)

Synthesis Example 18: Synthesis of Compound 95

Compound 95 was synthesized in substantially the same manner as in Synthesis of Compound 1, except that Intermediate I-14 was reacted with 4-bromo-9-phenyl-9H-carbazole (yield: 80%). The obtained compound was identified by LC-MS and $^1$H NMR. ($C_{42}H_{28}FN_3$ M+ cal.: 593.2. found 594.2).

$^1$H NMR (CDCl$_3$, 400 MHz) δ=8.07-8.03 (m, 1H), 7.98 (d, 1H), 7.95 (d, 1H), 7.61-7.17 (m, 17H), 7.10-6.98 (m, 3H), 6.87-6.72 (m, 4H), 6.68-6.65 (m, 1H)

Synthesis Example 19: Synthesis of Compound 98

Compound 98 was synthesized in substantially the same manner as in Synthesis of Compound 1, except that Intermediate I-17 was reacted with 1-bromo-9-(4-fluorophenyl)-9H-carbazole (yield: 78%). The obtained compound was identified by LC-MS and $^1$H NMR. ($C_{42}H_{27}F_2N_3$ M+ cal.: 611.2. found 612.2).

$^1$H NMR (CDCl$_3$, 400 MHz) δ=8.16 (d, 2H), 7.65 (d, 2H), 7.90 (d, 2H), 7.43 (dt, 2H), 7.29-7.11 (m, 12H), 7.04-6.96 (m, 2H), 6.84-6.74 (m, 3H), 6.69 (d, 2H)

Synthesis Example 20: Synthesis of Compound 111

Compound 111 was synthesized in substantially the same manner as in Synthesis of Compound 1, except that Intermediate I-17 was reacted with 2-bromo-9-phenyl-9H-carbazole (yield: 85%). The obtained compound was identified by LC-MS and $^1$H NMR. ($C_{42}H_{28}FN_3$ M+ cal.: 593.2. found 594.2).

$^1$H NMR (CDCl$_3$, 400 MHz) δ=8.16 (d, 1H), 8.07 (dd, 1H), 7.96 (d, 1H), 7.65-7.22 (m, 14H), 7.16-7.07 (m, 4H), 7.03-6.91 (m, 4H), 6.85-6.75 (m, 3H)

Synthesis Example 21: Synthesis of Compound 133

Compound 133 was synthesized in substantially the same manner as in Synthesis of Compound 1, except that Intermediate I-18 was reacted with 2-bromo-9-(4-fluorophenyl)-9H-carbazole (yield: 81%). The obtained compound was identified by LC-MS and $^1$H NMR. ($C_{48}H_{30}FN_3S$ M+ cal.: 699.2. found 700.2).

$^1$H NMR (CDCl$_3$, 400 MHz) δ=8.12-8.05 (d, 2H), 7.99 (d, 1H), 7.83-7.75 (m, 4H), 7.62-7.19 (m, 17H), 7.11-6.97 (m, 4H), 6.87 (t, 1H), 6.77 (d, 1H)

Synthesis Example 22: Synthesis of Compound 138

Compound 138 was synthesized in substantially the same manner as in Synthesis of Compound 1, except that Intermediate I-1 was reacted with 1-bromo-9-phenyl-9H-carbazole (yield: 77%). The obtained compound was identified by LC-MS and $^1$H NMR. ($C_{42}H_{28}FN_3S$ M+ cal.: 593.2. found 594.2).

$^1$H NMR (CDCl$_3$, 400 MHz) δ=8.12 (d, 2H), 7.62-7.25 (m, 19H), 7.14 (t, 1H), 7.05-6.95 (m, 3H), 6.86-6.74 (m, 3H)

Synthesis Example 23: Synthesis of Compound 140

Compound 140 was synthesized in substantially the same manner as in Synthesis of Compound 1, except that Intermediate I-3 was reacted with 1-bromo-9-phenyl-9H-carbazole (yield: 76%). The obtained compound was identified by LC-MS and $^1$H NMR. ($C_{42}H_{28}FN_3S$ M+ cal.: 593.2. found 594.2).

$^1$H NMR (CDCl$_3$, 400 MHz) δ=8.12 (dd, 2H), 7.59-7.23 (m, 16H), 7.18-7.04 (m, 5H), 7.02 (d, 1H), 6.95-6.90 (m, 2H), 6.84-6.80 (m, 2H)

Synthesis Example 24: Synthesis of Compound 163

Compound 163 was synthesized in substantially the same manner as in Synthesis of Compound 1, except that Intermediate I-19 was reacted with 1-bromo-9-phenyl-9H-carbazole (yield: 77%). The obtained compound was identified by LC-MS and $^1$H NMR. ($C_{48}H_{30}FN_3O$ M+ cal.: 683.2. found 684.2).
$^1$H NMR (CDCl$_3$, 400 MHz) δ=8.12 (d, 1H), 7.94 (s, 1H), 7.87-7.81 (m, 2H), 7.74 (d, 1H), 7.59-7.24 (m, 20H), 7.11-7.04 (m, 3H), 6.89-6.84 (m, 2H)

Synthesis Example 25: Synthesis of Compound 166

Compound 166 was synthesized in substantially the same manner as in Synthesis of Compound 1, except that Intermediate I-20 was reacted with 1-bromo-9-phenyl-9H-carbazole (yield: 78%). The obtained compound was identified by LC-MS and $^1$H NMR. ($C_{42}H_{28}FN_3$ M+ cal.: 593.2. found 594.2).
$^1$H NMR (CDCl$_3$, 400 MHz) δ=8.12 (d, 1H), 8.01 (d, 1H), 7.60-7.07 (m, 20H), 6.99-6.93 (m, 3H), 6.83-6.79 (m, 2H), 6.74 (d, 1H)

Synthesis Example 26: Synthesis of Compound 168

Compound 168 was synthesized in substantially the same manner as in Synthesis of Compound 1, except that Intermediate I-21 was reacted with 4-bromo-9-(4-fluorophenyl)-9H-carbazole (yield: 77%). The obtained compound was identified by LC-MS and $^1$H NMR. ($C_{42}H_{28}FN_3$ M+ cal.: 593.2. found 594.2).
$^1$H NMR (CDCl$_3$, 400 MHz) δ=8.12 (d, 1H), 8.02 (d, 1H), 7.60-7.22 (m, 14H), 7.15-7.05 (m, 7H), 7.01 (d, 1H), 6.84-6.74 (m, 4H)

Synthesis Example 27: Synthesis of Compound 180

Compound 180 was synthesized in substantially the same manner as in Synthesis of Compound 1, except that Intermediate I-22 was reacted with 9-([1,1'-biphenyl]-3-yl)-1-bromo-9H-carbazole (yield: 75%). The obtained compound was identified by LC-MS and $^1$H NMR. ($C_{54}H_{36}FN_3$ M+ cal.: 745.3. found 746.3).
$^1$H NMR (CDCl$_3$, 400 MHz) δ=8.16 (d, 1H), 8.05 (d, 1H), 7.75-7.50 (m, 13H), 7.45-7.08 (m, 15H), 6.98-6.92 (m, 3H), 6.86-6.82 (m, 2H), 6.75 (d, 1H)

Synthesis Example 28: Synthesis of Compound 193

Compound 193 was synthesized in substantially the same manner as in Synthesis of Compound 1, except that Intermediate I-23 was reacted with 4-bromo-9-phenyl-9H-carbazole (yield: 77%). The obtained compound was identified by LC-MS and $^1$H NMR. ($C_{42}H_{28}FN_3$ M+ cal.: 593.2. found 594.2).
$^1$H NMR (CDCl$_3$, 400 MHz) δ=8.03 (d, 2H), 7.59-7.40 (m, 12H), 7.34-7.15 (m, 6H), 7.08 (t, 2H), 6.94-6.89 (m, 2H), 6.80-6.74 (m, 4H)

Synthesis Example 29: Synthesis of Compound 205

Compound 205 was synthesized in substantially the same manner as in Synthesis of Compound 1, except that Intermediate I-24 was reacted with 4-bromo-9-phenyl-9H-carbazole (yield: 77%). The obtained compound was identified by LC-MS and $^1$H NMR. ($C_{48}H_{32}FN_3$ M+ cal.: 669.3. found 670.3).
$^1$H NMR (CDCl$_3$, 400 MHz) δ=8.01 (d, 2H), 7.61-7.22 (m, 19H), 7.17-7.04 (m, 7H), 6.95 (t, 1H), 6.87 (d, 2H), 6.73-6.69 (m, 1H)

Synthesis Example 30: Synthesis of Compound 220

Compound 220 was synthesized in substantially the same manner as in Synthesis of Compound 1, except that Intermediate I-25 was reacted with 5-bromo-3-fluoro-9-phenyl-9H-carbazole (yield: 72%). The obtained compound was identified by LC-MS and $^1$H NMR. ($C_{42}H_{28}FN_3$ M+ cal.: 593.2. found 594.2).
$^1$H NMR (CDCl$_3$, 400 MHz) δ=8.01 (d, 1H), 7.81 (d, 1H), 7.70 (d, 1H), 7.59-7.41 (m, 10H), 7.34-7.15 (m, 5H), 7.11-7.01 (m, 5H), 6.96-6.87 (m, 3H), 6.71-6.67 (m, 2H)

Synthesis Example 31: Synthesis of Compound 221

Compound 221 was synthesized in substantially the same manner as in Synthesis of Compound 1, except that Intermediate I-26 was reacted with 1-bromo-9-(4-fluorophenyl)-9H-carbazole (yield: 70%). The obtained compound was identified by LC-MS and $^1$H NMR. ($C_{42}H_{27}F_2N_3$ M+ cal.: 611.2. found 612.2).
$^1$H NMR (CDCl$_3$, 400 MHz) δ=8.12 (d, 2H), 7.60-7.56 (m, 4H), 7.43 (dt, 2H), 7.30-7.23 (m, 6H), 7.18-7.06 (m, 8H), 6.99 (d, 2H), 6.84-6.69 (m, 3H)

Synthesis Example 32: Synthesis of Compound 225

Compound 225 was synthesized in substantially the same manner as in Synthesis of Compound 1, except that Intermediate I-27 was reacted with 1-bromo-9-(4-fluorophenyl)-9H-carbazole (yield: 75%). The obtained compound was identified by LC-MS and $^1$H NMR. ($C_{51}H_{35}F_2N_3$ M+ cal.: 727.3. found 728.3).
$^1$H NMR (CDCl$_3$, 400 MHz) δ=12 (d, 2H), 8.08 (s, 1H), 7.78 (d, 1H), 7.60-7.23 (m, 14H), 7.14-7.04 (m, 7H), 6.94-6.83 (m, 3H), 6.64 (d, 1H), 1.61 (s, 6H)

Synthesis Example 33: Synthesis of Compound 227

Compound 227 was synthesized in substantially the same manner as in Synthesis of Compound 1, except that Intermediate I-28 was reacted with 2-bromo-9-(4-fluorophenyl)-9H-carbazole (yield: 81%). The obtained compound was identified by LC-MS and $^1$H NMR. ($C_{42}H_{27}F_2N_3$ M+ cal.: 611.2. found 612.2).
$^1$H NMR (CDCl$_3$, 400 MHz) δ=8.07 (d, 2H), 7.87 (d, 2H), 7.39-7.24 (m, 10H), 7.11-7.05 (m, 6H), 6.98 (dd, 2H), 6.87 (d, 2H), 6.77-6.68 (m, 3H)

Synthesis Example 34: Synthesis of Compound 228

Compound 228 was synthesized in substantially the same manner as in Synthesis of Compound 1, except that Intermediate I-29 was reacted with 2-bromo-9-(4-fluorophenyl)-9H-carbazole (yield: 80%). The obtained compound was identified by LC-MS and $^1$H NMR. ($C_{42}H_{26}F_3N_3$ M+ cal.: 629.2. found 630.2).
$^1$H NMR (CDCl$_3$, 400 MHz) δ=8.06 (d, 2H), 7.87 (d, 2H), 7.40-7.24 (m, 10H), 7.12-7.04 (m, 4H), 6.99-6.87 (m, 6H), 6.80-6.75 (m, 2H)

Synthesis Example 35: Synthesis of Compound 229

Compound 229 was synthesized in substantially the same manner as in Synthesis of Compound 1, except that Intermediate I-30 was reacted with 2-bromo-9-(4-fluorophenyl)-

9H-carbazole (yield: 79%). The obtained compound was identified by LC-MS and $^1$H NMR. ($C_{48}H_{29}F_2N_3O$ M+ cal.: 701.2. found 702.2).

$^1$H NMR (CDCl$_3$, 400 MHz) δ=8.06 (dd, 2H), 7.84 (dd, 1H), 7.73-7.70 (m, 3H), 7.55 (dd, 1H), 7.48-7.24 (m, 12H), 7.14-7.02 (m, 8H), 6.86 (d, 2H)

Synthesis Example 36: Synthesis of Compound 232

Compound 232 was synthesized in substantially the same manner as in Synthesis of Compound 1, except that Intermediate I-31 was reacted with 4-bromo-9-(4-fluorophenyl)-9H-carbazole (yield: 72%). The obtained compound was identified by LC-MS and $^1$H NMR. ($C_{42}H_{26}F_3N_3$ M+ cal.: 629.2. found 630.2).

$^1$H NMR (CDCl$_3$, 400 MHz) δ=8.01 (d, 2H), 7.59 (d, 2H), 7.45-7.22 (m, 8H), 7.15-7.03 (m, 8H), 6.94-6.89 (m, 2H), 6.80-6.73 (m, 4H)

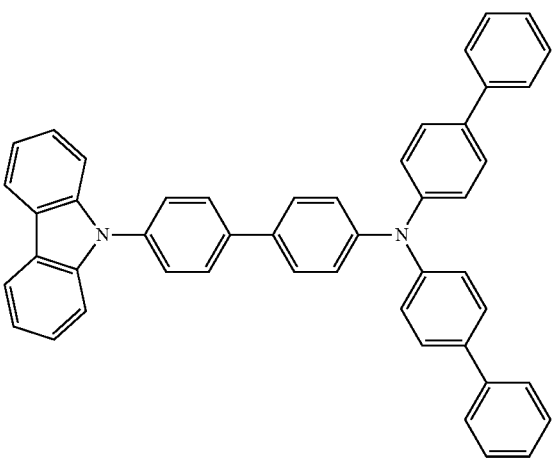

A

EXAMPLES

Example 1

A substrate, on which ITO, Ag, and ITO were deposited at a thickness of about 70 Å, 1,000 Å, and 70 Å, respectively, was cut to a size of 50 millimeters (mm)×50 mm×0.5 mm, sonicated in isopropyl alcohol and pure water for 5 minutes in each solvent, and cleaned by exposure to ultraviolet rays for 30 minutes and then exposed to ozone to use the glass substrate as an anode. Then, the glass substrate was mounted on a vacuum-deposition device.

Compound 1 and F4-TCNQ were co-vacuum-deposited on the ITO substrate at a weight ratio of 98:2 to form a hole injection layer having a thickness of 100 Å. Subsequently, Compound 1 was vacuum-deposited on the hole injection layer to form a first hole transport layer having a thickness of 1,200 Å. N,N-di([1,1'-biphenyl]-4-yl)-4'-(9H-carbazol-9-yl)-[1,1'-biphenyl]-4-amine (Compound A) was vacuum-deposited on the first hole transport layer to form a second hole transport layer having a thickness of 100 Å. Then, 9,10-di-naphthalene-2-yl-anthracene (hereinafter, referred to as "ADN") as a blue fluorescent host and N1,N1,N6,N6-tetraphenylpyrene-1,6-diamine (hereinafter, referred to as "TPA") as a blue fluorescent dopant were co-deposited on the second hole transport layer at a weight ratio of about 98:2 to form an emission layer having a thickness of about 300 Å. Next, 2-(4-(9,10-di(naphthalen-2-yl)anthracen-2-yl)phenyl)-1-phenyl-1H-benzo[d] imidazole (Compound B), i.e., an electron transport compound, and LiQ were co-deposited at a ratio of 5:5 on the emission layer to form an electron transport layer having a thickness of 300 Å. LiF, i.e., halogenated alkaline metal, was then deposited on the electron transport layer to form an electron injection layer having a thickness of 10 Å. MgAg was vacuum-deposited at a weight ratio of 90:10 on the electron injection layer to form a cathode having a thickness of 120 Å, thereby completing the manufacture of an organic light-emitting device.

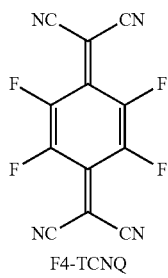

F4-TCNQ

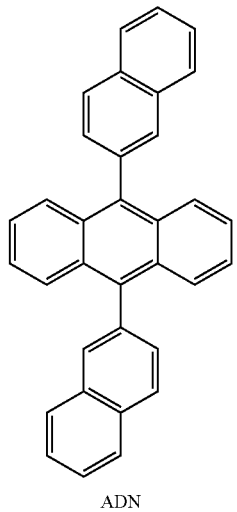

ADN

-continued

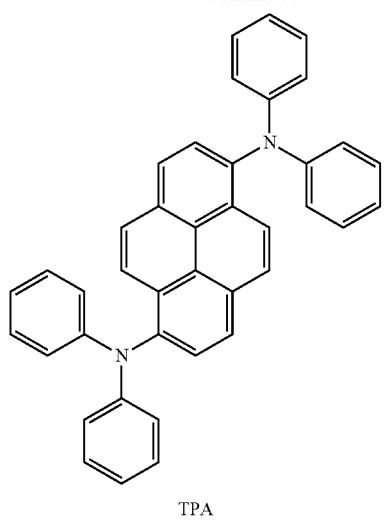

TPA

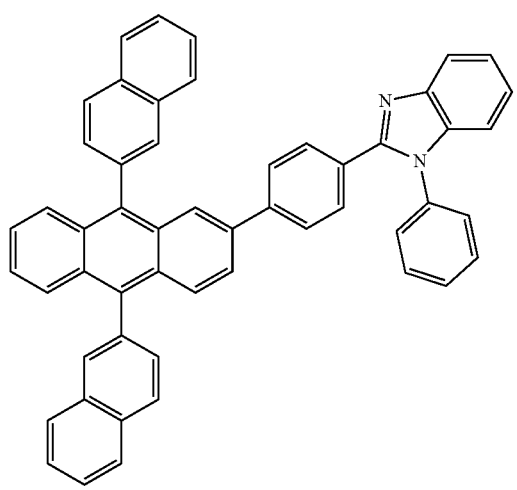

B

Examples 2 to 30

Organic light-emitting devices were manufactured in substantially the same manner as in Example 1, except that the compounds shown in Table 1 were used instead of Compound 1 in the formation of the first hole transport layer.

Comparative Examples 1 to 7

Organic light-emitting devices were manufactured in substantially the same manner as in Example 1, except that N4,N4'-di(naphthalen-1-yl)-N4,N4'-diphenyl-[1,1'-biphenyl]-4,4'-diamine (NPB), Compounds C to G, and Compound A8 were used instead of Compound 1 in the formation of the first hole transport layer.

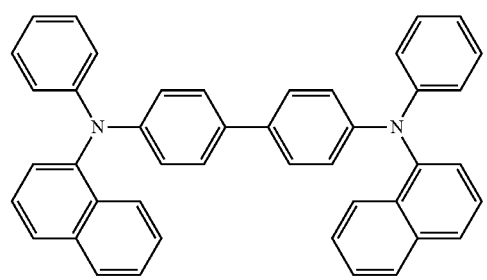

NPB

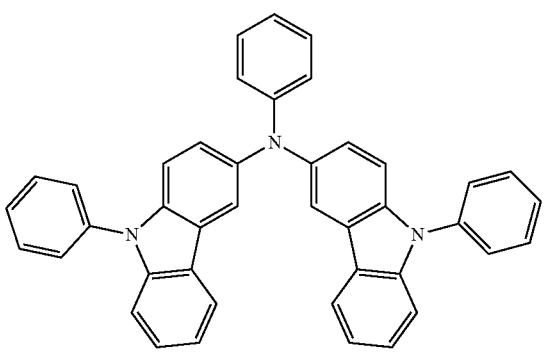

C

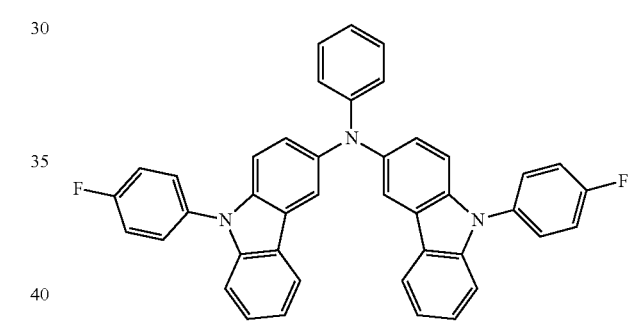

D

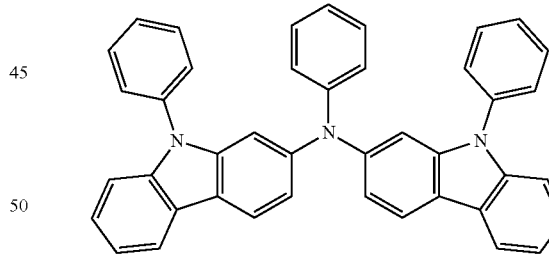

E

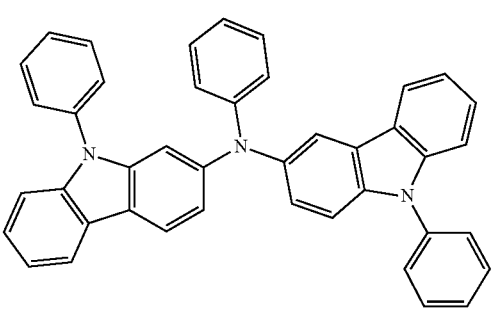

F

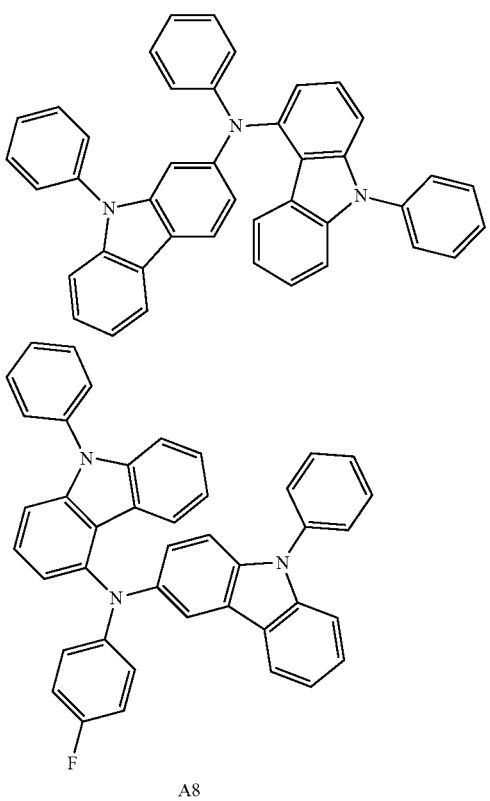

A8

Example 31

Compound 1 and F4-TCNQ were co-vacuum-deposited on the ITO substrate at a weight ratio of 98:2 to form a hole injection layer having a thickness of 100 Å. Subsequently, Compound 1 was vacuum-deposited on the hole injection layer to form a first hole transport layer having a thickness of 1,200 Å. Compound 221 was vacuum-deposited on the first hole transport layer to form a second hole transport layer having a thickness of 100 Å. Then, ADN as a blue fluorescent host and TPA as a blue fluorescent dopant were co-deposited on the second hole transport layer at a weight ratio of about 98:2 to form an emission layer having a thickness of about 300 Å. Next, Compound B, i.e., an electron transport compound, and LiQ were co-deposited at a ratio of 5:5 on the emission layer to form an electron transport layer having a thickness of 300 Å. LiF, i.e., halogenated alkaline metal, was then deposited on the electron transport layer to form an electron injection layer having a thickness of 10 Å. MgAg was vacuum-deposited at a weight ratio of 90:10 on the electron injection layer to form a cathode having a thickness of 120 Å, thereby completing the manufacture of an organic light-emitting device.

Examples 32 to 36

Organic light-emitting devices were manufactured in substantially the same manner as in Example 31, except that the compounds shown in Table 2 were used instead of Compound 221 in the formation of the second hole transport layer.

The performances (driving voltage, luminance, efficiency, and color-coordinate) of the organic light-emitting devices manufactured in Examples 1 to 36 and Comparative Examples 1 to 7 while driving at a current density of 10 mA/cm$^2$ were evaluated. T97 lifespan was also measured at a current density of 1.0 mA/cm$^2$, which indicates time (hour) for the luminance of each organic light-emitting device to decline to 97% of its initial luminance. The evaluation results are shown in Tables 1 and 2.

TABLE 1

| | First hole transport layer | Driving voltage (V) | Current density (mA/cm$^2$) | Efficiency (cd/A) | Color-coordinate CIE (x, y) | T97 lifespan (@1.0 mA/cm$^2$) |
|---|---|---|---|---|---|---|
| Example 1 | Compound 1 | 4.4 | 10 | 4.87 | 0.140, 0.051 | 133 |
| Example 2 | Compound 2 | 4.3 | 10 | 4.92 | 0.141, 0.052 | 158 |
| Example 3 | Compound 4 | 4.2 | 10 | 5.01 | 0.141, 0.050 | 163 |
| Example 4 | Compound 5 | 4.4 | 10 | 4.96 | 0.140, 0.052 | 143 |
| Example 5 | Compound 7 | 4.4 | 10 | 4.93 | 0.141, 0.052 | 165 |
| Example 6 | Compound 8 | 4.2 | 10 | 5.10 | 0.141, 0.052 | 118 |
| Example 7 | Compound 10 | 4.6 | 10 | 5.35 | 0.142, 0.051 | 79 |
| Example 8 | Compound 16 | 4.5 | 10 | 4.98 | 0.140, 0.053 | 175 |
| Example 9 | Compound 27 | 4.4 | 10 | 5.19 | 0.141, 0.052 | 149 |
| Example 10 | Compound 30 | 4.5 | 10 | 5.21 | 0.141, 0.054 | 141 |
| Example 11 | Compound 35 | 4.2 | 10 | 5.36 | 0.141, 0.052 | 177 |
| Example 12 | Compound 43 | 4.3 | 10 | 5.24 | 0.141, 0.052 | 137 |
| Example 13 | Compound 56 | 4.3 | 10 | 4.79 | 0.141, 0.052 | 141 |
| Example 14 | Compound 71 | 4.3 | 10 | 5.13 | 0.141, 0.052 | 152 |

TABLE 1-continued

|  | First hole transport layer | Driving voltage (V) | Current density (mA/cm$^2$) | Efficiency (cd/A) | Color-coordinate CIE (x, y) | T97 lifespan (@1.0 mA/cm$^2$) |
|---|---|---|---|---|---|---|
| Example 15 | Compound 79 | 4.5 | 10 | 4.99 | 0.141, 0.052 | 133 |
| Example 16 | Compound 82 | 4.4 | 10 | 4.85 | 0.141, 0.052 | 126 |
| Example 17 | Compound 90 | 4.5 | 10 | 5.01 | 0.141, 0.052 | 141 |
| Example 18 | Compound 95 | 4.4 | 10 | 4.93 | 0.141, 0.052 | 132 |
| Example 19 | Compound 98 | 4.4 | 10 | 4.97 | 0.141, 0.052 | 143 |
| Example 20 | Compound 111 | 4.5 | 10 | 4.86 | 0.141, 0.052 | 119 |
| Example 21 | Compound 133 | 4.6 | 10 | 5.09 | 0.141, 0.052 | 134 |
| Example 22 | Compound 138 | 4.5 | 10 | 4.97 | 0.141, 0.052 | 121 |
| Example 23 | Compound 140 | 4.4 | 10 | 4.91 | 0.141, 0.052 | 139 |
| Example 24 | Compound 163 | 4.4 | 10 | 5.12 | 0.141, 0.052 | 145 |
| Example 25 | Compound 166 | 4.5 | 10 | 4.97 | 0.141, 0.052 | 128 |
| Example 26 | Compound 168 | 4.4 | 10 | 5.01 | 0.141, 0.052 | 132 |
| Example 27 | Compound 180 | 4.6 | 10 | 5.03 | 0.141, 0.052 | 122 |
| Example 28 | Compound 193 | 4.5 | 10 | 5.01 | 0.141, 0.052 | 127 |
| Example 29 | Compound 205 | 4.4 | 10 | 5.06 | 0.141, 0.052 | 134 |
| Example 30 | Compound 220 | 4.6 | 10 | 4.97 | 0.141, 0.052 | 129 |
| Comparative Example 1 | NPB | 4.6 | 10 | 4.72 | 0.141, 0.051 | 70 |
| Comparative Example 2 | C | 5.1 | 10 | 4.55 | 0.141, 0.052 | 85 |
| Comparative Example 3 | D | 4.7 | 10 | 4.85 | 0.141, 0.051 | 122 |
| Comparative Example 4 | E | 4.5 | 10 | 4.54 | 0.141, 0.053 | 91 |
| Comparative Example 5 | F | 4.5 | 10 | 4.62 | 0.141, 0.052 | 89 |
| Comparative Example 6 | G | 4.6 | 10 | 4.57 | 0.141, 0.051 | 102 |
| Comparative Example 7 | A8 | 4.6 | 10 | 4.83 | 0.141, 0.052 | 119 |

TABLE 2

|  | First hole transport layer | Second hole transport layer | Driving voltage (V) | Current density (mA/cm$^2$) | Efficiency (cd/A) | Color-coordinate CIE(x, y) | T97 lifespan (@1.0 mA/cm$^2$) |
|---|---|---|---|---|---|---|---|
| Example 31 | Compound 1 | Compound 221 | 4.2 | 10 | 5.42 | 0.141, 0.052 | 197 |
| Example 32 | Compound 1 | Compound 225 | 4.2 | 10 | 5.52 | 0.141, 0.052 | 182 |
| Example 33 | Compound 1 | Compound 227 | 4.2 | 10 | 5.38 | 0.141, 0.050 | 179 |
| Example 34 | Compound 1 | Compound 228 | 4.2 | 10 | 5.41 | 0.140, 0.052 | 163 |
| Example 35 | Compound 1 | Compound 229 | 4.2 | 10 | 5.56 | 0.141, 0.052 | 199 |
| Example 36 | Compound 1 | Compound 232 | 4.2 | 10 | 5.43 | 0.141, 0.052 | 185 |

As apparent from Tables 1 and 2, when the compound according to one or more embodiments is used as a hole transport material in organic light-emitting devices, the organic light-emitting device of the Examples including the compound according to one or more embodiments were found to have improved driving voltage, excellent I-V-L characteristics with improved luminescence efficiency, and for example, significant improvement of lifespan due to lifespan improving effects, as compared with the organic light-emitting device of the Comparative Example 1 including NPB. In addition, even in comparison with Comparative Examples 2 to 7 in which Compounds C to G and A8 were used, the organic light-emitting device of the Examples were found to have improved driving voltage, improved luminescence efficiency, and improved T97 lifespan.

As apparent from the foregoing description, an organic light-emitting device including the amine-based compound may have a low driving voltage, high efficiency, long lifespan, and high maximum quantum efficiency.

It should be understood that embodiments described herein should be considered in a descriptive sense only and not for purposes of limitation. Descriptions of features or aspects within each embodiment should typically be considered as available for other similar features or aspects in other embodiments.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical, range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more embodiments have been described with reference to the figures, it will be understood by those of ordinary skill in the art that various changes in form and details may be made therein without departing from the spirit and scope as defined by the following claims, and equivalents thereof.

What is claimed is:

1. An amine-based compound represented by one of Formulae 1-1, 1-2, and 1A-5:

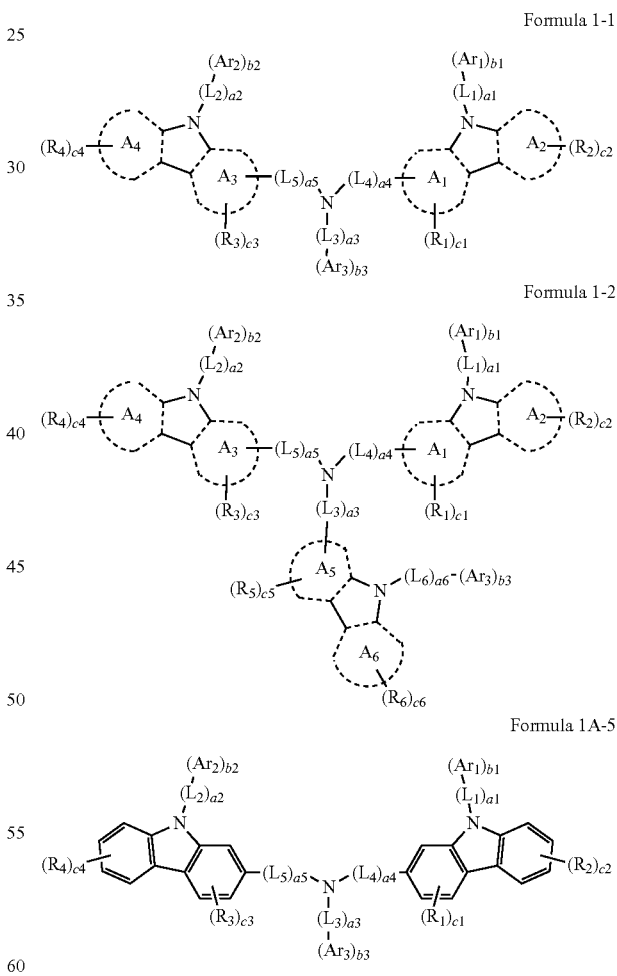

wherein, in Formulae 1-1, 1-2, and 1A-5,
$A_1$ to $A_6$ are each independently selected from a $C_5$-$C_{30}$ cyclic group and a $C_1$-$C_{30}$ heterocyclic group,
$L_1$ to $L_6$ are each independently selected from a substituted or unsubstituted $C_5$-$C_{60}$ carbocyclic group and a substituted or unsubstituted $C_1$-$C_{60}$ heterocyclic group, $a_1$ to $a_6$ are each independently an integer from 0 to 5, when a1 is 2 or greater, at least two $L_1$ groups are identical to or different from each other; when a2 is 2 or greater, at least two $L_2$ groups are identical to or different from each other; when a3 is 2 or greater, at least two $L_3$ groups are identical to or different from each other; when a4 is 2 or greater, at least two $L_4$ groups are identical to or different from each other; when a5 is 2 or greater, at least two $L_5$ groups are identical to or different from each other; when a6 is 2 or greater, at least two $L_6$ groups are identical to or different from each other, when a1 is 0, *-$(L_1)_{a1}$-*' is a single bond; when a2 is 0, *-$(L_2)_{a2}$-*' is a single bond; when a3 is 0, *-$(L_3)_{a3}$-*' is a single bond; when a4 is 0, *-$(L_4)_{a4}$-*' is a single bond; when a5 is 0, *-$(L_5)_{a5}$-*' is a single bond; when a6 is 0, *-$(L_6)_{a6}$-*' is a single bond, $Ar_1$ to $Ar_3$ and $R_1$ to $R_6$ are each independently selected from hydrogen, deuterium, —F, —Cl, —Br, —I, a hydroxyl group, a cyano group, a nitro group, an amino group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —B$(Q_1)(Q_2)$, —C(=O)$(Q_1)$, —N$(Q_1)(Q_2)$, —P(=O)$(Q_1)(Q_2)$, —P(=S)$(Q_1)(Q_2)$, —S(=O)$(Q_1)(Q_2)$, and —S(=O)$_2(Q_1)(Q_2)$, b1 to b3 are each independently an integer from 1 to 5, when b1 is 2 or greater, at least two $Ar_1$ groups are identical to or different from each other; when b2 is 2 or greater, at least two $Ar_2$ groups are identical to or different from each other; when b3 is 2 or greater, at least two $Ar_3$ groups are identical to or different from each other, c1 to c6 are each independently an integer from 1 to 10, when c1 is 2 or greater, at least two $R_1$ groups are identical to or different from each other; when c2 is 2 or greater, at least two $R_2$ groups are identical to or different from each other; when c3 is 2 or greater, at least two $R_3$ groups are identical to or different from each other; when c4 is 2 or greater, at least two $R_4$ groups are identical to or different from each other, when c5 is 2 or greater, at least two $R_5$ groups are identical to or different from each other; when c6 is 2 or greater, at least two $R_6$ groups are identical to or different from each other, the amine-based compound represented by one of Formulae 1-1 and 1-2 comprises at least one —F, wherein when the amine-based compound is represented by Formula 1A-5, $L_1$ to $L_3$ and $Ar_1$ to $Ar_3$ are each independently not a substituted or unsubstituted pyridine group, a substituted or unsubstituted pyrazine group, a substituted or unsubstituted pyrimidine group, a substituted or unsubstituted pyridazine group, or a substituted or unsubstituted triazine group, provided that the amine-based compound represented by one of Formulae 1A-9 and 1A-10 is excluded from Formulae 1-1 and 1-2:

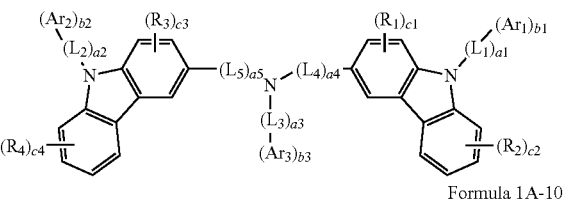

Formula 1A-9

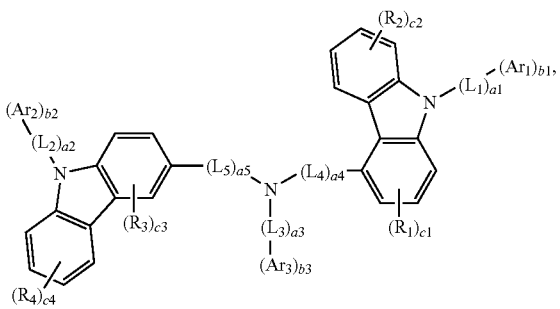

Formula 1A-10 and at least one substituent of the substituted $C_5$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ heteroaryloxy group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amino group, an amidino group, a hydrazino group, a hydrazono group, a C1-C60 alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{11})(Q_{12})(Q_{13})$, —N$(Q_{11})(Q_{12})$, —B$(Q_{11})(Q_{12})$, —C(=O)$(Q_{11})$, —S(=O)$_2(Q_{11})$, and —P(=O)$(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* and *' each indicate a binding site to an adjacent atom.

2. The amine-based compound of claim 1, wherein $A_1$ to $A_6$ are each independently selected from a benzene group, an indene group, a naphthalene group, an anthracene group, a fluorene group, a phenanthrene group, a triphenylene group, a pyrene group, a chrysene group, a naphthacene group, a pyrrole group, an imidazole group, a pyrazole group, a pyridine group, a pyrimidine group, a pyrazine group, a pyridazine group, an indole group, an isoindole group, an indazole group, a quinoline group, an isoquinoline group, a benzoquinoline group, a naphthyridine group, a quinoxaline group, a quinazoline group, a cinnoline group, a carbazole group, a phenanthridine group, an acridine group, a phenanthroline group, a phenazine group, a benzimidazole group, a furan group, a benzofuran group, a thiophene group, a benzothiophene group, a thiazole group, an isothiazole group, a benzothiazole group, an isoxazole group, an oxazole group, a triazole group, an oxadiazole group, a triazine group, a benzoxazole group, a dibenzofuran group, a dibenzothiophene group, a benzocarbazole group, and a dibenzocarbazole group.

3. The amine-based compound of claim 1, wherein $L_1$ to $L_6$ and $Ar_1$ to $Ar_3$ are each independently selected from a benzene group, a pentalene group, an indene group, a naphthalene group, an azulene group, a heptalene group, an indacene group, an acenaphthalene group, a fluorene group, a spiro-bifluorene group, a benzofluorene group, a phenalene group, a phenanthrene group, an anthracene group, a fluoranthene group, a triphenylene group, a pyrene group, a chrysene group, a naphthacene group, a picene group, a perylene group, a pentaphenylene group, a hexacene group, a pentacene group, a rubicene group, a coronene group, an ovalene group, a pyrrole group, an imidazole group, a pyrazole group, a pyridine group, a pyrazine group, a pyrimidine group, a pyridazine group, an isoindole group, an indole group, an indazole group, a purine group, a quinoline group, an isoquinoline group, a benzoquinoline group, a phthalazine group, a naphthyridine group, a quinoxaline group, a quinazoline group, a cinnoline group, a carbazole group, a phenanthridine group, an acridine group, a phenanthroline group, a phenazine group, a benzoxazole group, a benzimidazole group, a furan group, a benzofuran group, a thiophene group, a benzothiophene group, a thiazole group, an isothiazole group, a benzothiazole group, an isoxazole group, an oxazole group, a triazole group, a tetrazole group, an oxadiazole group, a triazine group, a benzoxazole group, a dibenzofuran group, a dibenzothiophene group, a benzocarbazole group, and a dibenzocarbazole group; and a benzene group, a pentalene group, an indene group, a naphthalene group, an azulene group, a heptalene group, an indacene group, an acenaphthalene group, a fluorene group, a spiro-bifluorene group, a benzofluorene group, a phenalene group, a phenanthrene group, an anthracene group, a fluoranthene group, a triphenylene group, a pyrene group, a chrysene group, a naphthacene group, a picene group, a perylene group, a pentaphenylene group, a hexacene group, a pentacene group, a rubicene group, a coronene group, an ovalene group, a pyrrole group, an imidazole group, a pyrazole group, a pyridine group, a pyrazine group, a pyrimidine group, a pyridazine group, an isoindole group, an indole group, an indazole group, a purine group, a quinoline group, an isoquinoline group, a benzoquinoline group, a phthalazine group, a naphthyridine group, a quinoxaline group, a quinazoline group, a cinnoline group, a carbazole group, a phenanthridine group, an acridine group, a phenanthroline group, a phenazine group, a benzoxazole group, a benzimidazole group, a furan group, a benzofuran group, a thiophene group, a benzothiophene group, a thiazole group, an isothiazole group, a benzothiazole group, an isoxazole group, an oxazole group, a triazole group, a tetrazole group, an oxadiazole group, a triazine group, a benzoxazole group, a dibenzofuran group, a dibenzothiophene group, a benzocarbazole group, and a dibenzocarbazole group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzoxazolyl group, a dibenzofuranyl group, a dibenzothiophenyl group, a benzocarbazolyl group, and a dibenzocarbazolyl group, and wherein when the amine-based compound is represented by Formula 1A-5, $L_1$ to $L_3$ and $Ar_1$ to $Ar_3$ are each independently not a substituted or unsubstituted pyridine group, a substituted or unsubstituted pyrazine group, a substituted or unsubstituted pyrimidine group, a substituted or unsubstituted pyridazine group, or a substituted or unsubstituted triazine group.

4. The amine-based compound of claim 1, wherein a4 and a5 in Formula 1-1 are each 0; or a3 to a5 in Formula 1-2 are each 0.

5. The amine-based compound of claim 1, wherein $Ar_1$ to $Ar_3$ are each independently selected from groups represented by Formulae 5-1 to 5-79, wherein when the amine-based compound is represented by Formula 1A-5, $Ar_1$ to $Ar_3$ are each independently selected from groups represented by Formulae 5-1 to 5-20:

Formula 5-1
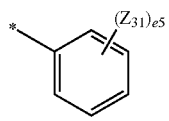

Formula 5-2
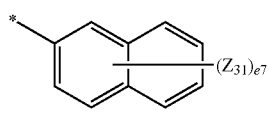

Formula 5-3
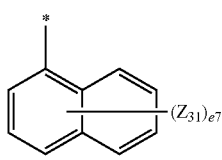

Formula 5-4
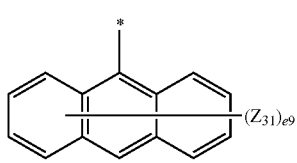

Formula 5-5
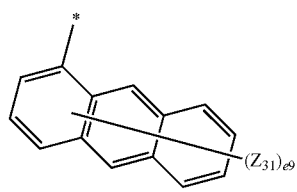

Formula 5-6
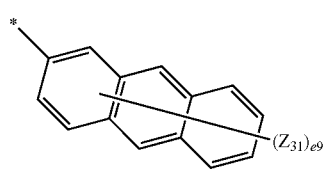

Formula 5-7
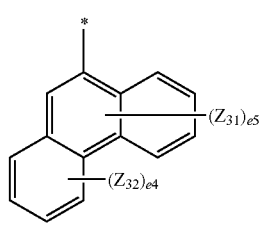

Formula 5-8
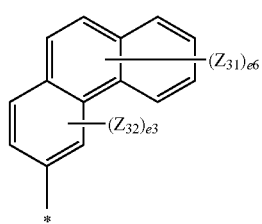

Formula 5-9
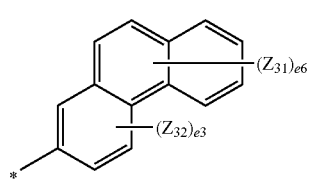

Formula 5-10
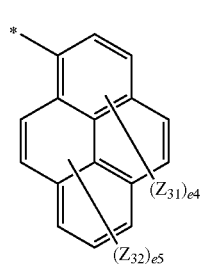

Formula 5-11
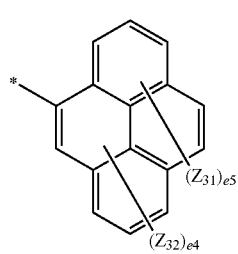

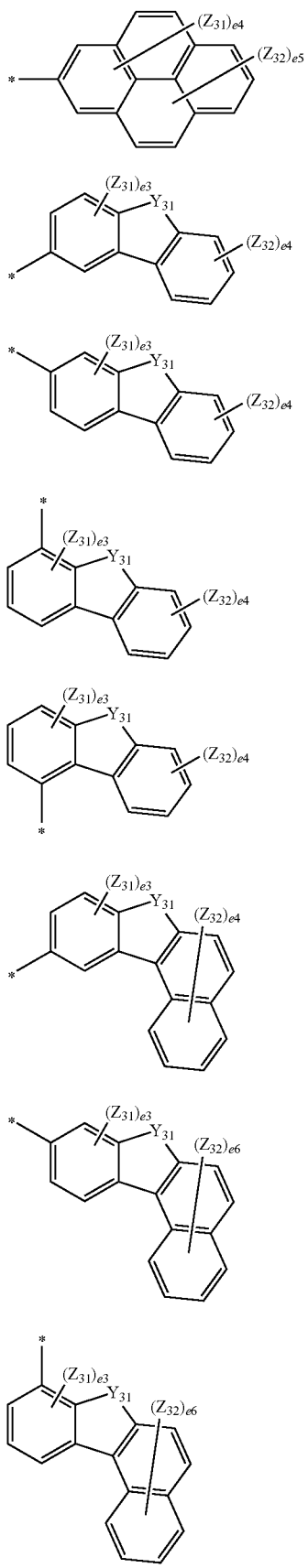
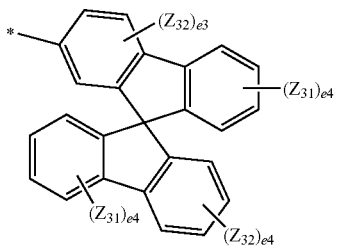
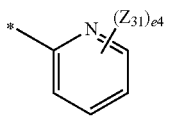
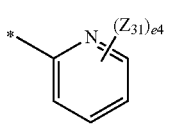
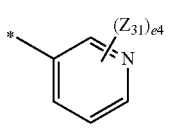
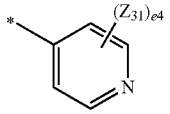
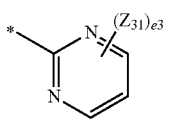
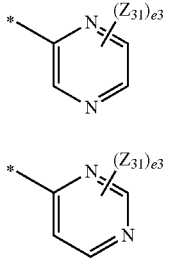
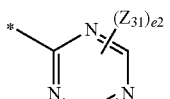
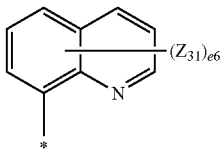

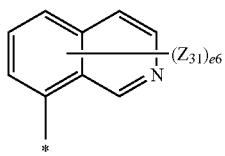
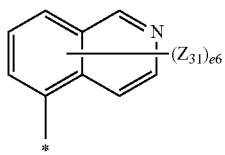
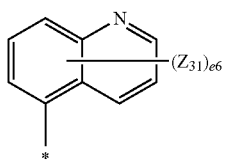
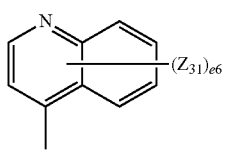
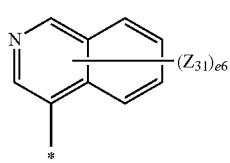
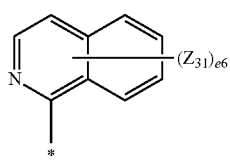
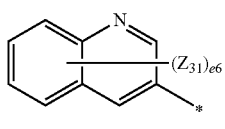
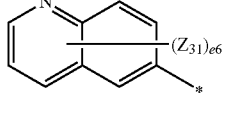
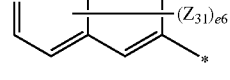
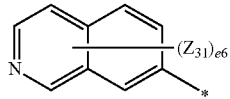
Formula 5-30
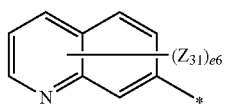
Formula 5-31
Formula 5-32
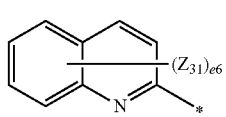
Formula 5-33
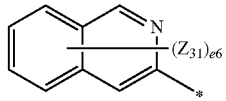
Formula 5-34
Formula 5-35
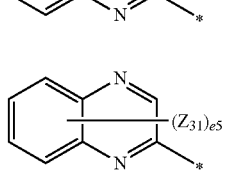
Formula 5-36
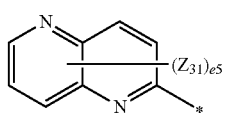
Formula 5-37
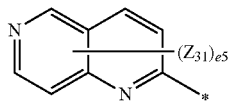
Formula 5-38
Formula 5-39
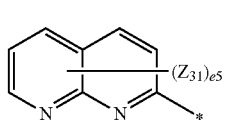
Formula 5-40
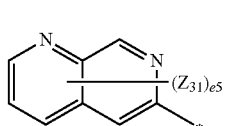
Formula 5-41
Formula 5-42
Formula 5-43
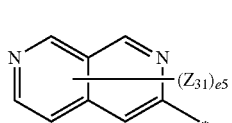
Formula 5-44
Formula 5-45
Formula 5-46
Formula 5-47
Formula 5-48
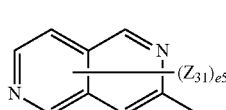
Formula 5-49
Formula 5-50
Formula 5-51
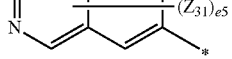

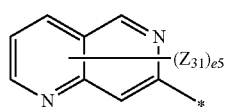
Formula 5-52
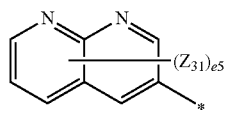
Formula 5-53
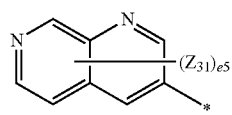
Formula 5-54
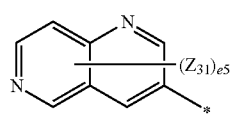
Formula 5-55
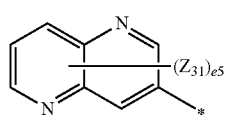
Formula 5-56
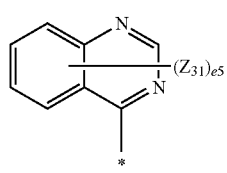
Formula 5-57
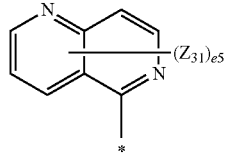
Formula 5-58
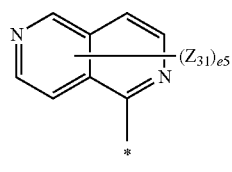
Formula 5-59
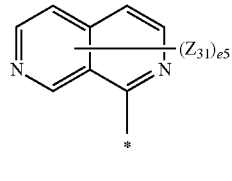
Formula 5-60
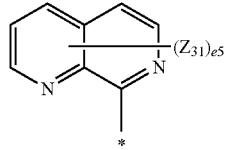
Formula 5-61
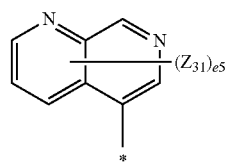
Formula 5-62
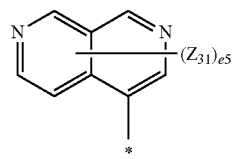
Formula 5-63
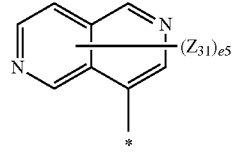
Formula 5-64
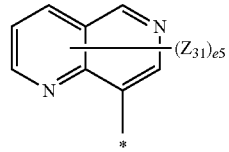
Formula 5-65
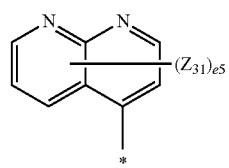
Formula 5-66
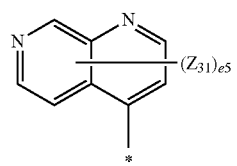
Formula 5-67
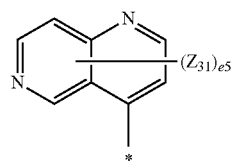
Formula 5-68
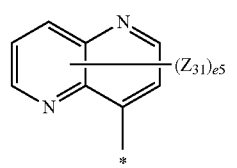
Formula 5-69
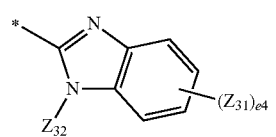
Formula 5-70

-continued

Formula 5-71
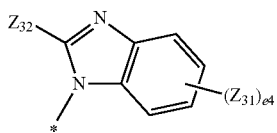

Formula 5-72
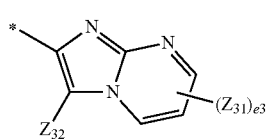

Formula 5-73
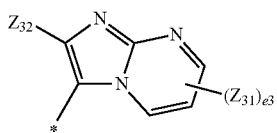

Formula 5-74
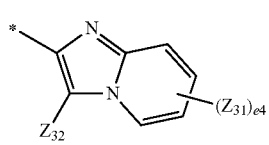

Formula 5-75
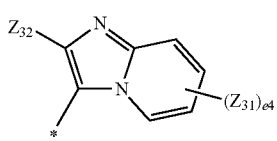

Formula 5-76
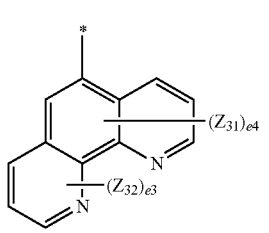

Formula 5-77
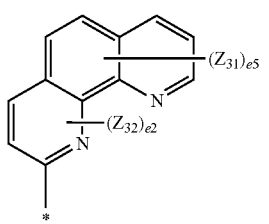

Formula 5-78
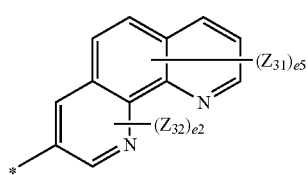

Formula 5-79
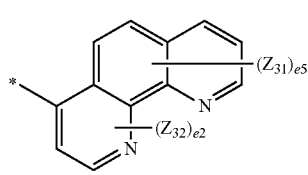

wherein, in Formulae 5-1 to 5-79, $Y_{31}$ is selected from O, S, $C(Z_{33})(Z_{34})$, $N(Z_{35})$, and $Si(Z_{36})(Z_{37})$, $Z_{31}$ to $Z_{37}$ are each independently selected from hydrogen, deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group, e2 is an integer from 0 to 2; when e2 is 2 or greater, at least two of each of groups represented by $Z_{31}$ and groups represented by $Z_{32}$ are identical to or different from each other, e3 is an integer from 0 to 3; when e3 is 2 or greater, at least two of each of groups represented by $Z_{31}$ and groups represented by $Z_{32}$ are identical to or different from each other, e4 is an integer from 0 to 4; when e4 is 2 or greater, at least two of each of groups represented by $Z_{31}$ and groups represented by $Z_{32}$ are identical to or different from each other, e5 is an integer from 0 to 5; when e5 is 2 or greater, at least two of each of groups represented by $Z_{31}$ and groups represented by $Z_{32}$ are identical to or different from each other, e6 is an integer from 0 to 6; when e6 is 2 or greater, at least two of each of groups represented by $Z_{31}$ and groups represented by $Z_{32}$ are identical to or different from each other, e7 is an integer from 0 to 7; when e7 is 2 or greater, at least two $Z_{31}$ groups are identical to or different from each other, e9 is an integer from 0 to 9; when e9 is 2 or greater, at least two $Z_{31}$ groups are identical to or different from each other, and

* indicates a binding site to an adjacent atom.

6. The amine-based compound of claim 1, wherein at least one of $Ar_1$ to $Ar_3$ is selected from groups represented by Formulae 7-1 to 7-9:

Formula 7-1

Formula 7-2

-continued

Formula 7-3
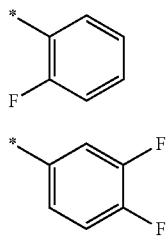

Formula 7-4
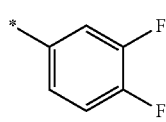

Formula 7-5
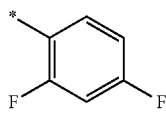

Formula 7-6
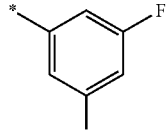

Formula 7-7
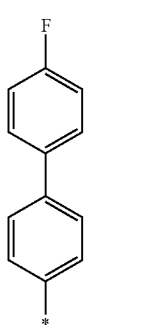

Formula 7-8
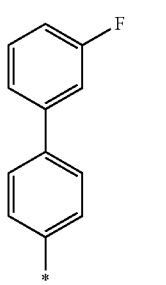

Formula 7-9
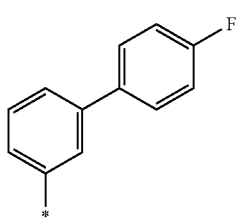

wherein, in Formulae 7-1 to 7-9, * indicates a binding site to an adjacent atom.

7. The amine-based compound of claim 1, wherein $R_1$ to $R_6$ are each independently selected from hydrogen, deuterium, —F, —Cl, —Br, —I, a hydroxyl group, a cyano group, a nitro group, an amino group, an amidino group, a hydrazino group, a hydrazono group, a methyl group, an ethyl group, a propyl group, an iso-propyl group, an n-butyl group, an iso-butyl group, a sec-butyl group, a ter-butyl group, a pentyl group, an iso-amyl group, a hexyl group, a phenyl group, and a biphenyl group.

8. The amine-based compound of claim 1, wherein:
in Formula 1-1, at least one selected from $R_1$ group(s) in the number of c1, $R_2$ group(s) in the number of c2, $R_3$ group(s) in the number of c3, and $R_4$ group(s) in the number of c4 is —F; or
in Formula 1-2, at least one selected from $R_1$ group(s) in the number of c1, $R_2$ group(s) in the number of c2, $R_3$ group(s) in the number of c3, $R_4$ group(s) in the number of c4, $R_5$ group(s) in the number of c5, and $R_6$ group(s) in the number of c6 is —F.

9. The amine-based compound of claim 1, represented by one of Formulae 1A-1 to 1A-4 and 1A-6 to 1A-8:

Formula 1A-1
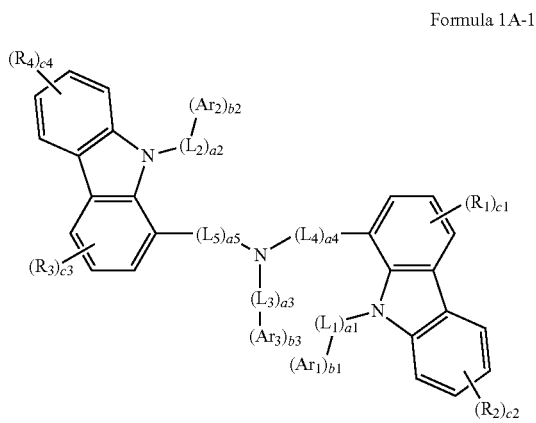

Formula 1A-2
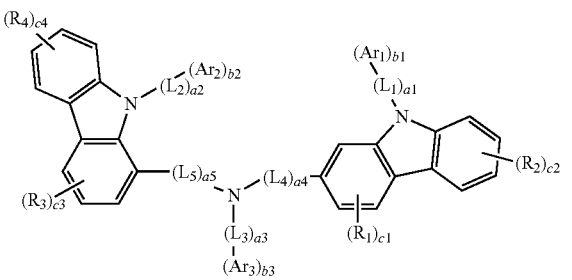

Formula 1A-3
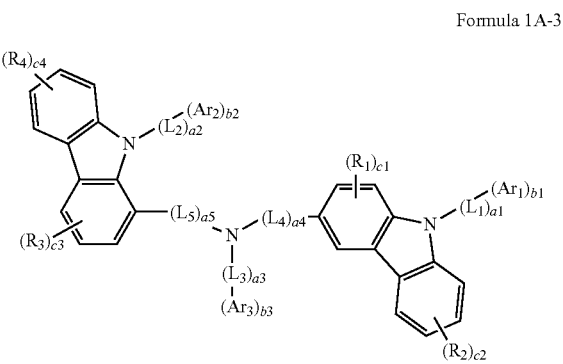

-continued

Formula 1A-4

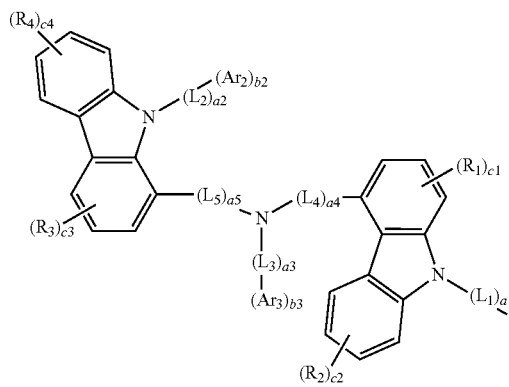

Formula 1A-6

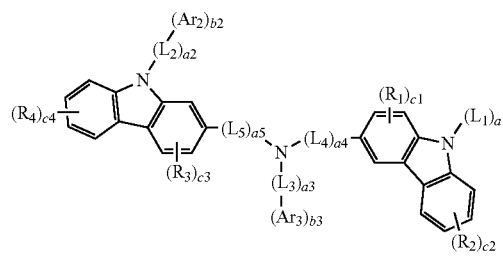

Formula 1A-7

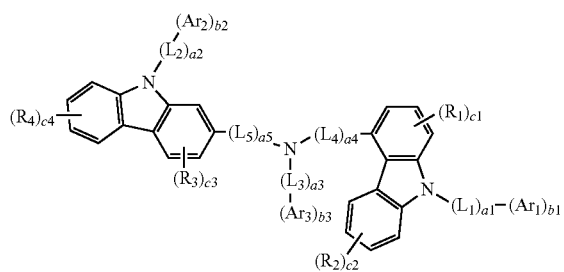

Formula 1A-8

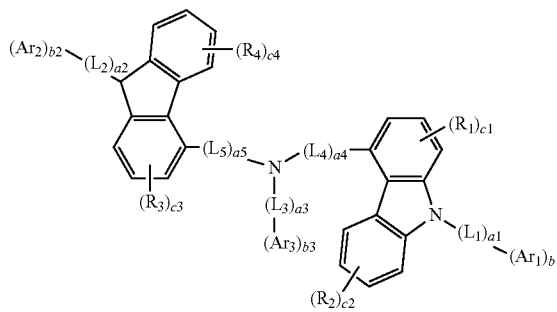

wherein in Formulae 1A-1 to 1A-4 and 1A-6 to 1A-8, $L_1$ to $L_5$, a1 to a5, $Ar_1$ to $Ar_3$, b1 to b3, and $R_1$ to $R_4$ are defined the same as those of Formulae 1-1 and 1-2, c1 and c3 are each independently an integer from 1 to 3, and c2 and c4 are each independently an integer from 1 to 4.

10. The amine-based compound of claim 1, represented by one of Formulae 1A-11 to 1A-18:

Formula 1A-11

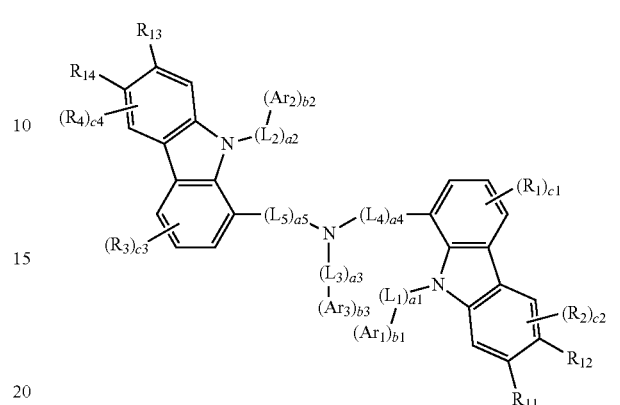

Formula 1A-12

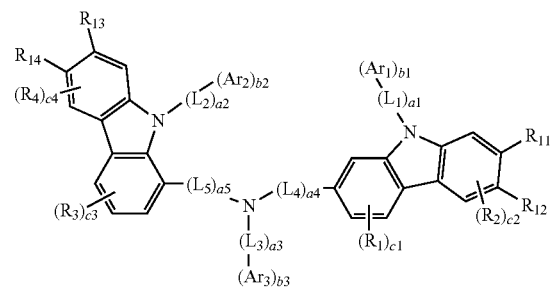

Formula 1A-13

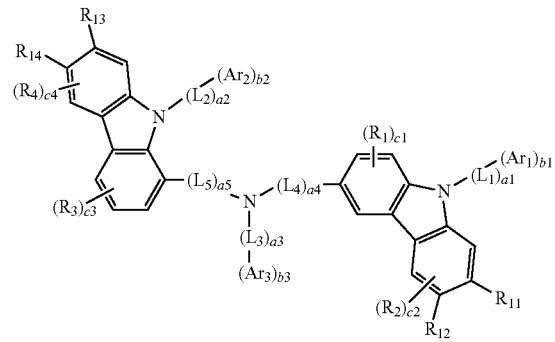

Formula 1A-14

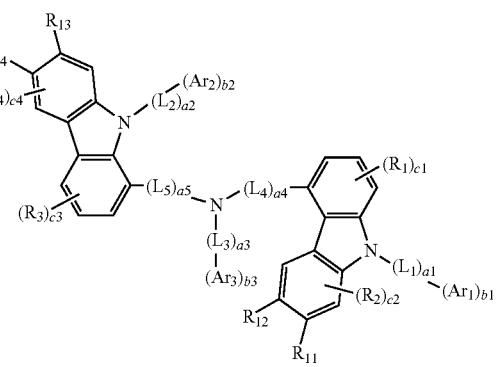

-continued

Formula 1A-15
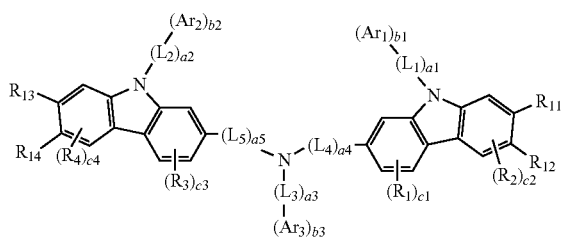

Formula 1A-16
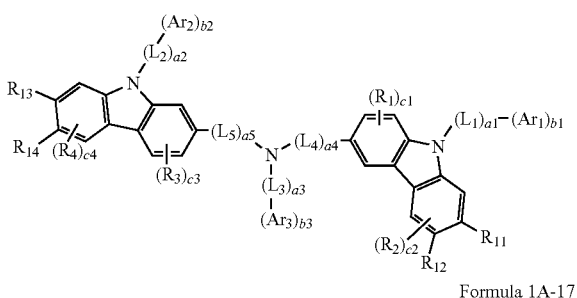

Formula 1A-17
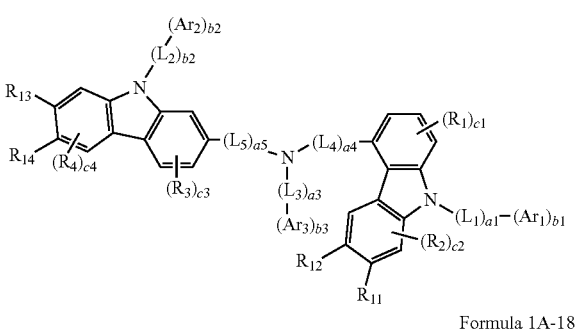

Formula 1A-18
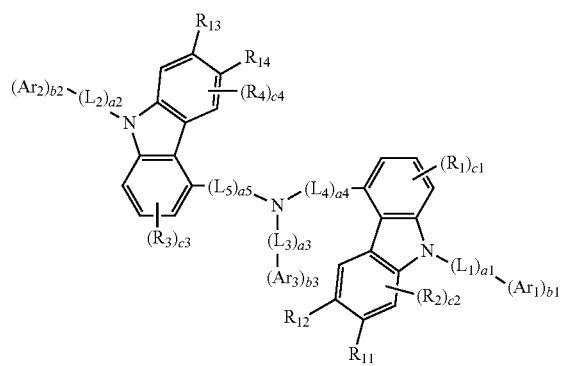

wherein, in Formulae 1A-11 to 1A-18,

L$_1$ to L5, a1 to a5, Ar$_1$ to Ar$_3$, b1 to b3, and R$_1$ to R$_4$ are define the same as those of Formulae 1-1 and 1-2, wherein when the amine-based compound is represented by Formula 1A-15, L$_1$ to L$_3$ and Ar$_1$ to Ar$_3$ are each independently not a substituted or unsubstituted pyridine group, a substituted or unsubstituted pyrazine group, a substituted or unsubstituted pyrimidine group, a substituted or unsubstituted pyridazine group, or a substituted or unsubstituted triazine group, c1 and c3 are each independently an integer from 1 to 3, c2 and c4 are each independently an integer selected from 1 and 2, R$_{11}$ to R$_{14}$ are each defined the same as R$_1$ of Formula 1, and i) at least one of Ar$_1$ to Ar$_3$ is selected from groups represented by Formulae 7-1 to 7-9;

ii) R$_{11}$ and/or R$_{13}$ is —F;

iii) R$_{12}$ and/or R$_{14}$ is —F;

iv) at least one of Ar$_1$ to Ar$_3$ is selected from groups represented by Formulae 7-1 to 7-9, and R$_{11}$ and/or R$_{13}$ is —F; or v) at least one of Ar$_1$ to Ar$_3$ is selected from groups represented by Formulae 7-1 to 7-9, and R$_{12}$ and/or R$_{14}$ is —F, Formula 7-1
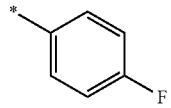

Formula 7-2
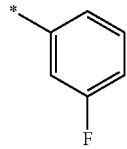

Formula 7-3
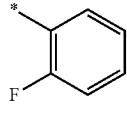

Formula 7-4
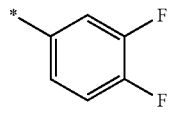

Formula 7-5
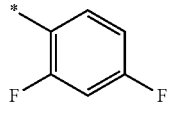

Formula 7-6
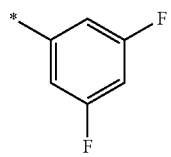

Formula 7-7
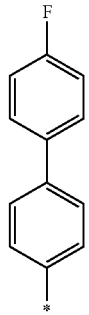

237
-continued
Formula 7-8
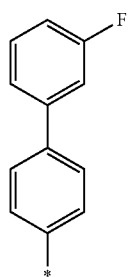
Formula 7-9
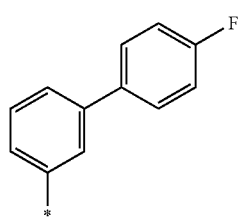
wherein, in Formulae 7-1 to 7-9, * indicates a binding site to an adjacent atom.
11. The amine-based compound of claim 1, wherein the number of —F(s) is selected from 1, 2, 3, 4, and 5.
12. The amine-based compound of claim 1, being selected from Compounds 1 to 232:
1
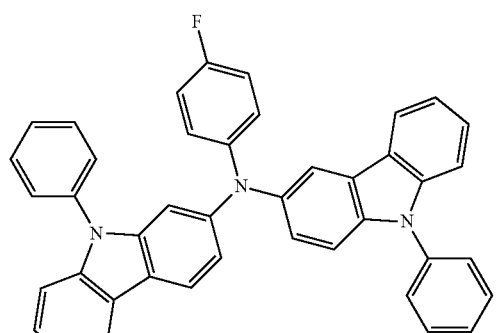
2
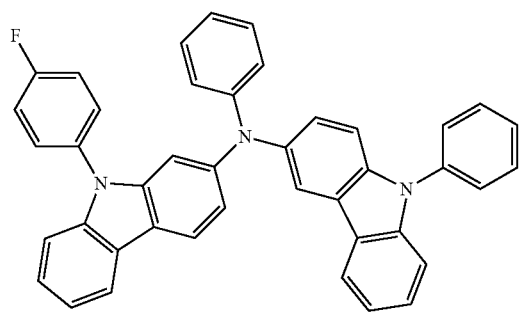
238
-continued
3
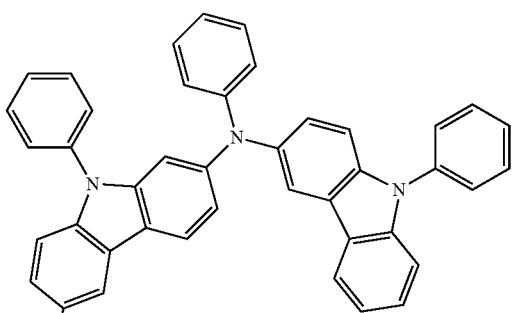
4
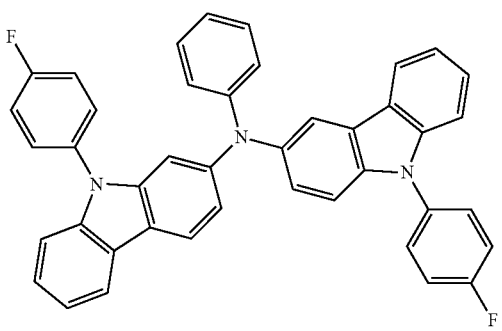
5
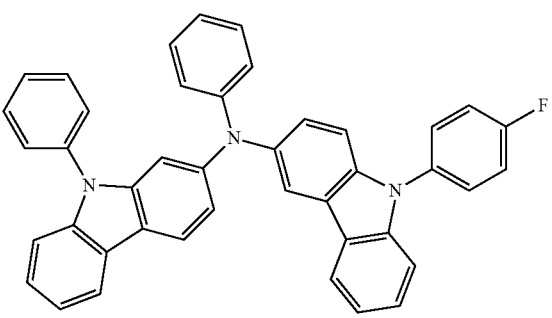
6
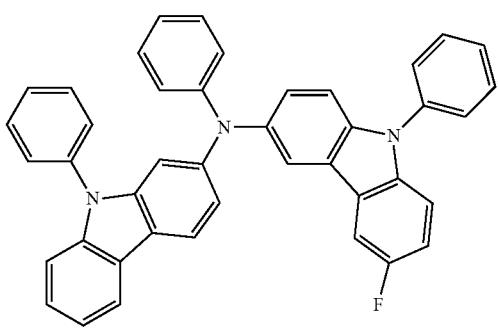

7
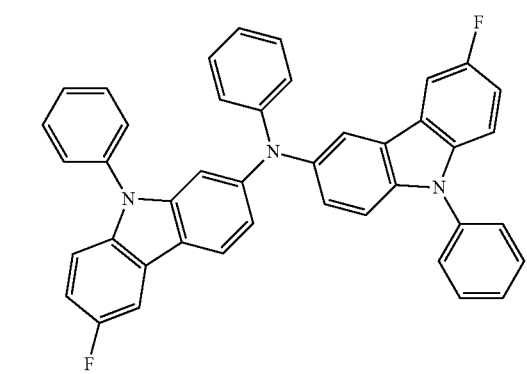
8
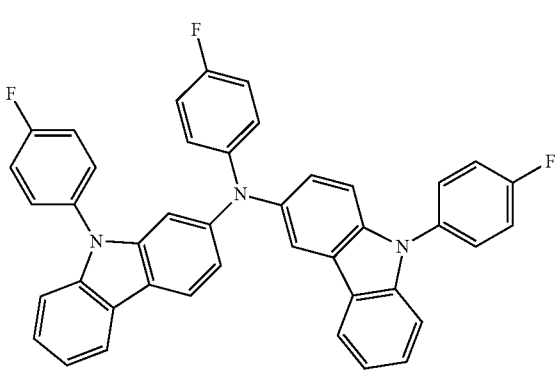
9
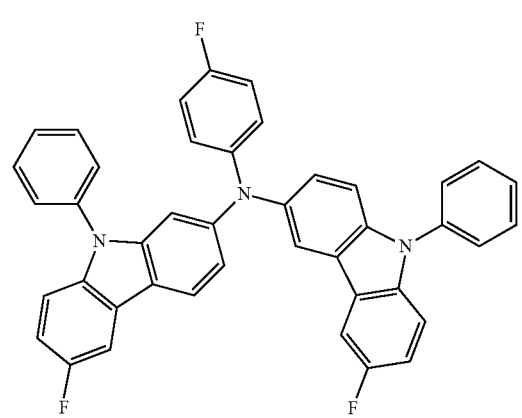
10
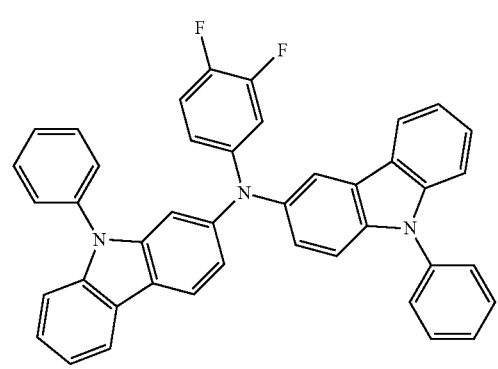
11
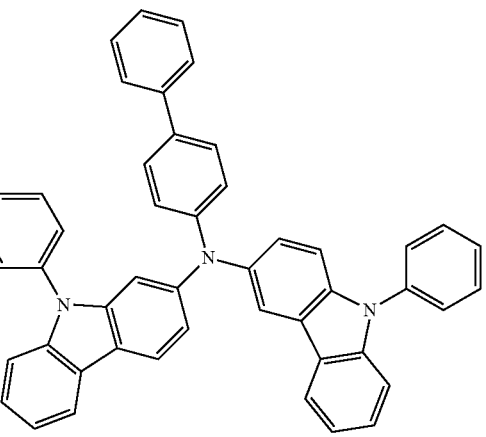
12
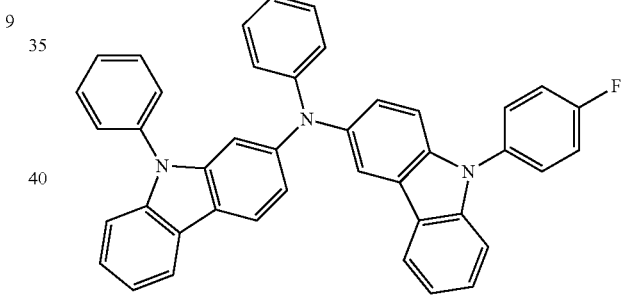
13
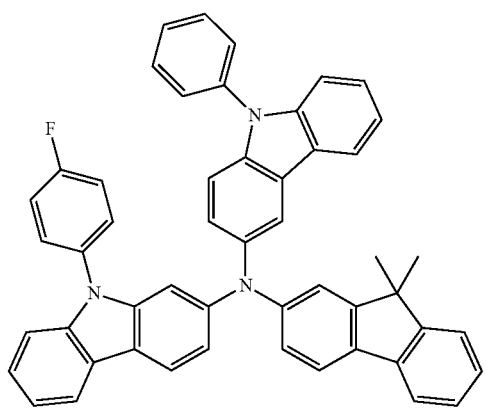

14
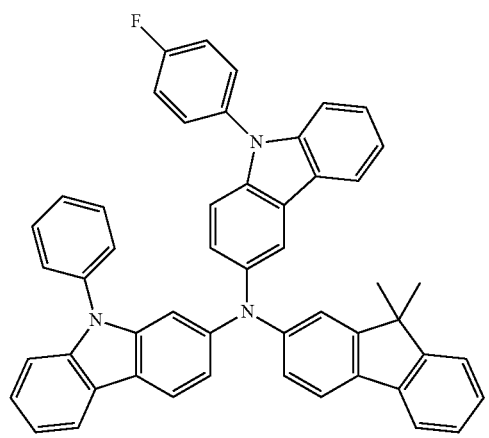
15
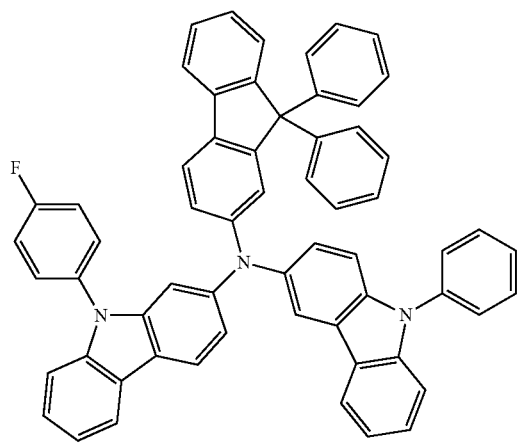
16
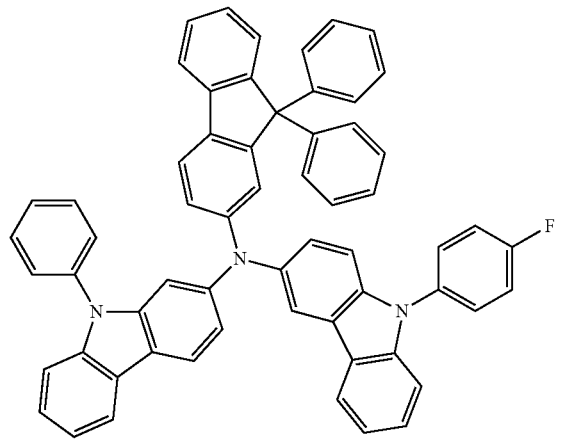
17
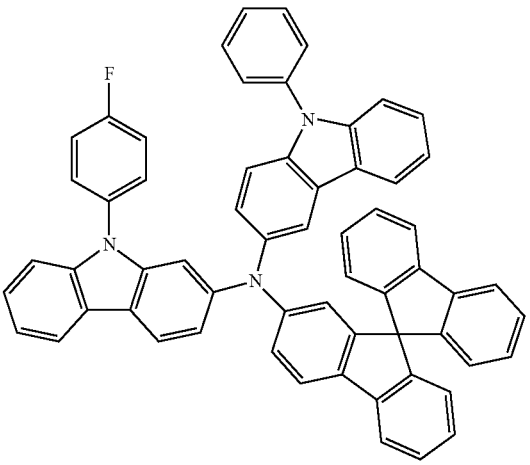
18
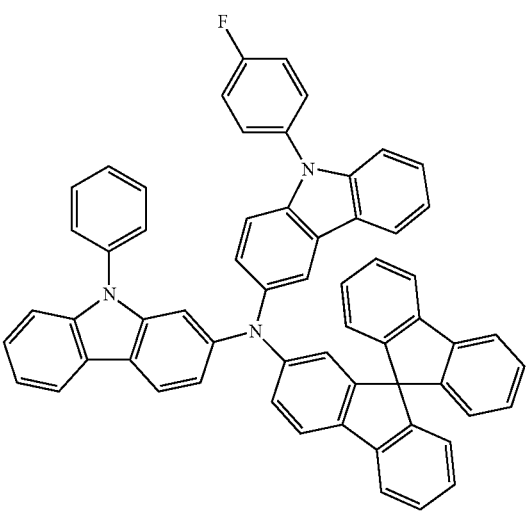
19
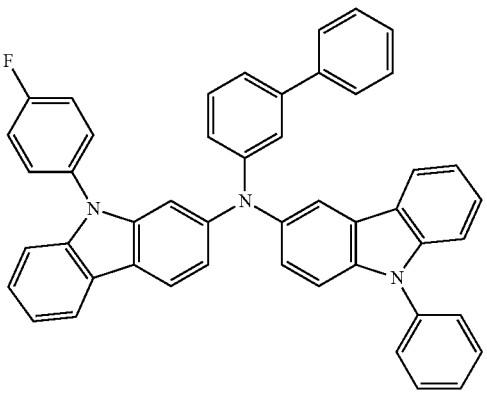

-continued
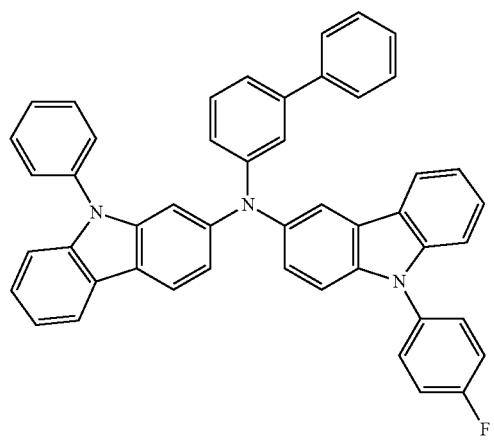
20
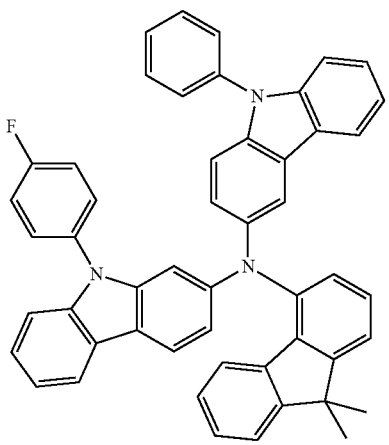
23
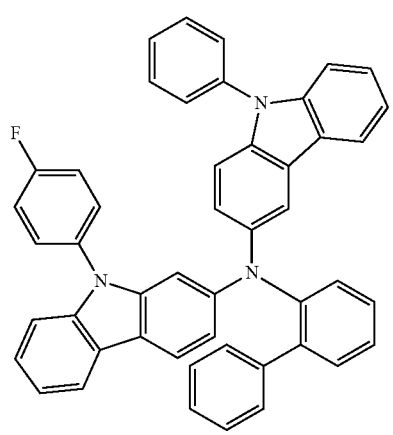
21
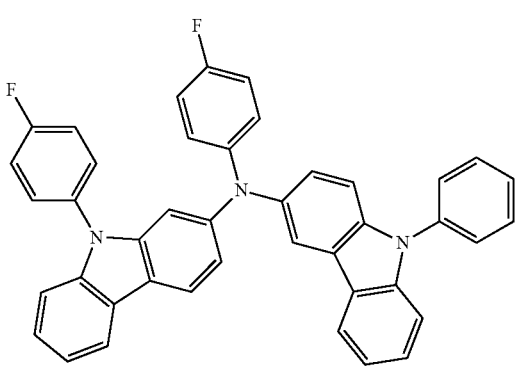
24
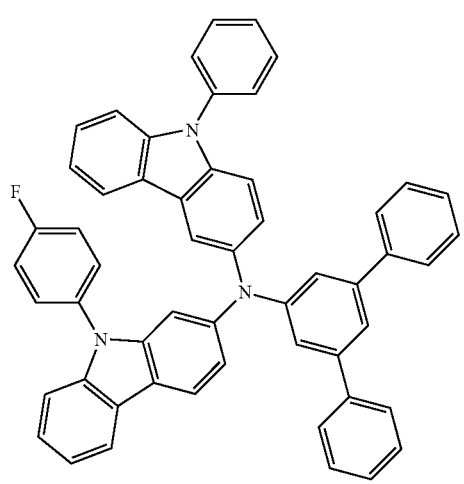
22
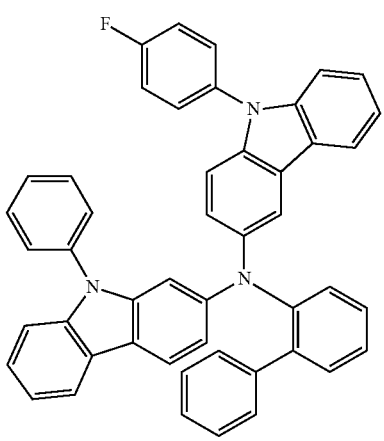
25

26
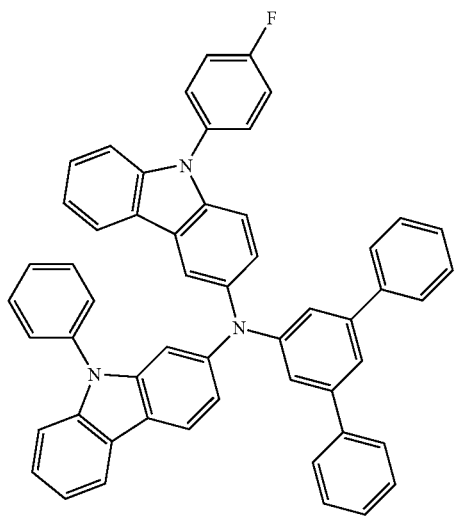
27
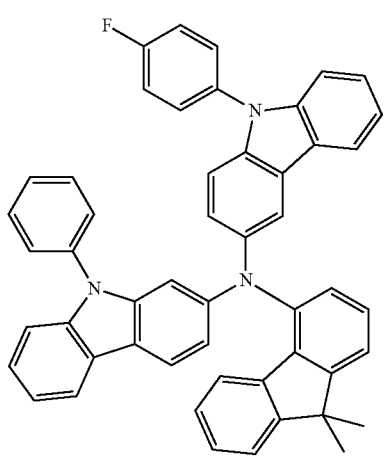
28
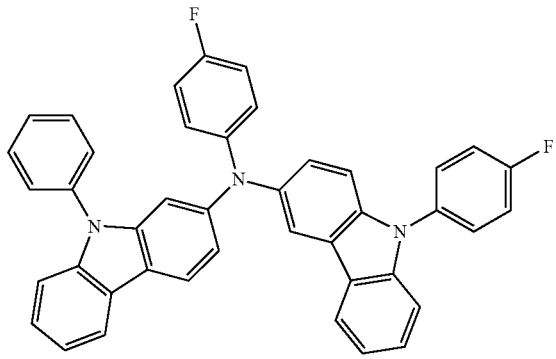
29
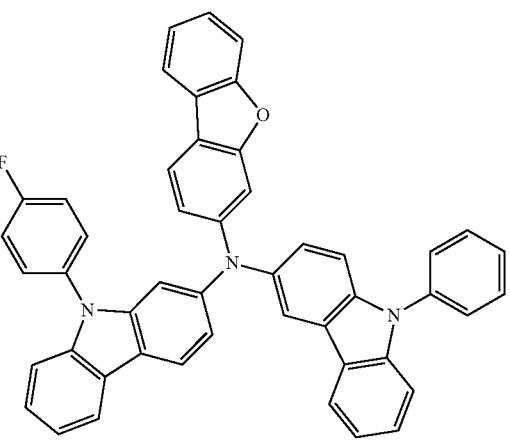
30
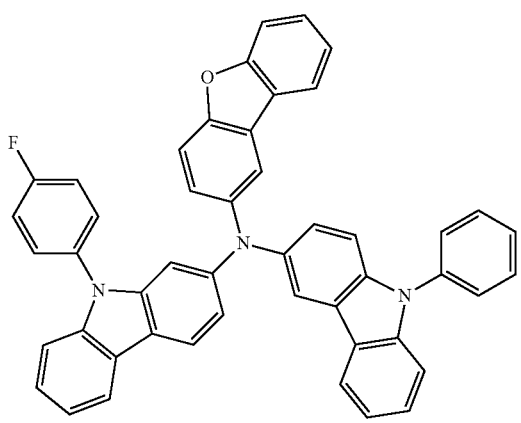
31
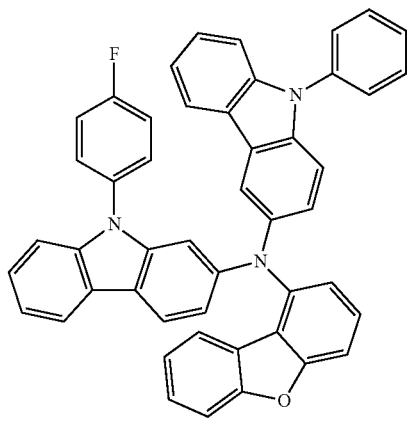

32
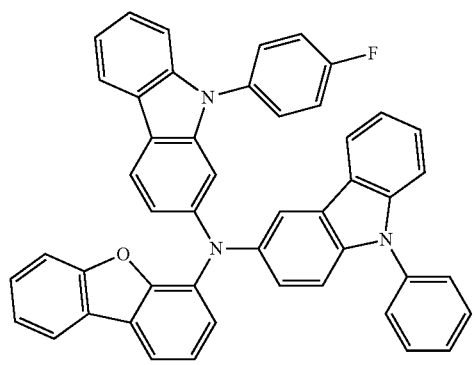
33
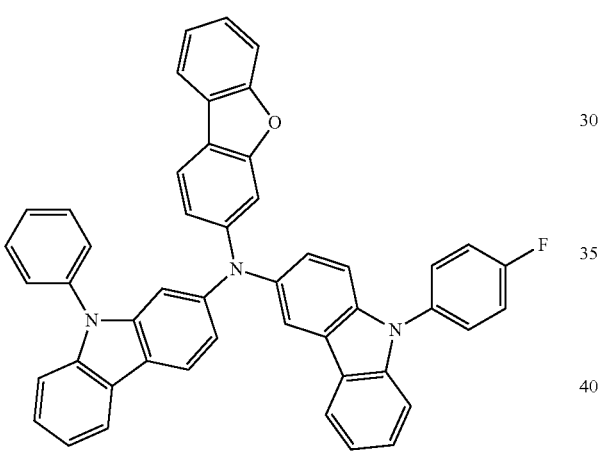
34
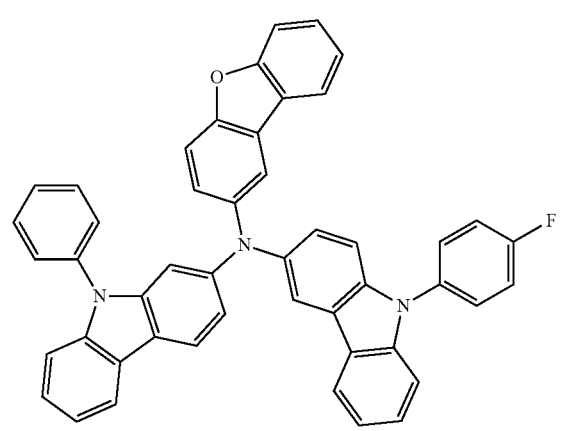
35
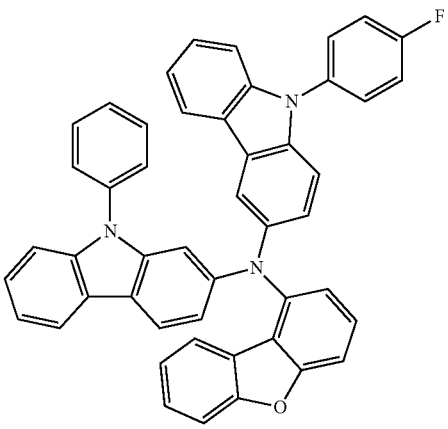
36
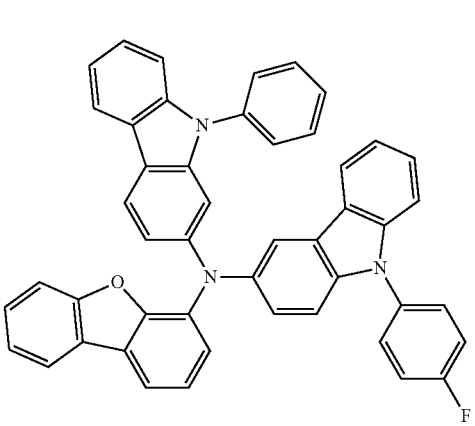
37
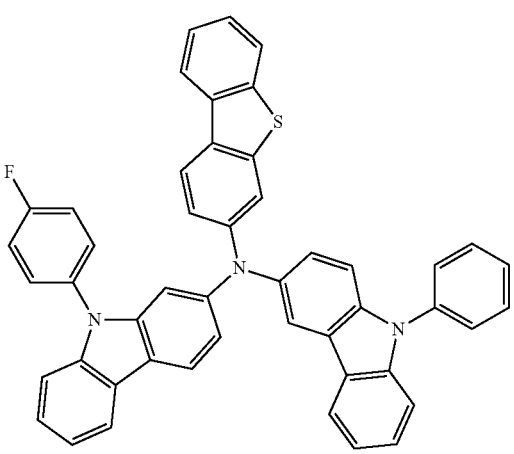

38
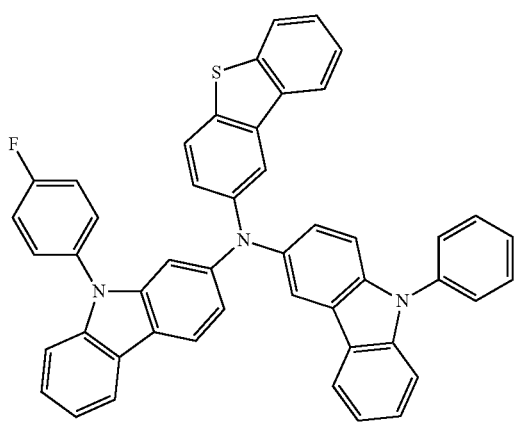
39
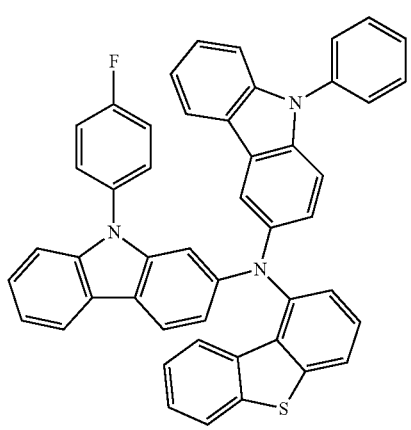
41
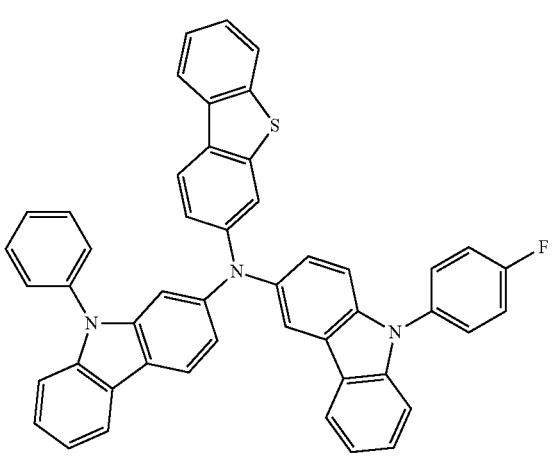
42
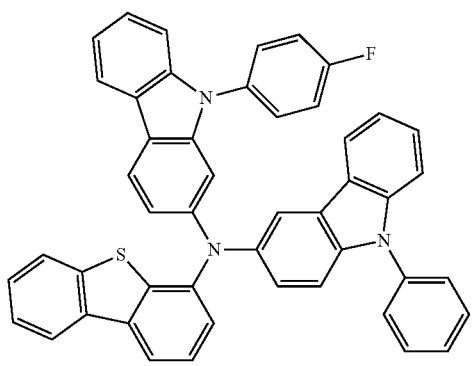
43
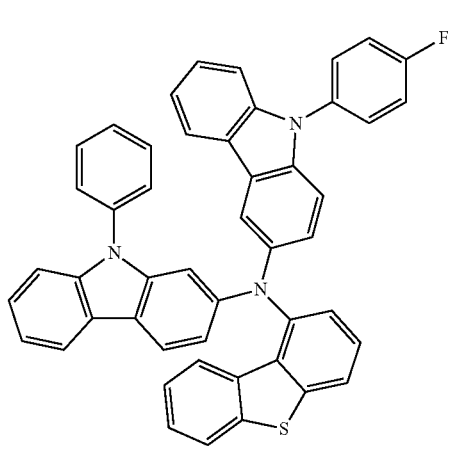

251
-continued
252
-continued
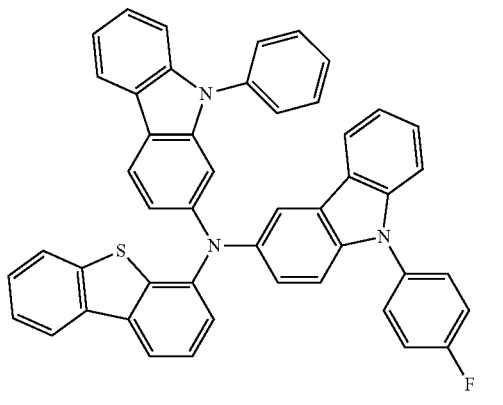
44
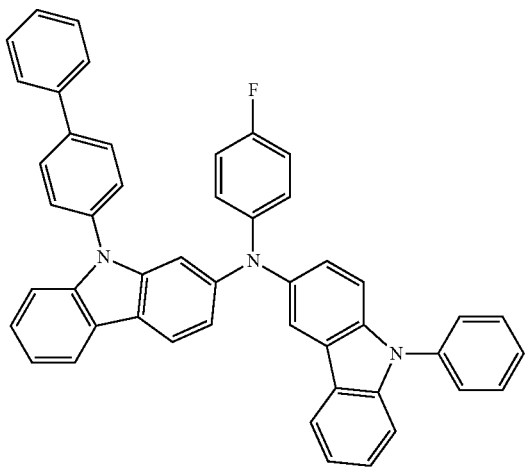
48
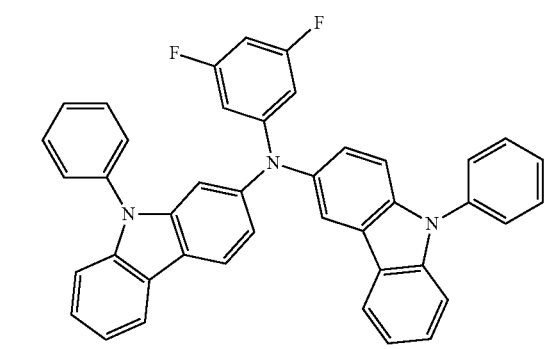
46
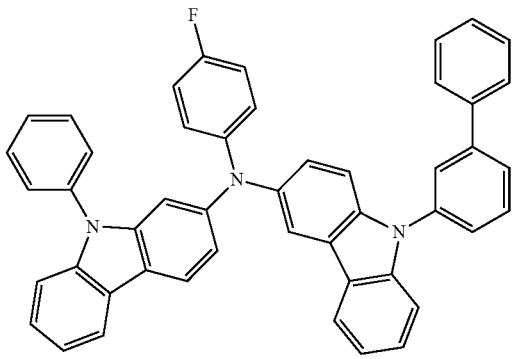
49
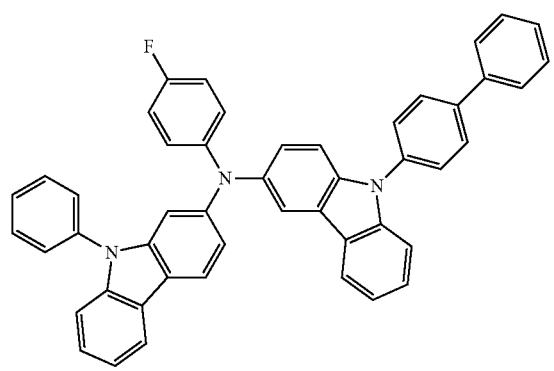
47
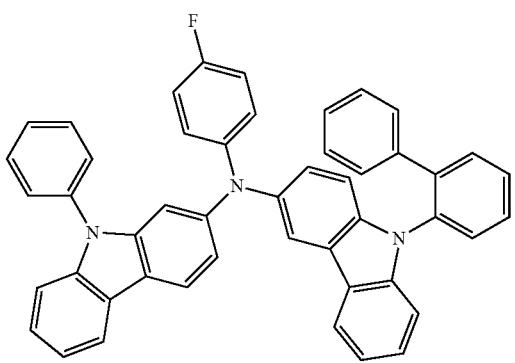
50

51
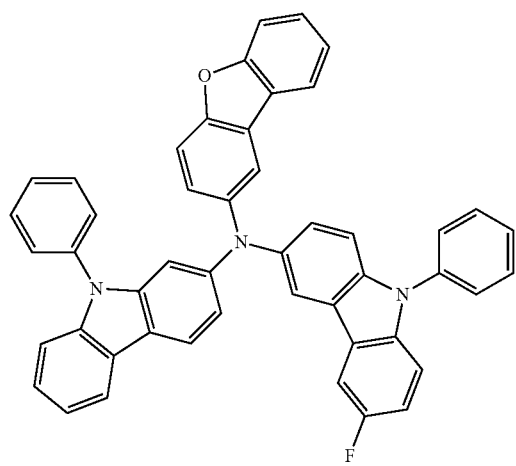
52
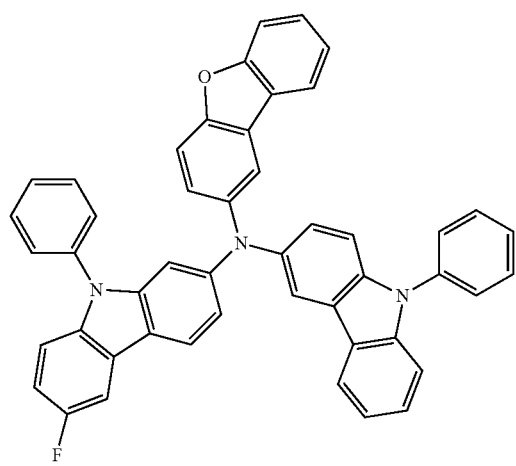
53
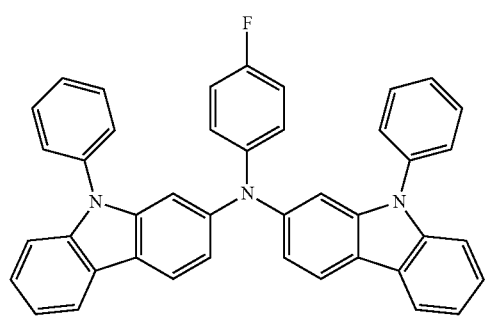
54
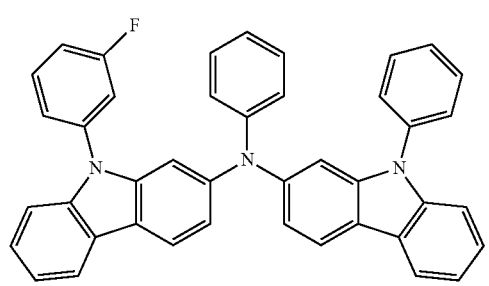
55
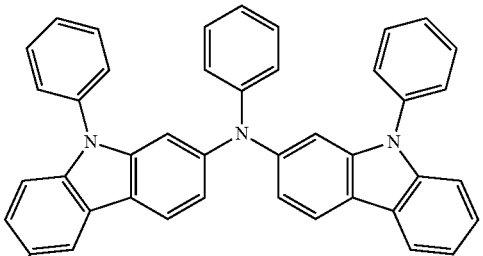
56
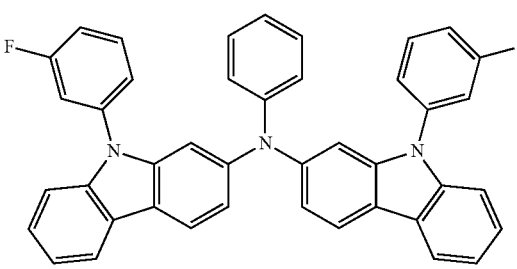
57
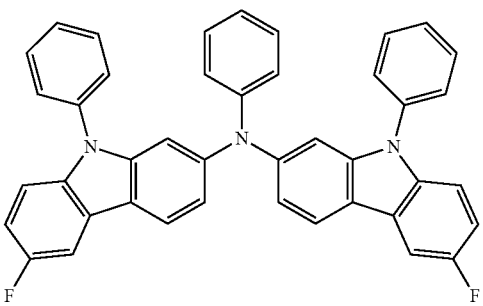
58
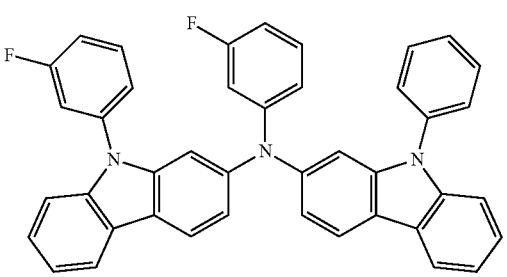
59
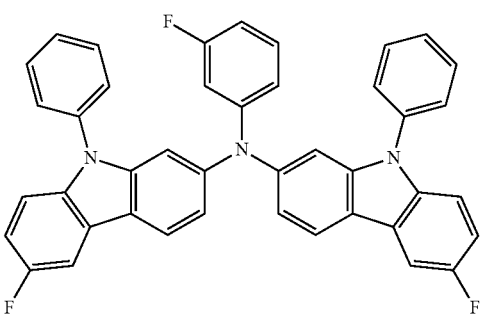

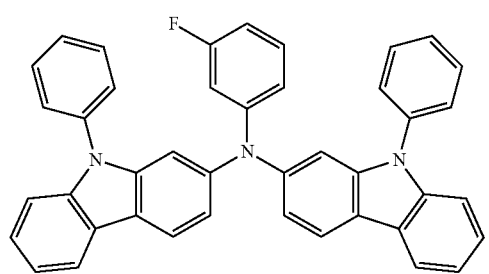
60
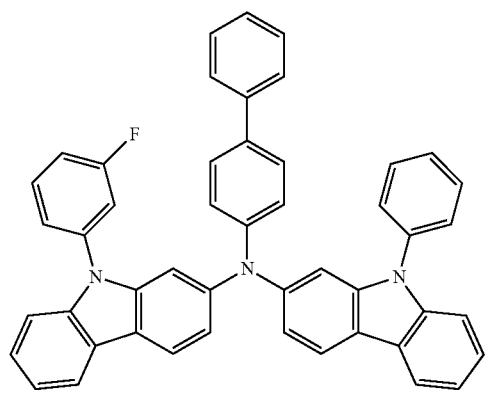
61
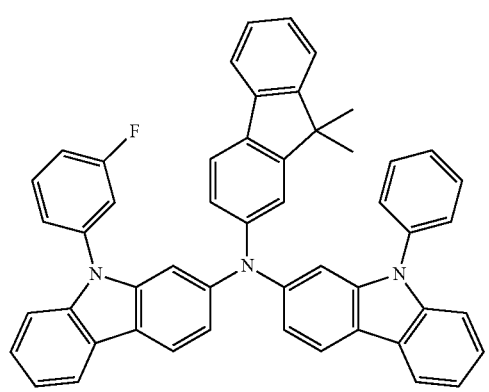
62
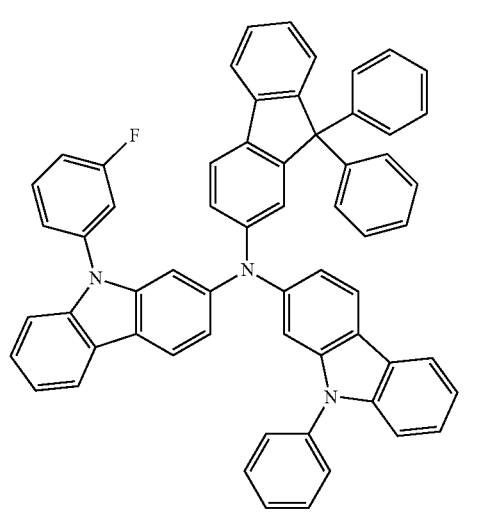
63
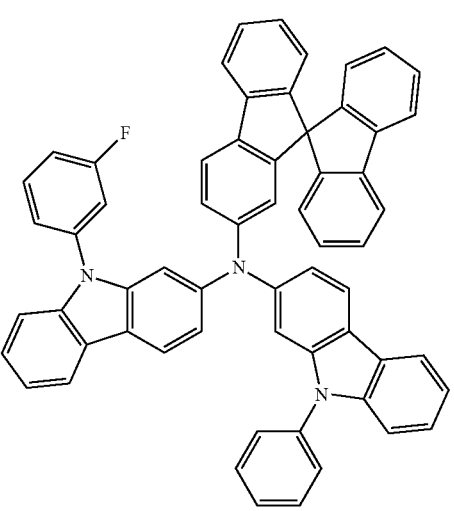
64
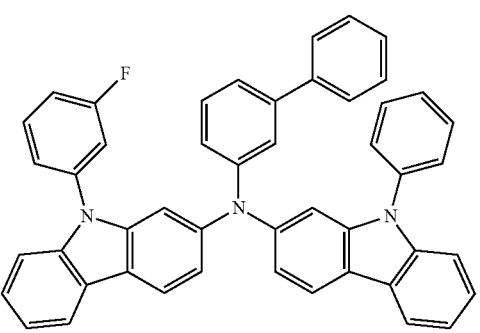
65
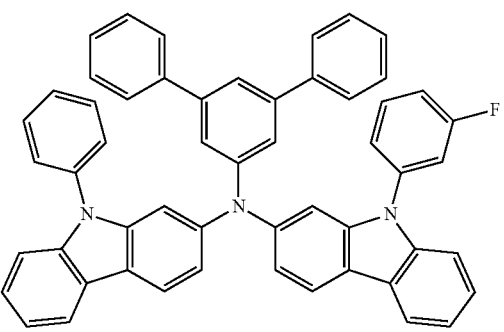
66
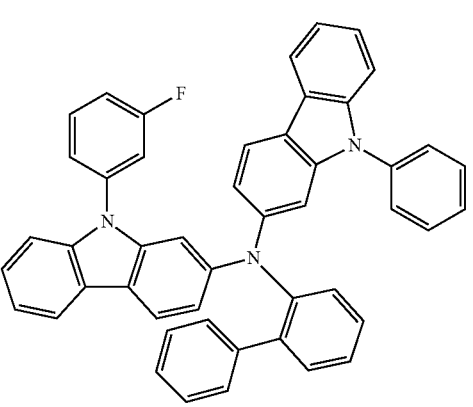
67

68
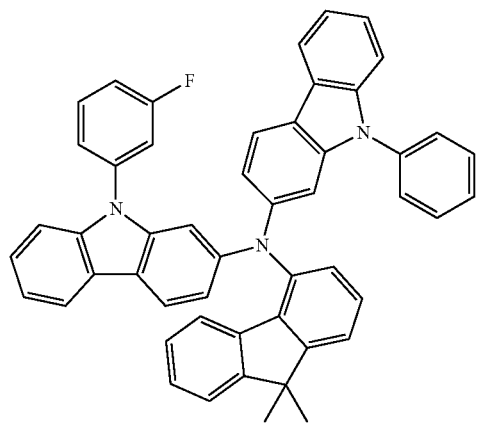
69
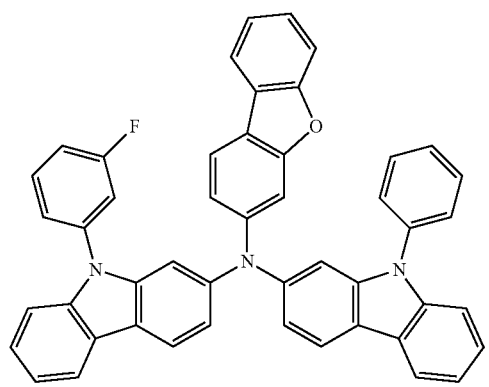
70
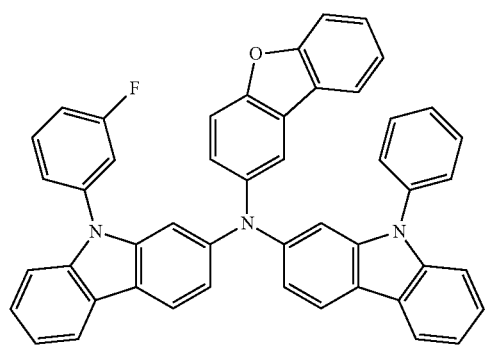
71
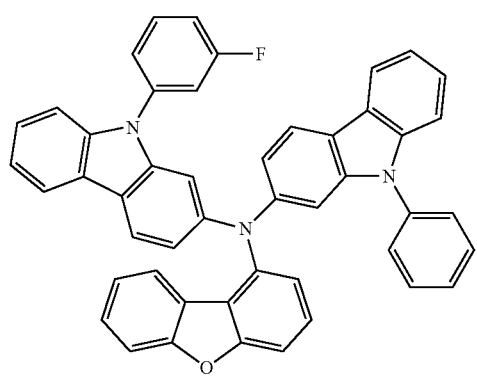
72
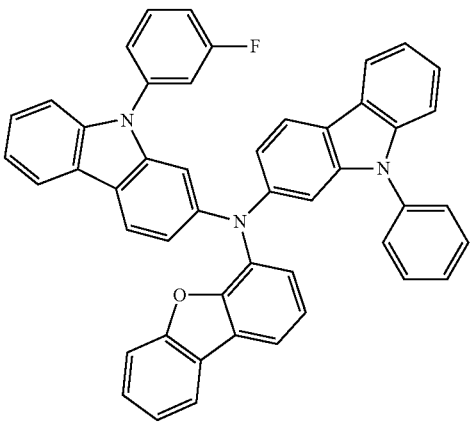
73
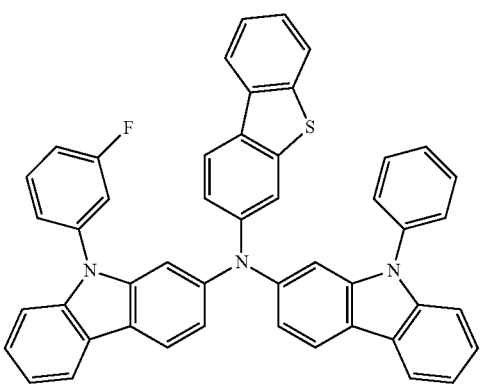
74
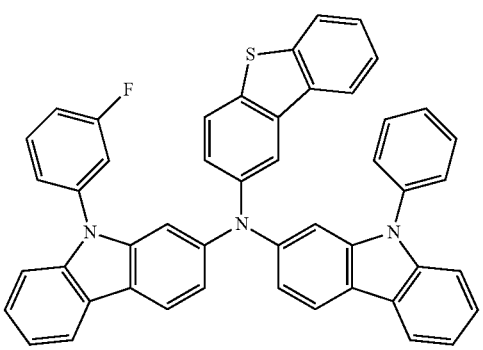
75
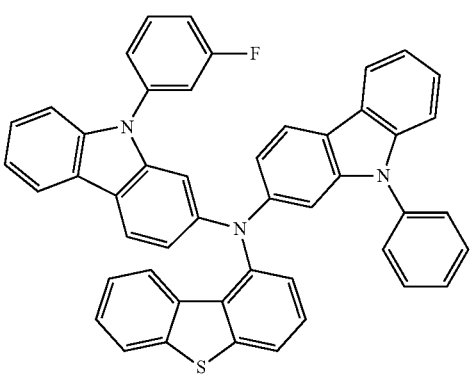

76
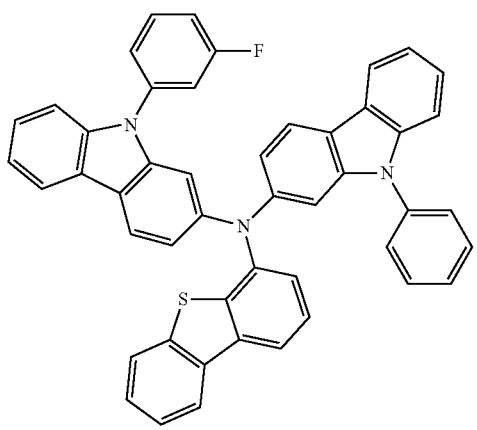
77
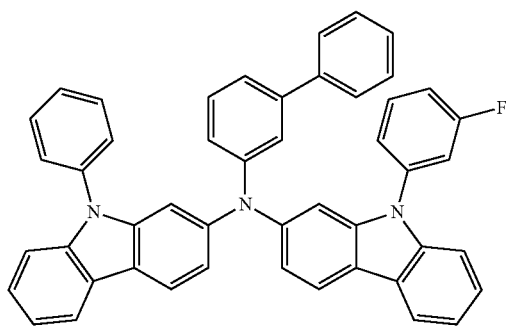
78
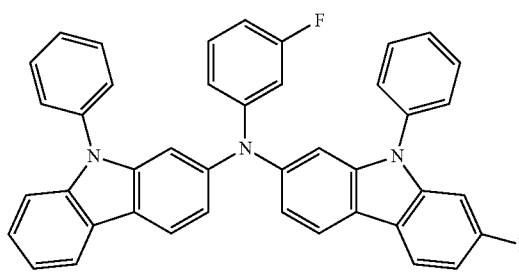
79
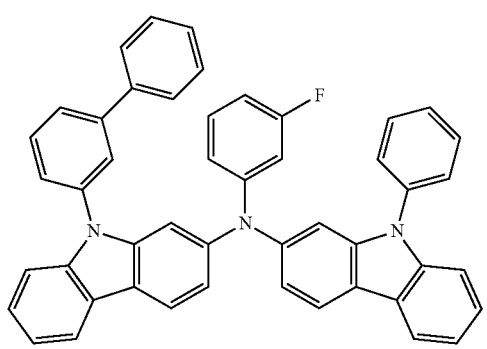
80
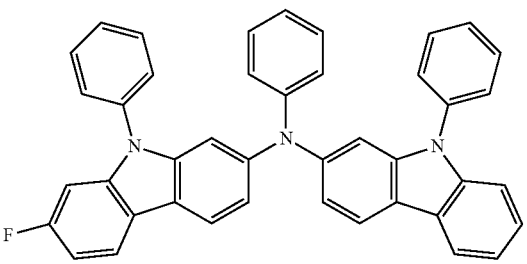
81
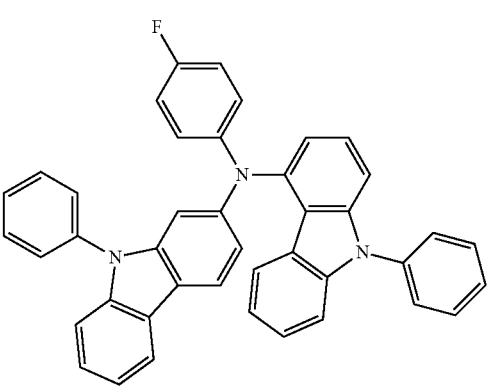
82
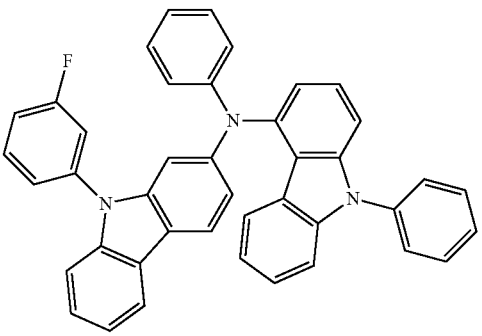
83
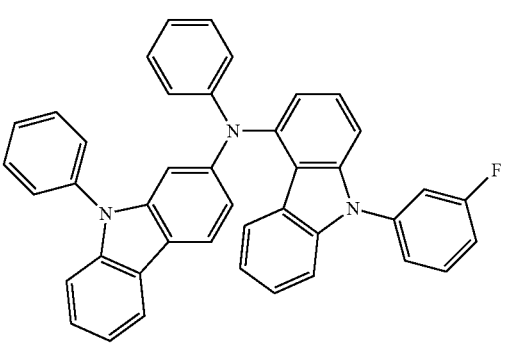

84
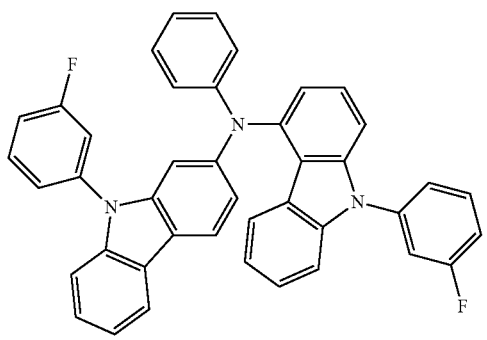
85
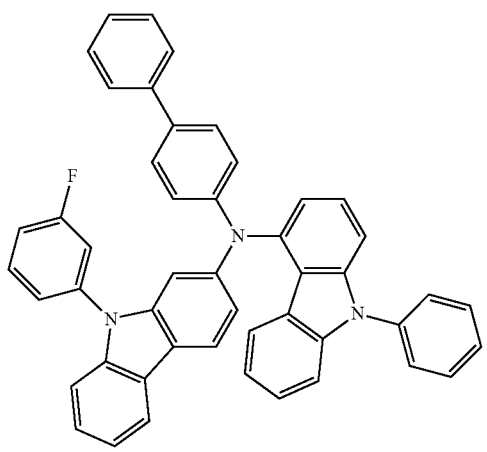
86
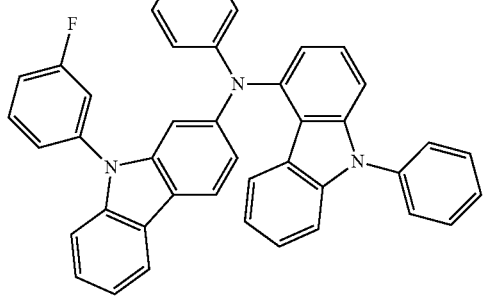
87
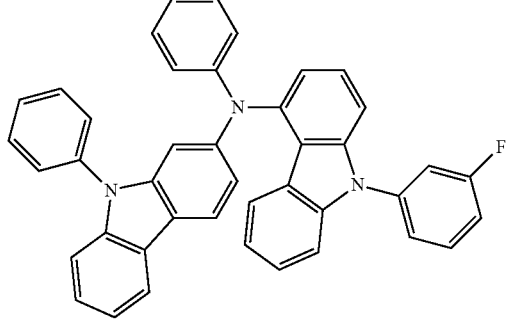
88
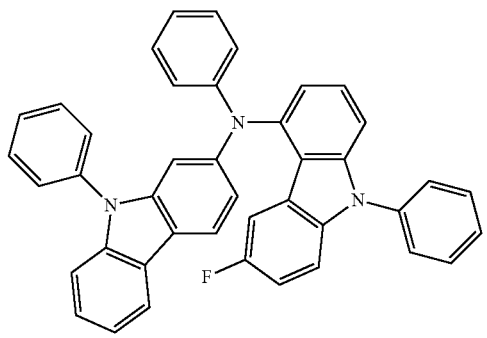
89
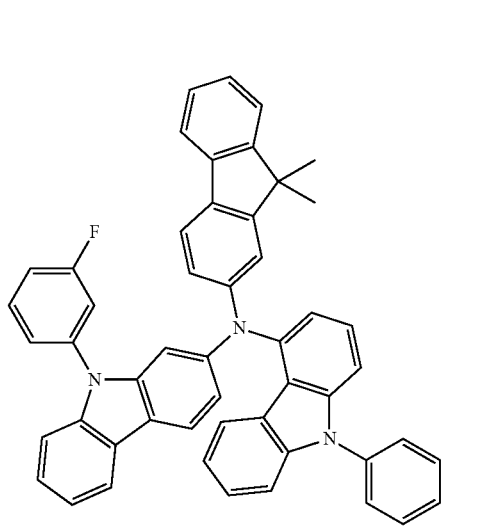
90
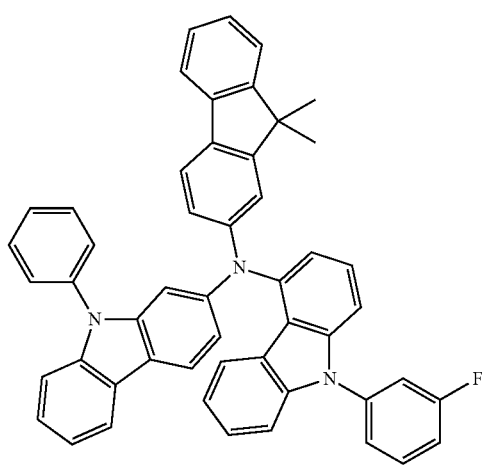

91
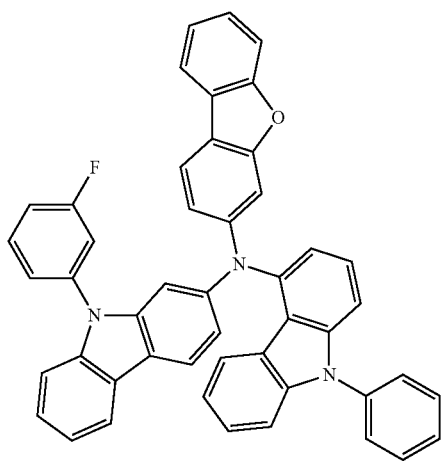
94
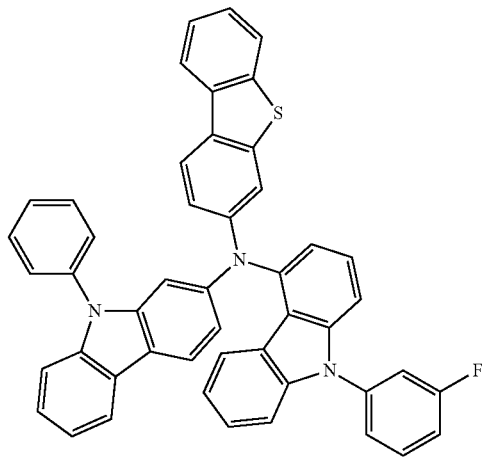
92
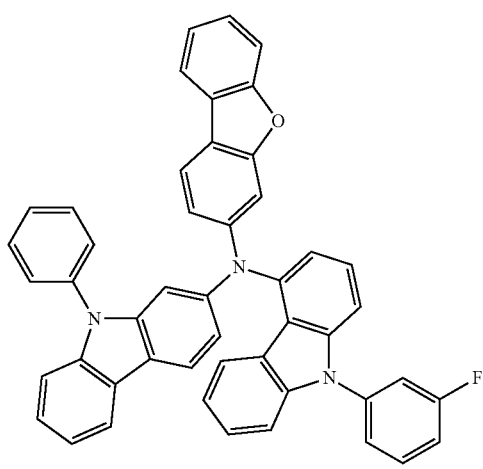
95
96
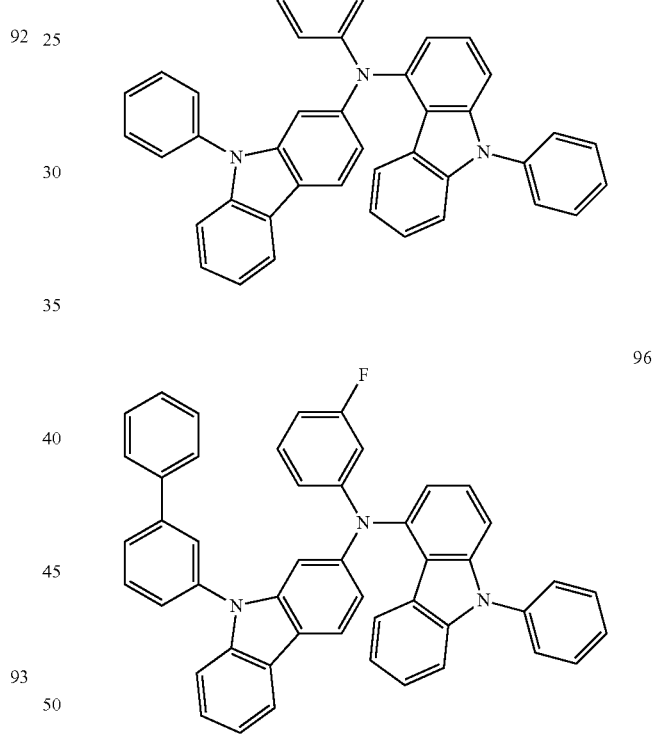
93
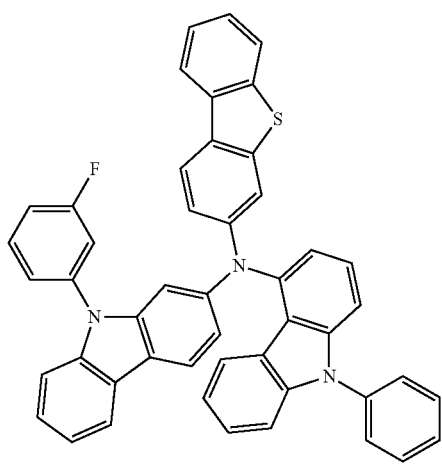
97
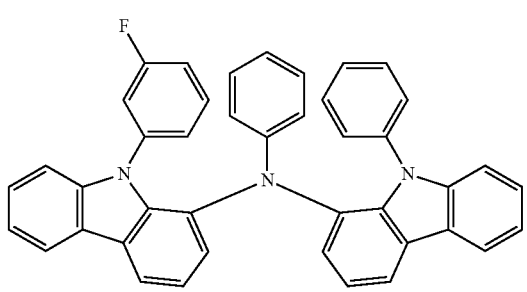

265
-continued
98
99
100
101
102
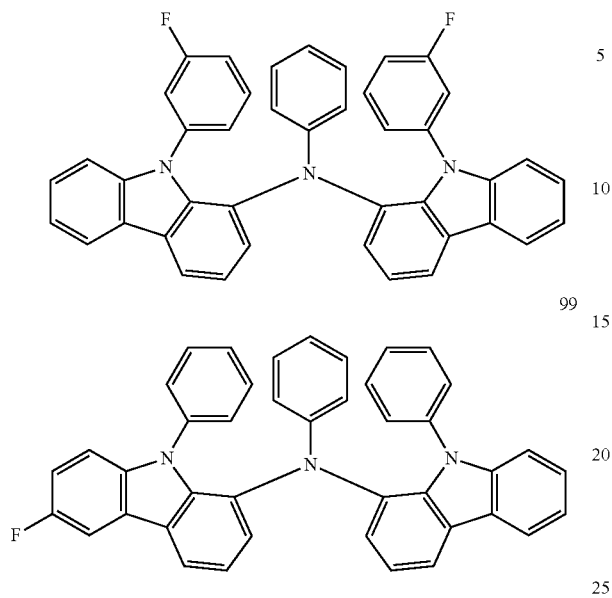
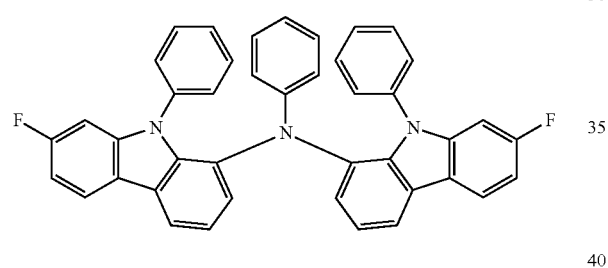
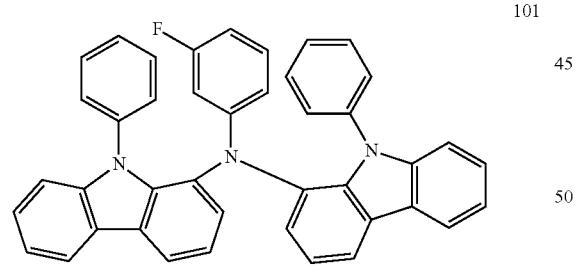
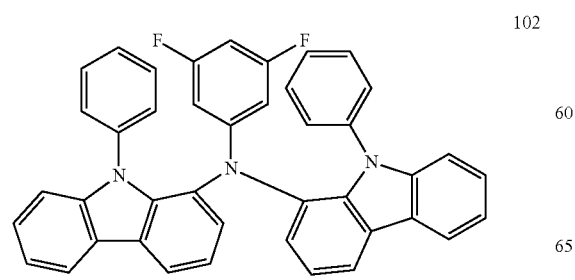
266
-continued
103
104
105
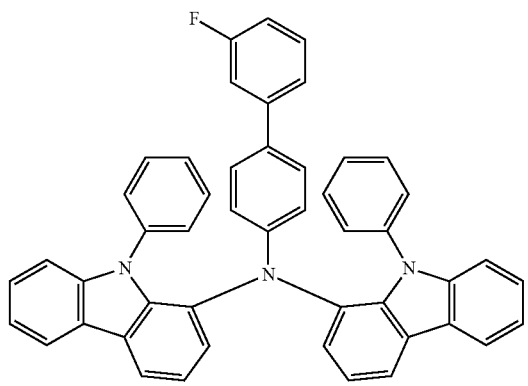
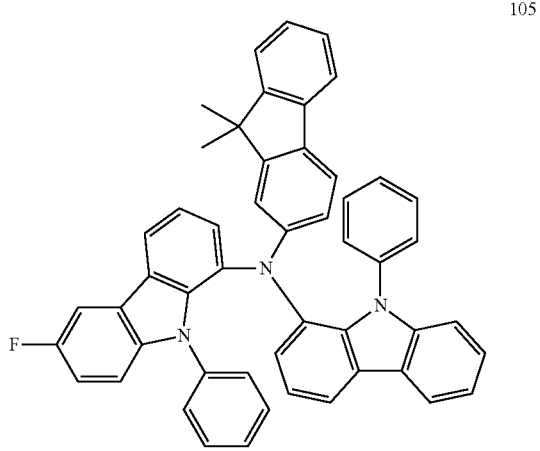

106
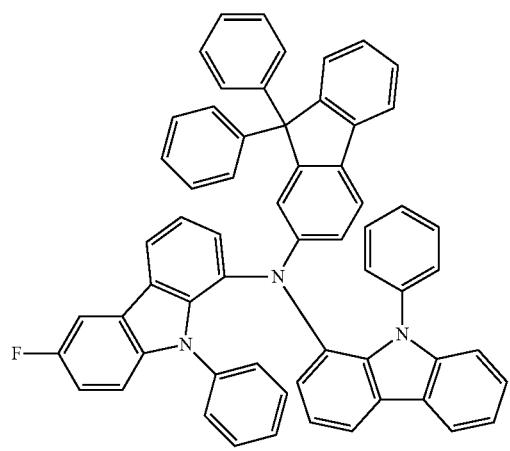
107
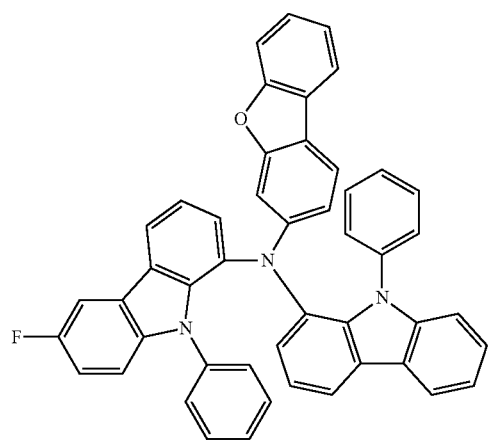
108
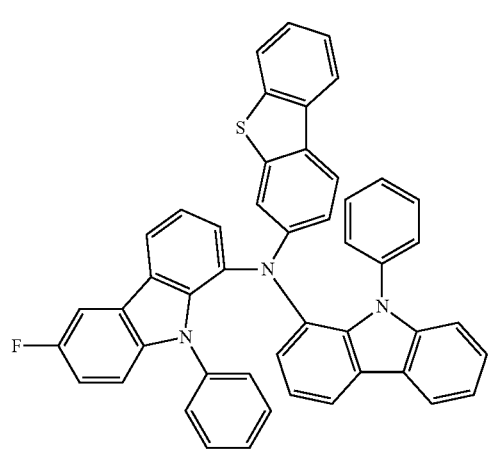
109
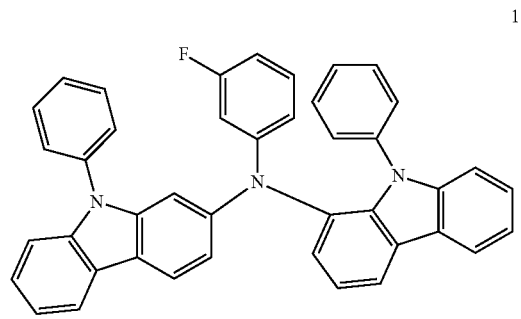
110
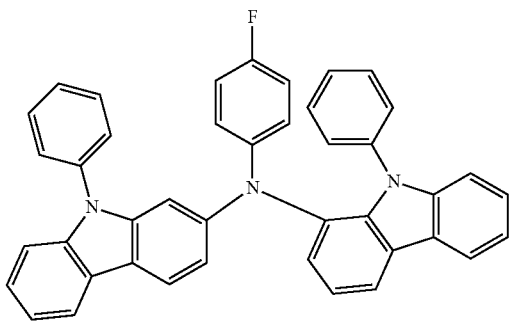
111
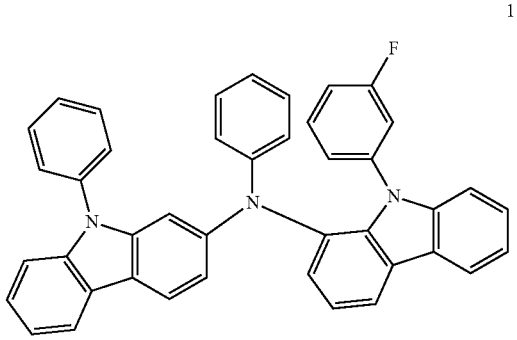
112
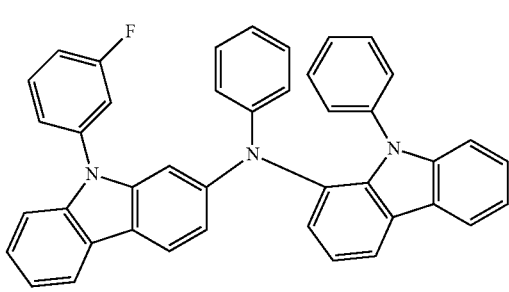
113
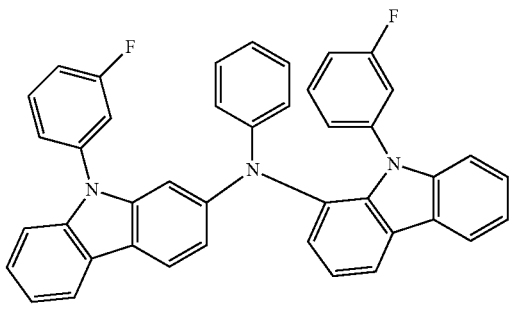
114
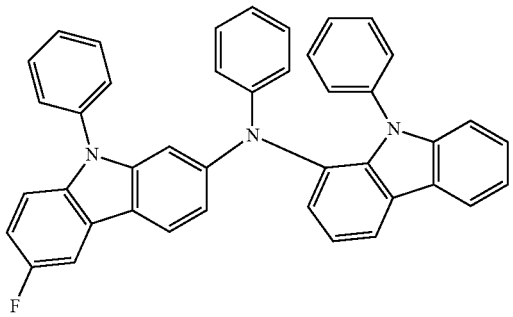

-continued
115
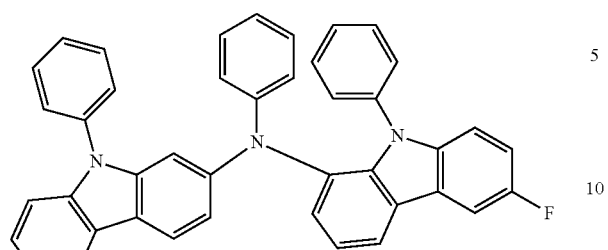
116
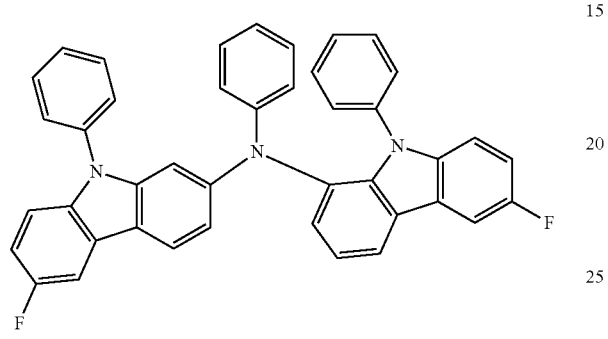
117
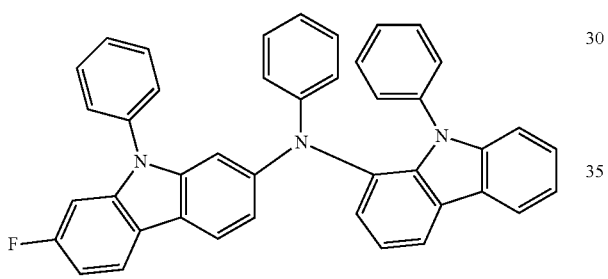
118
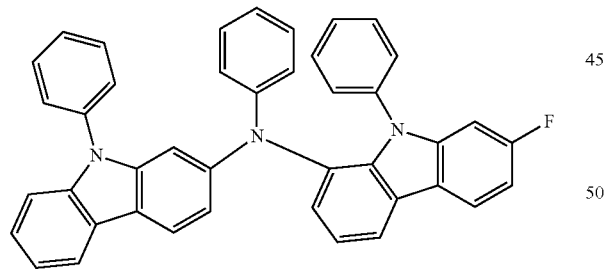
119
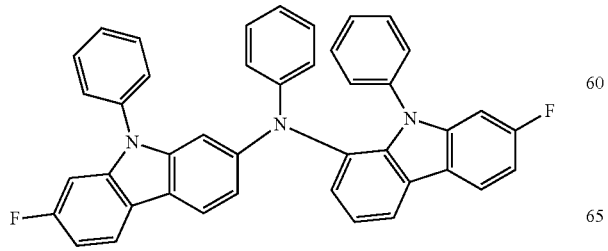
-continued
120
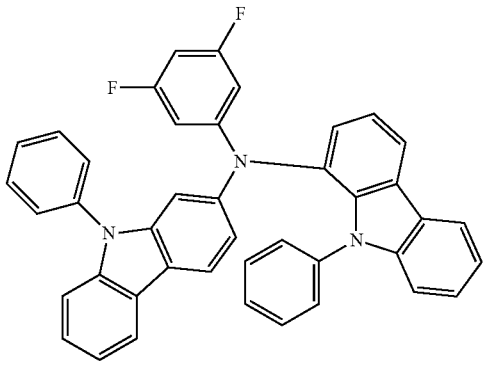
121
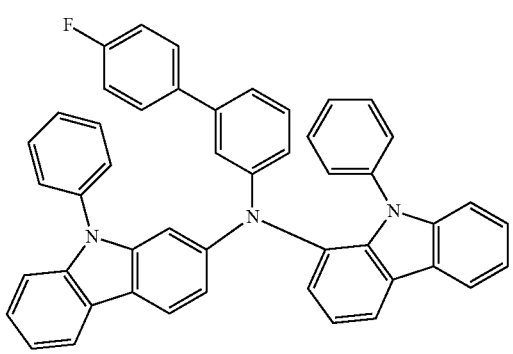
122
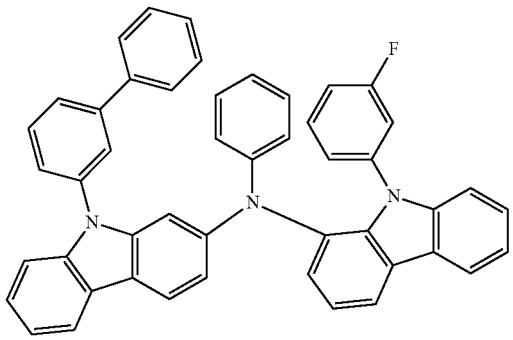
123
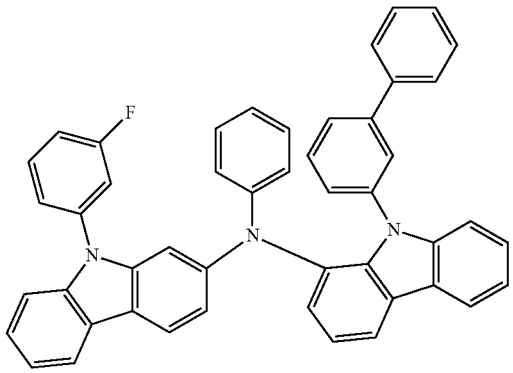

124
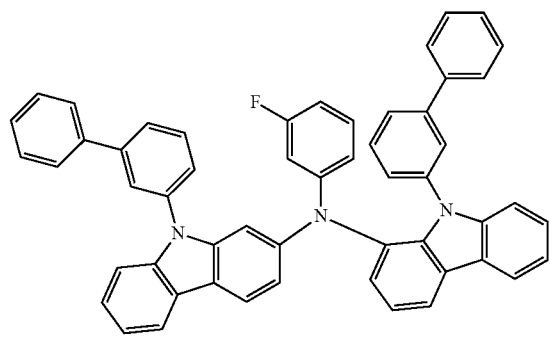
125
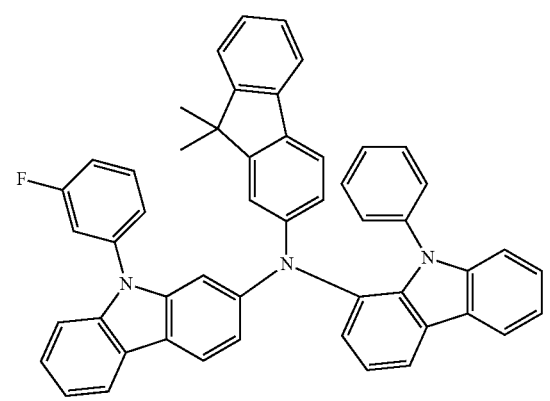
126
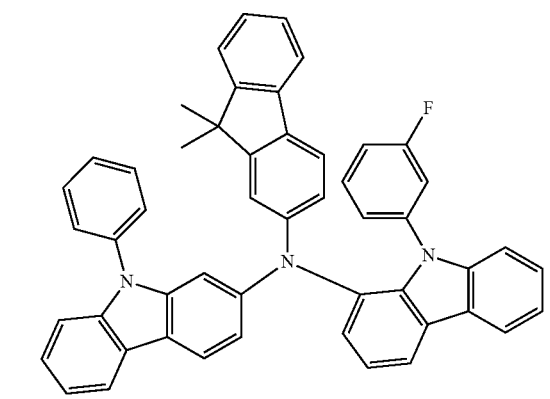
127
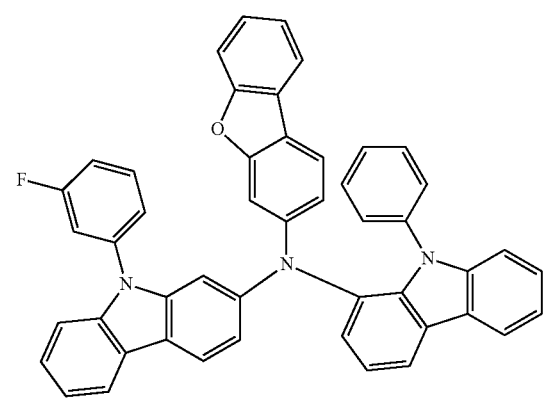
128
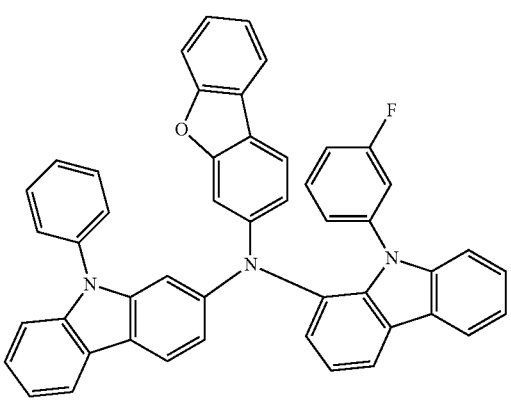
129
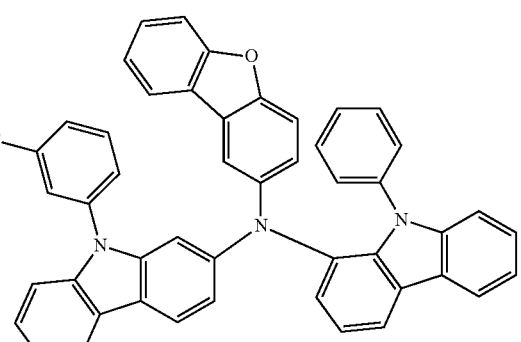
130
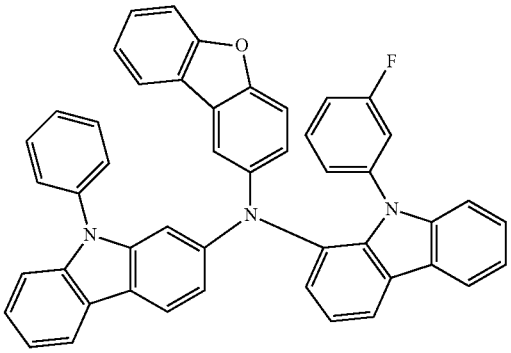
131
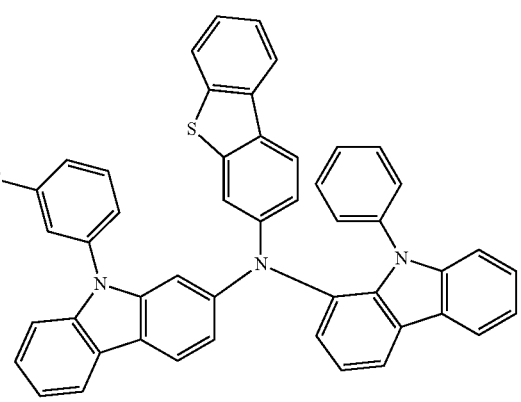

132
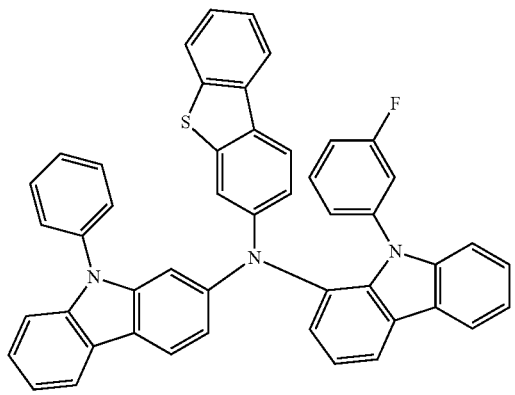
133
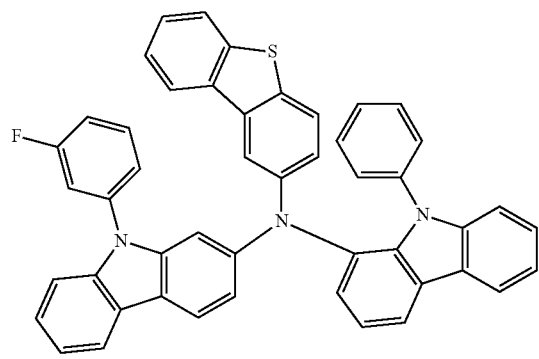
134
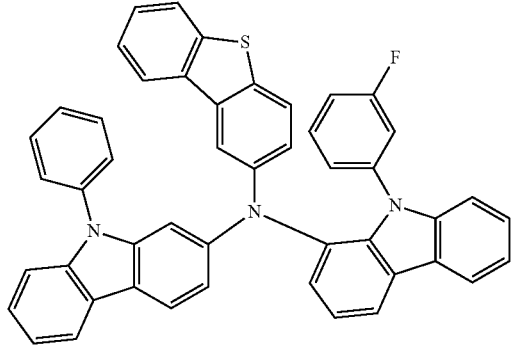
135
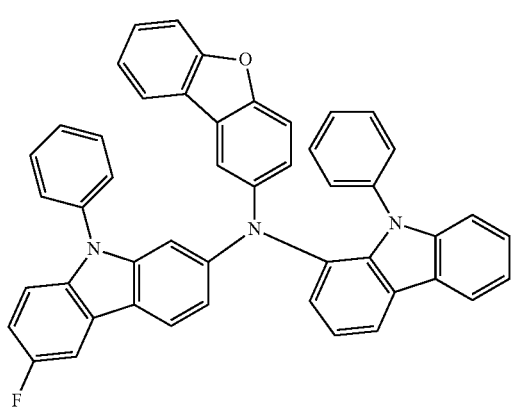
136
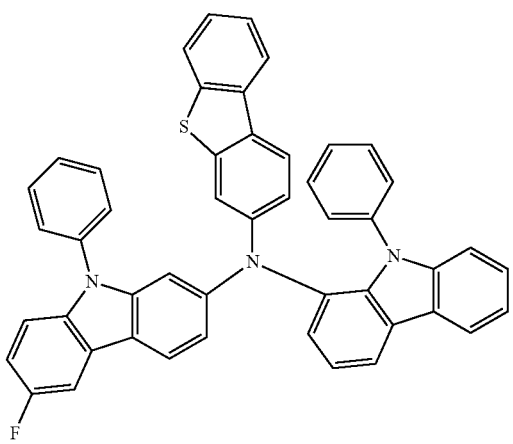
137
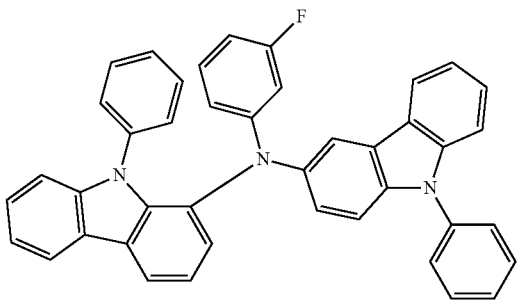
138
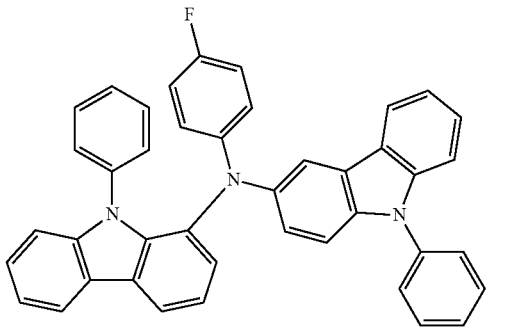
139
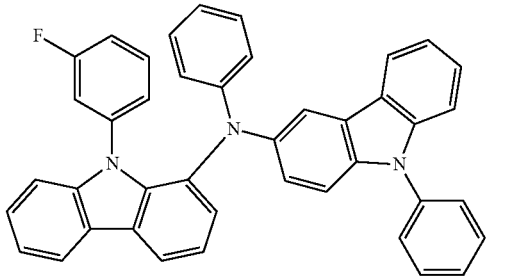

275
-continued
140
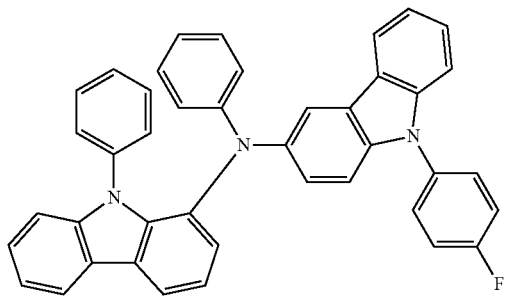
141
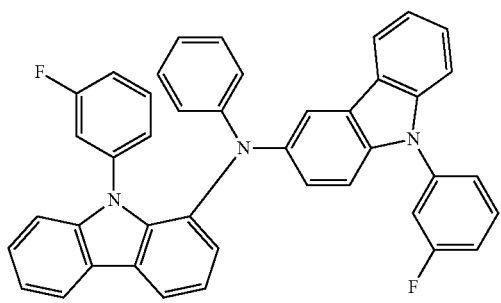
142
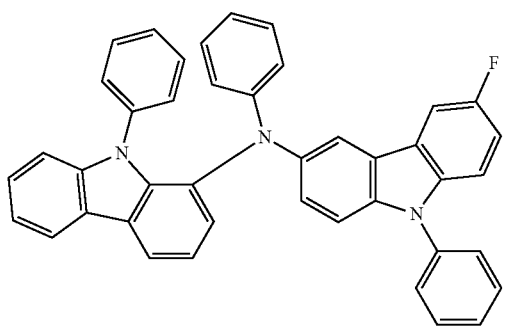
143
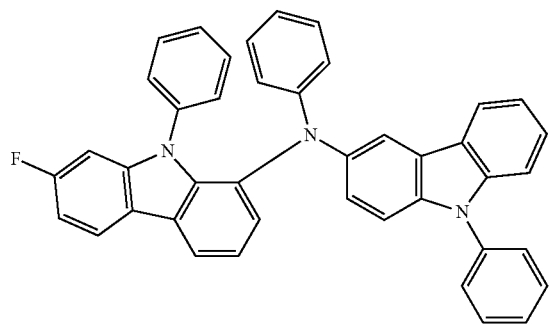
276
-continued
144
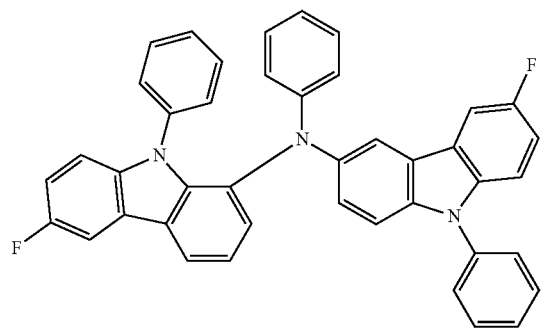
145
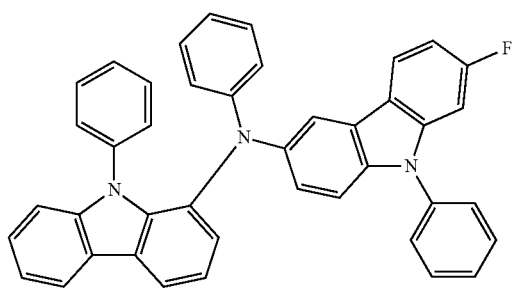
146
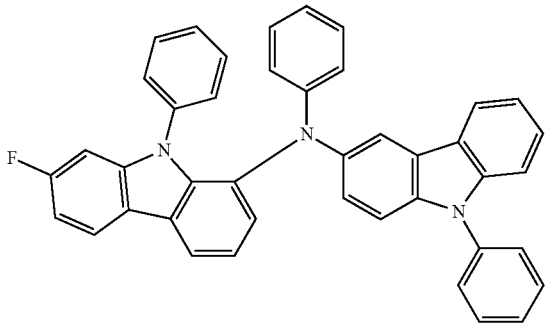
147
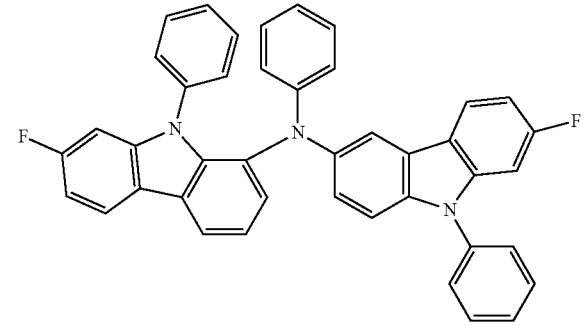

148
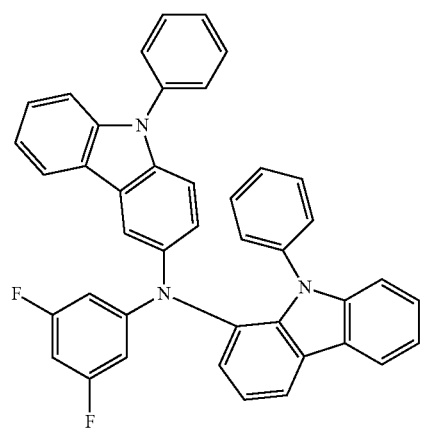
149
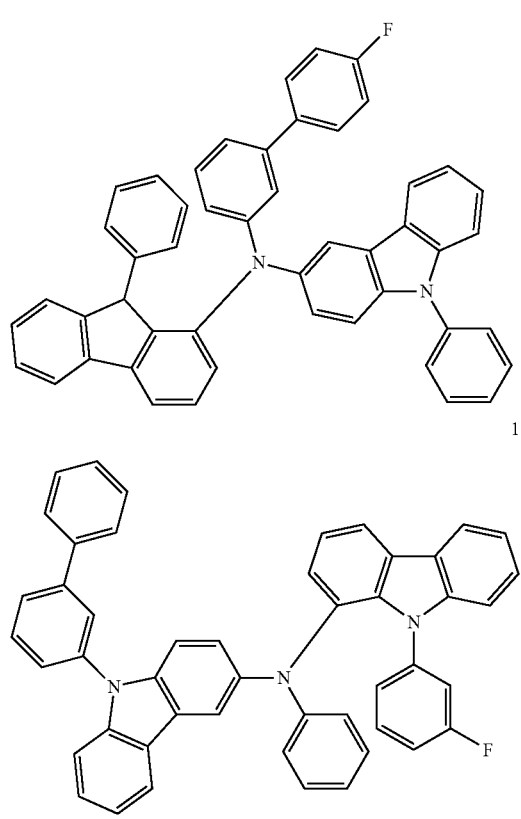
150
151
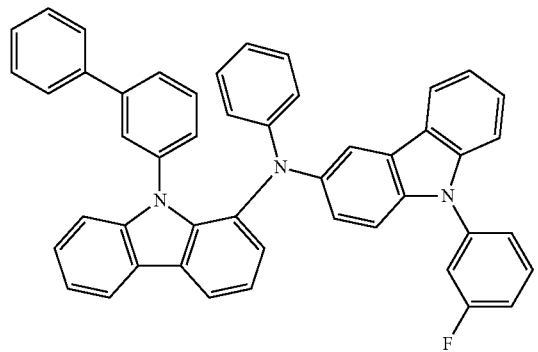
152
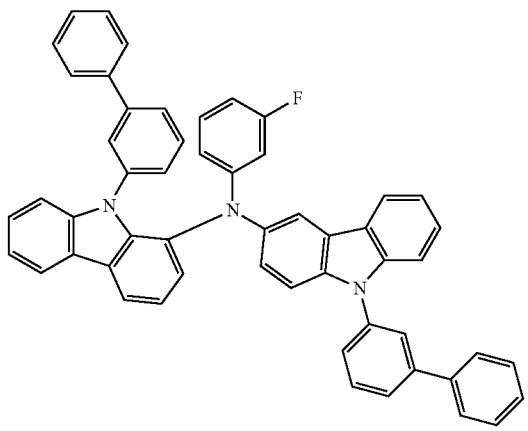
153
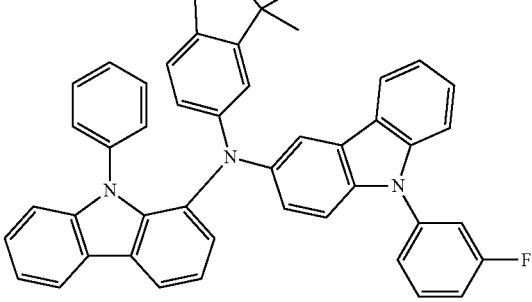
154
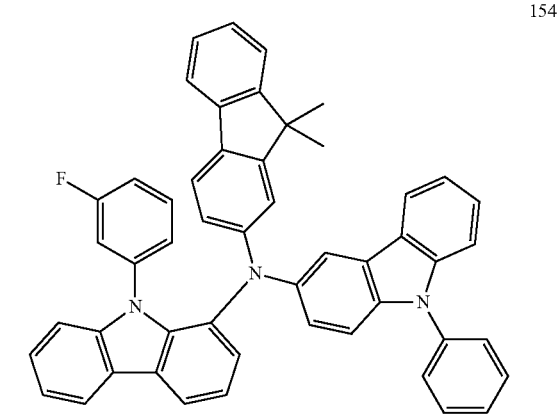

155
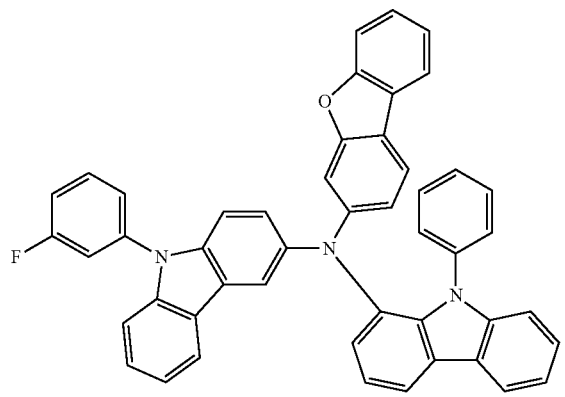
156
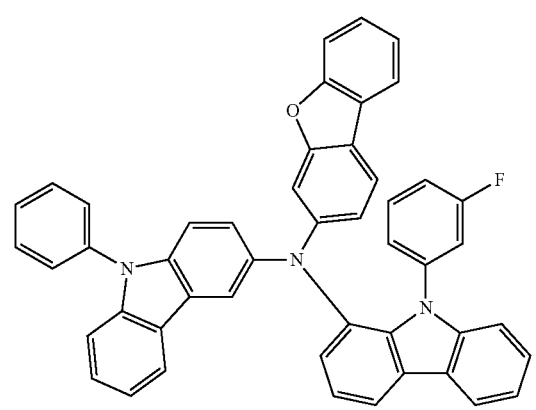
157
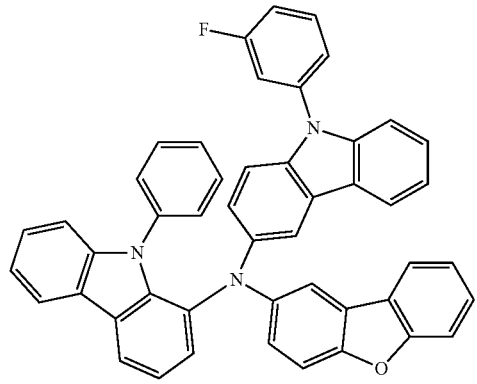
158
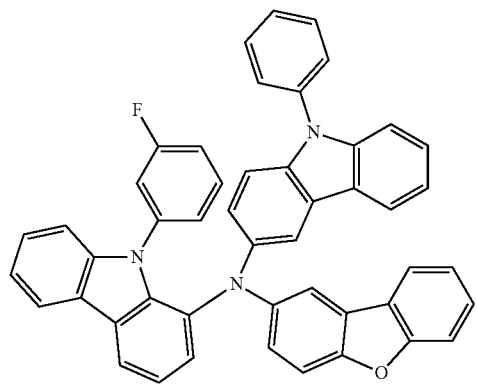
159
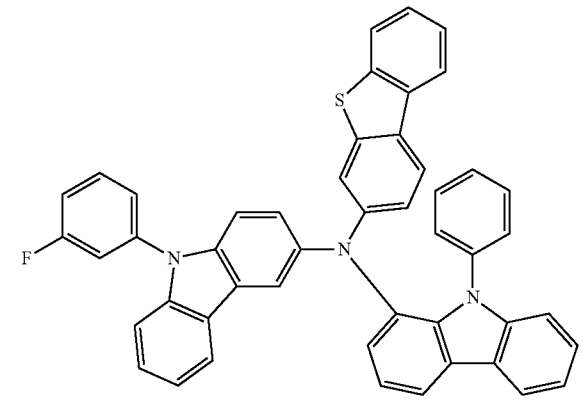
160
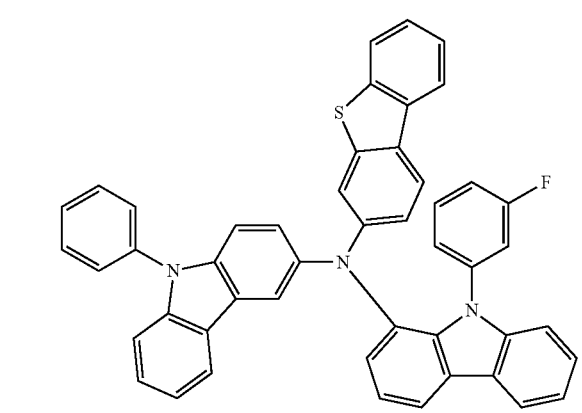
161
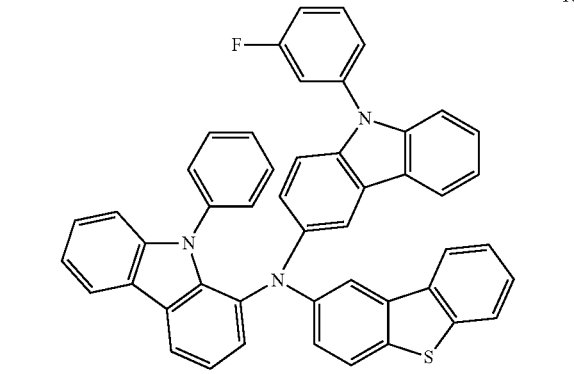
162
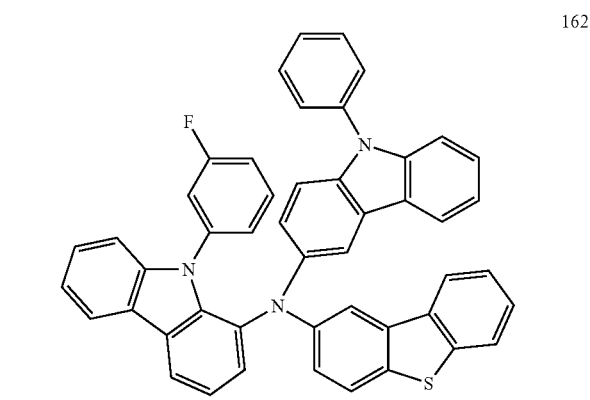

-continued
163
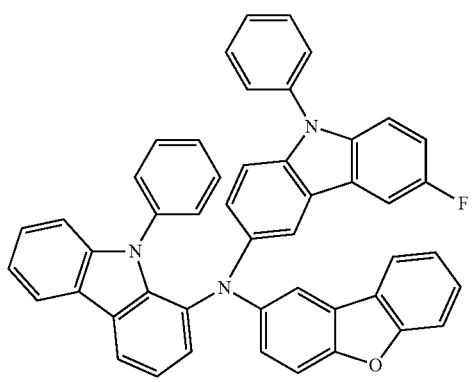
164
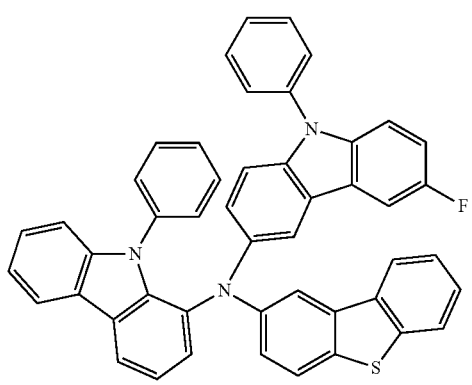
165
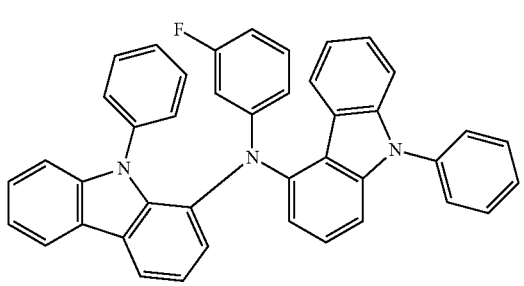
166
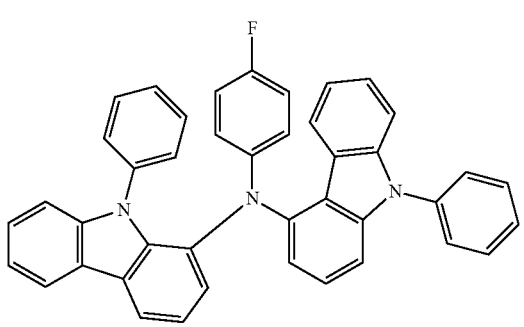
-continued
167
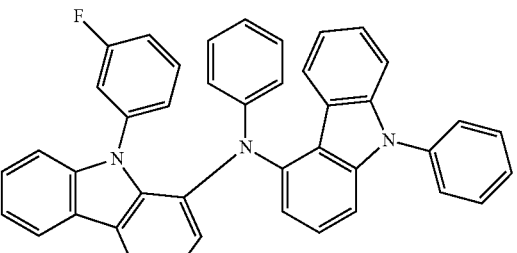
168
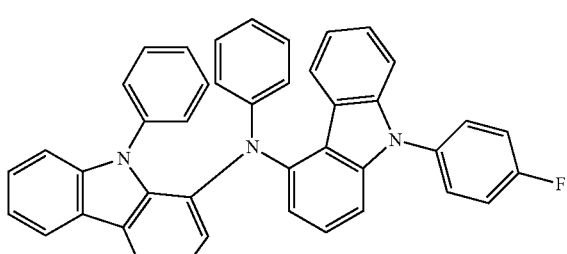
169
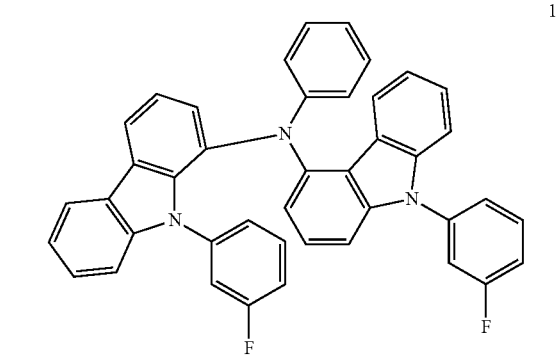
170
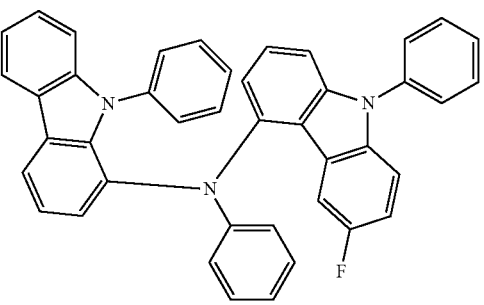
171
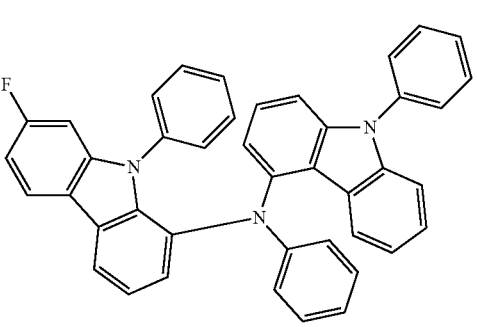

172
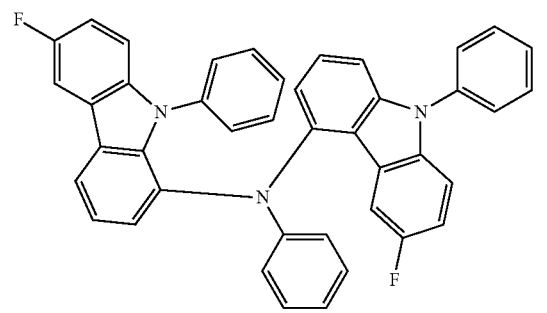
173
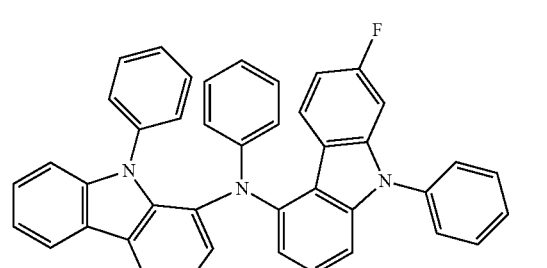
174
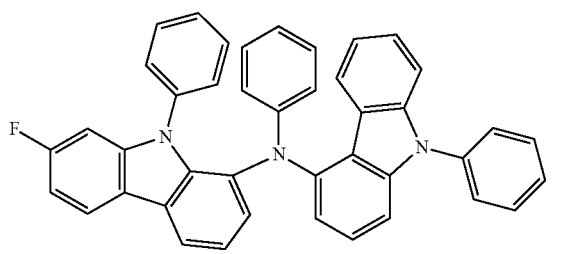
175
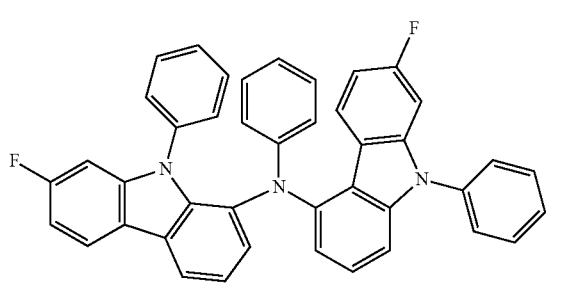
176
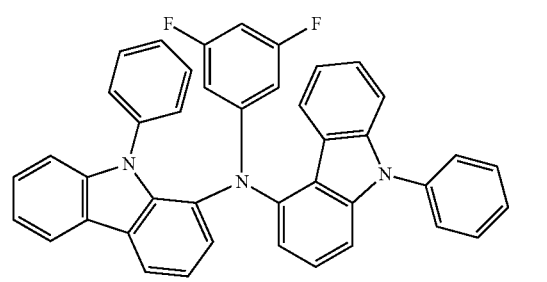
177
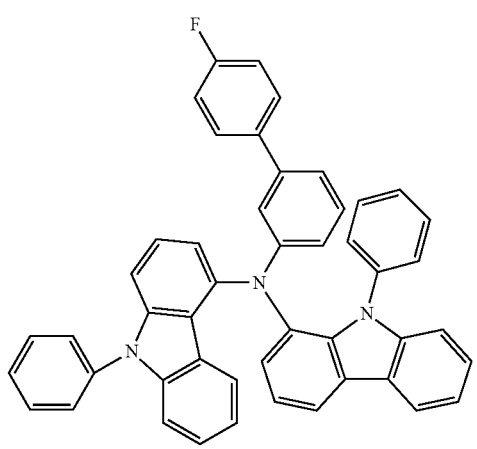
178
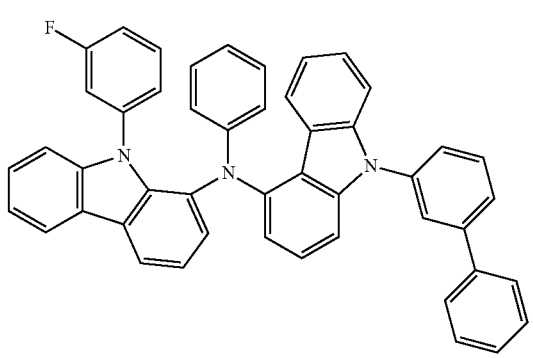
179
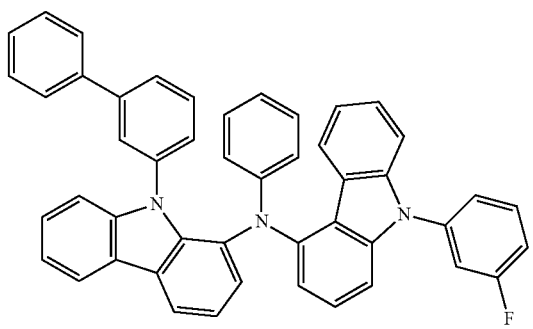
180
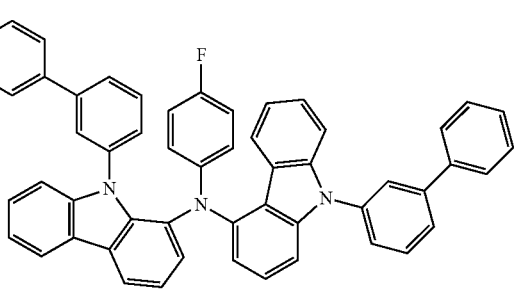

285
-continued
181
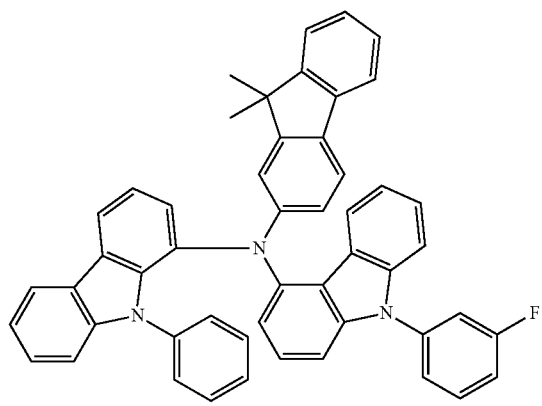
182
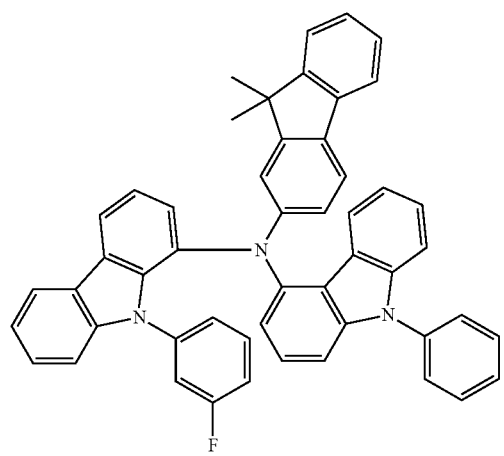
183
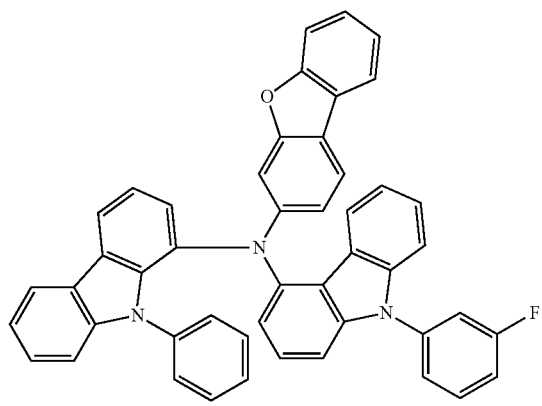
286
-continued
184
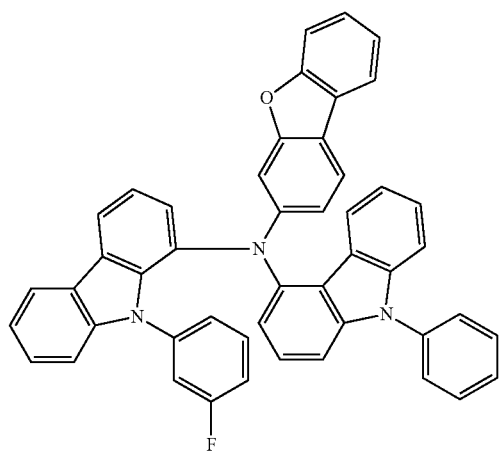
185
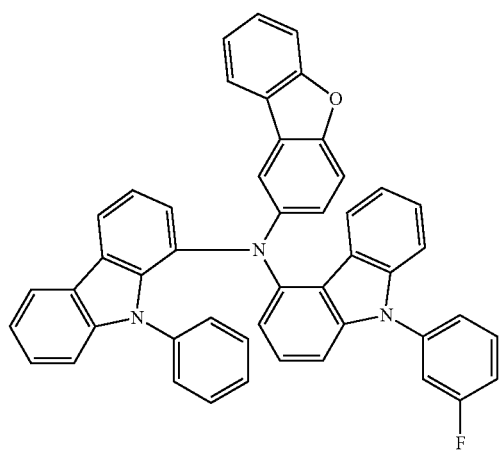
186
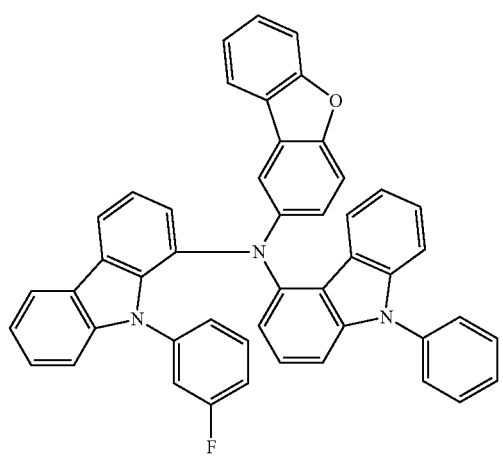

187
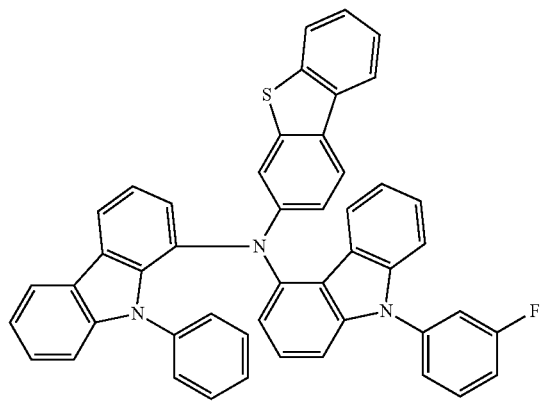
188
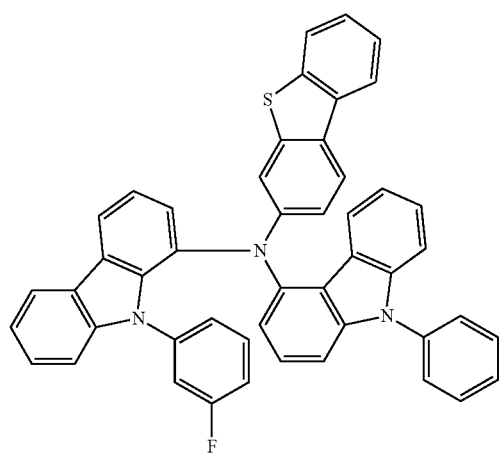
189
190
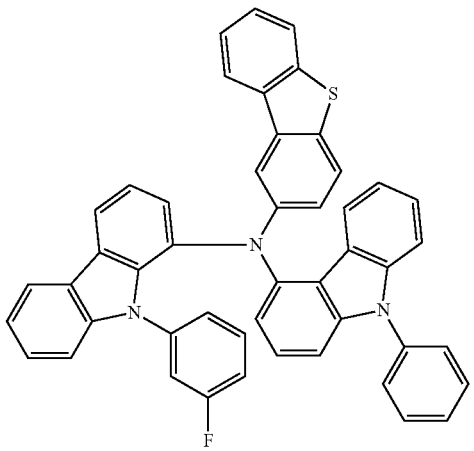
191
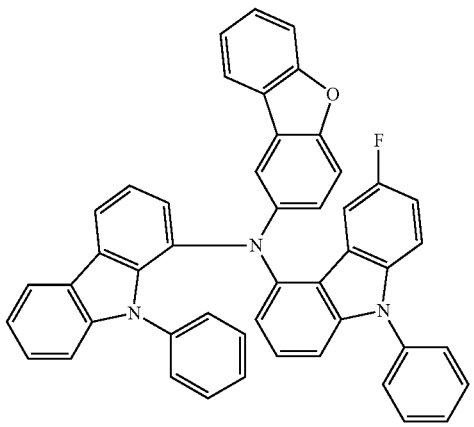
192
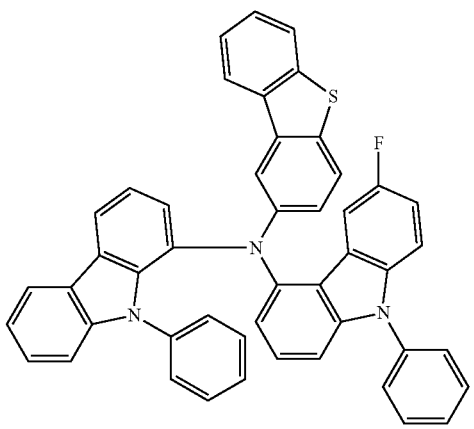
193
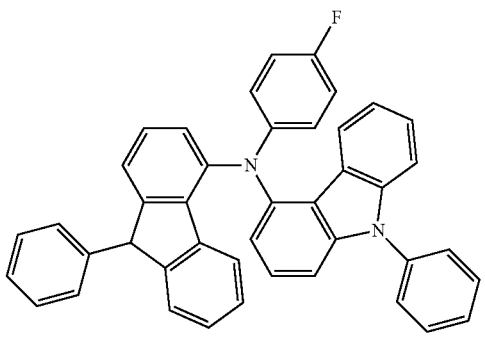

-continued
194
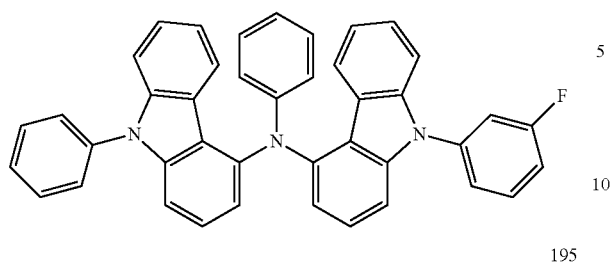
195
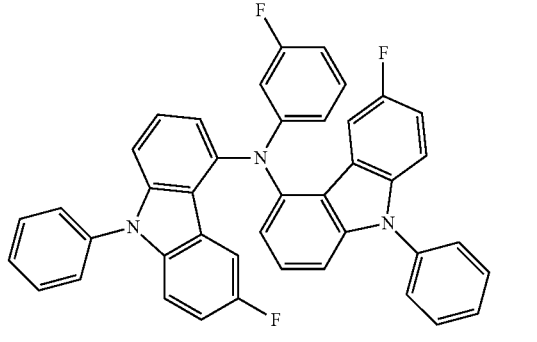
196
197
198
199
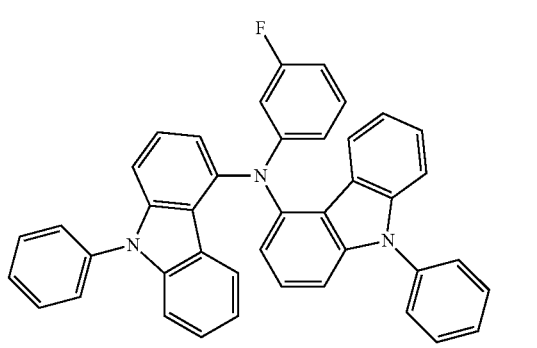
200
201
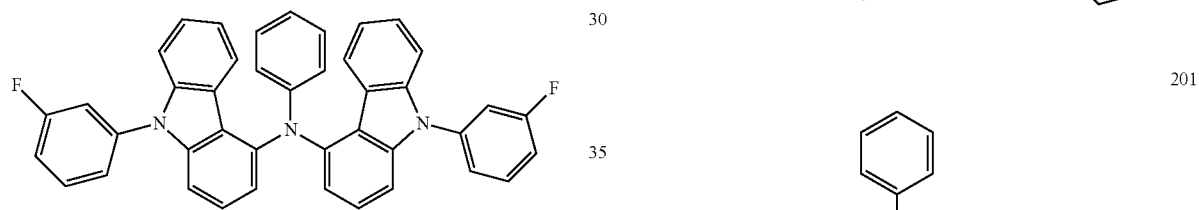
202
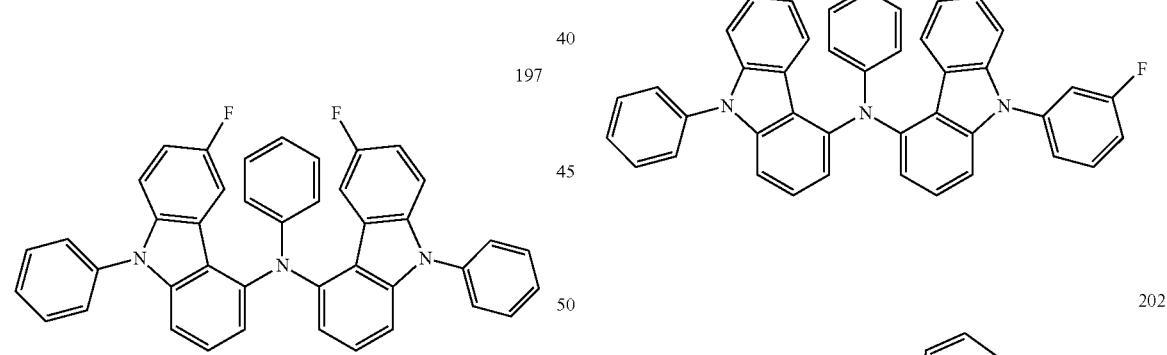
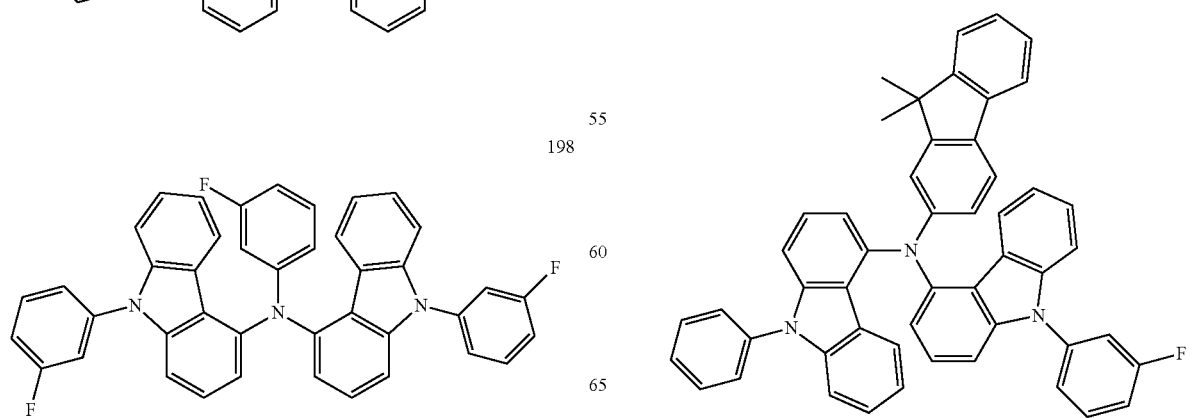

291
-continued
203
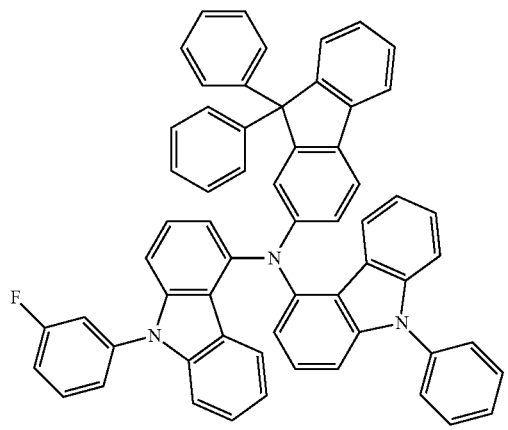
204
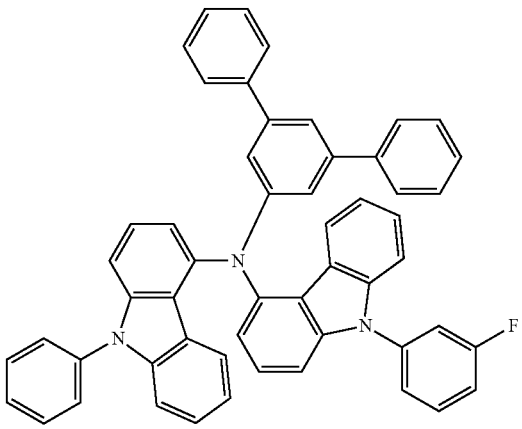
206
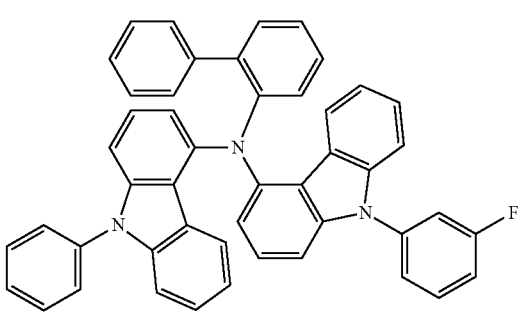
207
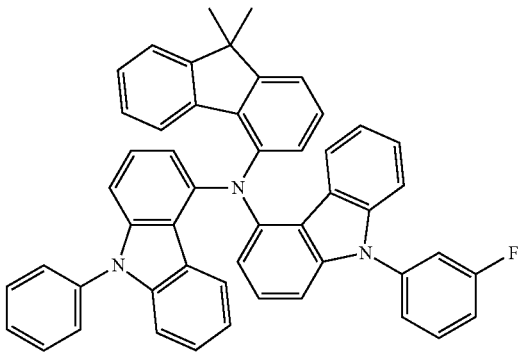
208
205
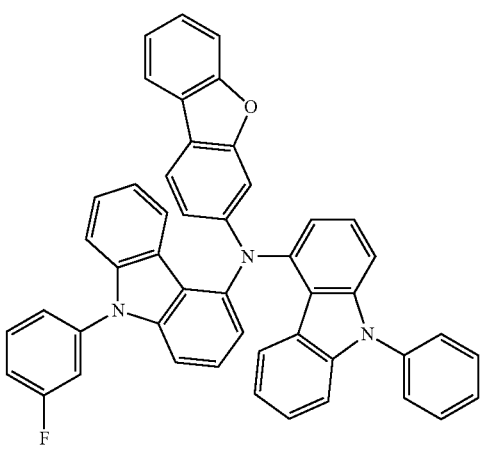
209
292
-continued 210
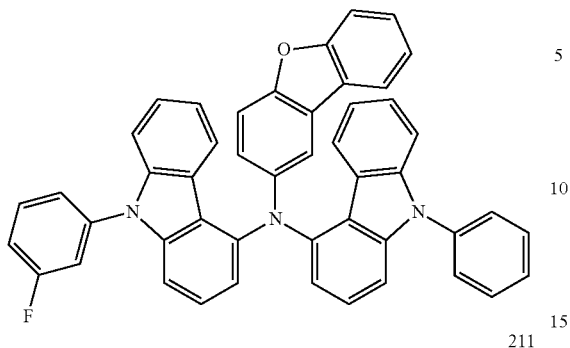
211
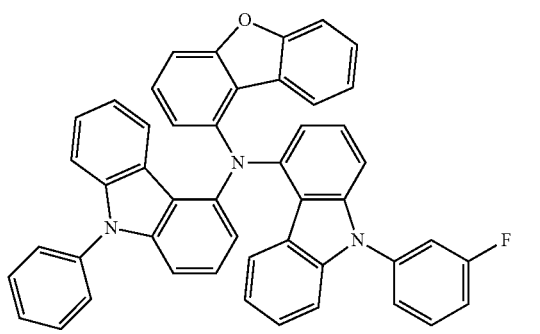
212
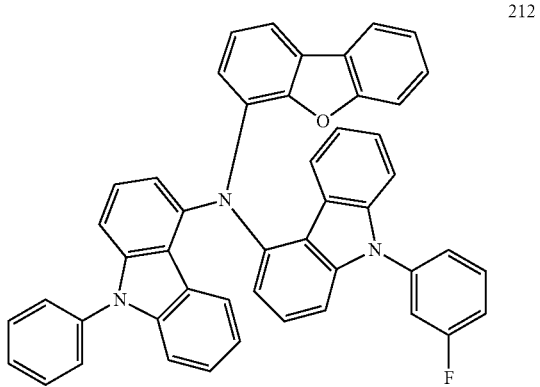
213
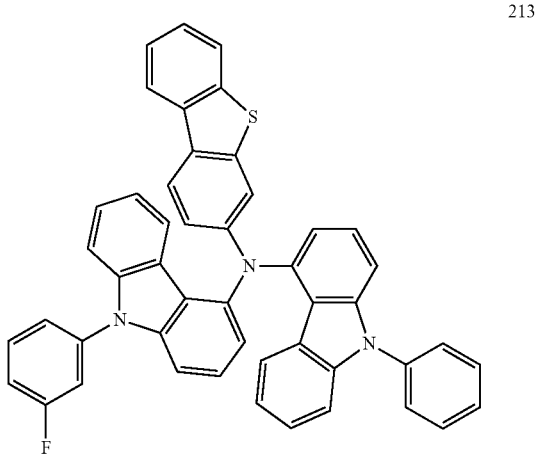
214
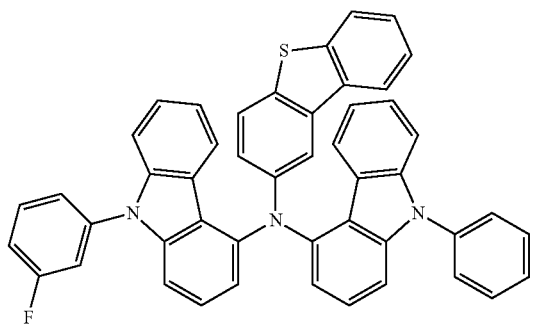
215
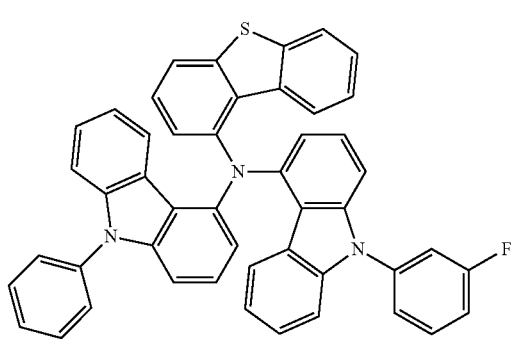
216
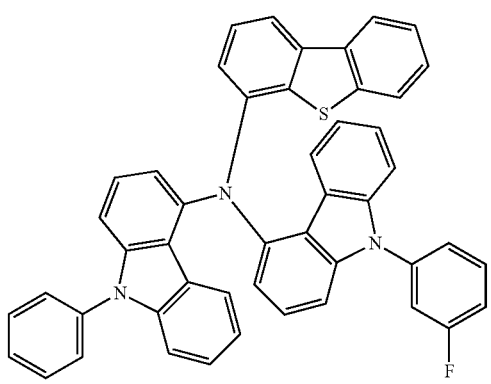
217
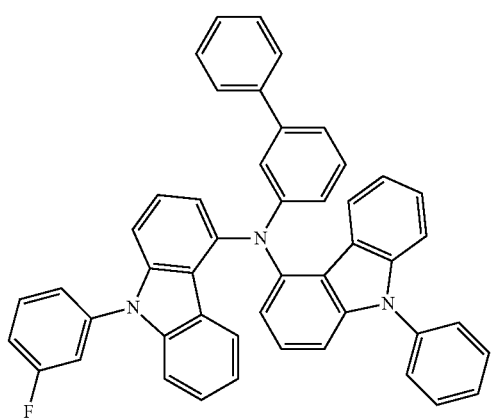

218
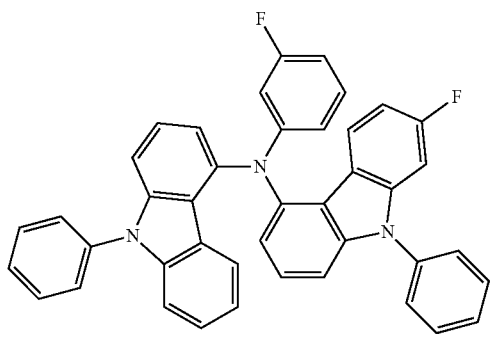
219
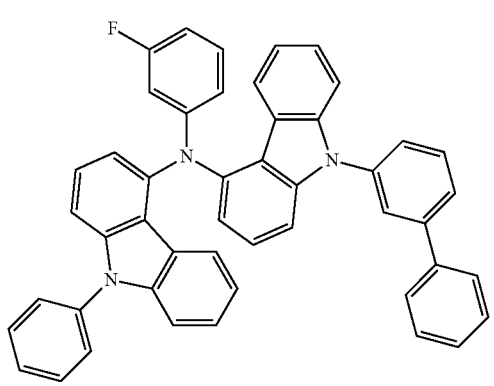
220
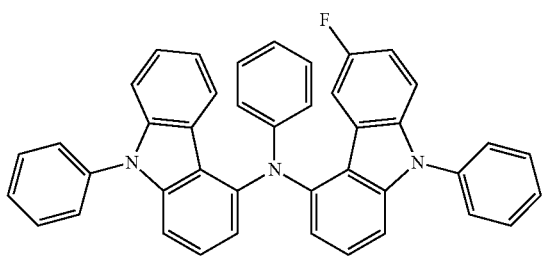
221
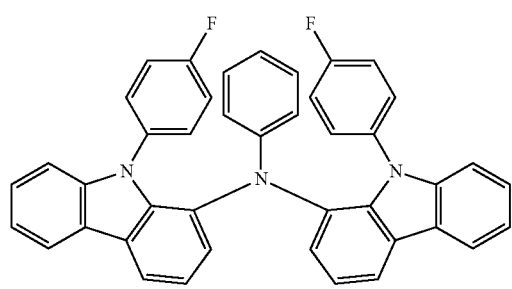
222
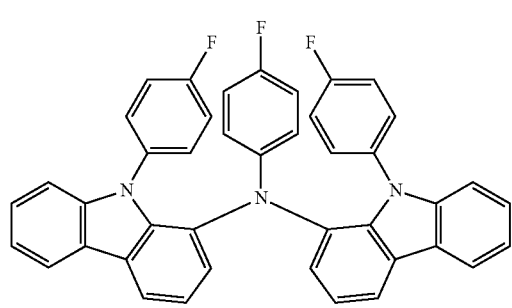
223
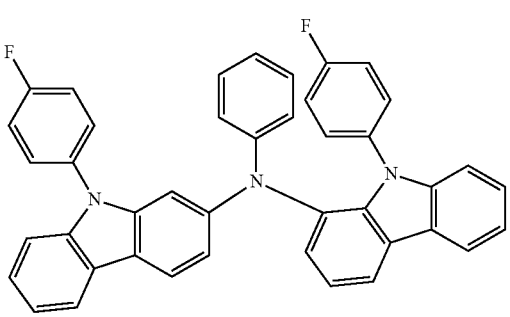
224
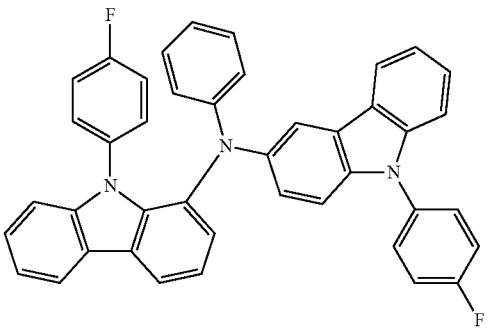
225
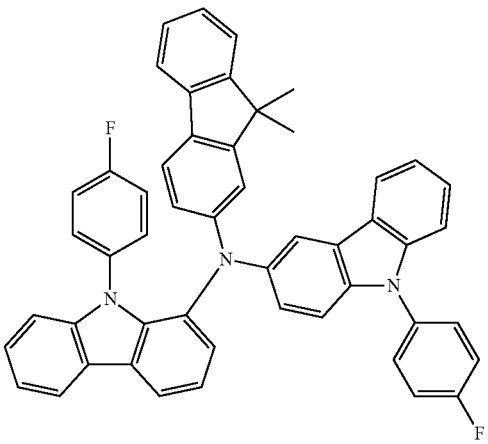
226
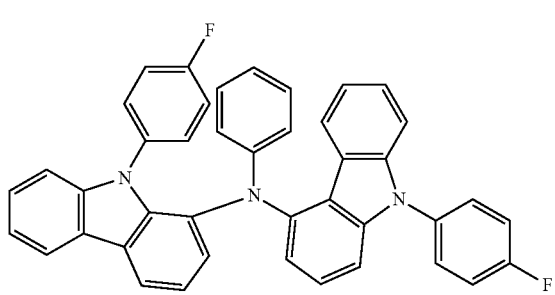

227 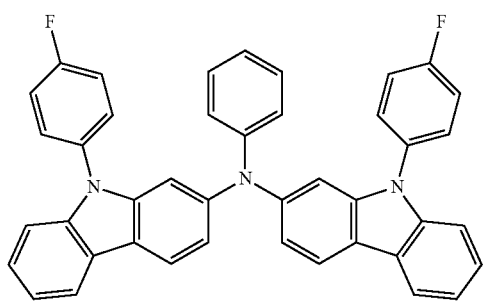

228 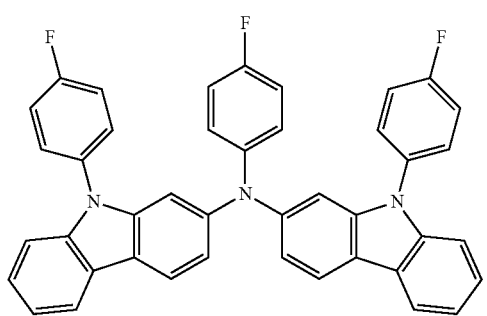

229 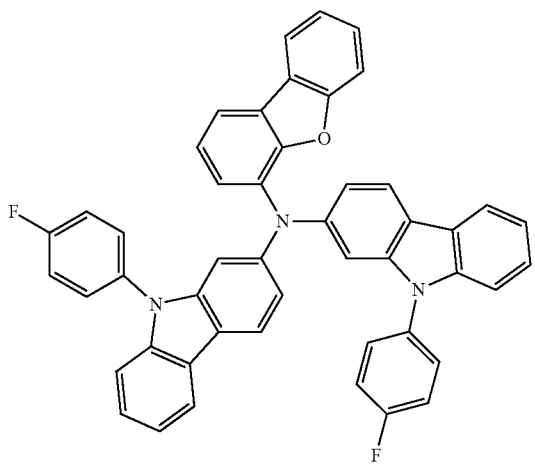

230 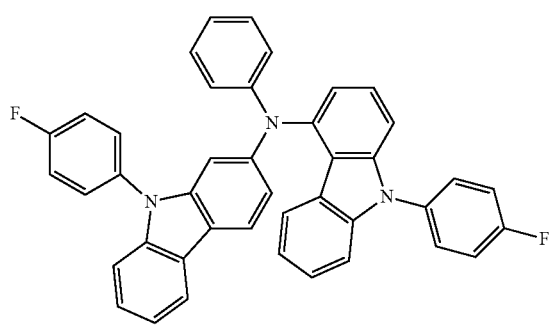

231 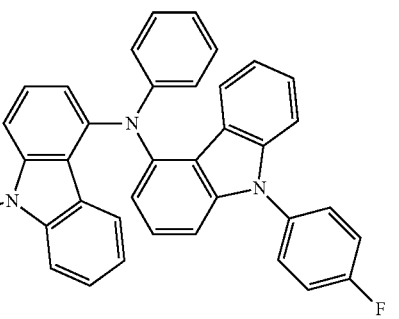

232

13. An organic light-emitting device comprising:
a first electrode;
a second electrode facing the first electrode; and
an organic layer disposed between the first electrode and the second electrode, wherein the organic layer comprises an emission layer and at least one of the amine-based compound of claim 1.

14. The organic light-emitting device claim 13, wherein:
the first electrode is an anode,
the second electrode is a cathode,
the organic layer further comprises a hole transport region disposed between the first electrode and the emission layer and an electron transport region disposed between the emission layer and the second electrode,
wherein the hole transport region comprises a hole injection layer, a first hole transport layer, a second hole transport layer, an emission auxiliary layer, an electron blocking layer, or a combination thereof, and
the electron transport region comprises a hole blocking layer, an electron transport layer, an electron injection layer, or a combination thereof.

15. The organic light-emitting device of claim 14, wherein the hole transport region further comprises the at least one of the amine-based compound.

16. The organic light-emitting device of claim 14, wherein the hole transport region comprises the first hole transport layer, wherein the first hole transport layer comprises the at least one of the amine-based compound.

17. The organic light-emitting device of claim 14, wherein:
the hole transport region comprises the hole injection layer, the first hole transport layer, and the second hole transport layer,
the second hole transport layer is disposed between the first hole transport layer and the emission layer, the hole injection layer and the first hole transport layer each comprise the at least one of the amine-based compound, and the at least one of the amine-based compound comprised in the hole injection layer and the at least one of the amine-based compound comprised in the first hole transport layer are identical to or different from each other.

18. The organic light-emitting device of claim 17, wherein the second hole transport layer comprises the at least one of the amine-based compound, the at least one of the amine-based compound comprised in the hole injection layer and the at least one of the amine-based compound comprised in the second hole transport layer are identical to or different from each other, and the at least one of the amine-based compound comprised in the first hole transport layer and the at least one of the amine-based compound comprised in the second hole transport layer are identical to or different from each other.

19. The organic light-emitting device of claim 14, wherein the hole transport region further comprises a p-dopant, wherein a lowest unoccupied molecular orbital (LUMO) energy level of the p-dopant is −3.5 eV or less.

20. The organic light-emitting device of claim 19, wherein the p-dopant comprises a quinone derivative.

\* \* \* \* \*